(12) United States Patent
Horne et al.

(10) Patent No.: US 6,974,667 B2
(45) Date of Patent: Dec. 13, 2005

(54) GENE EXPRESSION PROFILES IN LIVER CANCER

(75) Inventors: Darci T. Horne, Gaithersburg, MD (US); Uwe Scherf, Gaithersburg, MD (US); Joseph Vockley, Damascus, MD (US)

(73) Assignee: Gene Logic, Inc., Gaithersburg, MD (US)

( * ) Notice: Subject to any disclaimer, the term of this patent is extended or adjusted under 35 U.S.C. 154(b) by 503 days.

(21) Appl. No.: 09/880,107

(22) Filed: Jun. 14, 2001

(65) Prior Publication Data

US 2002/0142981 A1 Oct. 3, 2002

Related U.S. Application Data

(60) Provisional application No. 60/211,379, filed on Jun. 14, 2000, and provisional application No. 60/237,054, filed on Oct. 2, 2000.

(51) Int. Cl.[7] ........................... C12Q 1/68; C12P 19/34; C07H 21/04
(52) U.S. Cl. ........................ 435/6; 435/91.1; 536/23.1; 536/24.3
(58) Field of Search .......................... 435/6, 91.1, 91.2; 536/23.1, 24.3, 22.1; 935/6; 436/518

(56) References Cited

PUBLICATIONS

Timothy J. Yeatman et al., Identification of a differentially-expressed message associated with colon cancer liver metastasis . . . , (1995) Oxford University Press, Nucleic Acids Research, vol. 23, No. 19, pp. 4007–4008.*
Naohiro Tomita, Expression of pancreatic secretory trypsin inhibitor gene in neoplastic tissue, (Dec. 1987), vol. 225, pp. 113–119.*
Yoshitaka Ohmachi et al., Expression of the pancreatic secretory trypsin inhibitor gene in the liver infected with hepatitis B virus, Journal of Hepatology (1994), pp. 1012–1016.*
Chen CJ, Yu MW and Liaw YF. Epidemiological characteristics and risk factors of hepatocellular carcinoma. J Gastroenterol Hepatol. Oct. 1997;12(9–10):S294–308.
Di Carlo V, Ferrari G, Castoldi R, Nadalin S, Marenghi C, Molteni B, Taccagni G and Castrucci M. Surgical treatment and prognostic variables of hepatocellular carcinoma in 122 cirrhotics. Hepatogastroenterology. Jul. 1995;42(3):222–9.
Hsu DK, Dowling CA, Jeng KC, Chen JT, Yang RY and Liu FT. Galectin–3 expression is induced in cirrhotic liver and hepatocellular carcinoma. Int J Cancer. May 17, 1999;81(4):519–26.
Iurisci I, Tinari N, Natoli C, Angelucci D, Cianchetti E and Iacobelli S. Concentrations of galectin–3 in the sera of normal controls and cancer patients. Clin Cancer Res. Apr. 2000;6(4):1389–93.

Jiang WG, Bryce RP, Horrobin DF and Mansel RE. Regulation of tight junction permeability and occludin expression by polyunsaturated fatty acids. Biochem Biophys Res Commun. Mar. 17, 1998;244(2):414–20.
Johnson RC. Hepatocellular carcinoma. Hepatogastroenterology. Jan.–Feb. 1997;44(13):307–12.
Kurata T, Oguri T, Isobe T, Ishioka S and Yamakido M. Differential expression of facilitative glucose transporter (GLUT) genes in primary lung cancers and their liver metastases. Jpn J Cancer Res. Nov. 1999;90(11):1238–43.
Li D and Mrsny RJ. Oncogenic Raf–1 disrupts epithelial tight junctions via downregulation of occludin. J Cell Biol. Feb. 21, 2000;148(4):791–800.
Morita K, Furuse M, Fujimoto K and Tsukita S. Claudin multigene family encoding four–transmembrane domain protein components of tight junction strands. Proc Natl Acad Sci U S A. Jan. 19, 1999;96(2):511–6.
Nakamura M, Inufusa H, Adachi T, Aga M, Kurimoto M, Nakatani Y, Wakano T, Nakajima A, Hida JI, Miyake M, Shindo K and Yasutomi M. Involvement of galectin–3 expression in colorectal cancer progression and matastasis. Int J Oncol. Jul. 1999;15(1):143–8.
Ohmachi Y, Murata A, Matsuura N, Yasuda T, Yasuda T, Monden M, Mori T, Ogawa M and Matsubara K. Specific expression of the pancreatic–secretory–trypsin–inhibitor (PSTI) gene in hepatocellular carcinoma. Int J Cancer. Nov. 11, 1993;55(5):728–34.
Simon DB, Lu Y, Choate KA, Velazquez H, Al–Sabban E, Praga M, Casari G, Bettinelli A, Colussi G, Rodriguez–Soriano J, McCredie D, Milford D, Sanjad S and Lifton RP. Paracellin–1, a renal tight junction protein required for paracellular Mg2+ resorption. Science. Jul. 2, 1999;285(5424):103–6.
Weinberg RA. Tumor suppressor genes. Science. Nov. 22, 1991;254(5035):1138–46.
Zak J, Schneider SW, Eue I, Ludwig T and Oberleithner H. High–resistance MDCK–C7 monolayers used for measuring invasive potency of tumour cells. Pflugers Arch. May 2000;440(1):179–83.

* cited by examiner

*Primary Examiner*—Jehanne Sitton
(74) *Attorney, Agent, or Firm*—Morgan Lewis & Bockius LLP

(57) ABSTRACT

The present invention identifies the global changes in gene expression associated with liver cancer by examining gene expression in tissue from normal liver, metastatic malignant liver and hepatocellular carcinoma. The present invention also identifies expression profiles which serve as useful diagnostic markers as well as markers that can be used to monitor disease states, disease progression, drug toxicity, drug efficacy and drug metabolism.

18 Claims, 4 Drawing Sheets

GENE EXPRESSION PROFILES IN LIVER CANCER

RELATED APPLICATIONS

This application claims priority to U.S. Provisional Application No. 60/211,379, filed Jun. 14, 2000 and U.S. Provisional Application No. 60/237,054, filed Oct. 2, 2000, both of which are herein incorporated by reference in their entirety.

BACKGROUND OF THE INVENTION

Primary hepatocellular carcinoma (HCC) is a widespread cancer throughout the world, especially prevalent where the incidence of chronic hepatitis B (HBV) and hepatitis C (HCV) viral infections are endemic (Groen, (1999) Semin. Oncol. Nurs. 15, 48–57; Idilman et al., (1998) J. Viral. Hepat. 5, 110–117; Di Bisceglie et al., (1998) Hepatol. 28, 1161–1165; Johnson, (1997) Hepatogastroenerology 44, 307–312; Sheu, (1997) J. Gastroeneterol. Hepatol. 12, S309–313). Hepatocellular carcinomas are very malignant tumors that generally offer a poor prognosis, dependent on the size of the tumor, the effect on normal liver functions, and the involvement of metastases. They are best treated by surgical resection, when the tumors are diagnosed at a stage where this is a viable possibility, but the recurrence rate for these cancers remains high (Johnson, (1997) Hepatogastroenterology 44, 307–312; Schafer & Sorrell, (1999) Lancet 353, 1253–1257; Groen, (1999) Semin. Oncol. Nurs. 15, 48–57; Sitzman, (1995) World. J. Surg. 19, 790–794; DiCarlo, (1995) Hepato-Gastroenterol. 42, 222–259; Tanaka et al., (1996) Hepato-Gastroenterol. 43, 1172–1181; El-Assal et al., (1997) Surgery 122, 571–577).

Numerous risk factors for the development of HCC have been identified: cirrhosis, HBV or HCV infection, being male, alcohol-related liver disease, exposure to aflatoxins, vinyl chloride and radioactive thorium dioxide, cigarette smoking, ingestion of inorganic arsenic, the use of oral contraceptives and anabolic steroids, iron accumulation, and various inherited metabolic disorders (hemochromatosis, glycogen storage disease, porphyria, tyrosinemia, $\alpha$-1-antitrypsin deficiency) (Di Bisceglie et al., (1998) Hepatol. 28, 1161–1165; Chen et al., (1997) J. Gastroenterol. Hepatol. 12, S294–308; Schafer & Sorrell (1999) Lancet 353, 1253–1257; Groen, (1999) Semin. Oncol. Nurs. 15, 48–57; Idilman et al., (1998) J. Viral. Hepat. 5, 110–117; Johnson, (1997) Hepato-Gastroenterol. 44, 307–312).

In addition to liver tumors attributed to hepatocellular carcinoma, there are liver tumors that arise as metastases from primary tumors in other parts of the body. These tumors most often metastasize from the gastrointestinal organs, primarily the colon and rectum, but it is possible for metastatic liver cancers to occur from primary cancers throughout the body (Sitzman 1990, Groen 1999). These cancers can be treated using the routine therapies such as chemotherapy, radiotherapy, surgical resection, liver transplantation, chemoembolization, cryosurgery, or a combination of therapies (Sitzman, (1990) Hepatic Neoplasia, in Bayless (editor) Current Therapy in Gastroenterology and Liver Disease, Marcel Dekker; Groen, (1999) Semin. Oncol. Nurs. 15, 48–57).

The characterization of genes that are differentially expressed in tumorigenesis is an important step in identifying those that are intimately involved in the details of a cell's transformation from normal to cancerous. Studies examining the gene expression of metastatic liver tumors and hepatocellular carcinomas in comparison with a set of normal liver tissues would produce data identifying genes that are not expressed in normal livers but have been switched on in tumors, as well as genes that have been completely turned off in these tumors during the progression from a normal to a malignant state. Such studies would also lead to the identification of genes that are expressed in tumor tissue at differing levels, but not expressed at any level in normal liver tissue. The identification of genes and ESTs that are expressed in both types of tumors, i.e., primary hepatocellular carcinomas as well as metastatic tumors of a different origin, and not in normal liver cells would be extremely valuable for the diagnosis of liver cancer.

SUMMARY OF THE INVENTION

The present invention identifies the global changes in gene expression associated with liver cancer by examining gene expression in tissue from normal liver, metastatic malignant liver and hepatocellular carcinoma. The present invention also identifies expression profiles which serve as useful diagnostic markers as well as markers that can be used to monitor disease states, disease progression, drug toxicity, drug efficacy and drug metabolism.

The invention includes methods of diagnosing the presence or absence of liver cancer in a patient comprising the step of detecting the level of expression in a tissue sample of two or more genes from Tables 3–9; wherein differential expression of the genes in Tables 3–9 is indicative of liver cancer. In some preferred embodiments, one or more genes may be selected from a group consisting of the genes listed in Tables 3–5. In some preferred embodiments, the method may include detecting the expression level of one or more genes selected from a group consisting Tetraspan NET-6 protein; collagen, type V, alpha; and glypican 3.

The invention also includes methods of detecting the progression of liver cancer and/or differentiating nonmetastatic from metastatic disease. For instance, methods of the invention include detecting the progression of liver cancer in a patient comprising the step of detecting the level of expression in a tissue sample of two or more genes from 3–9; wherein differential expression of the genes in Tables 3–9 is indicative of liver cancer progression. In some preferred embodiments, one or more genes may be selected from a group consisting of the genes listed in Tables 3–5.

In some aspects, the present invention provides a method of monitoring the treatment of a patient with liver cancer, comprising administering a pharmaceutical composition to the patient and preparing a gene expression profile from a cell or tissue sample from the patient and comparing the patient gene expression profile to a gene expression from a cell population comprising normal liver cells or to a gene expression profile from a cell population comprising liver cancer cells or to both. In some preferred embodiments, the gene profile will include the expression level of one or more genes in Tables 3–9. In other preferred embodiments, one or more genes may be selected from a group consisting of the genes listed in Tables 3–5.

In another aspect, the present invention provides a method of treating a patient with liver cancer, comprising administering to the patient a pharmaceutical composition, wherein the composition alters the expression of at least one gene in Tables 3–9, preparing a gene expression profile from a cell or tissue sample from the patient comprising tumor cells and comparing the patient expression profile to a gene expression profile from an untreated cell population comprising liver cancer cells. In some preferred embodiments, one or more genes may be selected from a group consisting of the genes listed in Tables 3–5.

In one aspect, the present invention provides a method of diagnosing hepatocellular carcinoma in a patient, comprising detecting the level of expression in a tissue sample of two or more genes from Tables 3–9, wherein differential expression of the genes in Tables 3–9 is indicative of hepatocellular carcinoma. In some preferred embodiments, one or more genes may be selected from a group consisting of the genes listed in Tables 3 or 5

In another aspect, the present invention provides a method of detecting the progression of hepatocellular carcinoma in a patient, comprising detecting the level of expression in a tissue sample of two or more genes from Tables 3–9; wherein differential expression of the genes in Tables 3–9 is indicative of hepatocellular carcinoma progression. In some preferred embodiments, one or more genes may be selected from a group consisting of the genes listed in Tables 3 or 5.

The present invention also provides materials and methods for monitoring the treatment of a patient with a hepatocellular caricnoma. The present invention provides a method of monitoring the treatment of a patient with hepatocellular carcinoma, comprising administering a pharmaceutical composition to the patient, preparing a gene expression profile from a cell or tissue sample from the patient and comparing the patient gene expression profile to a gene expression from a cell population comprising normal liver cells or to a gene expression profile from a cell population comprising hepatocellular carcinoma cells or to both. In some preferred embodiments, the method may include detecting the level of expression of one or more genes from the genes listed in Tables 3–9. In some preferred embodiments, one or more genes may be selected from a group consisting of the genes listed in Tables 3 or 5.

In a related aspect, the present invention provides a method of treating a patient with hepatocellular carcinoma, comprising administering to the patient a pharmaceutical composition, wherein the composition alters the expression of at least one gene in Tables 3-9, preparing a gene expression profile from a cell or tissue sample from the patient comprising hepatocellular carcinoma cells and comparing the patient expression profile to a gene expression profile from an untreated cell population comprising hepatocellular carcinoma cells. In some preferred embodiments, one or more genes may be selected from a group consisting of the genes listed in Tables 3 or 5.

The present invention provides a method of diagnosing a metastatic liver tumor in a patient, comprising detecting the level of expression in a tissue sample of two or more genes from Tables 3–9, wherein differential expression of the genes in Tables 3–9 is indicative of hepatocellular carcinoma. In some preferred embodiments, one or more genes may be selected from a group consisting of the genes listed in Tables 4 or 5.

The present invention provides a method of detecting the progression of a metastatic liver tumor in a patient, comprising detecting the level of expression in a tissue sample of two or more genes from Tables 3–9, wherein differential expression of the genes in Tables 3–9 is indicative of a metastatic liver tumor progression. In some preferred embodiments, one or more genes may be selected from a group consisting of the genes listed in Tables 4 or 5.

In a related aspect, the present invention provides a method of monitoring the treatment of a patient with a metastatic liver tumor, comprising administering a pharmaceutical composition to the patient, preparing a gene expression profile from a cell or tissue sample from the patient and comparing the patient gene expression profile to a gene expression from a cell population comprising normal liver cells or to a gene expression profile from a cell population comprising metastatic liver tumor cells or to both. In some preferred embodiments, the method of the present invention may include detecting the expression level of one or more genes selected from the genes listed in Tables 3–9. In some preferred embodiments, one or more genes may be selected from a group consisting of the genes listed in Tables 4 or 5.

In some preferred embodiments, the present invention provides a method of treating a patient with a metastatic liver tumor, comprising administering to the patient a pharmaceutical composition, wherein the composition alters the expression of at least one gene in Tables 3–9, preparing a gene expression profile from a cell or tissue sample from the patient comprising metastatic liver tumor cells and comparing the patient expression profile to a gene expression profile from an untreated cell population comprising metastatic liver tumor cells. In some preferred embodiments, one or more genes may be selected from a group consisting of the genes listed in Tables 4 or 5.

The invention also includes methods of differentiating metastatic liver cancer from hepatocellular carcinoma in a patient comprising the step of detecting the level of expression in a tissue sample of two or more genes from Tables 3–9; wherein differential expression of the genes in Tables 3–9 is indicative of metastatic liver cancer rather than hepatocellular carcinoma.

The invention further includes methods of screening for an agent capable of modulating the onset or progression of liver cancer, comprising the steps of exposing a cell to the agent; and detecting the expression level of two or more genes from Tables 3–9. In some preferred embodiments, one or more genes may be selected from a group consisting of the genes listed in Tables 3–5.

Any of the methods of the invention described above may include the detection of at least 2 genes from the tables. Preferred methods may detect all or nearly all of the genes in the tables. In some preferred embodiments, one or more genes may be selected from a group consisting of the genes listed in Tables 3–5.

The invention further includes compositions comprising at least two oligonucleotides, wherein each of the oligonucleotides comprises a sequence that specifically hybridizes to a gene in Tables 3–9 as well as solid supports comprising at least two probes, wherein each of the probes comprises a sequence that specifically hybridizes to a gene in Tables 3–9. In some preferred embodiments, one or more genes may be selected from a group consisting of the genes listed in Tables 3–5.

The invention further includes computer systems comprising a database containing information identifying the expression level in liver tissue of a set of genes comprising at least two genes in Tables 3–9; and a user interface to view the information. In some preferred embodiments, one or more genes may be selected from a group consisting of the genes listed in Tables 3–5. The database may further include sequence information for the genes, information identifying the expression level for the set of genes in normal liver tissue and malignant tissue (metastatic and nonmetastatic) and may contain links to external databases such as GenBank.

The invention further comprises kits useful for the practice of one or more of the methods of the invention. In some preferred embodiments, a kit may contain one or more solid supports having attached thereto one or more oligonucleotides. The solid support may be a high-density oligonucleotide array. Kits may further comprise one or more reagents for use with the arrays, one or more signal detection and/or array-processing instruments, one or more gene expression databases and one or more analysis and database management software packages.

Lastly, the invention includes methods of using the databases, such as methods of using the disclosed computer systems to present information identifying the expression level in a tissue or cell of at least one gene in Tables 3–9, comprising the step of comparing the expression level of at least one gene in Tables 3–9 in the tissue or cell to the level of expression of the gene in the database. In some preferred embodiments, one or more genes may be selected from a group consisting of the genes listed in Tables 3–5.

BRIEF DESCRIPTION OF THE DRAWINGS

FIG. 2A is the Gene Signature Curve for normal liver tissue. FIG. 2B is the Gene Signature Curve for metastatic liver tumor samples. FIG. 2C is the Gene Signature Curve for hepatocellular carinoma samples.

DETAILED DESCRIPTION

Many biological functions are accomplished by altering the expression of various genes through transcriptional (e.g., through control of initiation, provision of RNA precursors, RNA processing, etc.) and/or translational control. For example, fundamental biological processes such as cell cycle, cell differentiation and cell death, are often characterized by the variations in the expression levels of groups of genes.

Changes in gene expression also are associated with pathogenesis. For example, the lack of sufficient expression of functional tumor suppressor genes and/or the over expression of oncogene/protooncogenes could lead to tumorgenesis or hyperplastic growth of cells (Marshall, (1991) Cell, 64,313–326; Weinberg, (1991) Science, 254, 1138–1146). Thus, changes in the expression levels of particular genes (e.g., oncogenes or tumor suppressors) serve as signposts for the presence and progression of various diseases.

Monitoring changes in gene expression may also provide certain advantages during drug screening development. Often drugs are screened and prescreened for the ability to interact with a major target without regard to other effects the drugs have on cells. Often such other effects cause toxicity in the whole animal, which prevent the development and use of the potential drug.

Figure 1:
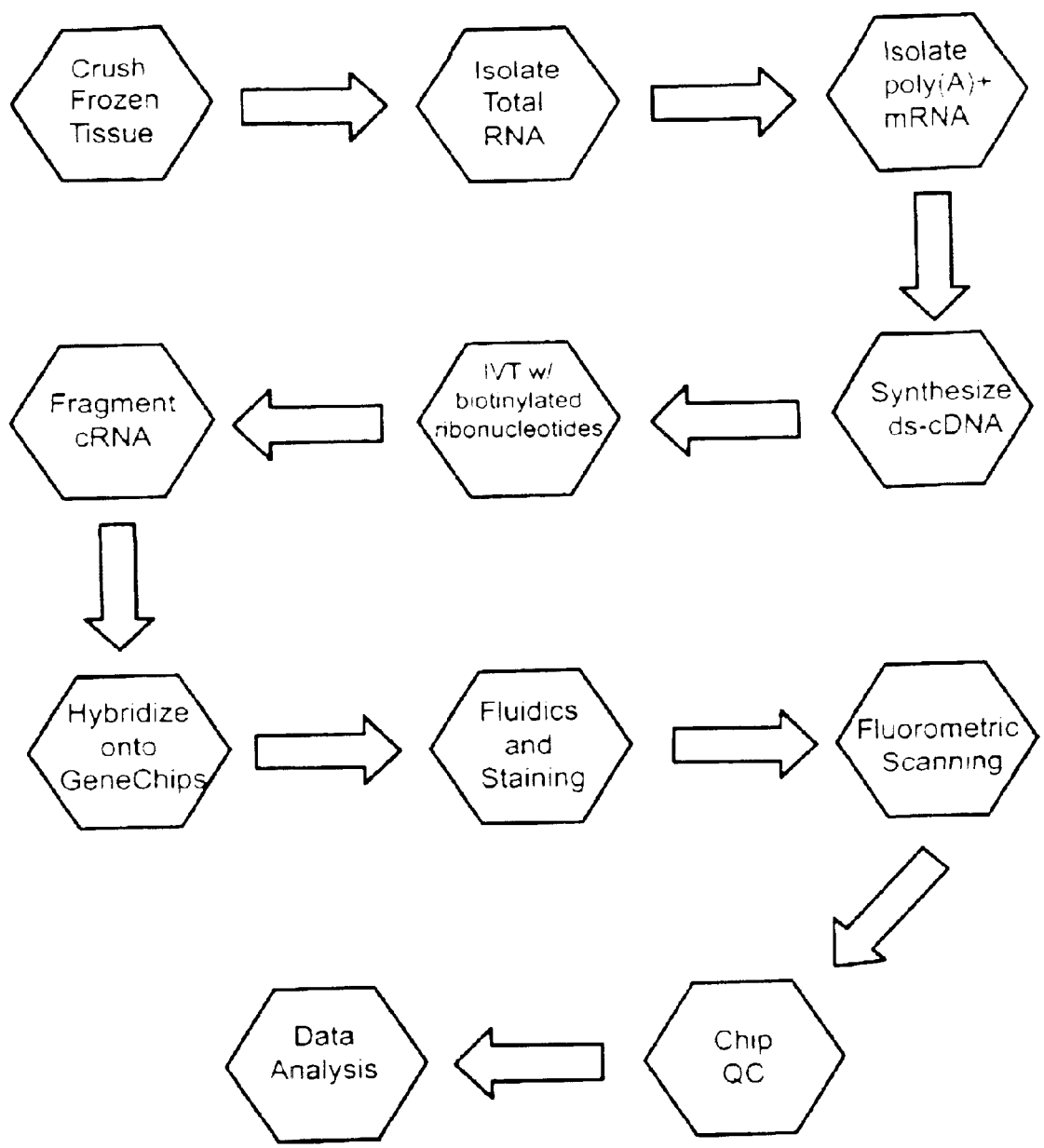
FIG. 1 is a flow chart showing a schematic representation of the experimental protocol.

The present inventors have examined tissue samples from normal liver, metastatic malignant liver and hepatocellular carcinoma to identify the global changes in gene expression associated with liver cancer. The protocol used is schematically represented in FIG. 1. These global changes in gene expression, also referred to as expression profiles, provide useful markers for diagnostic uses as well as markers that can be used to monitor disease states, disease progression, drug toxicity, drug efficacy and drug metabolism.

The present invention provides compositions and methods to detect the level of expression of genes that may be differentially expressed dependent upon the state of the cell, i.e., normal versus cancerous. As used herein, the phrase "detecting the level expression" includes methods that quantitate expression levels as well as methods that determine whether a gene of interest is expressed at all. Thus, an assay which provides a yes or no result without necessarily providing quantification of an amount of expression is an assay that requires "detecting the level of expression" as that phrase is used herein.

Assay Formats

The genes identified as being differentially expressed in liver cancer may be used in a variety of nucleic acid detection assays to detect or quantititate the expression level of a gene or multiple genes in a given sample. For example, traditional Northern blotting, nuclease protection, RT-PCR and differential display methods may be used for detecting gene expression levels. Those methods are useful for some embodiments of the invention. However, methods and assays of the invention are most efficiently designed with array or chip hybridization-based methods for detecting the expression of a large number of genes.

Any hybridization assay format may be used, including solution-based and solid support-based assay formats. Solid supports containing oligonucleotide probes for differentially expressed genes of the invention can be filters, polyvinyl chloride dishes, silicon or glass based chips, etc. Such wafers and hybridization methods are widely available, for example, those disclosed by Beattie (WO 95/11755). Any solid surface to which oligonucleotides can be bound, either directly or indirectly, either covalently or non-covalently, can be used. A preferred solid support is a high density array or DNA chip. These contain a particular oligonucleotide probe in a predetermined location on the array. Each predetermined location may contain more than one molecule of the probe, but each molecule within the predetermined location has an identical sequence. Such predetermined locations are termed features. There may be, for example, about 2, 10, 100, 1000 to 10,000; 100,000 or 400,000 of such features on a single solid support. The solid support, or the area within which the probes are attached may be on the order of a square centimeter.

Oligonucleotide probe arrays for expression monitoring can be made and used according to any techniques known in the art (see for example, Lockhart et al., (1996) Nat. Biotechnol. 14, 1675–1680; McGall et al., (1996) Proc. Nat. Acad. Sci. USA 93, 13555–13460). Such probe arrays may contain at least two or more oligonucleotides that are complementary to or hybridize to two or more of the genes described herein. Such arrays may also contain oligonucleotides that are complementary or hybridize to at least about 2, 3, 4, 5, 6, 7, 8, 9, 10, 20, 30, 50, 70, 100 or or more the genes described herein.

The genes which are assayed according to the present invention are typically in the form of mRNA or reverse transcribed mRNA. The genes may be cloned or not and the genes may be amplified or not. The cloning itself does not appear to bias the representation of genes within a population. However, it may be preferable to use polyA+RNA as a source, as it can be used with less processing steps.

The sequences of the expression marker genes are in the public databases. Tables 3-9 provide the GenBank accession number for the genes and ESTs identified called either Accession # (Tables 3, 4, and 5) or Fragment Name (Tables 6–9). The sequences of the genes in GenBank are expressly incorporated by reference as are equivalent and related sequences present in GenBank or other public databases. The column labeled "SEQ ID" refers to the sequence identification number correlating the listed gene or EST to its sequence information as provided within the sequence listing of this application.

Probes based on the sequences of the genes described herein may be prepared by any commonly available method. Oligonucleotide probes for assaying the tissue or cell sample are preferably of sufficient length to specifically hybridize only to appropriate, complementary genes or transcripts. Typically the oligonucleotide probes will be at least 10, 12, 14, 16, 18, 20 or 25 nucleotides in length. In some cases longer probes of at least 30, 40, or 50 nucleotides will be desirable.

As used herein, oligonucleotide sequences that are complementary to one or more of the genes described herein, refers to oligonucleotides that are capable of hybridizing under stringent conditions to at least part of the nucleotide sequence of said genes. Such hybridizable oligonucleotides will typically exhibit at least about 75% sequence identity at the nucleotide level to said genes, preferably about 80% or 85% sequence identity or more preferably about 90% or 95% or more sequence identity to said genes.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The terms "background" or "background signal intensity" refer to hybridization signals resulting from non-specific binding, or other interactions, between the labeled target nucleic acids and components of the oligonucleotide array (e.g., the oligonucleotide probes, control probes, the array substrate, etc.). Background signals may also be produced by intrinsic fluorescence of the array components themselves. A single background signal can be calculated for the entire array, or a different background signal may be calculated for each target nucleic acid. In a preferred embodiment, background is calculated as the average hybridization signal intensity for the lowest 5% to 10% of the probes in the array, or, where a different background signal is calculated for each target gene, for the lowest 5% to 10% of the probes for each gene. Of course, one of skill in the art will appreciate that where the probes to a particular gene hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g., probes directed to nucleic acids of the opposite sense or to genes not found in the sample such as bacterial genes where the sample is mammalian nucleic acids). Background can also be calculated as the average signal intensity produced by regions of the array that lack any probes at all.

The phrase "hybridizing specifically to" refers to the binding, duplexing or hybridizing of a molecule substantially to or only to a particular nucleotide sequence or sequences under stringent conditions when that sequence is present in a complex mixture (e.g., total cellular) DNA or RNA.

Assays and methods of the invention may utilize available formats to simultaneously screen at least about 100, preferably about 1000, more preferably about 10,000 and most preferably about 1,000,000 or more different nucleic acid hybridizations.

The term "mismatch control" or "mismatch probe" refer to a probe whose sequence is deliberately selected not to be perfectly complementary to a particular target sequence. For each mismatch (MM) control in a high-density array there typically exists a corresponding perfect match (PM) probe that is perfectly complementary to the same particular target sequence. The mismatch may comprise one or more bases.

While the mismatch(s) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

The term "perfect match probe" refers to a probe that has a sequence that is perfectly complementary to a particular target sequence. The test probe is typically perfectly complementary to a portion (subsequence) of the target sequence. The perfect match (PM) probe can be a "test probe", a "normalization control" probe, an expression level control probe and the like. A perfect match control or perfect match probe is, however, distinguished from a "mismatch control" or "mismatch probe."

As used herein a "probe" is defined as a nucleic acid, capable of binding to a target nucleic acid of complementary sequence through one or more types of chemical bonds, usually through complementary base pairing, usually through hydrogen bond formation. As used herein, a probe may include natural (i.e., A, G, U, C or T) or modified bases (7-deazaguanosine, inosine, etc.). In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

The term "stringent conditions" refers to conditions under which a probe will hybridize to its target subsequence, but with only insubstantial hybridization to other sequences or to other sequences such that the difference may be identified. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH.

Typically, stringent conditions will be those in which the salt concentration is at least about 0.01 to 1.0 M sodium ion concentration (or other salts) at pH 7.0 to 8.3 and the temperature is at least about 30° C. for short probes (e.g., 10 to 50 nucleotide). Stringent conditions may also be achieved with the addition of destabilizing agents such as formamide.

The "percentage of sequence identity" or "sequence identity" is determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical monomer unit (e.g., nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT (see below) is calculated using default gap weights.

Homology or identity may be determined by BLAST (Basic Local Alignment Search Tool) analysis using the algorithm employed by the programs blastp, blastn, blastx, tblastn and tblastx (Karlin et al., (1990) Proc. Natl. Acad. Sci. USA 87, 2264–2268 and Altschul, (1993) J. Mol. Evol. 36, 290–300, fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al., (1994) Nature Genet. 6, 119–129) which is filly incorporated by reference. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89, 10915–10919, fully incorporated by reference). Four blastn parameters were adjusted as follows: Q=10 (gap creation penalty); R=10 (gap extension penalty); wink=1 (generates word hits at every wink™ position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

Probe Design

One of skill in the art will appreciate that an enormous number of array designs are suitable for the practice of this invention. The high density array will typically include a number of probes that specifically hybridize to the sequences of interest. See WO 99/32660 for methods of producing probes for a given gene or genes. In addition, in a preferred embodiment, the array will include one or more control probes.

High density array chips of the invention include "test probes." Test probes may be oligonucleotides that range from about 5 to about 500 or about 5 to about 50 nucleotides, more preferably from about 10 to about 40 nucleotides and most preferably from about 15 to about 40 nucleotides in length. In other particularly preferred embodiments the probes are about 20 to 25 nucleotides in length. In another preferred embodiment, test probes are double or single strand DNA sequences. DNA sequences are isolated or cloned from natural sources or amplified from natural sources using natural nucleic acid as templates. These probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes fall into three categories referred to herein as (1) normalization controls; (2) expression level controls; and (3) mismatch controls.

Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g., fluorescence intensity) read from all other probes in the array are divided by the signal (e.g., fluorescence intensity) from the control probes thereby normalizing the measurements.

Virtually any probe may serve as a normalization control. However, it is recognized that hybridization efficiency varies with base composition and probe length. Preferred normalization probes are selected to reflect the average length of the other probes present in the array, however, they can be selected to cover a range of lengths. The normalization control(s) can also be selected to reflect the (average) base composition of the other probes in the array, however in a preferred embodiment, only one or a few probes are used and they are selected such that they hybridize well (i.e., no secondary structure) and do not match any target-specific probes.

Expression level controls are probes that hybridize specifically with constitutively expressed genes in the biological sample. Virtually any constitutively expressed gene provides a suitable target for expression level controls. Typical expression level control probes have sequences complementary to subsequences of constitutively expressed "housekeeping genes" including, but not limited to the β-actin gene, the transferrin receptor gene, the GAPDH gene, and the like.

Mismatch controls may also be provided for the probes to the target genes, for expression level controls or for normalization controls. Mismatch controls are oligonucleotide probes or other nucleic acid probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g., stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a twenty-mer, a corresponding mismatch probe will have the identical sequence except for a single base mismatch (e.g., substituting a G, a C or a T for an A) at any of positions 6 through 14 (the central mismatch).

Mismatch probes thus provide a control for non-specific binding or cross hybridization to a nucleic acid in the sample other than the target to which the probe is directed. Mismatch probes also indicate whether a hybridization is specific or not. For example, if the target is present the perfect match probes should be consistently brighter than the mismatch probes. In addition, if all central mismatches are present, the mismatch probes can be used to detect a mutation. The difference in intensity between the perfect match and the mismatch probe (I(BM)-I(MM)) provides a good measure of the concentration of the hybridized material.

Nucleic Acid Samples

As is apparent to one of ordinary skill in the art, nucleic acid samples used in the methods and assays of the invention may be prepared by any available method or process. Methods of isolating total mRNA are also well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I Theory and Nucleic Acid Preparation, Tijssen, (1993) (editor) Elsevier Press. Such samples include RNA samples, but also include cDNA synthesized from a mRNA sample isolated from a cell or tissue of interest. Such samples also include DNA amplified from the cDNA, and an RNA transcribed from the amplified DNA. One of skill in the art would appreciate that it is desirable to inhibit or destroy RNase present in homogenates before homogenates can be used.

Biological samples may be of any biological tissue or fluid or cells from any organism as well as cells raised in vitro, such as cell lines and tissue culture cells. Frequently the sample will be a "clinical sample" which is a sample derived from a patient. Typical clinical samples include, but are not limited to, sputum, blood, blood-cells (e.g., white cells), tissue or fine needle biopsy samples, urine, peritoneal fluid, and pleural fluid, or cells therefrom.

Biological samples may also include sections of tissues, such as frozen sections or formalin fixed sections taken for histological purposes.

Forming High Density Arrays

Methods of forming high density arrays of oligonucleotides with a minimal number of synthetic steps are known. The oligonucleotide analogue array can be synthesized on a solid substrate by a variety of methods, including, but not limited to, light-directed chemical coupling, and mechanically directed coupling (see Pirrung et al., (1992) U.S. Pat. No. 5,143,854; Fodor et al., (1998) U.S. Pat. No. 5,800,992; Chee et al, (1998) U.S. Pat. No. 5,837,832

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithogaphic mask is used selectively to expose functional groups which are then ready to react with incoming 5' photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In addition to the foregoing, additional methods which can be used to generate an array of oligonucleotides on a single substrate are described in Fodor et al., (1993). WO 93/09668. High density nucleic acid arrays can also be fabricated by depositing premade or natural nucleic acids in predetermined positions. Synthesized or natural nucleic acids are deposited on specific locations of a substrate by light directed targeting and oligonucleotide directed targeting. Another embodiment uses a dispenser that moves from region to region to deposit nucleic acids in specific spots.

Hybridization

Nucleic acid hybridization simply involves contacting a probe and target nucleic acid under conditions where the probe and its complementary target can form stable hybrid duplexes through complementary base pairing (see Lockhart et al., (1999) WO 99/32660). The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids.

Under low stringency conditions (e.g., low temperature and/or high salt) hybrid duplexes (e.g., DNA-DNA, RNA-RNA or RNA-DNA) will form even where the annealed sequences are not perfectly complementary.

Thus specificity of hybridization is reduced at lower stringency. Conversely, at higher stringency (e.g., higher temperature or lower salt) successful hybridization requires fewer mismatches. One of skill in the art will appreciate that hybridization conditions may be selected to provide any degree of stringency. In a preferred embodiment, hybridization is performed at low stringency, in this case in 6×SSPE-T at 37° C. (0.005% Triton x-100) to ensure hybridization and then subsequent washes are performed at higher stringency (e.g., 1×SSPE-T at 37° C.) to eliminate mismatched hybrid duplexes. Successive washes may be performed at increasingly higher stringency (e.g., down to as low as 0.25×SSPET at 37° C. to 50° C.) until a desired level of hybridization specificity is obtained. Stringency can also be increased by addition of agents such as formamide. Hybridization specificity may be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

Signal Detection

The hybridized nucleic acids are typically detected by detecting one or more labels attached to the sample nucleic acids. The labels may be incorporated by any of a number of means well known to those of skill in the art (see Lockhart et al., (1999) WO 99/32660).

Databases

The present invention includes relational databases containing sequence information, for instance for the genes of Tables 3–9, as well as gene expression information in various liver tissue samples. Databases may also contain information associated with a given sequence or tissue sample such as descriptive information about the gene associated with the sequence information, or descriptive information concerning the clinical status of the tissue sample, or the patient from which the sample was derived. The database may be designed to include different parts, for instance a sequences database and a gene expression database. Methods for the configuration and construction of such databases are widely available, for instance, see Akerblom et al., (1999) U.S. Pat. No. 5,953,727, which is herein incorporated by reference in its entirety.

The databases of the invention may be linked to an outside or external database. In a preferred embodiment, as described in Tables 3–9, the external database is GenBank and the associated databases maintained by the National Center for Biotechnology Information (NCBI).

Any appropriate computer platform may be used to perform the necessary comparisons between sequence information, gene expression information and any other information in the database or provided as an input. For example, a large number of computer workstations are available from a variety of manufacturers, such has those available from Silicon Graphics. Client-server environments, database servers and networks are also widely available and appropriate platforms for the databases of the invention.

The databases of the invention may be used to produce, among other things, electronic Northerns to allow the user to determine the cell type or tissue in which a given gene is expressed and to allow determination of the abundance or expression level of a given gene in a particular tissue or cell.

The databases of the invention may also be used to present information identifying the expression level in a tissue or cell of a set of genes comprising at least one gene in Tables 3–9 comprising the step of comparing the expression level of at least one gene in Tables 3–9 in the tissue to the level of expression of the gene in the database. Such methods may be used to predict the physiological state of a given tissue by comparing the level of expression of a gene or genes in Tables 3–9 from a sample to the expression levels found in tissue from normal liver, malignant liver or hepatocellular carcinoma. Such methods may also be used in the drug or agent screening assays as described below.

Kits

The invention further includes kits combining, in different combinations, high-density oligonucleotide arrays, reagents for use with the arrays, signal detection and array-processing instruments, gene expression databases and analysis and database management software described above. The kits may be used, for example, to predict or model the toxic response of a test compound, to monitor the progression of liver disease states, to identify genes that show promise as new drug targets and to screen known and newly designed drugs as discussed above.

The databases packaged with the kits are a compilation of expression patterns from human or laboratory animal genes and gene fragments (corresponding to the genes of Table 3–9). Data is collected from a repository of both normal and diseased animal tissues and provides reproducible, quantitative results, i.e., the degree to which a gene is up-regulated or down-regulated under a given condition.

The kits may used in the pharmaceutical industry, where the need for early drug testing is strong due to the high costs associated with drug development, but where bioinformatics, in particular gene expression informatics, is still lacking. These kits will reduce the costs, time and risks associated with traditional new drug screening using cell cultures and laboratory animals. The results of large-scale drug screening of pre-grouped patient populations, pharmacogenomics testing, can also be applied to select drugs with greater efficacy and fewer side-effects. The kits may also be used by smaller biotechnology companies and research institutes who do not have the facilities for performing such large-scale testing themselves.

Databases and software designed for use with use with microarrays is discussed in Balaban et al., U.S. Pat. No. Nos. 6,229,911, a computer-implemented method for managing information, stored as indexed tables, collected from small or large numbers of microarrays, and U.S. Pat. No. 6,185,561, a computer-based method with data mining capability for collecting gene expression level data, adding additional attributes and reformatting the data to produce answers to various queries. Chee et al., U.S. Pat. No. 5,974,164, disclose a software-based method for identifying mutations in a nucleic acid sequence based on differences in probe fluorescence intensities between wild type and mutant sequences that hybridize to reference sequences.

Diagnostic Uses for the Liver Cancer Markers

As described above, the genes and gene expression information provided in Tables 3–9 may be used as diagnostic markers for the prediction or identification of the malignant state of the liver tissue. For instance, a liver tissue sample or other sample from a patient may be assayed by any of the methods described above, and the expression levels from a gene or genes from the Tables, in particular the genes in Tables 3–5, may be compared to the expression levels found in normal liver tissue, tissue from metastatic liver cancer or hepatocellular carcinoma tissue. Expression profiles generated from the tissue or other sample that substantially resemble an expression profile from normal or diseased liver tissue may be used, for instance, to aid in disease diagnosis. Comparison of the expression data, as well as available sequence or other information may be done by researcher or diagnostician or may be done with the aid of a computer and databases as described above.

Use of the Liver Cancer Markers for Monitoring Disease Progression

As described above, the genes and gene expression information provided in Tables 3–9 may also be used as markers for the monitoring of disease progression, for instance, the development of liver cancer. For instance, a liver tissue sample or other sample from a patient may be assayed by any of the methods described above, and the expression levels in the sample from a gene or genes from or 3–9 may be compared to the expression levels found in normal liver tissue, tissue from metastatic liver cancer or hepatocellular carcinoma tissue. Comparison of the expression data, as well as available sequence or other information may be done by researcher or diagnostician or may be done with the aid of a computer and databases as described above.

Use of the Liver Cancer Markers for Drug Screening

According to the present invention, the genes identified in Tables 3–9 may be used as markers to evaluate the effects of a candidate drug or agent on a cell, particularly a cell undergoing malignant transformation, for instance, a liver cancer cell or tissue sample. A candidate drug or agent can be screened for the ability to simulate the transcription or expression of a given marker or markers (drug targets) or to down-regulate or counteract the transcription or expression of a marker or markers. According to the present invention, one can also compare the specificity of drugs' effects by looking at the number of markers which the drugs have and comparing them. More specific drugs will have fewer transcriptional targets. Similar sets of markers identified for two drugs indicates a similarity of effects.

Assays to monitor the expression of a marker or markers as defined in Tables 3–9 may utilize any available means of monitoring for changes in the expression level of the nucleic acids of the invention. As used herein, an agent is said to modulate the expression of a nucleic acid of the invention if it is capable of up- or down-regulating expression of the nucleic acid in a cell.

In one assay format, gene chips containing probes to at least two genes from Tables 3–9 may be used to directly monitor or detect changes in gene expression in the treated or exposed cell as described in more detail above. In another format, cell lines that contain reporter gene fusions between the open reading frame and/or the 3' or 5' regulatory regions of a gene in Tables 3–9 and any assayable fusion partner may be prepared. Numerous assayable fusion partners are known and readily available including the firefly luciferase gene and the gene encoding chloramphenicol acetyltransferase (Alam et al., (1990) Anal. Biochem. 188, 245–254). Cell lines containing the reporter gene fusions are then exposed to the agent to be tested under appropriate conditions and time. Differential expression of the reporter gene between samples exposed to the agent and control samples identifies agents which modulate the expression of the nucleic acid.

Additional assay formats may be used to monitor the ability of the agent to modulate the expression of a gene identified in Tables 3–9. For instance, as described above, mRNA expression may be monitored directly by hybridization of probes to the nucleic acids of the invention. Cell lines are exposed to the agent to be tested under appropriate conditions and time and total RNA or mRNA is isolated by standard procedures such those disclosed in Sambrook et al., (1989) Molecular Cloning—A Laboratory Manual, Cold Spring Harbor Laboratory Press).

In another assay format, cells or cell lines are first identified which express the gene products of the invention physiologically. Cell and/or cell lines so identified would be expected to comprise the necessary cellular machinery such that the fidelity of modulation of the transcriptional apparatus is maintained with regard to exogenous contact of agent with appropriate surface transduction mechanisms and/or the cytosolic cascades. Such cell lines may be, but are not required to be, derived from liver tissue. Further, such cells or cell lines may be transduced or transfected with an expression vehicle (e.g., a plasmid or viral vector) construct comprising an operable non-translated 5'-promoter containing end of the structural gene encoding the instant gene products fused to one or more antigenic fragments, which are peculiar to the instant gene products, wherein said fragments are under the transcriptional control of said promoter and are expressed as polypeptides whose molecular weight can be distinguished from the naturally occurring polypeptides or may further comprise an immunologically distinct tag. Such a process is well known in the art (see Sambrook et al., (1989) Molecular Cloning—A Laboratory Manual, Cold Spring Harbor Laboratory Press).

Cells or cell lines transduced or transfected as outlined above are then contacted with agents under appropriate conditions; for example, the agent comprises a pharmaceutically acceptable excipient and is contacted with cells comprised in an aqueous physiological buffer such as phosphate buffered saline (PBS) at physiological pH, Eagles balanced salt solution (BSS) at physiological pH, PBS or BSS comprising serum or conditioned media comprising PBS or BSS and serum incubated at 37° C. Said conditions may be modulated as deemed necessary by one of skill in the art. Subsequent to contacting the cells with the agent, said cells will be disrupted and the polypeptides of the lysate are fractionated such that a polypeptide fraction is pooled and contacted with an antibody to be further processed by immunological assay (e.g., ELISA, immunoprecipitation or Western blot). The pool of proteins isolated from the "agent-contacted" sample will be compared with a control sample where only the excipient is contacted with the cells and an increase or decrease in the immunologically generated signal from the "agent-contacted" sample compared to the control will be used to distinguish the effectiveness of the agent.

Another embodiment of the present invention provides methods for identifying agents that modulate the levels, concentration or at least one activity of a protein(s) encoded by the genes in Tables 3–9. Such methods or assays may utilize any means of monitoring or detecting the desired activity.

In one format, the relative amounts of a protein of the invention between a cell population that has been exposed to the agent to be tested compared to an unexposed control cell population may be assayed. In this format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe, such as a specific antibody.

Agents that are assayed in the above methods can be randomly selected or rationally selected or designed. As used herein, an agent is said to be randomly selected when the agent is chosen randomly without considering the specific sequences involved in the association of the a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agents action. Agents can be rationally selected or rationally designed by utilizing the peptide sequences that make up these sites.

For example, a rationally selected peptide agent can be a peptide whose amino acid sequence is identical to or a derivative of any functional consensus site.

The agents of the present invention can be, as examples, peptides, small molecules, vitamin derivatives, as well as carbohydrates. Dominant negative proteins, DNA encoding these proteins, antibodies to these proteins, peptide fragments of these proteins or mimics of these proteins may be introduced into cells to affect function. "Mimic" as used herein refers to the modification of a region or several regions of a peptide molecule to provide a structure chemically different from the parent peptide but topographically and functionally similar to the parent peptide (see Grant, (1995) in Molecular Biology and Biotechnology Meyers (editor) VCH Publishers). A skilled artisan can readily recognize that there is no limit as to the structural nature of the agents of the present invention.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

Example 1

Tissue Sample Acquisition and Preparation

FIG. 1 outlines the experimental protocol used. Liver tissue samples were excised and snap frozen in liquid nitrogen. The clinical data for each of the samples included in this study are outlined in Table 1. The sample set was composed of eight samples of normal liver tissue (N1–N8), five samples of metastatic adenocarcinoma arising from rectum (designated M1 and M3) and colon (M2, M4 and M5) tissues and six samples of primary hepatocellular carcinomas. Samples were named according to type of tissue: HCC=hepatocellular carcinoma, M=metastatic, N=normal. Table 1 include the TNM classification (the American Joint Committee on Cancer's system of classifying cancers) of the tissues used as samples where T refers to the extent of the primary tumor, N refers to the absence or presence and extent of regional lymph node metastasis, and M refers to the absence or presence of distant metastasis. Numbers following T, N, and M refer to the size of the primary tumor and the amount of vascular invasion, where 0=no evidence of tumor, lymph node involvement or metastasis, 4=multiple tumors involved, and x=cannot be assessed. Histopathologic grade (Table 1) is a qualitative assessment of differentiation of a tumor, where G1=most differentiated and G4=undifferentiated. Clinical stage (Table 1) characterizes the anatomic extent of disease in the patient from whom the sample was taken, where I and II are early stages, III and IV are late stages.

With minor modifications, the sample preparation protocol followed the Affymetrix GeneChip Expression Analysis Manual. Frozen tissue was first ground to powder using the Spex Certiprep 6800 Freezer Mill. Total RNA was then extracted using Trizol (Life Technologies). The total RNA yield for each sample (average tissue weight of 300 mg) was 200–500 $\mu$g. Next, mRNA was isolated using the Oligotex mRNA Midi kit (Qiagen). Since the mRNA was eluted in a final volume of 400 $\mu$l, an ethanol precipitation step was required to bring the concentration to 1 $\mu$g/$\mu$l. Using 1–5 $\mu$g of mRNA, double stranded cDNA was created using the SuperScript Choice system (Gibco-BRL). First strand cDNA synthesis was primed with a T7-(dT$_{24}$) oligonucleotide. The cDNA was then phenol-chloroform extracted and ethanol precipitated to a final concentration of 1 $\mu$g/$\mu$l.

From 2 $\mu$g of cDNA, cRNA was synthesized according to standard procedures. To biotin label the cRNA, nucleotides Bio-11 -CTP and Bio-16-UTP (Enzo Diagnostics) were added to the reaction. After a 37° C. incubation for six hours, the labeled cRNA was cleaned up according to the Rneasy Mini kit protocol (Qiagen). The cRNA was then fragmented (5×fragmentation buffer: 200 mM Tris-Acetate (pH 8.1), 500 mM KOAc, 150 mM MgOAc) for thirty-five minutes at 94° C. 55 $\mu$g of fragmented cRNA was hybridized on the human Hu35 k set and the HuGeneFL array for twenty-four hours at 60 rpm in a 45° C. hybridization oven The chips were washed and stained with Streptavidin Phycoerythrin (SAPE) (Molecular Probes) in Affymetrix fluidics stations. To amplify staining, SAPE solution was added twice with an anti-streptavidin biotinylated antibody (Vector Laboratories) staining step in between. Hybridization to the probe arrays was detected by fluorometric scanning (Hewlett Packard Gene Array Scanner). Following hybridization and scanning, the microarray images were analyzed for quality control, looking for major chip defects or abnormalities in hybridization signal. After all chips passed QC, the data was analyzed using Affymetrix GeneChip software (v3.0), and Experimental Data Mining Tool (EDMT) software (v1.0).

Example 2

Gene Expression Analysis

All samples were prepared as described and hybridized onto the Affymetrix HuGeneFL array and the Human Hu35k set of arrays. Each chip contains 16–20 oligonucleotide probe pairs per gene or cDNA clone. These probe pairs include perfectly matched sets and mismatched sets, both of which are necessary for the calculation of the average difference. The average difference is a measure of the intensity difference for each probe pair, calculated by subtracting the intensity of the mismatch from the intensity of the perfect match. This takes into consideration variability in hybridization among probe pairs and other hybridization artifacts that could affect the fluorescence intensities. Using the average difference value that has been calculated, the GeneChip software then makes an absolute call for each gene or EST.

The absolute call of present, absent or marginal is used to generate a Gene Signature, a tool used to identify those genes that are commonly present or commonly absent in a given sample set, according to the absolute call. For each set of samples, a median average difference was figured using the average differences of each individual sample within the set. The median average difference must be greater than 150 to assure that the expression level is well above the background noise of the hybridization. For the purposes of this study, only the genes and ESTs with a median average difference greater than 150 have been further studied in detail.

The Gene Signature for one set of samples is compared to the Gene Signature of another set of samples to determine the Gene Signature Differential. This comparison identifies the genes that are consistently present in one set of samples and consistently absent in the second set of samples.

The Gene Signature Curve is a graphic view of the number of genes consistently present in a given set of samples as the sample size increases, taking into account the genes commonly expressed among a particular set of samples, and discounting those genes whose expression is variable among those samples. The curve is also indicative of the number of samples necessary to generate an accurate Gene Signature. As the sample number increases, the number of genes common to the sample set decreases. The curve is generated using the positive Gene Signatures of the samples in question, determined by adding one sample at a time to the Gene Signature, beginning with the sample with the smallest number of present genes and adding samples in ascending order. The curve displays the sample size required for the most consistency and the least amount of expression variability from sample to sample. The point where this curve begins to level off represents the minimum number of samples required for the Gene Signature. Graphed on the x-axis is the number of samples in the set, and on the y-axis is the number of genes in the positive Gene Signature.

Example 3

Gene Expression Analysis of Normal Liver Tissue

Figure 2A:
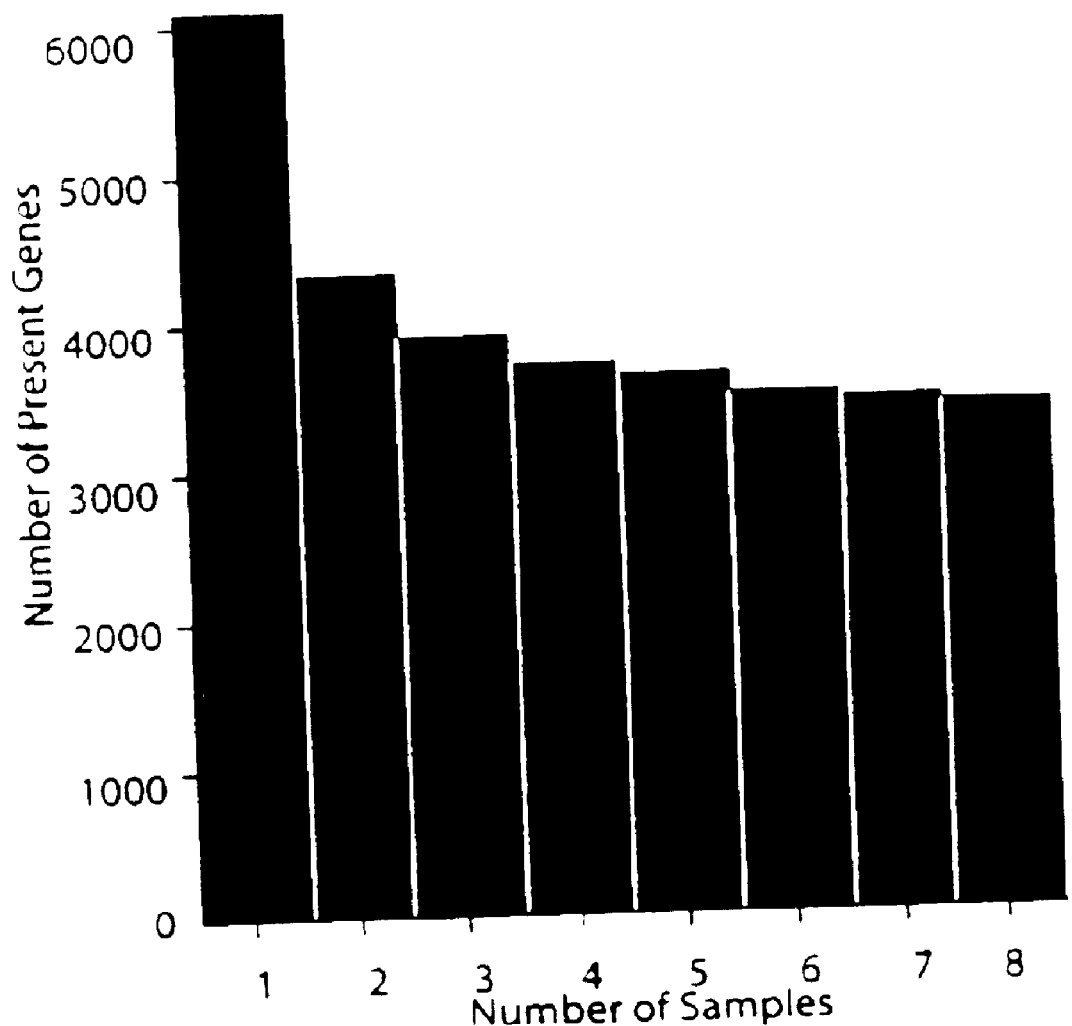
FIGS. 2A–2C are graphs of the number of genes present in all samples as a function of the number of samples for the second sample set.
Figure 2B:
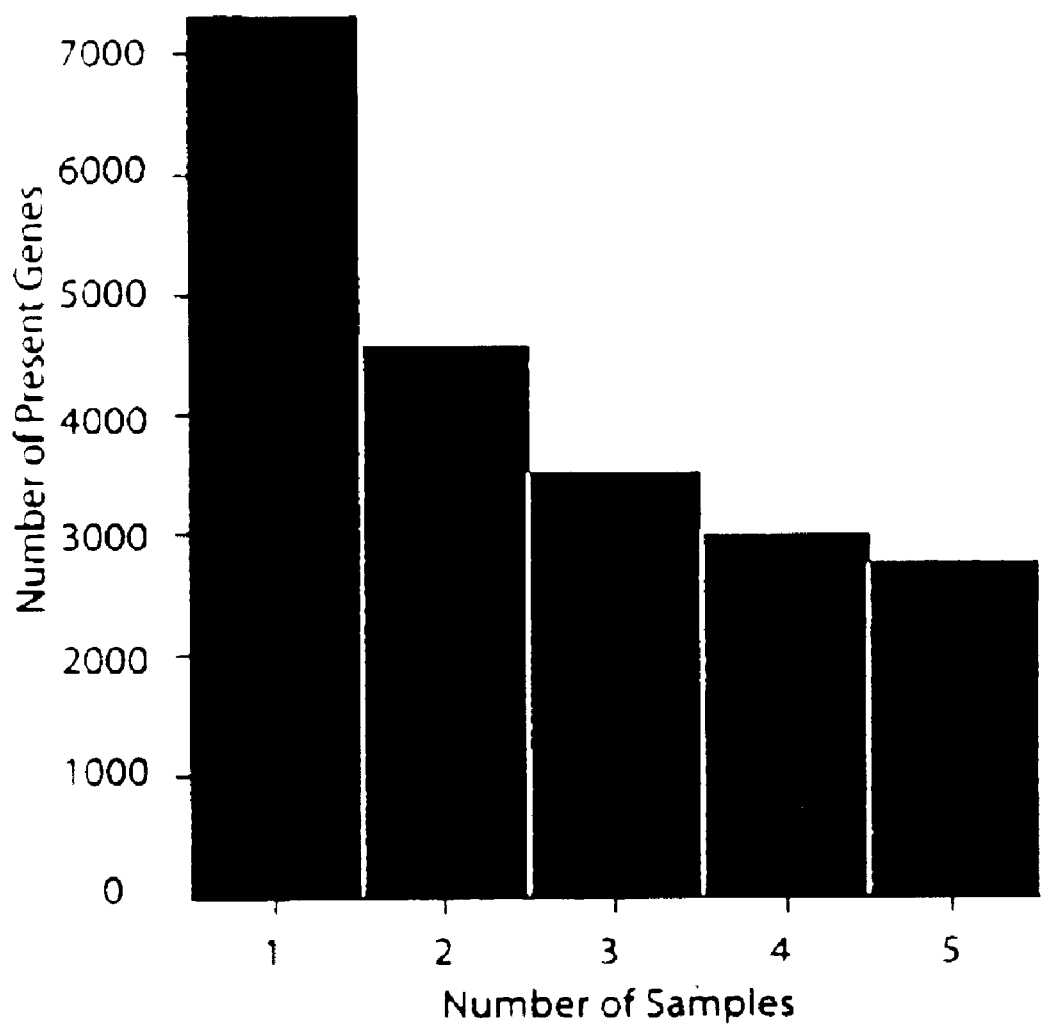
Figure 2C:
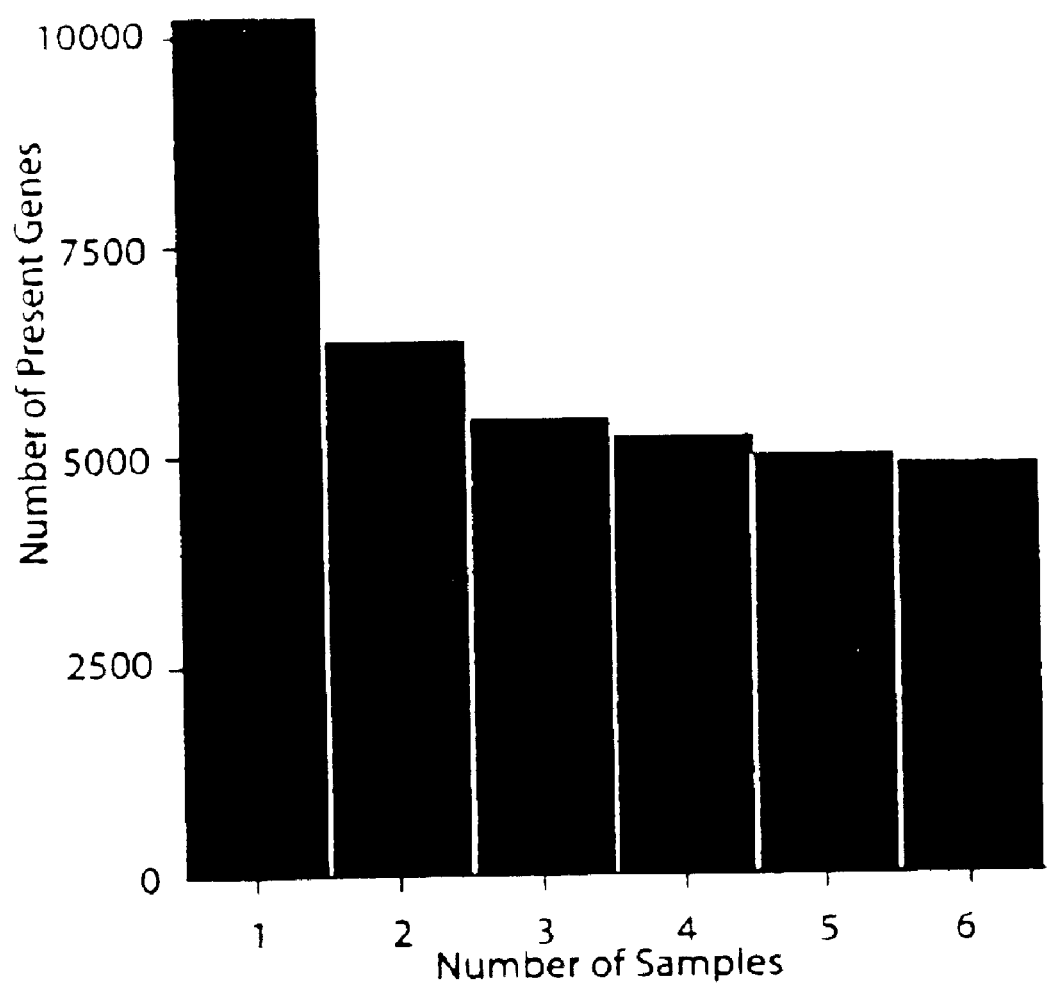

The gene expression patterns and Gene Signature were individually determined for each sample set: eight samples with normal liver pathology, six samples whose pathology indicated the primary malignancy to be hepatocellular carcinoma, and five samples whose primary colorectal adenocarcinoma had metastasized to the liver. The Gene Signatures obtained for the sample set are shown in FIG. 2

The Gene Signature considers the present and absent genes alone, and does not take into consideration those that have been called marginal. Table 2 shows the numbers of present genes, called the positive Gene Signature, and the number of absent genes, called the negative Gene Signature, for each of the three sets of samples.

The Gene Signature is the set of genes that are commonly present or commonly absent in N-1 samples of a given sample set. The positive Gene Signature for the normal liver tissues contains 6,213 genes and ESTs. This same set of normal samples did not show any detectable level of expression of 24,900 genes. Many of the genes and ESTs in this positive Gene Signature are housekeeping genes or structural genes that are not only expressed in the liver, but are ubiquitously expressed in tissues throughout the body. Within this positive Gene Signature are also those genes whose expression is specifically restricted to normal liver tissue and those genes required for the liver to function at its normal capacities. It is the group of genes unique to the liver whose expression levels are most likely to change during tumorigenesis. Whether up-regulated or down-regulated or turned completely on or turned completely off, the changes in expression of these vital genes very likely contributes to the drastic changes in liver function caused by the transformation of normal liver cells into cancerous cells.

Example 4

Gene Expression Analysis of Malignant Liver Tissue

There are 8,479 genes and ESTs in the positive Gene Signature for the HCC tumors, and a total of 23,233 genes and ESTs are included in the negative Gene Signature of the HCC samples. This negative Gene Signature includes all the genes that have been completely turned off during tumorigenesis, as well as those genes that are not usually expressed in liver tissue. These results include a number of genes and ESTs that are not regularly expressed in liver tissues, but through the process of tumor production, their expression patterns have been dramatically altered from no detectable level of expression to some significant level of expression in comparison with the normal liver.

The colorectal metastases in the liver commonly express 5,102 genes and ESTs, and do not show expression of 30,455 additional genes and ESTs. As with the negative Gene Signature for the HCC sample set, the genes included in this data set are generally not expressed in liver tissue, whether tumor or normal tissue. The 5,102 in the sample set of metastatic tumors also identify those genes with expression levels that have been changed from off to on as a result of tumor formation.

Example 5

Analysis of Gene Expression Profiles

A differential comparison of the genes and ESTs expressed in the normals and the two different types of liver tumors identifies a subset of the genes included in the positive Gene Signatures that are uniquely expressed in each sample set. This Gene Signature Differential highlights genes whose expression profiles have most dramatically changed in the transformation from normal to diseased liver cells. The parameters for these analyses were set to accommodate variation in expression of one eight normal samples and one of the six HCC samples or one of the 5 metastatic tumor samples, such that the genes categorized as unique to normal were called present by the software in seven of eight (87%) normal liver samples and were also called absent in five of six HCC (83%) or four of five (80%) metastatic liver tumor. Conversely, the genes categorized as unique to each set of tumors as compared to the normal livers were called present in five of six HCC (83%) or four of five (80%) metastatic tumor samples and absent in seven of eight normal livers (87%).

The Gene Signature Differential comparing the normal livers to those with metastatic tumors identified a total of 903 sequences expressed only in normal liver tissue. The number of genes or ESTs that meet the median average difference minimum of 150 is 449, of which 289 are genes and the number of ESTs is 160. The remaining ESTs and genes may be indistinguishable from the background noise of the hybridization. The same comparison of normals versus metastatic tumors demonstrates that in the metastatic tumor samples there are 296 uniquely expressed sequences. Those that meet the median average difference minimum requirement are 83 genes and 72 ESTs. Those genes and ESTs expressed in metastatic and not in normal liver tissue are shown in Table 9A and those present in normal liver tissue and not metastatic tissue Table 9B. Numerous genes with differing expression levels in metastatic liver tumor tissue compared to normal tissue were identified. The fifteen genes whose expression level was most different in metastatic as compared to normal tissue are shown in Table 4. Those with the most increased expression are in Table 4A and those with the most decreased expression are in Table 4B. Expression levels were determined by comparing the mean expression values of individual genes in tumor and normal liver samples. Fold change was calculated as a ratio with a p value given as a measure of statistical significance. Fold change is considered significant for a given gene or EST when it is greater than 3.0 with a p value <0.05. Only the characterized genes have been listed; the ESTs with similar fold changes are not presented here. Asterisk (*) in Table 4 denotes those genes that were also identified in the Gene Signature differential between metastatic liver carcinoma and normal liver tissue. A complete listing of all the genes and ESTs with at least a three-fold change in expression is shown in Table 6. Table 6A contains those genes and ESTs whose expression level increased in metastatic tissue relative to normal tissue and Table 6B contains those genes and ESTs whose expression level decreased.

The Gene Signature Differential between the normal liver samples and the HCC samples identifies a total of 47 unique expressers in the normals, 23 with an median average difference of 150, 13 of which are named gene and 10 of which are ESTs. When comparing the expression of the HCC samples with the normal livers, there are 243 genes and ESTs only expressed in the HCC samples.

Those genes and ESTs expressed in HCC and not in normal liver tissue are shown in Table 8A and those present in normal liver tissue and not HCC are shown in Table 8B. Numerous genes with differing expression levels in HCC compared to normal tissue were identified. The fifteen genes whose expression level was most different in HCC as compared to normal tissue are shown in Table 3. Those with the most increased expression are in Table 3A and those with the most decreased expression are in Table 3B. Expression levels were determined by comparing the mean expression values of individual genes in tumor and normal liver samples. Fold change was calculated as a ratio with a p value given as a measure of statistical significance. Fold change is considered significant for a given gene or EST when it is greater than 3.0 with a p value <0.05. Only the characterized genes have been listed; the ESTs with similar fold changes are not presented here. Asterisk (*) in Table 3 denotes those genes that were also identified in the Gene Signature differential between hepatocellular carcinoma and normal liver tissue. A complete listing of all the genes and ESTs with at least a three-fold change in expression is shown in Table 7. Table 7A contains those genes and ESTs whose expression level increased in hepatocellular carcinoma tissue relative to normal tissue and Table 7B contains those genes and ESTs whose expression level decreased.

Analysis of sample set identified 24 ESTs and 42 genes that are expressed in both metastatic liver tumors and hepatocellular carcinomas, but not in normal liver tissues. The fifteen genes with the most increase in expression level in both types of cancer are shown in Table 5. Expression levels were determined by comparing the mean expression values of individual genes in tumor and normal liver samples. The mean expression value for HCC and metastatic carcinomas was greater than 250, and included only those genes that showed a fold change greater than 3 with significant p values for both sets of tumors. No detectable level of expression was found in the normal liver tissues for these genes. Only the characterized genes have been listed; the ESTs with similar fold changes that are unique to the tumors are not presented here.

Differential gene expression patterns between normal liver samples and hepatocellular carcinomas and between normal livers and metastatic liver tumors were examined. Genes uniquely expressed by each of the groups individually were identified, as well as those genes that are commonly expressed among liver tumors, whether primary hepatocellular carcinomas or metastatic liver tumors.

Example 6

Association of Liver Cancer with Specific Gene Expression

The present inventors have closely examined a number of the tumor-expressing genes to determine if their expression patterns correlate with previous reports published in the literature, and to define a logical relationship between the gene and hepatocarcinogenesis. A number of genes that have previously been associated with either liver cancer or other types of cancers were identified, as well as numerous genes that have not been linked to cancers in any previous studies.

842 genes and ESTs that are up-regulated in hepatocellular carcinomas were identified when compared with normal liver tissue. One such gene is PTTG1, pituitary tumor-transforming gene 1, or securin, an oncogene that inhibits sister chromatid separation during anaphase. Normal tissues show little or no PTTG1 expression, but high levels of expression have been associated with various tumors, including liver tumors, and carcinoma cell lines. Overexpression in NIH3T3 cells resulted in transformation, and these cells caused the formation of tumors when injected into mice. The mechanism by which this tumorigenic activity takes place is postulated to be through the missegregation of sister chromatids, resulting in aneuploidy and, therefore, genetic instability. Our data further support this overexpression of PTTG1 in hepatocellular carcinoma, with a fold change of 10.7 (P=0.00052), and no detectable level of expression in normal tissues, as identified by the differential comparison of the consensus patterns of gene expression of these two sample sets.

Galectin 3, LGALS3, one of a family of beta-galactoside-binding animal lectins, is significantly overexpressed both in primary hepatocellular carcinoma and metastatic liver carcinomas with fold changes of 6.8 (P=0.00103) and 27.1 (P=0.00001), respectively. Expression of LGALS3 has been associated with tumor growth, progression, and metastasis, as well as cell-cell and cell-matrix interactions and inflammatory processes. Although expression studies have revealed no detectable level of galectin-3 in normal liver cells, samples from patients with hepatocellular carcinoma revealed considerable levels of LGALS3 expression. The abnormal expression of this lectin may be an early event in the process of transformation of normal cells to tumor cells, or it may impart an increased capacity for these tumor cells to survive and proliferate. Consistent with the reports in the art, an increased expression level was found in both types of tumor, but higher concentrations of galectin-3 were observed in liver metastates from colorectal tumors than in the primary HCC tumors.

Another gene that is overexpressed in both hepatocellular carcinoma and metastatic colorectal adenocarcinomas with fold changes of 12.2 (P=0.00169) and 58.0 (P=0.00063), respectively, is solute carrier family 2, member 3, or glucose transporter 3 (GLUT3). It is one of a family of transmembrane proteins that function as facilitative glucose transporters, which has a unique specificity for brain and neuronal tissues. Glucose uptake and metabolism are known to be increased in carcinoma cells compared to normal cells. Glucose transporter expression may be elevated in response to the increase in glucose utilization seen in actively proliferating cells, like those of tumors. Conversely, the high levels of glucose transporter expression may be responsible for the enhanced influx of glucose into the tumor cells. Various reports have indicated increased expression of one or more of the family of glucose transporters in malignancies, including those of the brain, esophagus, colon, pancreas, liver, breast, lung, bladder, ovary, testis, skin, head and neck, kidney, and gastric tumors. It has been reported that metastatic liver carcinomas have even higher levels of GLUT3 expression than primary tumors. Consistent with previous studies, the current data confirm the significant overexpression of GLUT3 both in primary liver cancer, hepatocellular carcinoma, and in tumors that have metastasized from the colon and rectum.

One of the significantly underexpressed genes identified by comparing the expression profiles of hepatocellular carcinomas and metastatic liver tumors with that of normal liver tissue is metallothionein 1L. The expression level in HCC is 26.9 fold lower than that of normal (P=0.00999), and in metastatic colorectal adenocarcinomas it is down-regulated 66.5 fold (P=0.00415). Metallothioneins are heavy metal binding proteins that are involved in detoxification of metals, zinc and copper metabolism cellular adaptation mechanisms, and may be involved in regulating apoptosis. Colorectal adenocarcinoma that has metastasized to the liver has been specifically reported to express less metallothionein than normal liver tissue. Comparison of the consensus patterns of gene expression between metastatic liver samples and normal liver samples show no significant level of MT1L expression in the tumors. Furthermore, additional work has determined that human hepatocellular carcinomas contain much lower levels of metallothioneins than normal liver tissue, and that this decrease correlates with the degree of differentiation and concentrations of copper and zinc in the cells. By comparing the expression profiles of hepatocellular carcinoma and normal liver tissue, this significant reduction in MT1L expression in HCC was confirmed.

A number of enzymes belonging to the family of cytochrome P450s are drastically underexpressed in the two sets of liver tumors in comparison with the normal liver tissue.

For example, expression of CYP2A6 is decreased in HCC with a fold change of 14.2 (P=0.0307), and in metastatic tumors with a fold change of 69.9 (P=O). CYP8B 1 is down-regulated 19.3 fold (P=0.00807) in HCC and 65.1 fold (P=0.0039) in liver metastases. In addition to these commonly down-regulated cytochrome P450s, in HCC samples CYP2B is underexpressed 17.9 fold (P=0.01469), and in the metastatic liver tumors CYP2C9 and CYP2A7 are underexpressed 84.7 fold (P=0.00327) and 72.0 fold (P=0), respectively. Several of these genes are also identified by the differential comparison between expression profiles of tumor and normal, confirming the significant decrease in expression in tumor tissues. Many of these P450 enzymes are critical players in the metabolism of carcinogens, drugs, and other chemical compounds, that are expressed in normal liver.

In addition to genes that are underexpressed in metastatic adenocarcinomas in the liver, more than 1000 genes and ESTs that are overexpressed specifically in these tumors were identified. Two of the most highly up-regulated are claudin 4, also known as clostridium perfringens enterotoxin receptor 1 (fold change 84.4, P=0) and occludin (fold change 43.1, P=0). Both of these genes are tight junction proteins, responsible for the formation and maintenance of continuous seals around epithelial cells to form a physical barrier that blocks the free passage of water and solutes through the paracellular space. More specifically, claudin-4 is one member of a family of transmembrane proteins that comprise tight junction strands, and occludin is a cell adhesion molecule. Claudins likely function as paracellular channels, regulating the flow of ions and solutes into and out of the paracellular space. Tight junction proteins also contribute to the regulation of the cellular processes of cell growth and differentiation. Permeability of tight junctions has been associated with tumor formation, where a breakdown in the barrier function of tight junctions allows an increase in the cellular permeability. This breakdown then opens the tight junction barrier, permitting invasion by tumor cells. It has been reported that tight junctions of colon tumors leak more than do the tight junctions of normal colon. A complete loss of tight junction function and a loss of cell-cell contact growth control has been seen in cells that had been transfected with oncogenic Raf-1, and expression levels of occludin and another claudin are lower in these cells. Occludin expression has been up-regulated in vitro by the addition of various fatty acids that have anti-cancer effects, decreasing the paracellular permeability. The extreme down-regulation of occludin and claudin-4 in metastatic liver tumors is strongly supported by the reports of tight junction breakdown in tumor tissues.

The present study identified 93 significantly up-regulated genes in both primary HCC and metastatic liver tumors that were not found to have any detectable level of expression in the normal samples. Serine protease inhibitor, Kazal type I (SPINK1), also called pancreatic secretory trypsin inhibitor (PSTI) or tumor-associated trypsin inhibitor (TATI), is one such gene. It is highly expressed in the cells of normal pancreas and in the mucosa of the gastrointestinal tract where it offers protection from proteolytic breakdown. A marked increase in expression is seen in various pancreatic diseases and in tumors of different tissues, including gastric carcinomas, colorectal cancers, and other neoplastic tissues. This increase is presumably due to the elevated expression of trypsin in the tumors, and not related to amplification or rearrangements within the gene. SPINK1 is also considered a valuable marker for a number of solid tumors. An elevation of SPINK1 in the blood of patients with hepatocellular carcinoma has been seen. Furthermore, they suggest that the level of expression correlates with the extent of tumor, such that this heightened expression level could be indicative of HCC under certain conditions. In keeping with this report of overexpression in these tumors, the present expression data show the levels of expression of this gene in HCC samples to be 28.9 times higher than normal (P=0.00003), and in metastatic liver tumors the expression level is 9.8 times higher than normal (P=0.03697).

Midkine is one of a family of heparin-binding growth factors, inducible by retinoic acid, and is actively involved in cell-cell interactions and angiogenesis. The expression pattern of midkine is highly restricted in normal adult tissues, and no expression has been reported in normal adult liver, although its expression is required during embryogenesis for normal development. However, it is expressed in moderate to high levels in many tumors, including Wilm's tumors of the kidney, stomach, colon, pancreas, lung, esophagus, breast, and liver tumors. The present data confirm these reports, showing a significant overexpression of midkine in hepatocellular carcinoma samples (fold change 9.9, P=0.02104) and in liver metastases (fold change 10.4, P=0.01818), but no noticeable expression in normal liver.

Stathmin, leukemia-associated phosphoprotein 18, is a phosphoprotein whose expression pattern and phosphorylation status are controlled by extracellular signals responsible for the regulation of the processes of cell proliferation and differentiation. It is also involved in the regulation of cell division via the destabilization of microtubules. When comparing expression levels between non-malignant tissues and malignant tissues, the tumors generally show a significant up-regulation of this phosphoprotein, specifically lymphomas, leukemias, breast and prostate tumors. One reason proposed for this elevated expression in cancer cells is the dissimilarity in the rates of cell proliferation and states of differentiation between normal and tumor cells. In both HCC samples and metastatic adenocarcinomas, significant up-regulation of stathmin, 9.4 fold in HCC (P=0.00015) and 4.8 fold in metastatic tumors (P=0.005 14) was seen.

Both the genes and ESTs described here will provide valuable information for the identification of new drug targets against liver carcinomas, and that information may be extended for use in the study of carcinogenesis in other tissues. These sequences may be used in the methods of the invention or may be used to produce the probes and arrays of the invention.

Although the present invention has been described in detail with reference to examples above, it is understood that various modifications can be made without departing from the spirit of the invention. Accordingly, the invention is limited only by the following claims. All cited patents, applications and publications referred to in this application are herein incorporated by reference in their entirety.

TABLE 1

Clinical Information for Hepatocellular Carcinoma, Metastatic Liver Tumor, and Normal Liver Samples Included in this Study

| Sample | Pathology | Primary Tumor | Age | Gender | Race | TNM Classification | Histopathologic Grade | Clinical Stage |
|---|---|---|---|---|---|---|---|---|
| HCC1 | Hepatocellular Carcinoma | Liver | 64 | Male | Caucasian | T3, Nx, Mx | G2 | stage III |
| HCC2 | Hepatocellular Carcinoma | Liver | 27 | Female | Caucasian | T3, N0, Mx | G1 | stage III |
| HCC3 | Hepatocellular Carcinoma | Liver | 78 | Female | Caucasian | T4, Nx, Mx | G2 | stage III |
| HCC4 | Hepatocellular Carcinoma | Liver | 43 | Male | Asian | T4, N1, Mx | G2 | stage IV |
| HCC5 | Hepatocellular Carcinoma | Liver | 51 | Male | Caucasian | T4, N0, Mx | G2 | stage IV |
| HCC6 | Hepatocellular Carcinoma | Liver | 57 | Male | Caucasian | unavailable | G2 | stage III |
| M1 | Metastatic Adenocarcinoma | Rectum | 61 | Female | Caucasian | Tx, Nx, M1 | G3 | stage IV; Duke D |
| M2 | Metastatic Adenocarcinoma | Colon | 54 | Male | Caucasian | unavailable | G2 | stage IV; Duke D |
| M3 | Metastatic Adenocarcinoma | Rectum | 50 | Female | Caucasian | Tx, Nx, M1 | G2 | stage IV; Duke D |
| M4 | Metastatic Adenocarcinoma | Colon | 60 | Male | Caucasian | Tx, Nx, M1 | G2 | stage IV; Duke D |
| M5 | Metastatic Adenocarcinoma | Colon | 57 | Male | Caucasian | Tx, Nx, M1 | G2 | stage IV; Duke D |
| N1 | Normal liver | | 54 | Female | Caucasian | | | |
| N2 | Normal liver | | 55 | Female | Caucasian | | | |
| N3 | Normal liver | | 58 | Male | Caucasian | | | |
| N4 | Normal liver | | 44 | Female | Caucasian | | | |
| N5 | Normal liver | | 40 | Female | Caucasian | | | |
| N6 | Normal liver | | 72 | Female | Caucasian | | | |
| N7 | Normal liver | | 48 | Female | Unknown | | | |
| N8 | Normal liver | | 55 | Female | Caucasian | | | |

TABLE 2

Summary of Genes and ESTs Expressed in HCC, Metastatic Liver Tumors, and Normal Livers

| | Hepatocelluar Carcinoma | Colorectal Metastases | Normal Livers |
|---|---|---|---|
| I. Fingerprint of Gene Expression | | | |
| Genes and ESTs commonly expressed in sample set | 8479 | 5102 | 6213 |
| Genes and ESTs commonly unexpressed in sample set | 23233 | 30455 | 24900 |
| II. Fold Change | | | |
| Genes and ESTs overexpressed in tumors (fold change >3 and p < 0.05) | 842 | 1044 | |
| Number of Genes | 430 | 603 | |
| Number of ESTs | 412 | 441 | |
| Genes and ESTs underexpressed in tumors (fold change >3 and p < 0.05) | 393 | 1867 | |
| Number of Genes | 235 | 1016 | |
| Number of ESTs | 158 | 851 | |
| III. Differential Comparison between Normal and Tumor Expression | | | |
| Genes and ESTs turned ON in tumors | 243 | 296 | |
| Genes and ESTs with expression level above threshold in tumor | 77 | 155 | |
| Number of Genes | 38 | 83 | |
| Number of ESTs | 39 | 72 | |
| Genes and ESTs turned OFF in tumors | 47 | 903 | |
| Genes and ESTs with expression level above threshold in normal | 23 | 449 | |
| Number of Genes | 13 | 289 | |
| Number of ESTs | 10 | 160 | |

Table 3A

Top Fifteen Genes Overexpressed in Hepatocellular Carcinoma

| Accession # | SEQ ID: | Unigene Cluster | Gene Name | Fold Change | Pvalue |
|---|---|---|---|---|---|
| N33920 | 2492 | Hs.44532 | diubiquitin | 50.3 | 0 |
| Y00705 | 3847 | Hs.181286 | serine protease inhibitor, Kazal type 1 | 28.9 | 0.00003 |
| AA610116 | 1499 | Hs.102737 | tetraspan NET-6 protein | 16.4 | 0.00249 |
| AA505133 | 1417 | Hs.279905 | solute carrier family 2 (facilitated glucose transporter), member 3 | 12.2 | 0.00169 |
| AA055896 | 135 | Hs.146428 | collagen, type V, alpha 1 | 10.9* | 0.00907 |
| AA430032 | 1009 | Hs.252587 | pituitary tumor-transforming 1 | 10.7* | 0.00052 |
| Z37987 | 3879 | Hs.119651 | glypican 3 | 10.7 | 0.02304 |
| J03464 | 2094 | Hs.179573 | collagen, type I, alpha 2 | 10.4 | 0.00979 |
| W45320 | 3520 | Hs.228059 | KRAB-associated protein 1 | 10.1* | 0.00002 |
| M94250 | 2425 | Hs.82045 | midkine (neurite growth-promoting factor 2) | 9.9* | 0.02104 |

Table 3A-continued

Top Fifteen Genes Overexpressed in Hepatocellular Carcinoma

| Accession # | SEQ ID: | Unigene Cluster | Gene Name | Fold Change | Pvalue |
|---|---|---|---|---|---|
| AA428172 | 986 | Hs.8546 | Notch (Drosophila) homolog 3 | 9.6* | 0.00195 |
| AA620881 | 1510 | Hs.21858 | trinucleotide repeat containing 3 | 9.5 | 0.00062 |
| D51276 | 1678 | Hs.81915 | leukemia-associated phosphoprotein p18 (stathmin) | 9.4 | 0.00015 |
| AA156187 | 399 | Hs.81634 | ATP synthase, H+ transporting, mitochondrial F0 complex subunit b, isoform 1 | 9.4 | 0.02007 |
| D31094 | 1639 | Hs.109798 | G8 protein | 9.4 | 0.0048 |

TABLE 3B

Top Fifteen Genes that are Underexpressed in Hepatocellular Carcinoma

| Accession # | SEQ ID: | Unique Cluster | Gene Name | Fold Change | Pvalue |
|---|---|---|---|---|---|
| HB1070 | 2006 | Hs.8765 | RNA helicase-related protein | 39.6 | 0.00002 |
| AA007395 | 17 | Hs.1219 | alcohol dehydrogenase 4 (class II), pi polypeptide | 37.8 | 0.00939 |
| T48075 | 3129 | Hs.251577 | hemoglobin, alpha 1 | 35.8 | 0.00471 |
| N80129 | 2702 | Hs.94360 | metallothionein 1 L | 26.9 | 0.00999 |
| AA010605 | 26 | Hs.2899 | 4-hydroxyphenylpyruvate dioxygenase | 25.5 | 0.00855 |
| W88946 | 3636 | Hs.18508 | putative glycine-N-acyltransferase | 25.3 | 0.00221 |
| T95813 | 3261 | Hs.137476 | KIAA1051 protien | 20.4 | 0.01361 |
| H58692 | 1960 | Hs.9520 | formyltetrahydrofolate dehydrogenase | 20.2 | 0.00485 |
| R97419 | 3003 | Hs.35718 | cyctochrome P450, subfamily VIIIB (sterol 12-alpha-hydroxylase), polypeptide 1 | 19.3 | 0.00807 |
| H80901 | 2005 | Hs.272576 | ficolin (collagen/fibrinogen domain-containing) 3 (Hakata antigen) | 18.6 | 0 |
| M29873 | 2318 | Hs.1360 | cytochrome P450, subfamily IIB (phenobarbital-inducible) | 17.9 | 0.01469 |
| U56814 | 3392 | Hs.88646 | deoxyribonuclease I-like 3 | 17.7 | 0.00007 |
| T67931 | 3183 | Hs.7645 | fibrinogen, B beta polypeptide | 17.3 | 0.00128 |
| K03192 | 2127 | Hs/183584 | cytochrome P450, subfamily IIA (phenobarbital-inducible), polypeptide 6 | 14.2 | 0.0307 |
| AA448002 | 1113 | Hs.23759 | putative type II membrane protein | 14.1* | 0 |

TABLE 4A

Top Fifteen Genes Overexpressed in Metastatic Carcinomas in the Liver

| Accession # | SEQ ID: | Unigene Cluster | Gene Name | Fold Change | Pvalue |
|---|---|---|---|---|---|
| AA427468 | 973 | Hs.5372 | Claudin 4 | 84.4* | 0 |
| H58873 | 1961 | Hs.169902 | Solute carrier family 2 (facilitated glucose transporter), member 3 | 58.0* | 0.00063 |
| AA421562 | 934 | Hs.91011 | Anterior gradient 2 (Xenopus leavis) homolog | 56.3* | 0.0041 |
| AA100719 | 212 | Hs.73848 | Carcinoembroyonic antigne-related cell adhesion molecule 6 (non-specific cross reacting antigen) | 50.9* | 0.00081 |
| AA335191 | 741 | Hs.173724 | Creatine kinase, brain | 47.4* | 0.00419 |
| H95233 | 2048 | Hs.31439 | Serine protease inhibitor, Kunitz type 2 | 47.1 | 0 |
| H94471 | 2042 | Hs.171952 | Occludin | 43.1 | 0 |
| X93036 | 3827 | Hs.92323 | FXYD domain-containing ion transport reglator 3 | 42.4* | 0.00167 |
| AA156243 | 340 | Hs.154737 | Serine protease, umbillcal endothelium | 41.4* | 0.00139 |
| M35252 | 2343 | Hs.84072 | Transmembrane 4 superfamily membrane 3 | 39.1 | 0 |
| M29540 | 2317 | Hs.220529 | Carcinoembryonic antigen-related cell adhesion molecule 5 | 36.6* | 0.0116 |
| N92934 | 2724 | Hs.17409 | Cysteine-rich protein 1 (intestinal) | 35.5 | 0.002 |
| AA610116 | 1149 | Hs.102737 | Tetraspan NET-6 protein | 33.7 | 0.00171 |
| HG2788-HT2896 | | Hs.27258 | Calycyclin binding protein | 33.2 | 0 |
| AA429009 | 994 | Hs.233950 | Serine protease inhibitor, Kunitz type 1 | 30.0* | 0.00001 |

TABLE 4B

Top Fifteen Genes that are Underexpressed in Metastatic Carcinomas in the Liver

| Accession # | SEQ ID: | Unigene Cluster | Gene Name | Fold Change | Pvalue |
|---|---|---|---|---|---|
| N54417 | 2566 | Hs.90765 | Fibrinogen, A alpha polypeptide | 99.3 | 0.00001 |
| N53031 | 2555 | Hs.89691 | UDP glycosyltransferase 2 family, polypeptide B4 | 97.6 | 0.00022 |

TABLE 4B-continued

Top Fifteen Genes that are Underexpressed in Metastatic Carcinomas in the Liver

| Accession # | SEQ ID: | Unigene Cluster | Gene Name | Fold Change | Pvalue |
|---|---|---|---|---|---|
| M15656 | 2268 | Hs.234234 | Aldolase B, fructose-bisphosphate | 96.7* | 0 |
| T59148 | 3157 | Hs.550966 | Carbamoyl-phosphate synthetase 1, mitochondrial | 88.9* | 0 |
| R49459 | 2881 | Hs.63758 | Transferrin receptor 2 | 85.6 | 0.00048 |
| X55283 | 3731 | Hs.1259 | Asialoglycoprotein receptor 2 | 85.0 | 0.00084 |
| L16883 | 2166 | Hs.167529 | Cytochrome P450, subfamily IIC (menphenytoin 4-hydroxylase), polypeptide 9 | 84.7 | 0.00327 |
| T48039 | 3128 | Hs.2351 | Protien C (inactivator of coagulation factors Va and VIIIa) | 84.4 | 0.00112 |
| H58692 | 1960 | Hs.9520 | Formyltetrahydrofolate dehydrogenase | 81.4* | 0 |
| M81349 | 2404 | Hs.1955 | Serum amyloid A4, constitutive | 76.2 | 0.00015 |
| R43174 | 2847 | Hs.1898 | Paraoxonase 1 | 74.0* | 0.00038 |
| M16594 | 2272 | Hs.89552 | glutathione S-transferase A2 | 73.2* | 0 |
| U22029 | 3326 | Hs.250615 | Cytochrome P450, subfamily IIA (phenobarbital-inducible), polypeptide 7 | 72.0* | 0 |
| AA256367 | 579 | Hs.107966 | Paraoxonase 3 | 70.3 | 0.00192 |
| K03192 | 2127 | Hs.183584 | Cytochrome P450, subfamily IIA (phenobarbital-inducible), polypeptide 6 | 69.9* | 0 |

TABLE 5

Top Fifteen Genes Expressed in Both Hepatocellular Carcinomas and Metastatic Liver Tumors, not in Normal Liver Tissue

| Accession # | SEQ ID: | Unigene Cluster | Gene Name | HCC Fold Change | HCC p value | Metastatics Fold Change | Metastatic p value |
|---|---|---|---|---|---|---|---|
| Y00705 | 3847 | Hs.181286 | serine protease inhibitor, Kazal type 1 | 28.9 | 0.00003 | 9.8 | 0.03697 |
| AA610116 | 1499 | Hs.102737 | tetraspan NET-6 protein | 16.4 | 0.00249 | 33.7 | 0.00171 |
| AA055896 | 135 | Hs.146428 | collagen, type V, alpha 1 | 10.9 | 0.00907 | 18.2 | 0.00146 |
| J03464 | 2094 | Hs.179573 | collagen, type I, alpha 2 | 10.4 | 0.00979 | 9.8 | 0.00028 |
| M94250 | 2425 | Hs.82045 | midkine (neurite growth-promoting factor 2) | 9.9 | 0.02104 | 10.4 | 0.01818 |
| AA620881 | 1510 | Hs.21858 | trinucleotide repeat containing 3 | 9.5 | 0.00062 | 8.7 | 0.00735 |
| D51276 | 1678 | Hs.81915 | leukemia-associated phosphoprotein p18 (stathmin) | 9.4 | 0.00015 | 4.8 | 0.00514 |
| D31094 | 1639 | Hs.109798 | G8 protein | 9.4 | 0.0048 | 4.4 | 0.04845 |
| AA429472 | 997 | Hs.236522 | DKFZP434P106 protein | 8.8 | 0.00063 | 8.3 | 0.00208 |
| AA452724 | 1149 | Hs.166468 | programmed cell death 5 | 7.7 | 0.00085 | 7.2 | 0.00908 |
| D26129 | 1635 | Hs.78224 | ribonuclease, RNase A family, 1 (pancreatic) | 6.9 | 0.00008 | 5.7 | 0.03827 |
| AA434418 | 1036 | Hs.72172 | KIAA1115 protein | 6.8 | 0.0032 | 5.1 | 0.00498 |
| AA335191 | 741 | Hs.173724 | creatine kinase, brain | 6.5 | 0.01462 | 47.4 | 0.00419 |
| AA204927 | 425 | Hs.77899 | tropomyosin 1 (alpha) | 6.1 | 0.0014 | 7.1 | 0.00074 |
| H27188 | 1908 | Hs.9930 | collagen-binding protein 2 (colligen 2) | 5.8 | 0.01826 | 4.2 | 0.02073 |

TABLE 6A

Up in Metastatics vs Normal Sample Set 2

| Fragment Name | SEQ ID: | Known Gene Name | Fold Change | Direction | Pvalue |
|---|---|---|---|---|---|
| AA427468 | 973 | claudin 4 | 84.43 | up | 0 |
| H58873 | 1961 | solute carrier family 2 (facilitated glucose transporter), member 1 | 57.98 | up | 0.00063 |
| AA421562 | 934 | anterior gradient 2 (Xenepus laevis) homolog | 56.3 | up | 0.0041 |
| J04423 | 2109 | EST | 54.11 | up | 0.02774 |
| AA100719 | 212 | carcinoembryonic antigen-related cell adhesion molecule 6 (non-specific cross reacting antigen) | 50.88 | up | 0.00081 |
| AA159525 | 354 | EST | 49.39 | up | 0.00062 |
| J04423 | 2109 | EST | 48.05 | up | 0.02203 |
| AA335191 | 741 | creatine kinase, brain | 47.35 | up | 0.00419 |
| H95233 | 2048 | serine protease inhibitor, Kunitz type, 2 | 47.06 | up | 0 |
| N22015 | 2447 | EST | 46.61 | up | 0.00025 |
| M18728 | 2285 | carcinoembryonic antigen-related cell adhesion molecule 6 (non-specific cross reacting antigen) | 44.82 | up | 0.00291 |
| AA211483 | 435 | EST | 44.07 | up | 0.00175 |
| H94471 | 2042 | occludin | 43.09 | up | 0 |
| N54841 | 2571 | EST | 42.96 | up | 0.00002 |
| AA055805 | 132 | EST | 42.83 | up | 0.00142 |
| X93036 | 3827 | FXYD domain-containing ion transport regulator 3 | 42.36 | up | 0.00167 |
| AA156243 | 340 | serine protease, umbilical endothelium | 41.44 | up | 0.00139 |
| R33498 | 2819 | EST | 41.34 | up | 0.00001 |
| AA291168 | 696 | EST | 40.67 | up | 0.00065 |
| M35252 | 2343 | transmembrane 4 superfamily member 3 | 39.12 | up | 0 |

TABLE 6A-continued

Up in Metastatics vs Normal Sample Set 2

| Fragment Name | SEQ ID: | Known Gene Name | Fold Change | Direction | Pvalue |
|---|---|---|---|---|---|
| AA398908 | 801 | EST | 38.69 | up | 0.01089 |
| AA424487 | 945 | EST | 38.41 | up | 0.00002 |
| M29540 | 2317 | carcinoembryonic antigen-related cell adhesion molecule 5 | 36.57 | up | 0.0116 |
| N92934 | 2724 | cysteine-rich protein 1 (intestinal) | 35.52 | up | 0.002 |
| AA075299 | 164 | EST | 34.27 | up | 0.00002 |
| AA610116 | 1499 | tetraspan NET-6 protein | 33.68 | up | 0.00171 |
| HG2788-HT2896 | | calcyclin binding protein | 33.15 | up | 0 |
| W92449 | 3649 | EST | 31.67 | up | 0.00011 |
| T26366 | 3092 | EST | 30.43 | up | 0.00153 |
| AA429009 | 994 | serine protease inhibitor, Kunitz type I | 30.04 | up | 0.00001 |
| AA099404 | 208 | EST | 29.07 | up | 0 |
| AA011134 | 29 | EST | 28.79 | up | 0.00602 |
| W72276 | 3580 | EST | 27.39 | up | 0.00183 |
| M57710 | 2357 | lectin, galactoside-binding, soluble, 3 (galectin 3) | 27.12 | up | 0.00001 |
| AA053102 | 125 | cadherin 17, LI cadherin (liver-intestine) | 26.63 | up | 0.01745 |
| W95477 | 3661 | EST | 26.51 | up | 0.00161 |
| M27826 | 2313 | endogenous retroviral protease | 26.36 | up | 0.00342 |
| AA157818 | 349 | endogenous retroviral protease | 25.99 | up | 0.00153 |
| A372630 | 769 | differentially expressed in hematopoietic lineages | 25.49 | up | 0.01743 |
| T03580 | 3045 | pyruvate kinase, muscle | 24.91 | up | 0.0001 |
| AA463861 | 1251 | EST | 24.79 | up | 0.00096 |
| AA101551 | 216 | EST | 24.78 | up | 0 |
| AA284879 | 679 | EST | 24.68 | up | 0.00001 |
| AA213696 | 437 | poly(A)-binding protein, cytoplasmic 1 | 24.65 | up | 0.00001 |
| AA394121 | 778 | laminin receptor 1 (67kD, ribosomal protein SA) | 23.78 | up | 0.00099 |
| AA234096 | 479 | EST | 23.72 | up | 0.00018 |
| AA156187 | 339 | ATP synthase, H+ transporting, mitochondrial FO complex, subunit b, isoform 1 | 23.24 | up | 0.00006 |
| X56494 | 3735 | pyruvate kinase, muscle | 22.97 | up | 0.00001 |
| F09394 | 1803 | K1AA0715 protein | 22.89 | up | 0.01753 |
| M94345 | 2426 | capping protein (actin filament), gelsolin-like | 22.38 | up | 0.00003 |
| AA428964 | 993 | kallikrein 10 | 21.83 | up | 0.02324 |
| J04423 | 2109 | EST | 21.46 | up | 0.04283 |
| L08044 | 2149 | trefoil factor 3 (intestinal) | 21.42 | up | 0.01674 |
| AA405791 | 864 | EST | 21.22 | up | 0 |
| LI7131 | 2168 | high-mobility group (nonhistone chromosomal) protein isoforms I and Y | 20.57 | up | 0.00058 |
| AA233959 | 477 | EST | 19.69 | up | 0.00101 |
| AA427636 | 976 | EST | 19.23 | up | 0.00145 |
| U78095 | 3429 | serine protease inhibitor, Kunitz type, 2 | 18.85 | up | 0 |
| AA161043 | 356 | tetraspan 1 | 18.8 | up | 0.00015 |
| D38583 | 1656 | S100 calcium-binding protein A11 (calgizzarin) | 18.7 | up | 0.00003 |
| AA055896 | 135 | collagen, type V, alpha 1 | 18.16 | up | 0.00146 |
| AA143763 | 311 | EST | 18.09 | up | 0.00347 |
| AA171760 | 367 | EST | 17.86 | up | 0 |
| H18442 | 1891 | creatine kinase, brain | 17.42 | up | 0.02391 |
| AA422150 | 939 | cytochrome P540 family member predicted from ESTs | 17.14 | up | 0.00108 |
| AA158234 | 351 | EST | 17.04 | up | 0.00711 |
| AA442054 | 1067 | phospholipase C, gamma 1 (formerly subtype 148) | 16.89 | up | 0.00205 |
| AA430032 | 1009 | pituitary tumor-transforming 1 | 16.87 | up | 0.00659 |
| AA251299 | 541 | KIAA0014 gene product | 16.86 | up | 0.00046 |
| AA331393 | 739 | EST | 16.73 | up | 0.00848 |
| W93726 | 3653 | protease inhibitor 5 (maspin) | 16.48 | up | 0.00014 |
| M93036 | 2421 | membrane component, chromosomal 4, surface marker (35kD glycoprotein) | 16.45 | up | 0.00308 |
| AA411502 | 889 | EST | 16.42 | up | 0.00241 |
| AA410508 | 885 | EST | 16.04 | up | 0.02635 |
| AA053660 | 128 | EST | 15.98 | up | 0.00003 |
| N98464 | 2743 | EST | 15.95 | up | 0.00004 |
| AA215299 | 439 | U6 snRNA-associated Sm-like protein LSm7 | 15.84 | up | 0.00001 |
| M27830 | 2314 | EST | 15.53 | up | 0.00022 |
| AA131919 | 270 | putative type II membrane protein | 15.36 | up | 0.00027 |
| T24068 | 3087 | EST | 15.26 | up | 0.00046 |
| AA253473 | 567 | EST | 15.23 | up | 0.00171 |
| W42957 | 3513 | calmodulin 2 (phosphorylase kinase, delta) | 15.22 | up | 0.00007 |
| AA430674 | 1018 | EST | 15.11 | up | 0.00293 |
| M38591 | 2350 | S100 calcium-binding protein A10 (annexin II ligand, calpactin I, light polypeptide (p 11)) | 14.87 | up | 0 |
| M27830 | 2314 | EST | 14.86 | up | 0.00043 |
| AA485697 | 1346 | EST | 14.74 | up | 0.00102 |
| AA451676 | 1135 | EST | 14.72 | up | 0.00056 |
| X68314 | 3775 | glutathione peroxidase 2 (gastrointestinal) | 14.4 | up | 0.00222 |
| AA372018 | 768 | EST | 14.3 | up | 0.00178 |
| AA135894 | 295 | retinoic acid induced 3 | 14.27 | up | 0.00558 |
| Y00503 | 3846 | keratin 19 | 14.19 | up | 0.00217 |
| L08044 | 2149 | trefoil factor 3 (intestinal) | 14.18 | up | 0.02124 |
| AA161292 | 357 | interferon, alpha-inducible protein 27 | 13.84 | up | 0.00004 |

TABLE 6A-continued

Up in Metastatics vs Normal Sample Set 2

| Fragment Name | SEQ ID: | Known Gene Name | Fold Change | Direction | Pvalue |
|---|---|---|---|---|---|
| AA412405 | 901 | EST | 13.82 | up | 0.01021 |
| C01766 | 1559 | EST | 13.67 | up | 0.00003 |
| AA262943 | 611 | EST | 13.42 | up | 0.00234 |
| U09770 | 3295 | cysteine-rich protein 1 (intestinal) | 13.03 | up | 0.0072 |
| AA227560 | 458 | EST | 12.81 | up | 0.01693 |
| M16364 | 2269 | creatine kinase, brain | 12.69 | up | 0.03633 |
| X57348 | 3741 | stratifin | 12.53 | up | 0.0013 |
| AA429890 | 1004 | cisplatin resistance associated | 12.51 | up | 0.00053 |
| J04164 | 2108 | interferon induced transmembrane protein 1(9-27) | 12.37 | up | 0.00001 |
| X65614 | 3764 | S100 calcium-binding protein P | 12.2 | up | 0.00065 |
| AA134968 | 289 | EST | 12.11 | up | 0.00079 |
| AA134985 | 290 | EST | 12.11 | up | 0.00318 |
| J05257 | 2118 | dipeptidase 1 (renal) | 12.02 | up | 0.02099 |
| T23490 | 3081 | EST | 11.86 | up | 0.03242 |
| N49284 | 2536 | v-myb avian myeloblastosis viral oncogene homolog | 11.82 | up | 0.01981 |
| X76180 | 3792 | sodium channel, nonvoltage-gated 1 alpha | 11.68 | up | 0 |
| AA290674 | 692 | eukaryotic translation initiation factor 4E binding protein 1 | 11.59 | up | 0.00036 |
| M10098 | 2231 | EST | 11.55 | up | 0.00099 |
| AA447687 | 1104 | EST | 11.42 | up | 0.00362 |
| D00017 | 1587 | annexinA2 | 11.38 | up | 0 |
| H20989 | 1899 | pyruvate kinase, muscle | 11.37 | up | 0.0375 |
| AF003521 | 1545 | jagged 2 | 11.26 | up | 0.00008 |
| AA126044 | 245 | EST | 11.23 | up | 0.00041 |
| R95966 | 2996 | EST | 11.22 | up | 0.00682 |
| AA256642 | 582 | EST | 11.17 | up | 0.00035 |
| AA497031 | 1407 | EST | 11.05 | up | 0.04381 |
| R92994 | 2989 | matrix metalloproteinase 12 (macrophage elastase) | 11.05 | up | 0.00248 |
| L33842 | 2197 | IMP (inosine monophosphate) dehydrogenase 2 | 11.03 | up | 0.00001 |
| AA026030 | 53 | EST | 11.01 | up | 0.01649 |
| R49476 | 2882 | EST | 10.95 | up | 0.00014 |
| AA404338 | 849 | EST | 10.9 | up | 0.00668 |
| W95348 | 3660 | HSPC113 protein | 10.89 | up | 0.01065 |
| M12125 | 2241 | tropomyosin 2 (beta) | 10.83 | up | 0.00191 |
| U07969 | 3288 | cadherin 17, LI cadherin (liver-intestine) | 10.78 | up | 0.02002 |
| AA338889 | 745 | actin related protein 2/3 complex, subunit 4 (20 kD) | 10.77 | up | 0.03782 |
| AA460017 | 1225 | EST | 10.76 | up | 0.00106 |
| K03195 | 2128 | solute carrier family 2 (facilitated glucose transporter), member 1 | 10.73 | up | 0.00139 |
| AA422086 | 938 | EST | 10.71 | up | 0.03418 |
| T53404 | 3142 | EST | 10.68 | up | 0.00582 |
| M27830 | 2314 | EST | 10.64 | up | 0.00213 |
| AA113149 | 226 | tumor suppressing subtransferable candidate 3 | 10.58 | up | 0.00543 |
| X83228 | 3807 | cadherin 17, LI cadherin (liver-intestine) | 10.58 | up | 0.02147 |
| X12447 | 3693 | aldolase A, fructose-bisphosphate | 10.52 | up | 0.00038 |
| D51112 | 1675 | collapsin response mediator protein 1 | 10.48 | up | 0.00076 |
| Z74615 | 3946 | collagen, type I, alpha 1 | 10.47 | up | 0.00064 |
| AA429636 | 1001 | hexokinase 2 | 10.43 | up | 0.00597 |
| R71395 | 2951 | EST | 10.42 | up | 0.00422 |
| D83735 | 1747 | calponin 2 | 10.42 | up | 0.00001 |
| N31570 | 2485 | TNF receptor-associated factor 5 | 10.39 | up | 0.00018 |
| T95057 | 3258 | EST | 10.39 | up | 0.00003 |
| M94250 | 2425 | midkine (neurite growth-promoting factor 2) | 10.39 | up | 0.01818 |
| M10098 | 2231 | EST | 10.2 | up | 0.00027 |
| M24485 | 2304 | glutathione 5-transferase pi | 10.2 | up | 0.00003 |
| AA609013 | 1477 | dipeptidase 1 (renal) | 10.17 | up | 0.00109 |
| J03592 | 2096 | solute carrier family 25 (mitochondrial carrier; adenine nucleotide translocator) member 6 | 10.05 | up | 0 |
| AA001504 | 2 | EST | 9.98 | up | 0.00336 |
| H89551 | 2024 | EST | 9.94 | up | 0.00137 |
| AA608897 | 1473 | EST | 9.92 | up | 0.00087 |
| X89960 | 3815 | EST | 9.87 | up | 0 |
| Y00705 | 3847 | serine protease inhibitor, Kazal type 1 | 9.83 | up | 0.03697 |
| J03464 | 2094 | collagen, type I, alpha 2 | 9.81 | up | 0.00028 |
| M27830 | 2314 | EST | 9.8 | up | 0.00041 |
| AA132986 | 275 | EST | 9.72 | up | 0.00552 |
| X67325 | 3772 | interferon, alpha-inducible protein 27 | 9.67 | up | 0.03245 |
| AA280734 | 639 | KIAA0618 gene product | 9.64 | up | 0.00003 |
| N46423 | 2520 | EST | 9.64 | up | 0.00027 |
| T03313 | 3041 | dyskeratosis congenita 1, dyskerin | 9.63 | up | 0.00001 |
| AA188378 | 392 | EST | 9.56 | up | 0.00271 |
| AA428172 | 986 | Notch (Drosophila) homolog 3 | 9.53 | up | 0.02562 |
| AA454908 | 1171 | KIAA0144 gene product | 9.3 | up | 0.00539 |
| N39237 | 2510 | EST | 9.29 | up | 0.00001 |
| AA133936 | 284 | EST | 9.19 | up | 0.00088 |
| AA235707 | 500 | EST | 9.17 | up | 0.00005 |
| L33930 | 2198 | CD24 antigen (small cell lung carcinoma cluster 4 antigen) | 9.16 | up | 0.01252 |

TABLE 6A-continued

Up in Metastatics vs Normal Sample Set 2

| Fragment Name | SEQ ID: | Known Gene Name | Fold Change | Direction | Pvalue |
|---|---|---|---|---|---|
| H97013 | 2059 | ephrin-A4 | 9.14 | up | 0.00346 |
| AA084901 | 181 | ribosomal protein S6 kinase, 70kD, polypeptide 2 | 9.13 | up | 0.00003 |
| M38690 | 2351 | CD9 antigen (p24) | 9.08 | up | 0.00059 |
| W78057 | 3597 | EST | 9.06 | up | 0.0034 |
| N72116 | 2667 | solute carrier family 11 (proton-coupled divalent metal ion transporters), member 2 | 9.01 | up | 0.00051 |
| R91819 | 2983 | EST | 8.95 | up | 0.00009 |
| Z39191 | 3898 | EST | 8.84 | up | 0.00011 |
| AA116036 | 233 | chromosome 20 open reading frame 1 | 8.81 | up | 0.00133 |
| M27830 | 2314 | EST | 8.78 | up | 0.00003 |
| AA053424 | 127 | EST | 8.76 | up | 0.01775 |
| AA243173 | 526 | EST | 8.75 | up | 0.00003 |
| AA291139 | 695 | EST | 8.69 | up | 0.04573 |
| AA424029 | 943 | EST | 8.68 | up | 0.00081 |
| L09604 | 2151 | proteolipid protein 2 (colonic epithelium-enriched) | 8.68 | up | 0. |
| AA620881 | 1510 | trinucleotide repeat containing 3 | 8.66 | up | 0.00735 |
| AA435665 | 1040 | EST | 8.66 | up | 0.00001 |
| AA451877 | 1138 | EST | 8.63 | up | 0.00489 |
| U79725 | 3437 | glycoprotein A33 (transmembrane) | 8.57 | up | 0.00299 |
| AA043959 | 101 | tropomyosin 4 | 8.54 | up | 0.02222 |
| 080946 | 1737 | SERS protein kinase 1 | 8.53 | up | 0.00455 |
| L21954 | 2177 | benzodiazapine receptor (peripheral) | 8.53 | up | 0.00001 |
| X54667 | 3728 | cystatin S,cystatin SN | 8.53 | up | 0.00059 |
| U47025 | 3367 | phosphorylase, glycogen; brain | 8.52 | up | 0.00134 |
| N62126 | 2588 | EST | 8.51 | up | 0.00016 |
| N73808 | 2678 | EST | 8.46 | up | 0.01886 |
| HG371-HT26388 | | mucin 1, transmembrane | 8.44 | up | 0.00268 |
| T30193 | 3097 | protease, serine, 8 (prostasin) | 8.39 | up | 0.00043 |
| M32886 | 2335 | sorcin | 8.35 | up | 0.00215 |
| U73379 | 3417 | ubiquitin carrier protein E2-C | 8.32 | up | 0.00101 |
| AA429472 | 997 | DKFZP434P106 protein | 8.27 | up | 0.00208 |
| AA406542 | 878 | EST | 8.27 | up | 0.00724 |
| F04674 | 1793 | K1AA0746 protein | 8.2 | up | 0.00028 |
| M27830 | 2314 | EST | 8.2 | up | 0.00294 |
| T03438 | 3042 | EST | 8.18 | up | 0.00032 |
| R56095 | 2905 | EST | 8.16 | up | 0.00023 |
| AA461187 | 1236 | EST | 8.15 | up | 0.00068 |
| 578187 | 3035 | cell division cycle 25B | 8.07 | up | 0.00009 |
| T33489 | 3104 | EST | 8.04 | up | 0.00469 |
| R02036 | 2753 | EST | 8.01 | up | 0.01012 |
| AA295819 | 722 | EST | 8 | up | 0.01793 |
| AA282247 | 657 | EST | 8 | up | 0.00014 |
| U09117 | 3293 | phospholipase C, delta 1 | 7.96 | up | 0.00001 |
| AA479797 | 1316 | EST | 7.93 | up | 0.00006 |
| J04469 | 2111 | creatine kinase, mitochondrial 1 (ubiquitous) | 7.9 | up | 0.00705 |
| Z39429 | 3903 | EST | 7.84 | up | 0.00045 |
| AA053033 | 124 | EST | 7.83 | up | 0.00379 |
| Z40945 | 3924 | trinucleotide repeat containing 15 | 7.82 | up | 0.00007 |
| R45994 | 2866 | EST | 7.81 | up | 0.0018 |
| F04531 | 1791 | Kell blood group precursor (McLeod phenotype) | 7.79 | up | 0.03205 |
| AA425852 | 958 | EST | 7.78 | up | 0.00239 |
| R48447 | 2870 | EST | 7.75 | up | 0.00049 |
| AA243133 | 525 | serine/threonine kinase 15 | 7.73 | up | 0.04328 |
| AA074514 | 160 | EST | 7.69 | up | 0 |
| AA292788 | 714 | EST | 7.69 | up | 0.00967 |
| AA433930 | 1032 | chondroitin 4-sulfotransferase | 7.68 | up | 0.02445 |
| Z23090 | 3865 | heat shock 27kD protein 1 | 7.67 | up | 0.00008 |
| AA196790 | 421 | EST | 7.64 | up | 0.00287 |
| F13809 | 1828 | tropomyosin 1 (alpha) | 7.62 | up | 0.00012 |
| U21049 | 3324 | epithelial protein up-regulated in carcinoma, membrane associated protein 17 | 7.53 | up | 0.01667 |
| K03460 | 2129 | tubulin, alpha 1 (testis specific) | 7.5 | up | 0.00002 |
| D13639 | 1607 | cyclin D2 | 7.49 | up | 0.01641 |
| M31303 | 2327 | leukemia-associated phosphoprotein p18 (stathmin) | 7.48 | up | 0.00021 |
| N69263 | 2647 | EST | 7.47 | up | 0.00004 |
| AF001294 | 1544 | tumor suppressing subtransferable candidate 3 | 7.45 | up | 0.00009 |
| U01062 | 3272 | inositol 1,4,5-triphosphate receptor, type 3 | 7.41 | up | 0 |
| AA463725 | 1249 | mannosyl (alpha-1,6-)-glycoprotein beta-1,2-N-acetylglucosaminyltransferas | 7.4 | up | 0.04715 |
| AA403159 | 845 | Ste-20 related kinase | 7.33 | up | 0.00187 |
| M86752 | 2411 | stress-induced-phosphoprotein 1 (Hsp70/Hsp90-organizing protein) | 7.32 | up | 0.00001 |
| W38044 | | myeloid/lymphoid or mixed-lineage leukemia (trithorax (Drosophila) homolog); translocated to, 7 | 7.28 | up | 0.00105 |
| X04347 | 3677 | heterogeneous nuclear ribonucleoprotein A1 | 7.26 | up | 0.00018 |
| AA452724 | 1149 | programmed cell death 5 | 7.2 | up | 0.00908 |
| AA151428 | 335 | matrix metalloproteinase 23B | 7.15 | up | 0.00056 |
| R38239 | 2829 | EST | 7.14 | up | 0.00249 |

TABLE 6A-continued

Up in Metastatics vs Normal Sample Set 2

| Fragment Name | SEQ ID: | Known Gene Name | Fold Change | Direction | Pvalue |
|---|---|---|---|---|---|
| AA292765 | 712 | ZW10 interactor | 7.14 | up | 0.02623 |
| AA204927 | 425 | tropomyosin 1 (alpha) | 7.09 | up | 0.00074 |
| D80710 | 1734 | integral type I protein | 7.08 | up | 0.00213 |
| AB006781 | 1540 | lectin, galactoside-binding, soluble, 4 (galectin 4) | 7.05 | up | 0.00913 |
| S54005 | 3019 | thymosin, beta 10 | 7.03 | up | 0.00334 |
| AA053248 | 126 | EST | 7.01 | up | 0.00003 |
| AA610053 | 1496 | EST | 7.01 | up | 0.00003 |
| N71781 | 2665 | EST | 7.01 | up | 0.02952 |
| M14199 | 2258 | laminin receptor 1 (67kD, ribosomal protein SA) | 7.01 | up | 0 |
| M55998 | 2356 | collagen, type I, alpha 1 | 6.99 | up | 0.00103 |
| T32108 | 3102 | EST | 6.96 | up | 0.00723 |
| AA479044 | 1307 | EST | 6.9 | up | 0.04668 |
| AA449073 | 1117 | EST | 6.89 | up | 0.01445 |
| N22107 | 2448 | EST | 6.88 | up | 0.04259 |
| AA055811 | 133 | glycoprotein A33 (transmembrane) | 6.86 | up | 0.02152 |
| AA226932 | 453 | DKFZP564F0923 protein | 6.84 | up | 0.00405 |
| AA131584 | 268 | DKFZP564O0463 protein | 6.83 | up | 0.00025 |
| R56880 | 2908 | EST | 6.82 | up | 0.02559 |
| AA227926 | 460 | EST | 6.81 | up | 0.01701 |
| U42408 | 3360 | ladinin 1 | 6.8 | up | 0.00305 |
| F01444 | 1770 | KIAA0440 protein | 6.78 | up | 0.00028 |
| AA419217 | 923 | DKFZP586E1422 protein | 6.77 | up | 0.00045 |
| W92207 | 3648 | EST | 6.77 | up | 0.00002 |
| Z41740 | 3932 | EST | 6.76 | up | 0.00049 |
| AA411813 | 893 | postmeiotic segregation increased 2-like 11 | 6.76 | up | 0.03499 |
| AA053007 | 123 | putative receptor protein | 6.76 | up | 0.00061 |
| AA599522 | 1452 | squamous cell carcinoma antigen recognised by T cells | 6.75 | up | 0.04229 |
| L11669 | 2157 | tetracycline transporter-like protein | 6.75 | up | 0.00101 |
| H78211 | 2001 | EST | 6.73 | up | 0.02488 |
| W81540 | 3611 | serine/threonine kinase 24 (Ste20, yeast homolog) | 6.72 | up | 0.00164 |
| R69700 | 2942 | EST | 6.71 | up | 0.0021 |
| AA406145 | 870 | EST | 6.71 | up | 0.00047 |
| X79882 | 3802 | lung resistance-related protein | 6.71 | up | 0.0362 |
| N73762 | 2677 | EST | 6.65 | up | 0.0023 |
| AA429825 | 1003 | DKFZP566B023 protein | 6.63 | up | 0.00032 |
| D55716 | 1686 | minichromosome maintenance deficient (*S. cerevisiae*) 7 | 6.6 | up | 0.00151 |
| AA127712 | 255 | EST | 6.59 | up | 0.03706 |
| W80730 | 3604 | EST | 6.59 | up | 0.00425 |
| Z38266 | 3883 | EST | 6.58 | up | 0.01909 |
| D83783 | 1748 | trinucleotide repeat containing 11 (THR-associated protein, 230 kDa subunit) | 6.55 | up | 0.00176 |
| Z28407 | 3873 | ribosomal protein L8 | 6.53 | up | 0.00004 |
| AA078862 | 173 | EST | 6.52 | up | 0.00025 |
| AA609614 | 1487 | EST | 6.5 | up | 0.00406 |
| HG2797-HT2906 | | clathrin, light polypeptide (Lcb) | 6.5 | up | 0.00013 |
| X64364 | 3761 | basigin | 6.45 | up | 0.00041 |
| AA179787 | 380 | polyglutamine binding protein 1 | 6.44 | up | 0.00206 |
| R61297 | 2919 | eukaryotic translation initiation factor 3, subunit 6 (48kD) | 6.42 | up | 0.00126 |
| C13992 | 1564 | EST | 6.39 | up | 0.00059 |
| AA148885 | 320 | minichromosome maintenance deficient (*S. cerevisiae*) 4 | 6.39 | up | 0.0125 |
| D28124 | 1636 | neuroblastoma candidate region, suppression of tumorigenicity 1 | 6.38 | up | 0.00015 |
| L19605 | 2170 | annexin A11 | 6.38 | up | 0.00017 |
| AB002533 | 1539 | karyopherin alpha 4 (importin alpha 3) | 6.38 | up | 0.00003 |
| R70801 | 2949 | EST | 6.36 | up | 0.00563 |
| N47956 | 2523 | eukaryotic translation initiation factor 3, subunit 3 (gamma, 40kD) | 6.34 | up | 0.00251 |
| L41351 | 2214 | protease, serine, 8 (prostasin) | 6.34 | up | 0.01132 |
| D63486 | 1712 | KIAA0152 gene product | 6.33 | up | 0.00078 |
| HG1153-HT1153 | | non-metastatic cells 2, protein (NM23B) expressed in | 6.31 | up | 0 |
| AA410469 | 883 | EST | 6.3 | up | 0.00103 |
| AA424881 | 949 | EST | 6.3 | up | 0.00556 |
| AA449456 | 1126 | EST | 6.29 | up | 0.00087 |
| AA430048 | 1012 | KIAAOI6O protein | 6.27 | up | 0.00631 |
| X99133 | 3839 | lipocalin 2 (oncogene 24p3) | 6.27 | up | 0.0453 |
| R79580 | 2969 | EST | 6.25 | up | 0.00593 |
| AA028132 | 62 | EST | 6.25 | up | 0.00646 |
| N66624 | 2617 | homolog of mouse quaking QKI (KH domain RNA binding protein) | 6.25 | up | 0 |
| AA010065 | 22 | CDC28 protein kinase 2 | 6.25 | up | 0.02752 |
| M27830 | 2314 | EST | 6.25 | up | 0.00046 |
| W90146 | 3641 | EST | 6.23 | up | 0.01558 |
| AA062721 | 146 | nuclear factor (erythroid-derived 2)-like 1 | 6.2 | up | 0.00024 |
| R96924 | 3000 | EST | 6.18 | up | 0.03417 |
| L23808 | 2179 | matrix metalloproteinase 12 (macrophage elastase) | 6.18 | up | 0.02195 |
| AA053248 | 126 | EST | 6.16 | up | 0.00191 |
| AA453783 | 1158 | EST | 6.16 | up | 0.00167 |
| AA478300 | 1298 | CD39-like 2 | 6.15 | up | 0.01625 |
| N26186 | 2467 | EST | 6.15 | up | 0.00135 |

TABLE 6A-continued

Up in Metastatics vs Normal Sample Set 2

| Fragment Name | SEQ ID: | Known Gene Name | Fold Change | Direction | Pvalue |
|---|---|---|---|---|---|
| AA425279 | 951 | quiescin Q6 | 6.15 | up | 0.00083 |
| AA441911 | 1066 | EST | 6.14 | up | 0.00003 |
| U93205 | 3460 | chloride intracellular channel 1 | 6.14 | up | 0.00058 |
| W67251 | 3567 | EST | 6.13 | up | 0.01463 |
| D87953 | 1765 | N-myc downstream regulated | 6.12 | up | 0.00033 |
| U20758 | 3322 | secreted phosphoprotein 1 (osteopontin, bone sialoprotein I, early T-lymphocyte activation 1) | 6.12 | up | 0.03448 |
| M62895 | 2375 | annexin A2,annexin A2 pseudogene 2 | 6.11 | up | 0.00013 |
| AA128561 | 261 | collagen, type XVII, alpha 1 | 6.09 | up | 0.0433 |
| U58682 | 3395 | ribosomal protein S28 | 6.09 | up | 0.00001 |
| AA479727 | 1315 | EST | 6.06 | up | 0.00389 |
| N80703 | 2703 | EST | 6.06 | up | 0.00003 |
| AA279177 | 624 | lymphocyte antigen 75 | 6.05 | up | 0.01821 |
| AA292379 | 708 | EST | 6.04 | up | 0.00568 |
| W74233 | 3594 | related RAS viral (r-ras) oncogene homolog | 6.02 | up | 0.01815 |
| AA007160 | 16 | EST | 6 | up | 0.01035 |
| H09281 | 1863 | EST | 6 | up | 0.00966 |
| Z41798 | 3934 | EST | 6 | up | 0.00073 |
| R97759 | 3005 | serum/glucocorticoid regulated kinase | 5.99 | up | 0.00221 |
| AA284945 | 680 | EST | 5.98 | up | 0.00026 |
| W49574 | 3535 | EST | 5.97 | up | 0.00045 |
| T32072 | 3101 | EST | 5.95 | up | 0.00029 |
| D82558 | 1746 | novel centrosomal protein RanBPM | 5.94 | up | 0.00752 |
| AA463234 | 1246 | KIAA0792 gene product | 5.94 | up | 0.01182 |
| U48705 | 3369 | discoidin domain receptor family, member 1 | 5.94 | up | 0.01323 |
| R52161 | 2892 | EST | 5.84 | up | 0.03253 |
| R76782 | 2962 | O-linked N-acetylglucosamine (GlcNAc) transferase (UDP-N-acetylglucosamine:polypeptide-N-acetylglucosaminyl transferase) | 5.83 | up | 0.01126 |
| R40254 | 2839 | EST | 5.82 | up | 0.00304 |
| H81413 | 2007 | high-mobility group (nonhistone chromosomal) protein isoforms I andY | 5.82 | up | 0.00769 |
| H75933 | 1998 | laminin receptor 1 (67kD, ribosomal protein SA) | 5.81 | up | 0.00024 |
| T15473 | 3057 | muscle specific gene | 5.81 | up | 0.02404 |
| M27830 | 2314 | EST | 5.78 | up | 0.0017 |
| AA478017 | 1295 | zyxin | 5.77 | up | 0.00484 |
| AA179845 | 381 | EST | 5.77 | up | 0.01414 |
| AA151778 | 338 | claudin 7 | 5.77 | up | 0.00002 |
| U78556 | 3432 | cisplatin resistance associated | 5.77 | up | 0.00241 |
| U51478 | 3384 | ATPase, Na+/K+ transporting, beta 3 polypeptide | 5.75 | up | 0.00007 |
| U73843 | 3420 | E74-like factor 3 (ets domain transcription factor) | 5.75 | up | 0.00017 |
| AA236037 | 506 | EST | 5.74 | up | 0.0091 |
| M60784 | 2366 | small nuclear ribonucleoprotein polypeptide A | 5.74 | up | 0.00126 |
| R44538 | 2855 | EST | 5.73 | up | 0.01015 |
| AA287393 | 688 | EST | 5.68 | up | 0.00062 |
| D26129 | 1635 | ribonuclease, RNase A family, 1 (pancreatic) | 5.68 | up | 0.03827 |
| L76191 | 2222 | interleukin-1 receptor-associated kinase 1 | 5.66 | up | 0.00089 |
| N52168 | 2550 | EST | 5.65 | up | 0.00003 |
| D51393 | 1681 | ribosomal protein L4 | 5.64 | up | 0.00074 |
| T47325 | 3124 | EST | 5.63 | up | 0.01015 |
| M10098 | 2231 | EST | 5.62 | up | 0.00251 |
| M86400 | 2409 | tyrosine 3-monooxygenase/tryptophan 5-monooxygenase activation protein, zeta polypeptide | 5.62 | up | 0.00016 |
| M10098 | 2231 | EST | 5.61 | up | 0.01238 |
| D11086 | 1595 | interleukin 2 receptor, gamma (severe combined immunodeficiency) | 5.61 | up | 0.00873 |
| AA093497 | 199 | DEK oncogene (DNA binding) | 5.6 | up | 0.02551 |
| AA452536 | 1145 | v-ral simian leukemia viral oncogene homolog A (ras related) | 5.6 | up | 0.00481 |
| AA279840 | 632 | titin-cap (telethonin) | 5.58 | up | 0.01253 |
| N71072 | 2663 | EST | 5.57 | up | 0.03881 |
| R06251 | 2763 | tumor protein D52-like 2 | 5.57 | up | 0.00037 |
| N66951 | 2620 | EST | 5.54 | up | 0.02442 |
| AA188378 | 392 | EST | 5.54 | up | 0.01359 |
| U46692 | 3366 | cystatin B (stefin B) | 5.54 | up | 0.00016 |
| U20499 | 3320 | sulfotransferase family 1A, phenol-preferring, member 3 | 5.5 | up | 0.00299 |
| AA287347 | 687 | EST | 5.47 | up | 0.00034 |
| M81757 | 2405 | ribosomal protein S19 | 5.46 | up | 0 |
| S81914 | 3037 | immediate early response 3 | 5.46 | up | 0.01798 |
| AA262887 | 610 | EST | 5.4 | up | 0.04719 |
| D63487 | 1713 | KIAA0153 protein | 5.4 | up | 0.00027 |
| J05582 | 2121 | mucin 1, transmembrane | 5.39 | up | 0.00056 |
| T23516 | 3082 | 3-phosphoglycerate dehydrogenase | 5.38 | up | 0.00001 |
| AA181600 | 384 | EST | 5.38 | up | 0.03316 |
| H99473 | 2077 | regulator of nonsense transcripts 1 | 5.37 | up | 0.00177 |
| AA459254 | 1211 | EST | 5.36 | up | 0.0259 |
| C14756 | 1570 | MLN51 protein | 5.36 | up | 0.00001 |
| M10098 | 2231 | EST | 5.35 | up | 0.00186 |
| AA485405 | 1343 | EST | 5.35 | up | 0.03475 |

TABLE 6A-continued

Up in Metastatics vs Normal Sample Set 2

| Fragment Name | SEQ ID: | Known Gene Name | Fold Change | Direction | Pvalue |
|---|---|---|---|---|---|
| N69252 | 2646 | ferritin, light polypeptide | 5.33 | up | 0.01554 |
| HG1612-HT1612 | | MARCKS-like protein | 5.32 | up | 0.00007 |
| M20471 | 2289 | clathrin, light polypeptide (Lca) | 5.32 | up | 0.00344 |
| AA126719 | 250 | EST | 5.31 | up | 0.00026 |
| T16308 | 3068 | EST | 5.29 | up | 0.00119 |
| AA335091 | 740 | EST | 5.28 | up | 0.0009 |
| AA189015 | 394 | EST | 5.27 | up | 0.00004 |
| AA450247 | 1133 | EST | 5.27 | up | 0.02833 |
| HG1614-HT1614 | | protein phosphatase 1, catalytic subunit, alpha isoform | 5.27 | up | 0.00257 |
| L19686 | 2171 | macrophage migration inhibitory factor (glycosylation-inhibiting factor) | 5.26 | up | 0.00562 |
| J04152 | 2107 | membrane component, chromosome 1, surface marker I (40kD glycoprotein, identified by monoclonal antibody GA733) | 5.26 | up | 0.02466 |
| U14972 | 3306 | ribosomal protein S10 | 5.24 | up | 0.00077 |
| AA459388 | 1215 | copine I | 5.23 | up | 0.00691 |
| T16983 | 3073 | cleavage and polyadenylation specific factor 4, 30kD subunit | 5.23 | up | 0.00075 |
| C15324 | 1574 | EST | 5.22 | up | 0.00344 |
| L04490 | 2137 | NADH dehydrogenase (ubiquinone) 1 alpha subcomplex, 9 (39kD) | 5.22 | up | 0.02192 |
| AA291137 | 694 | EST | 5.21 | up | 0.00685 |
| R38511 | 2831 | protein similar to *E. coli* yhdg and R. capsulatus nifR3 | 5.19 | up | 0.00015 |
| R06866 | 2773 | EST | 5.18 | up | 0.00187 |
| D20906 | 1627 | EST | 5.18 | up | 0.02189 |
| H05625 | 1847 | EST | 5.17 | up | 0.04551 |
| AA011383 | 31 | EST | 5.17 | up | 0.00008 |
| N20198 | 2439 | ubiquitin-conjugating enzyme E2 variant 1 | 5.17 | up | 0.00508 |
| AA490494 | 1377 | EST | 5.16 | up | 0.01696 |
| S69272 | 3027 | protease inhibitor 6 (placental thrombin inhibitor) | 5.15 | up | 0.00003 |
| AA471278 | 1277 | BUB3 (budding uninhibited by benzimidazoles 3, yeast) homolog | 5.14 | up | 0.00873 |
| AA026150 | 55 | EST | 5.14 | up | 0.01072 |
| AA086232 | 186 | kangai 1 (suppression of tumorigenicity 6, prostate; CD82 antigen (R2 leukocyte antigen, antigen detected by monoclonal and antibody IA4)) | 5.14 | up | 0.01916 |
| AA620466 | 1502 | EST | 5.14 | up | 0.00004 |
| X17206 | 3715 | ribosomal protein S2 | 5.14 | up | 0 |
| J04423 | 2109 | EST | 5.13 | up | 0.02791 |
| W92608 | 3650 | BAI1-associated protein 3 | 5.12 | up | 0.00075 |
| AA434418 | 1036 | KIAA1115 protein | 5.12 | up | 0.00498 |
| AA482319 | 1335 | putative type II membrane protein | 5.11 | up | 0.00177 |
| AA249819 | 535 | EST | 5.09 | up | 0.00136 |
| AA442763 | 1072 | cyclin B2 | 5.09 | up | 0.02168 |
| T26513 | 3094 | protein phosphatase 2 (formerly 2A), regulatory subunit A (PR 65), alpha isoform | 5.07 | up | 0.0016 |
| H09271 | 1862 | EST | 5.06 | up | 0.0016 |
| H88674 | 2021 | collagen, type I, alpha 2 | 5.06 | up | 0.00866 |
| X98482 | 3838 | EST | 5.03 | up | 0.00002 |
| H43286 | 1929 | gamma-aminobutyric acid (GABA) B receptor, 1 | 5.02 | up | 0.01972 |
| AA364267 | 762 | EST | 5.01 | up | 0.00255 |
| AA464963 | 1265 | EST | 5.01 | up | 0.00107 |
| AA147439 | 315 | EST | 5.01 | up | 0.00336 |
| T15442 | 3056 | calpain, large polypeptide L1 | 5.01 | up | 0.00255 |
| N77947 | 2697 | EST | 5 | up | 0.00117 |
| L06505 | 2142 | ribosomal protein L12 | 5 | up | 0.00163 |
| AA280283 | 637 | EST | 4.99 | up | 0.02644 |
| AA447991 | 1112 | EST | 4.99 | up | 0.00173 |
| AA464414 | 1258 | EST | 4.99 | up | 0.00529 |
| AA075580 | 165 | EST | 4.98 | up | 0.02083 |
| U17077 | 3313 | BENE protein | 4.98 | up | 0.00366 |
| AA476216 | 1279 | EST | 4.97 | up | 0.00359 |
| AA132554 | 273 | EST | 4.96 | up | 0.02076 |
| AA504270 | 1411 | EST | 4.96 | up | 0.01919 |
| R48589 | 2873 | EST | 4.95 | up | 0.01346 |
| R58974 | 2909 | EST | 4.95 | up | 0.00498 |
| AA283085 | 667 | EST | 4.93 | up | 0.00382 |
| AA489712 | 1372 | EST | 4.93 | up | 0.00726 |
| AA496981 | 1404 | v-erb-b2 avian erythroblastic leukemia viral oncogene homolog 3 | 4.93 | up | 0.01096 |
| D14520 | 1613 | basic transcription element binding protein 2 | 4.93 | up | 0.00004 |
| AA402495 | 838 | EST | 4.91 | up | 0.00235 |
| U15008 | 3308 | small nuclear ribonucleoprotein D2 polypeptide (16.5kD) | 4.9 | up | 0.00396 |
| AA406218 | 872 | EST | 4.88 | up | 0.02194 |
| AA482127 | 1333 | protein kinase related to *S. cerevisiae* STE20, effector for Cdc42Hs | 4.88 | up | 0.00017 |
| M79463 | 2401 | promyelocytic leukemia | 4.88 | up | 0.01821 |
| AA146619 | 312 | EST | 4.87 | up | 0.00863 |
| AA262477 | 608 | ribonuclease HI, large subunit | 4.87 | up | 0.00005 |
| AA121315 | 237 | KIAA1077 protein | 4.86 | up | 0.02438 |
| H38568 | 1918 | EST | 4.86 | up | 0.0003 |
| AA306121 | 729 | EST | 4.85 | up | 0.00381 |
| D51133 | 1676 | tubulin, beta, 4 | 4.84 | up | 0.02875 |

TABLE 6A-continued

Up in Metastatics vs Normal Sample Set 2

| Fragment Name | SEQ ID: | Known Gene Name | Fold Change | Direction | Pvalue |
|---|---|---|---|---|---|
| W02041 | 3465 | EST | 4.83 | up | 0.00158 |
| T55004 | 3145 | EST | 4.83 | up | 0.00156 |
| Z74616 | 3947 | collagen, type I, alpha 2 | 4.83 | up | 0.02364 |
| X17093 | 3713 | EST | 4.82 | up | 0.00176 |
| D51276 | 1678 | leukemia-associated phosphoprotein p18 (stathmin) | 4.81 | up | 0.00514 |
| M77349 | 2399 | transforming growth factor, beta-induced, 68kD | 4.81 | up | 0.00546 |
| AA425852 | 958 | EST | 4.8 | up | 0.03874 |
| R22565 | 2799 | EST | 4.8 | up | 0.0424 |
| M10098 | 2231 | EST | 4.79 | up | 0.00328 |
| D13413 | 1604 | heterogeneous nuclear ribonucleoprotein U (scaffold attachment factor A) | 4.79 | up | 0.00092 |
| H46486 | 1932 | nesca protein | 4.77 | up | 0.00421 |
| U51095 | 3381 | caudal type homeo box transcription factor 1 | 4.76 | up | 0.02664 |
| AA609786 | 1491 | nucleolar protein 1 (l20kD) | 4.75 | up | 0.00261 |
| AA251230 | 540 | EST | 4.75 | up | 0.00054 |
| AA459703 | 1222 | v-myc avian myelocytomatosis viral oncogene homolog | 4.75 | up | 0.02413 |
| AA131084 | 265 | procollagen-lysine, 2-oxoglutarate 5-dioxygenase 3 | 4.74 | up | 0.00427 |
| D50914 | 1673 | KIAA0124 protein | 4.74 | up | 0.00752 |
| T35341 | 3111 | EST | 4.73 | up | 0.00057 |
| AA253011 | 558 | KIAA0713 protein | 4.73 | up | 0.01944 |
| X74929 | 3789 | keratin 8 | 4.73 | up | 0.00018 |
| D25560 | 1634 | EST | 4.72 | up | 0.00661 |
| X62535 | 3753 | diacylglycerol kinase, alpha (80kD) | 4.72 | up | 0.00315 |
| X66899 | 3769 | Ewing sarcoma breakpoint region 1 | 4.72 | up | 0.00011 |
| X68688 | 3777 | zinc finger protein 33a (KOX 31) | 4.7 | up | 0.00062 |
| AB000584 | 1533 | prostate differentiation factor | 4.7 | up | 0.00071 |
| AA293719 | 720 | EST | 4.69 | up | 0.02181 |
| R39191 | 2833 | KIAA1020 protein | 4.69 | up | 0.00456 |
| AA598405 | 1424 | membrane interacting protein of RGS16 | 4.69 | up | 0.0122 |
| U12465 | 3299 | ribosomal protein L35 | 4.69 | up | 0.00001 |
| AA405715 | 862 | hypothetical protein | 4.68 | up | 0.00898 |
| AA131162 | 266 | EST | 4.68 | up | 0.00042 |
| U78525 | 3431 | eukaryotic translation initiation factor 3, subunit 9 (eta, 116kD) | 4.68 | up | 0.00132 |
| AA171939 | 368 | EST | 4.67 | up | 0.00104 |
| M10098 | 2231 | EST | 4.66 | up | 0.00405 |
| AA298786 | 727 | EST | 4.65 | up | 0.02821 |
| N93798 | 2737 | protein tyrosine phosphatase type IVA, member 3 | 4.65 | up | 0.00118 |
| R06254 | 2764 | tumor protein D52-like 2 | 4.64 | up | 0.00039 |
| L20591 | 2173 | annexin A3 | 4.64 | up | 0.00065 |
| U14969 | 3303 | ribosomal protein L28 | 4.63 | up | 0.00004 |
| AA482224 | 1334 | putative type II membrane protein | 4.62 | up | 0.0105 |
| T26471 | 3093 | EST | 4.62 | up | 0.01091 |
| R70005 | 2943 | EST | 4.61 | up | 0.00037 |
| HG3548-HT3749 | | cut (Drosophila)-like 1 (CCAAT displacement protein) | 4.61 | up | 0.00824 |
| H43646 | 1930 | H2A histone family, member Y | 4.6 | up | 0.00147 |
| AA455521 | 1178 | E2F transcription factor 5, p130-binding | 4.6 | up | 0.00773 |
| H05525 | 1846 | hypothetical protein | 4.6 | up | 0.0033 |
| S56151 | 3020 | milk fat globule-EGF factor 8 protein | 4.59 | up | 0.0091 |
| AA143493 | 310 | pleckstrin 2 (mouse) homolog | 4.58 | up | 0.01037 |
| F04444 | 1788 | EST | 4.57 | up | 0.01132 |
| AA412301 | 899 | EST | 4.57 | up | 0.00026 |
| D31417 | 1645 | secreted protein of unknown function | 4.56 | up | 0.00014 |
| AA025277 | 51 | EST | 4.56 | up | 0.03136 |
| AA478415 | 1299 | EST | 4.56 | up | 0.00095 |
| HG3364-HT3541 | | ribosomal protein L37 | 4.55 | up | 0.00005 |
| M24194 | 2302 | guanine nucleotide binding protein (G protein), beta polypeptide 2-like 1 | 4.55 | up | 0.00017 |
| AA261907 | 603 | DKFZP566E144 protein | 4.54 | up | 0.02289 |
| U04313 | 3283 | protease inhibitor 5 (maspin) | 4.54 | up | 0.02986 |
| AA287022 | 685 | thymidine kinase 1, soluble | 4.51 | up | 0.02582 |
| M34182 | 2340 | protein kinase, cAMP-dependent, catalytic, gamma | 4.51 | up | 0.00043 |
| D38548 | 1655 | KIAA0076 gene product | 4.5 | up | 0.00036 |
| X69150 | 3779 | ribosomal protein S18 | 4.5 | up | 0.00003 |
| AA262969 | 613 | ferritin, heavy polypeptide 1 | 4.49 | up | 0.00013 |
| M22960 | 2296 | protective protein for beta-galactosidase (galactosialidosis) | 4.49 | up | 0.00898 |
| AA094752 | 203 | hypothetical 43.2 Kd protein | 4.47 | up | 0.00243 |
| J04423 | 2109 | EST | 4.47 | up | 0.02754 |
| T98284 | 3267 | EST | 4.47 | up | 0.00054 |
| HG2873-HT3017 | | ribosomal protein L30 | 4.47 | up | 0.00009 |
| Z24727 | 3868 | tropomyosin 1 (alpha) | 4.47 | up | 0.00121 |
| U75285 | 3421 | apoptosis inhibitor 4 (survivin) | 4.46 | up | 0.02212 |
| M14483 | 2261 | prothymosin, alpha (gene sequence 28) | 4.46 | up | 0.00686 |
| J03827 | 2100 | nuclease sensitive element binding protein 1 | 4.45 | up | 0.00015 |
| X15940 | 3706 | ribosomal protein L31 | 4.45 | up | 0.00004 |
| N31597 | 2486 | DKFZP564G2022 protein | 4.44 | up | 0.00085 |
| N21359 | 2441 | EST | 4.43 | up | 0.00078 |
| Z26876 | 3871 | ribosomal protein L38 | 4.43 | up | 0.00022 |

TABLE 6A-continued

Up in Metastatics vs Normal Sample Set 2

| Fragment Name | SEQ ID: | Known Gene Name | Fold Change | Direction | Pvalue |
|---|---|---|---|---|---|
| N39099 | 2507 | EST | 4.42 | up | 0.00643 |
| N39254 | 2511 | EST | 4.42 | up | 0.00478 |
| T77733 | 3218 | tubulin, gamma 1 | 4.42 | up | 0.00049 |
| D31094 | 1639 | G8 protein | 4.41 | up | 0.04845 |
| AA482546 | 1336 | KIAA0124 protein | 4.41 | up | 0.00604 |
| N70903 | 2661 | EST | 4.41 | up | 0.0078 |
| AA070827 | 157 | EST | 4.41 | up | 0.01902 |
| Z25749 | 3869 | nuclear factor of kappa light polypeptide gene enhancer in B-cells inhibitor-like 2 | 4.41 | up | 0.00031 |
| N68921 | 2638 | EST | 4.4 | up | 0.00989 |
| T23465 | 3080 | EST | 4.4 | up | 0.017 |
| AA147084 | 314 | proliferation-associated 2G4, 38kD | 4.4 | up | 0.0045 |
| W52858 | 3542 | DKFZPS64F0522 protein | 4.38 | up | 0.00088 |
| R49395 | 2880 | EST | 4.38 | up | 0.00112 |
| D53139 | 1684 | ribosomal protein S28 | 4.38 | up | 0.0009 |
| H18412 | 1890 | isocitrate dehydrogenase 3 (NAD+) gamma | 4.37 | up | 0.00262 |
| U25789 | 3333 | ribosomal protein L21 | 4.37 | up | 0.00045 |
| J04423 | 2109 | EST | 4.35 | up | 0.01245 |
| AA236714 | 516 | nuclear mitotic apparatus protein 1 | 4.35 | up | 0.00083 |
| U90913 | 3458 | Tax interaction protein 1 | 4.35 | up | 0.00159 |
| L44538 | 2217 | EST | 4.34 | up | 0.04319 |
| L06499 | 2141 | ribosomal protein L37a | 4.34 | up | 0.01103 |
| M17886 | 2282 | ribosomal protein, large, P1 | 4.34 | up | 0.00044 |
| AA320369 | 735 | chromosome 19 open reading frame 3 | 4.33 | up | 0.00554 |
| AA598988 | 1442 | EST | 4.32 | up | 0.00044 |
| R26744 | 2803 | midline 1 (Opitz/BBB syndrome) | 4.32 | up | 0.00532 |
| W44557 | 3515 | chromosome 1 open reading frame 2 | 4.32 | up | 0.00128 |
| AA173430 | 371 | EST | 4.32 | up | 0.04362 |
| L34587 | 2200 | transcription elongation factor B (SIII), polypeptide 1 (15kD, elongin C) | 4.32 | up | 0.00287 |
| X06617 | 3684 | ribosomal protein S11 | 4.32 | up | 0.0002 |
| W93943 | 3654 | EST | 4.3 | up | 0.00296 |
| AA608579 | 1464 | paired-like homeodomain transcription factor 2 | 4.29 | up | 0.04435 |
| W60486 | 3555 | EST | 4.29 | up | 0.00964 |
| L11566 | 2156 | ribosomal protein L18 | 4.29 | up | 0.00014 |
| HG1980-HT2023 | | tubulin, beta polypeptide | 4.29 | up | 0.00408 |
| AA122386 | 239 | collagen, type V, alpha 2 | 4.28 | up | 0.005 |
| H38240 | 1916 | thrombospondin 2 | 4.28 | up | 0.0066 |
| X64707 | 3762 | ribosomal protein L13 | 4.28 | up | 0.00257 |
| Y10807 | 3857 | HMT1 (hnRNP methyltransferase, *S. cerevisiae*)-like 2 | 4.28 | up | 0.00124 |
| AA070206 | 155 | EST | 4.26 | up | 0.00018 |
| N89670 | 2708 | EST | 4.26 | up | 0.00002 |
| D63880 | 1715 | KIAA0159 gene product | 4.26 | up | 0.00253 |
| AA431719 | 1025 | EST | 4.25 | up | 0.00015 |
| Z40583 | 3919 | EST | 4.24 | up | 0.02375 |
| AA426447 | 965 | EST | 4.23 | up | 0.0309 |
| AA453477 | 1153 | X-prolyl aminopeptidase (aminopeptidase P)-Iike | 4.23 | up | 0.0001 |
| AA278817 | 618 | EST | 4.22 | up | 0.00061 |
| HG2239-HT2324 | | potassium voltage-gated channel, Shaw-related subfamily, member 3 | 4.22 | up | 0.0065 |
| AA033790 | 74 | apolipoprotein D | 4.21 | up | 0.03247 |
| N70678 | 2659 | TAR (HIV) RNA-binding protein 1 | 4.2 | up | 0.00119 |
| W45487 | 3521 | dynamin 2 | 4.2 | up | 0.00325 |
| L04483 | 2136 | ribosomal protein S21 | 4.2 | up | 0.00057 |
| AA132032 | 271 | trinucleotide repeat containing 1 | 4.19 | up | 0.00295 |
| AA282149 | 654 | huntingtin interacting protein-1-related | 4.19 | up | 0.00091 |
| R59352 | 2914 | KIAA0296 gene product | 4.19 | up | 0.00393 |
| D88154 | 1766 | villin-like | 4.18 | up | 0.00051 |
| D59322 | 1694 | EST | 4.18 | up | 0.00006 |
| U12404 | 3298 | ribosomal protein L10a | 4.18 | up | 0.00004 |
| S73885 | 3031 | transcription factor AP-4 (activating enhancer-binding protein 4) | 4.18 | up | 0.00005 |
| AA398205 | 789 | EST | 4.17 | up | 0.00004 |
| H09241 | 1861 | EST | 4.17 | up | 0.00727 |
| HG1800-HT1823 | | ribosomal protein S20 | 4.17 | up | 0.00001 |
| H27188 | 1908 | collagen-binding protein 2 (colligen 2) | 4.16 | up | 0.02073 |
| H56345 | 1950 | EST | 4.15 | up | 0.00488 |
| M17733 | 2280 | thymosin, beta 4, X chromosome | 4.15 | up | 0.00009 |
| U78027 | 3428 | EST | 4.15 | up | 0.00295 |
| AA482613 | 1338 | DKFZP434B203 protein | 4.14 | up | 0.00186 |
| F09788 | 1808 | procollagen-proline, 2-oxoglutarate 4-dioxygenase (proline 4-hydroxylase), alpha polypeptide II | 4.14 | up | 0.00003 |
| R44479 | 2854 | KIAA0552 gene product | 4.14 | up | 0.0181 |
| AA075722 | 166 | nuclear transport factor 2 (placental protein 15) | 4.14 | up | 0.00374 |
| U31556 | 3345 | E2F transcription factor 5, p130-binding | 4.14 | up | 0.01157 |
| AA263044 | 615 | H2A histone family, memberY | 4.13 | up | 0.00024 |
| AA256273 | 577 | EST | 4.13 | up | 0.03874 |
| AA443316 | 1075 | v-Ha-ras Harvey rat sarcoma viral oncogene homolog | 4.13 | up | 0.01729 |

TABLE 6A-continued

Up in Metastatics vs Normal Sample Set 2

| Fragment Name | SEQ ID: | Known Gene Name | Fold Change | Direction | Pvalue |
|---|---|---|---|---|---|
| X80822 | 3805 | ribosomal protein L18a | 4.13 | up | 0.0006 |
| AA224502 | 451 | EST | 4.12 | up | 0.00694 |
| AA461476 | 1243 | EST | 4.12 | up | 0.00871 |
| R31107 | 2811 | EST | 4.12 | up | 0.00003 |
| R43952 | 2852 | homeo box B5 | 4.11 | up | 0.04316 |
| R36947 | 2824 | calcium channel, voltage-dependent, beta 3 subunit | 4.11 | up | 0.00006 |
| T40849 | 3115 | maternal G10 transcript | 4.11 | up | 0.00449 |
| X14850 | 3703 | H2A histone family, member X | 4.11 | up | 0.0001 |
| AA026356 | 57 | EST | 4.1 | up | 0.00133 |
| D50663 | 1671 | t-complex-associated-testis-expressed 1-like 1 | 4.09 | up | 0.00208 |
| X03342 | 3672 | ribosomal protein L32 | 4.09 | up | 0.00008 |
| X62691 | 3754 | ribosomal protein S15a | 4.09 | up | 0.00005 |
| R38076 | 2827 | EST | 4.08 | up | 0.00374 |
| Z39079 | 3897 | KIAA1058 protein | 4.08 | up | 0.01781 |
| D57489 | 1689 | chaperonin containing TCP1, subunit 7 (eta) | 4.08 | up | 0.00001 |
| N50048 | 2541 | EST | 4.08 | up | 0.00085 |
| M87339 | 2414 | replication factor C (activator 1)4 (37kD) | 4.07 | up | 0.00316 |
| C14348 | 1568 | EST | 4.06 | up | 0.00111 |
| H05394 | 1845 | K1AA0266 gene product | 4.06 | up | 0.0015 |
| H97809 | 2063 | EST | 4.05 | up | 0.00111 |
| T47601 | 3125 | EST | 4.05 | up | 0.00878 |
| U62962 | 3403 | eukaryotic translation initiation factor 3, subunit 6 (48kD) | 4.05 | up | 0.0047 |
| T55196 | 3146 | EST | 4.04 | up | 0.00012 |
| AA431873 | 1028 | EST | 4.03 | up | 0.00785 |
| N66139 | 2614 | neurochondrin | 4.03 | up | 0.00118 |
| HG3214-HT3391 | | ribosomal protein S27 (metallopanstimulin 1) | 4.03 | up | 0.00238 |
| AA405460 | 857 | EST | 4.02 | up | 0.03492 |
| AA236533 | 514 | ecotropic viral integration site 1 | 4.01 | up | 0.02882 |
| T91116 | 3251 | EST | 4.01 | up | 0.02721 |
| AA034378 | 77 | endogenous retroviral protease | 4.01 | up | 0.00974 |
| D49400 | 1667 | ATPase, vacuolar, 14 kD | 4.01 | up | 0.00287 |
| M32405 | 2334 | ribosomal protein S15 | 4.01 | up | 0.00055 |
| U14968 | 3302 | ribosomal protein L27a | 4.01 | up | 0.00003 |
| W31382 | 3494 | EST | 4 | up | 0.00058 |
| D86956 | 1753 | heat shock 105kD | 4 | up | 0.03013 |
| X70040 | 3785 | macrophage stimulating 1 receptor (c-met-related tyrosine kinase) | 4 | up | 0.00402 |
| M13934 | 2255 | ribosomal protein S14 | 3.99 | up | 0 |
| H53657 | 1945 | adenylate cyclase 3 | 3.98 | up | 0.0045 |
| W28362 | 3487 | K1AA0974 protein | 3.98 | up | 0.00626 |
| W20391 | 3478 | kinesin-like 2 | 3.98 | up | 0.01788 |
| AA292931 | 715 | EST | 3.97 | up | 0.00067 |
| H13532 | 1881 | ribosomal protein L18a | 3.97 | up | 0.00061 |
| T66935 | 3178 | EST | 3.97 | up | 0.00188 |
| L03411 | 2134 | RD RNA-binding protein | 3.97 | up | 0.00422 |
| AA291456 | 700 | EST | 3.96 | up | 0.03633 |
| AA496245 | 1398 | EST | 3.96 | up | 0.0039 |
| U85773 | 3448 | phosphomannomutase 2 | 3.94 | up | 0.00288 |
| F09297 | 1800 | EST | 3.94 | up | 0.0016 |
| H93492 | 2037 | EST | 3.94 | up | 0.01136 |
| U53830 | 3390 | interferon regulatory factor 7 | 3.94 | up | 0.03147 |
| 82348 | 1744 | 5-aminoimidazole-4-carboxamide ribonucleotide formyltransferase/IMP cyclohydrolase | 3.93 | up | 0.00037 |
| U14971 | 3305 | ribosomal protein S9 | 3.93 | up | 0.00026 |
| X52966 | 3723 | ribosomal protein L35a | 3.93 | up | 0.00217 |
| AF004709 | 1547 | mitogen-activated protein kinase 13 | 3.92 | up | 0.0009 |
| D87735 | 1764 | ribosomal protein L14 | 3.92 | up | 0.00015 |
| M17885 | 2281 | ribosomal protein, large, P0 | 3.92 | up | 0.00003 |
| D63391 | 1710 | platelet-activating factor acetyihydrolase, isoform Ib, gamma subunit (29kD) | 3.91 | up | 0.00062 |
| X77588 | 3796 | N-acetyltransferase, homolog of S. cerevisiae ARD1 | 3.91 | up | 0.0221 |
| M29277 | 2316 | melanoma adhesion molecule | 3.91 | up | 0.00112 |
| C14412 | 1569 | HSPC038 protein | 3.9 | up | 0.00036 |
| AA215468 | 441 | ADP-ribosylation factor-related protein 1 | 3.9 | up | 0.04549 |
| H29565 | 1913 | EST | 3.89 | up | 0.01856 |
| AA234362 | 481 | EST | 3.89 | up | 0.03524 |
| X51521 | 3718 | villin 2 (ezrin) | 3.89 | up | 0.00001 |
| AA253330 | 562 | adaptor-related protein complex 1, gamma 1 subunit | 3.87 | up | 0.00708 |
| AA191708 | 400 | EST | 3.87 | up | 0.01904 |
| N91023 | 2715 | EST | 3.87 | up | 0.00008 |
| N98758 | 2744 | EST | 3.87 | up | 0.0074 |
| L40379 | 2210 | thyroid receptor interacting protein 10 (CDC42-interacting protein) | 3.87 | up | 0.00207 |
| N92775 | 2722 | amyloid beta (A4) precursor protein-binding, family A, member 3 (X11-like 2) | 3.86 | up | 0.00577 |
| AA187938 | 391 | EST | 3.86 | up | 0.00512 |
| Z30643 | 3876 | chloride channel Ka | 3.86 | up | 0.00204 |
| C21248 | 1585 | pituitary tumor-transforming I | 3.85 | up | 0.00456 |
| D86974 | 1756 | K1AA0220 protein | 3.85 | up | 0.0161 |

TABLE 6A-continued

Up in Metastatics vs Normal Sample Set 2

| Fragment Name | SEQ ID: | Known Gene Name | Fold Change | Direction | Pvalue |
|---|---|---|---|---|---|
| HG821-HT821 | | ribosomal protein S13 | 3.84 | up | 0.00003 |
| X80909 | 3806 | nascent-polypeptide-associated complex alpha polypeptide | 3.84 | up | 0.00399 |
| W76097 | 3596 | EST | 3.83 | up | 0.00001 |
| AA291659 | 702 | EST | 3.83 | up | 0.01934 |
| W80763 | 3605 | EST | 3.83 | up | 0.01319 |
| AA026092 | 54 | EST | 3.83 | up | 0.04596 |
| AA411685 | 890 | EST | 3.83 | up | 0.00417 |
| Z41103 | 3926 | trinucleotide repeat containing 15 | 3.83 | up | 0.00444 |
| AA455522 | 1179 | EST | 3.83 | up | 0.00017 |
| D21063 | 1628 | minichromosome maintenance deficient (*S. cerevisiae*) 2 (mitotin) | 3.83 | up | 0.00983 |
| D42085 | 1658 | KIAA0095 gene product | 3.83 | up | 0.00036 |
| HG3039-HT3200 | | ADP-ribosylation factor 1 | 3.83 | up | 0.00077 |
| L33075 | 2195 | IQ motif containing GTPase activating protein 1 | 3.83 | up | 0.00015 |
| M77232 | 2398 | ribosomal protein S6 | 3.82 | up | 0.00045 |
| R56678 | 2907 | EST | 3.81 | up | 0.02242 |
| AA621277 | 1520 | EST | 3.81 | up | 0.00194 |
| AA437387 | 1064 | EST | 3.81 | up | 0.01478 |
| N49738 | 2538 | EST | 3.81 | up | 0.02479 |
| AA504264 | 1410 | EST | 3.81 | up | 0.00684 |
| U53347 | 3388 | solute carrier family 1 (neutral amino acid transporter), member 5 | 3.81 | up | 0.00273 |
| X55954 | 3733 | ribosomal protein L23 | 3.81 | up | 0.00025 |
| D54296 | 1685 | KIAA0255 gene product | 3.8 | up | 0.01059 |
| M30496 | 2324 | ubiquitin carboxyl-terminal esterase L3 (ubiquitin thiolesterase) | 3.8 | up | 0.00478 |
| U11861 | 3297 | maternal G10 transcript | 3.8 | up | 0.00001 |
| N27186 | 2469 | EST | 3.79 | up | 0.00112 |
| H49637 | 1940 | EST | 3.79 | up | 0.01092 |
| M18000 | 2283 | ribosomal protein S17 | 3.79 | up | 0.00004 |
| U09564 | 3294 | SFRS protein kinase 1 | 3.79 | up | 0.00765 |
| F09684 | 1805 | EST | 3.78 | up | 0.00277 |
| AA128407 | 259 | EST | 3.78 | up | 0.01081 |
| R28636 | 2808 | UDP-Gal:betaGlcNAc beta 1,4- galactosyltransferase, polypeptide 3 | 3.78 | up | 0.00765 |
| L12350 | 2160 | thrombospondin 2 | 3.78 | up | 0.00061 |
| N93105 | 2727 | EST | 3.77 | up | 0.02195 |
| HG3945-HT4215 | | phospholipid transfer protein | 3.77 | up | 0.03169 |
| AA131894 | 269 | EST | 3.76 | up | 0.00384 |
| T48195 | 3130 | eukaryotic translation initiation factor 3, subunit 3 (gamma, 40kD) | 3.75 | up | 0.00012 |
| N68038 | 2631 | phorbolin (similar to apolipoprotein B mRNA editing protein) | 3.75 | up | 0.01041 |
| AA437368 | 1063 | EST | 3.75 | up | 0.01317 |
| M15205 | 2265 | thymidine kinase 1, soluble | 3.75 | up | 0.00159 |
| AA620995 | 1512 | EST | 3.74 | up | 0.03414 |
| M10098 | 2231 | EST | 3.73 | up | 0.01794 |
| AA113303 | 227 | transmembrane 4 superfamily member (tetraspan NET-7) | 3.73 | up | 0.00084 |
| X69908 | 3783 | ATP synthase, H +transporting, mitochondrial F0 complex, subunit c (subunit 9), isoform 2 | 3.73 | up | 0.00685 |
| AA179298 | 378 | stomatin-like protein 2 | 3.72 | up | 0.00299 |
| M96739 | 2433 | nescient helix loop helix 1 | 3.72 | up | 0.00015 |
| X55715 | 3732 | ribosomal protein S3 | 3.72 | up | 0.00755 |
| AA436027 | 1050 | EST | 3.71 | up | 0.03676 |
| H04799 | 1841 | EST | 3.71 | up | 0.04109 |
| Z40898 | 3922 | EST | 3.71 | up | 0.01168 |
| AA025166 | 50 | fusion, derived from t(12;16) malignant liposarcoma | 3.71 | up | 0.0052 |
| AA150053 | 327 | EST | 3.71 | up | 0.00102 |
| AA490212 | 1375 | H2A histone family, member Y | 3.71 | up | 0.01226 |
| AA307748 | 730 | EST | 3.7 | up | 0.00001 |
| N29888 | 2482 | EST | 3.7 | up | 0.00226 |
| AA034499 | 78 | zinc finger protein 198 | 3.7 | up | 0.02143 |
| D14657 | 1615 | KIAA0101 gene product | 3.7 | up | 0.04079 |
| L38696 | 2208 | RNA-binding protein (autoantigenic) | 3.7 | up | 0.00093 |
| AA416963 | 911 | EST | 3.69 | up | 0.03956 |
| AA496204 | 1397 | EST | 3.69 | up | 0.01097 |
| AA435526 | 1037 | transferrin receptor (p90, CD71) | 3.69 | up | 0.00139 |
| AA126459 | 248 | DKFZP566B023 protein | 3.69 | up | 0.00352 |
| H78323 | 2002 | transcription factor Dp-1 | 3.69 | up | 0.00326 |
| W73189 | 3586 | EphB2 | 3.68 | up | 0.02909 |
| AA029356 | 66 | EST | 3.68 | up | 0.01545 |
| C14051 | 1565 | phosphoprotein enriched in astrocytes 15 | 3.68 | up | 0.01453 |
| R38280 | 2830 | BCS1 (yeast homolog)-like | 3.68 | up | 0.0009 |
| X66401 | 3768 | proteasome (prosome, macropain) subunit, beta type, 9 (large multifunctional protease 2) | 3.68 | up | 0.01385 |
| X69398 | 3781 | CD47 antigen (Rh-related antigen, integrin-associated signal transducer) | 3.68 | up | 0.02332 |
| AA429470 | 996 | EST | 3.67 | up | 0.00782 |
| L25081 | 2180 | ras homolog gene family, member C | 3.67 | up | 0.00005 |
| M23613 | 2301 | nucleophosmin (nucleolar phosphoprotein B23, numatrin) | 3.67 | up | 0.00977 |
| AA328993 | 738 | EST | 3.66 | up | 0.00146 |
| W39183 | 3505 | KIAA0601 protein | 3.66 | up | 0.00018 |

TABLE 6A-continued

Up in Metastatics vs Normal Sample Set 2

| Fragment Name | SEQ ID: | Known Gene Name | Fold Change | Direction | Pvalue |
|---|---|---|---|---|---|
| AA211851 | 436 | EST | 3.66 | up | 0.00789 |
| X53331 | 3724 | matrix Gla protein | 3.66 | up | 0.04038 |
| AA621780 | 1530 | CGI-96 protein | 3.65 | up | 0.01582 |
| AA449122 | 1119 | EST | 3.65 | up | 0.00369 |
| W70336 | 3576 | EST | 3.65 | up | 0.01776 |
| AA029215 | 64 | adaptor-related protein complex 2, beta 1 subunit | 3.65 | up | 0.00037 |
| N27334 | 2470 | EST | 3.65 | up | 0.03437 |
| U37689 | 3355 | polymerase (RNA) II (DNA directed) polypeptide H | 3.65 | up | 0.00044 |
| D38073 | 1651 | minichromosome maintenance deficient (*S. cerevisiae*) 3 | 3.65 | up | 0.01869 |
| R49216 | 2879 | EST | 3.64 | up | 0.0004 |
| R87989 | 2978 | centrosome associated protein | 3.64 | up | 0.00008 |
| AA135407 | 292 | endogenous retroviral protease | 3.64 | up | 0.01086 |
| AA148977 | 322 | EST | 3.64 | up | 0.02911 |
| D63874 | 1714 | high-mobility group (nonhistone chromosomal) protein 1 | 3.64 | up | 0.00228 |
| AA454597 | 1166 | EST | 3.63 | up | 0.0067 |
| F04320 | 1786 | replication factor C (activator 1) 4 (37 kD) | 3.63 | up | 0.01119 |
| X68688 | 3777 | zinc finger protein 33a (KOX 31) | 3.62 | up | 0.00319 |
| R27432 | 2807 | EST | 3.62 | up | 0.00014 |
| AA401958 | 832 | EST | 3.62 | up | 0.01232 |
| HG2279-HT2375 | | triosephosphate isomerase 1 | 3.62 | up | 0.00192 |
| AA416973 | 913 | EST | 3.61 | up | 0.0091 |
| N62675 | 2593 | DEAD/H (Asp-Glu-Ala-Asp/His) box polypeptide 16 | 3.61 | up | 0.04034 |
| T15477 | 3058 | EST | 3.61 | up | 0.00005 |
| AA460017 | 1225 | EST | 3.61 | up | 0.00109 |
| D43950 | 1660 | chaperonin containing TCP1, subunit 5 (epsilon) | 3.61 | up | 0.00672 |
| N99505 | 2745 | EST | 3.6 | up | 0.04499 |
| AA443271 | 1073 | KIAA0546 protein | 3.6 | up | 0.01228 |
| N89937 | 2710 | LIM domain only 7 | 3.6 | up | 0.01375 |
| R71082 | 2950 | programmed cell death 5 | 3.6 | up | 0.01338 |
| AA412720 | 905 | EST | 3.6 | up | 0.01396 |
| X17567 | 3716 | small nuclear ribonucleoprotein polypeptides B and B1 | 3.59 | up | 0.00586 |
| AA399226 | 803 | tight junction protein 3 (zona occludens 3) | 3.59 | up | 0.02002 |
| R55470 | 2903 | EST | 3.59 | up | 0.00515 |
| X79234 | 3800 | ribosomal protein L11 | 3.58 | up | 0.00051 |
| D80917 | 1736 | KIAA0670 protein/acinus | 3.58 | up | 0.00007 |
| W81375 | 3610 | EST | 3.58 | up | 0.00322 |
| U89606 | 3451 | pyridoxal (pyridoxine, vitamin B6) kinase | 3.58 | up | 0.00322 |
| X05610 | 3682 | collagen, type IV, alpha 2 | 3.57 | up | 0.01351 |
| AA443941 | 1085 | tumor suppressing subtransferable candidate 1 | 3.57 | up | 0.01685 |
| N56935 | 2574 | EST | 3.57 | up | 0.00282 |
| N68385 | 2634 | ribosomal protein L13a | 3.57 | up | 0.00417 |
| R49084 | 2878 | KIAA0770 protein | 3.57 | up | 0.00447 |
| U83246 | 3442 | copine I | 3.56 | up | 0.01672 |
| AA182001 | 386 | EST | 3.56 | up | 0.00945 |
| N51342 | 2544 | EST | 3.56 | up | 0.0001 |
| W42627 | 3508 | EST | 3.56 | up | 0.00198 |
| X66364 | 3767 | cyclin-dependent kinase 5 | 3.55 | up | 0.02824 |
| AA451680 | 1136 | hepatocellular carcinoma associated protein; breast cancer associated gene 1 | 3.55 | up | 0.00708 |
| Z38909 | 3894 | EST | 3.55 | up | 0.03195 |
| T48293 | 3132 | EST | 3.55 | up | 0.01355 |
| W37680 | 3502 | EST | 3.55 | up | 0.01036 |
| AA252994 | 557 | apoptosis inhibitor 4 (survivin) | 3.55 | up | 0.00075 |
| AA134052 | 285 | Rab geranylgeranyltransferase, alpha subunit | 3.54 | up | 0.03062 |
| AA504806 | 1416 | EST | 3.54 | up | 0.00221 |
| T12599 | 3055 | ribosomal protein L21 | 3.54 | up | 0.01437 |
| L19527 | 2169 | ribosomal protein L27 | 3.54 | up | 0.00025 |
| U17760 | 3314 | laminin, beta 3 (nicein (125 kD), kalinin (140 kD), BM600 (125 kD)) | 3.54 | up | 0.01853 |
| AA056361 | 140 | integral membrane protein 2C | 3.53 | up | 0.02983 |
| H55437 | 1948 | kraken-like | 3.53 | up | 0.02344 |
| C14098 | 1566 | EST | 3.53 | up | 0.04401 |
| H98924 | 2072 | chromatin assembly factor 1, subunit A (p150) | 3.53 | up | 0.02106 |
| AA094517 | 202 | EST | 3.52 | up | 0.04805 |
| AA237017 | 521 | KIAA1068 protein | 3.52 | up | 0.00976 |
| T58607 | 3154 | EST | 3.52 | up | 0.04102 |
| AA028103 | 61 | EST | 3.52 | up | 0.01142 |
| M136547 | 302 | EST | 3.51 | up | 0.00308 |
| AA151182 | 332 | EST | 3.51 | up | 0.00043 |
| AA400271 | 814 | EST | 3.51 | up | 0.00742 |
| U93868 | 3462 | polymerase (RNA) III (DNA directed) (32 kD) | 3.5 | up | 0.01235 |
| W73914 | 3592 | EST | 3.5 | up | 0.04782 |
| AA482007 | 1331 | EST | 3.49 | up | 0.00167 |
| AA452259 | 1143 | EST | 3.49 | up | 0.00114 |
| HG3549-HT3549 | | ribosomal protein L10 | 3.49 | up | 0 |
| U79266 | 3433 | protein predicted by clone 23627 | 3.49 | up | 0.00004 |
| X07820 | 3692 | matrix metalloproteinase 10 (stromelysin 2) | 3.49 | up | 0.00689 |

TABLE 6A-continued

Up in Metastatics vs Normal Sample Set 2

| Fragment Name | SEQ ID: | Known Gene Name | Fold Change | Direction | Pvalue |
|---|---|---|---|---|---|
| H08863 | 1859 | hypothetical protein | 3.48 | up | 0.00205 |
| AA292659 | 710 | EST | 3.48 | up | 0.00037 |
| AA432162 | 1029 | DKFZP586B2022 protein | 3.48 | up | 0.03851 |
| T92935 | 3254 | EST | 3.48 | up | 0.03578 |
| X67247 | 3771 | mitogen-activated protein kinase kinase kinase kinase 3 | 3.48 | up | 0.00012 |
| AA426521 | 967 | Sjogren's syndrome nuclear autoantigen 1 | 3.47 | up | 0.01161 |
| AA489707 | 1371 | EST | 3.47 | up | 0.03433 |
| AA609008 | 1475 | EST | 3.46 | up | 0.02935 |
| L36720 | 2205 | bystin-like | 3.46 | up | 0.00094 |
| D21261 | 1629 | transgelin 2 | 3.46 | up | 0.00685 |
| AA446968 | 1097 | EST | 3.45 | up | 0.02232 |
| AA459310 | 1214 | EST | 3.45 | up | 0.00179 |
| N30436 | 2483 | EST | 3.45 | up | 0.02356 |
| AA410962 | 887 | peroxisome proliferative activated receptor, delta | 3.45 | up | 0.04574 |
| F02800 | 1780 | EST | 3.45 | up | 0.03238 |
| U14970 | 3304 | ribosomal protein S5 | 3.45 | up | 0.00915 |
| U26726 | 3335 | hydroxysteroid (11-beta) dehydrogenase 2 | 3.45 | up | 0.02342 |
| H17476 | 1889 | EST | 3.44 | up | 0.00479 |
| D19737 | 1623 | golgi autoantigen, golgin subfamily a, 3 | 3.44 | up | 0.02212 |
| U76366 | 3423 | Treacher Collins-Franceschetti syndrome 1 | 3.44 | up | 0.00021 |
| L40904 | 2212 | peroxisome proliferative activated receptor, gamma | 3.43 | up | 0.03511 |
| AA427442 | 971 | guanine nucleotide regulatory factor | 3.43 | up | 0.01547 |
| R77631 | 2966 | EST | 3.43 | up | 0.00006 |
| AA398761 | 799 | EST | 3.43 | up | 0.00726 |
| D80662 | 1733 | adaptor-related protein complex 1, gamma 2 subunit | 3.43 | up | 0.00108 |
| M77836 | 2400 | pyrroline-5-carboxylate reductase 1 | 3.43 | up | 0.00759 |
| T78922 | 3221 | stem cell growth factor; lymphocyte secreted C-type lectin | 3.42 | up | 0.02419 |
| N51053 | 2542 | eukaryotic translation initiation factor 5 | 3.42 | up | 0.01326 |
| AA134158 | 287 | EST | 3.42 | up | 0.0277 |
| AA454710 | 1168 | EST | 3.42 | up | 0.00653 |
| AA446949 | 1096 | EST | 3.41 | up | 0.03411 |
| AA164252 | 358 | VGF nerve growth factor inducible | 3.41 | up | 0.00154 |
| T59161 | 3158 | thymosin, beta 10 | 3.41 | up | 0.01885 |
| T35725 | 3112 | EST | 3.4 | up | 0.00149 |
| M60854 | 2367 | ribosomal protein S16 | 3.4 | up | 0.00001 |
| AA135871 | 294 | EST | 3.39 | up | 0.01544 |
| AA599244 | 1448 | KIAA0530 protein | 3.39 | up | 0.01246 |
| D25274 | 1632 | EST | 3.39 | up | 0.00238 |
| U33286 | 3348 | chromosome segregation 1 (yeast homolog)-like | 3.39 | up | 0.00939 |
| AA384184 | 774 | DKFZP586B0519 protein | 3.38 | up | 0.01209 |
| H04753 | 1839 | EST | 3.38 | up | 0.02447 |
| AA422049 | 937 | EST | 3.38 | up | 0.0067 |
| AA233886 | 475 | D site of albumin promoter (albumin D-box) binding protein | 3.38 | up | 0.0218 |
| U86409 | 3449 | EST | 3.38 | up | 0.00003 |
| X52851 | 3722 | EST | 3.38 | up | 0.0001 |
| U84720 | 3445 | RAE1 (RNA export 1, S.pombe) homolog | 3.37 | up | 0.03586 |
| M31520 | 2328 | ribosomal protein S24 | 3.37 | up | 0.00077 |
| AA458890 | 1206 | EST | 3.36 | up | 0.00303 |
| AA504413 | 1413 | EST | 3.35 | up | 0.00079 |
| AA001409 | 1 | EST | 3.35 | up | 0.04092 |
| AA251909 | 549 | EST | 3.35 | up | 0.03937 |
| AA461473 | 1242 | nebulette | 3.35 | up | 0.03855 |
| J04823 | 2115 | cytochrome c oxidase subunit VIII | 3.35 | up | 0.00075 |
| M26708 | 2311 | prothymosin, alpha (gene sequence 28) | 3.35 | up | 0.00064 |
| AA370163 | 766 | EST | 3.34 | up | 0.00643 |
| AA149889 | 326 | neighbor of A-kinase anchoring protein 95 | 3.34 | up | 0.02054 |
| U22376 | 3327 | v-myb avian myeloblastosis viral oncogene homolog | 3.34 | up | 0.03416 |
| C00021 | 1551 | stress-associated endoplasmic reticulum protein 1; ribosome associated membrane protein 4 | 3.33 | up | 0.00215 |
| AA156450 | 342 | EST | 3.33 | up | 0.00587 |
| AA338729 | 743 | EST | 3.33 | up | 0.00046 |
| D83783 | 1748 | trinucleotide repeat containing 11 (THR-associated protein, 230 kDa subunit) | 3.33 | up | 0.00748 |
| HG4542-HT4947 | | ribosomal protein L15 | 3.33 | up | 0.00023 |
| AA427825 | 981 | EST | 3.33 | up | 0.01615 |
| D43949 | 1659 | KIAA0082 protein | 3.32 | up | 0.0014 |
| D50913 | 1672 | KIAA0123 protein | 3.32 | up | 0.01202 |
| AA478599 | 1304 | G protein-coupled receptor 56 | 3.31 | up | 0.00182 |
| H93021 | 2033 | peptidylprolyl isomerase A (cyclophilin A) | 3.31 | up | 0.0183 |
| R53109 | 2898 | dimethylarginine dimethylaminohydrolase 2 | 3.31 | up | 0.02389 |
| AA132983 | 274 | DKFZP586G1517 protein | 3.31 | up | 0.01155 |
| H93652 | 2039 | ribosomal protein S5 | 3.31 | up | 0.00788 |
| T33508 | 3105 | phosphatidylinositol-4-phosphate 5-kinase, type II, beta | 3.31 | up | 0.00416 |
| M33197 | 2337 | glyceraldehyde-3-phosphate dehydrogenase | 3.31 | up | 0.00009 |
| H59617 | 1964 | EST | 3.3 | up | 0.04588 |
| D51287 | 1680 | ribosomal protein S12 | 3.3 | up | 0.02829 |

TABLE 6A-continued

Up in Metastatics vs Normal Sample Set 2

| Fragment Name | SEQ ID: | Known Gene Name | Fold Change | Direction | Pvalue |
|---|---|---|---|---|---|
| L20941 | 2174 | ferritin, heavy polypeptide 1 | 3.3 | up | 0.01172 |
| M91083 | 2418 | chromosome 11 open reading frame 13 | 3.3 | up | 0.00163 |
| Z68228 | 3944 | junction plakoglobin | 3.3 | up | 0.0237 |
| R73565 | 2958 | EST | 3.29 | up | 0.03489 |
| Z39200 | 3899 | EST | 3.29 | up | 0.00586 |
| AA084921 | 182 | ribosomal protein S10 | 3.29 | up | 0.04872 |
| T59668 | 3159 | lysyl oxidase | 3.28 | up | 0.00588 |
| AA280928 | 642 | EST | 3.27 | up | 0.04625 |
| AA397916 | 784 | EST | 3.27 | up | 0.02895 |
| D20464 | 1625 | bromodomain adjacent to zinc finger domain, 2B | 3.27 | up | 0.04897 |
| N73846 | 2679 | EST | 3.27 | up | 0.00012 |
| O80237 | 1729 | actin related protein 2/3 complex, subunit 4 (20 kD) | 3.27 | up | 0.00137 |
| T47032 | 3123 | partner of RAC1 (arfaptin 2) | 3.27 | up | 0.00503 |
| AA218663 | 444 | acid-inducible phosphoprotein | 3.26 | up | 0.03537 |
| T25725 | 3090 | EST | 3.26 | up | 0.00099 |
| X56932 | 3737 | ribosomal protein L13a | 3.26 | up | 0 |
| AA040465 | 95 | EST | 3.25 | up | 0.00146 |
| N62819 | 2594 | EST | 3.25 | up | 0.01137 |
| X51466 | 3717 | eukaryotic translation elongation factor 2 | 3.25 | up | 0.00019 |
| AA459961 | 1223 | EST | 3.24 | up | 0.00316 |
| AA488987 | 1365 | synaptogyrin 2 | 3.24 | up | 0.01444 |
| F01568 | 1772 | EST | 3.24 | up | 0.0018 |
| AA431776 | 1027 | EST | 3.24 | up | 0.01814 |
| AA464698 | 1262 | EST | 3.24 | up | 0.04854 |
| R54614 | 2901 | EST | 3.24 | up | 0.00526 |
| L76200 | 2223 | guanylate kinase 1 | 3.24 | up | 0.0097 |
| AA126429 | 247 | peroxisomal farnesylated protein | 3.23 | up | 0.00478 |
| AA405310 | 856 | EST | 3.23 | up | 0.00138 |
| AA427925 | 982 | EST | 3.23 | up | 0.01806 |
| AA133590 | 282 | EST | 3.23 | up | 0.03565 |
| H42321 | 1928 | ribosomal protein L18a | 3.23 | up | 0.01102 |
| T15903 | 3062 | EST | 3.23 | up | 0.01377 |
| AA127851 | 257 | EST | 3.23 | up | 0.01943 |
| R53109 | 2898 | dimethylarginine dimethylaminohydrolase 2 | 3.22 | up | 0.00724 |
| AA027946 | 60 | EST | 3.22 | up | 0.00098 |
| AA425401 | 954 | serine/threonine kinase 24 (Ste20, yeast homolog) | 3.22 | up | 0.00625 |
| AA449458 | 1127 | EST | 3.22 | up | 0.03098 |
| D60811 | 1704 | EST | 3.22 | up | 0.0098 |
| H96975 | 2057 | EST | 3.22 | up | 0.0141 |
| D23660 | 1630 | ribosomal protein L4 | 3.22 | up | 0.00316 |
| HG613-HT613 | | ribosomal protein S12 | 3.22 | up | 0.00761 |
| U01147 | 3274 | active BCR-related gene | 3.22 | up | 0.00103 |
| R26706 | 2802 | EST | 3.21 | up | 0.03858 |
| F02863 | 1782 | EST | 3.21 | up | 0.01039 |
| AA406385 | 876 | DKFZP564B0769 protein | 3.21 | up | 0.00724 |
| D78676 | 1719 | EST | 3.2 | up | 0.00635 |
| AA447732 | 1105 | EST | 3.2 | up | 0.00591 |
| AA458852 | 1203 | KIAA0440 protein | 3.2 | up | 0.00038 |
| AA397906 | 782 | DKFZP4341216 protein | 3.2 | up | 0.00138 |
| AA504111 | 1409 | EST | 3.2 | up | 0.00544 |
| U90549 | 3455 | high-mobility group (nonhistone chromosomal) protein 17-like 3 | 3.2 | up | 0.0401 |
| X13956 | 3698 | EST | 3.2 | up | 0.00321 |
| AA608965 | 1474 | Hermansky-Pudlak syndrome | 3.19 | up | 0.00204 |
| U62392 | 3402 | zinc finger protein 193 | 3.18 | up | 0.00269 |
| N58463 | 2579 | PCTAIRE protein kinase 1 | 3.18 | up | 0.00649 |
| AA436616 | 1056 | EST | 3.18 | up | 0.04402 |
| U40990 | 3358 | potassium voltage-gated channel, KQT-like subfamily, member 1 | 3.18 | up | 0.00093 |
| X56997 | 3738 | ubiquitin A-52 residue ribosomal protein fusion product 1 | 3.18 | up | 0.00006 |
| X69391 | 3780 | ribosomal protein L6 | 3.18 | up | 0.00003 |
| X78687 | 3797 | sialidase 1 (lysosomal sialidase) | 3.18 | up | 0.031 |
| X95404 | 3831 | cofilin 1 (non-muscle) | 3.18 | up | 0.00104 |
| AA258482 | 596 | zinc finger protein | 3.17 | up | 0.04606 |
| AA169837 | 364 | NADH dehydrogenase (ubiquinone) Fe-S protein 6 (13kD) (NADH-coenzyme Q reductase) | 3.17 | up | 0.03038 |
| AA479945 | 1319 | plakophilin 3 | 3.17 | up | 0.01767 |
| AA598506 | 1430 | KIAA0179 protein | 3.17 | up | 0.01694 |
| T26574 | 3095 | catenin (cadherin-associated protein), delta 1 | 3.17 | up | 0.00828 |
| D25216 | 1631 | KIAA0014 gene product | 3.17 | up | 0.02125 |
| D25328 | 1633 | phosphofructokinase, platelet | 3.17 | up | 0.04925 |
| X63527 | 3758 | ribosomal protein L19 | 3.17 | up | 0.02488 |
| M64716 | 2382 | ribosomal protein S25 | 3.16 | up | 0.00039 |
| HG1112-HT1112 | | EST | 3.15 | up | 0.04958 |
| HG2147-HT2217 | | mucin 3, intestinal | 3.15 | up | 0.0026 |
| D78361 | 1718 | EST | 3.14 | up | 0.00023 |
| Z38729 | 3891 | EST | 3.13 | up | 0.04514 |

TABLE 6A-continued

Up in Metastatics vs Normal Sample Set 2

| Fragment Name | SEQ ID: | Known Gene Name | Fold Change | Direction | Pvalue |
|---|---|---|---|---|---|
| AA192755 | 401 | EST | 3.13 | up | 0.00442 |
| AA194237 | 408 | EST | 3.13 | up | 0.00212 |
| M31520 | 2328 | ribosomal protein S24 | 3.13 | up | 0.00014 |
| AA410972 | 888 | EST | 3.12 | up | 0.00023 |
| D52632 | 1683 | ribosomal protein S6 | 3.12 | up | 0.00498 |
| HG2724-HT2820 | | DNA-damage-inducible transcript 3 | 3.12 | up | 0.03726 |
| X92518 | 3822 | high-mobility group (nonhistone chromosomal) protein isoform I-C | 3.12 | up | 0.00638 |
| AA402937 | 843 | EST | 3.11 | up | 0.00182 |
| N64616 | 2610 | EST | 3.11 | up | 0.0074 |
| H28333 | 1912 | melanoma adhesion molecule | 3.11 | up | 0.00172 |
| M14949 | 2264 | related RAS viral (r-ras) oncogene homolog | 3.11 | up | 0.00013 |
| U43901 | 3361 | laminin receptor 1 (67 kD, ribosomal protein SA) | 3.11 | up | 0.03145 |
| HG2815-HT2931 | | myosin, light polypeptide 6, alkali, smooth muscle and non-muscle | 3.11 | up | 0.00475 |
| X69654 | 3782 | ribosomal protein S26 | 3.11 | up | 0.02683 |
| AA402968 | 844 | EST | 3.1 | up | 0.00453 |
| N67205 | 2624 | EST | 3.1 | up | 0.00626 |
| N92915 | 2723 | brefeldin A-inhibited guanine nucleotide-exchange protein 1 | 3.1 | up | 0.00807 |
| D14530 | 1614 | ribosomal protein S23 | 3.1 | up | 0.00331 |
| M68864 | 2389 | ORF | 3.1 | up | 0.00603 |
| U14973 | 3307 | ribosomal protein S29 | 3.1 | up | 0.00028 |
| M36072 | 2347 | ribosomal protein L7a | 3.1 | up | 0.00006 |
| AA449479 | 1129 | EST | 3.09 | up | 0.03495 |
| D59847 | 1701 | EST | 3.09 | up | 0.02206 |
| AA194724 | 409 | endonuclease G | 3.09 | up | 0.04011 |
| AA412403 | 900 | EST | 3.09 | up | 0.00047 |
| U05875 | 3285 | interferon gamma receptor 2 (interferon gamma transducer 1) | 3.09 | up | 0.00549 |
| X80822 | 3805 | ribosomal protein L18a | 3.08 | up | 0.02481 |
| T58153 | 3153 | heatshock 105kD | 3.08 | up | 0.01317 |
| HG4319-HT4589 | | ribosomal protein L5 | 3.08 | up | 0.0017 |
| U67171 | 3408 | selenoprotein W, 1 | 3.08 | up | 0.0047 |
| L12711 | 2161 | transketolase (Wernicke-Korsakoff syndrome) | 3.08 | up | 0.03362 |
| N70577 | 2658 | EST | 3.07 | up | 0.01975 |
| Z39930 | 3911 | EST | 3.07 | up | 0.00002 |
| AA158795 | 352 | EST | 3.07 | up | 0.00057 |
| W37937 | | EST | 3.07 | up | 0.00776 |
| D79205 | 1721 | ribosomal protein L39 | 3.07 | up | 0.00021 |
| AA449475 | 1128 | EST | 3.06 | up | 0.00291 |
| N24899 | 2460 | EST | 3.06 | up | 0.00353 |
| Z38150 | 3880 | EST | 3.06 | up | 0.00049 |
| AA172076 | 369 | EST | 3.06 | up | 0.00326 |
| N90238 | 2711 | EST | 3.06 | up | 0.00354 |
| U27328 | 3337 | fucosyltransferase 3 (galactoside 3(4)-L-fucosyltransferase, Lewis blood group included) | 3.05 | up | 0.03224 |
| AA421638 | 935 | EST | 3.05 | up | 0.00487 |
| AA007158 | 15 | EST | 3.05 | up | 0.01964 |
| H24077 | 1900 | EST | 3.05 | up | 0.0324 |
| U36341 | 3350 | solute carrier family 6 (neurotransmitter transporter, creatine), member 8 | 3.05 | up | 0.02622 |
| U02493 | 3278 | non-Pou domain-containing octamer (ATGCAAAT) binding p | 3.04 | up | 0.0019 |
| N36432 | 2506 | erythrocyte membrane protein band 4.1-like 2 | 3.03 | up | 0.03086 |
| AA436473 | 1052 | EST | 3.03 | up | 0.00133 |
| AA598712 | 1436 | EST | 3.03 | up | 0.03656 |
| AA447118 | 1099 | EST | 3.03 | up | 0.01702 |
| H52673 | 1943 | BCL2-antagonist/killer 1 | 3.03 | up | 0.0393 |
| AA491223 | 1389 | EST | 3.03 | up | 0.00557 |
| T47969 | 3127 | ceroid-lipofuscinosis, neuronal 3, juvenile (Batten, Spielmeyer-Vogt disease) | 3.03 | up | 0.03452 |
| X03453 | 3674 | EST | 3.03 | up | 0.0025 |
| J03459 | 2093 | leukotriene A4 hydrolase | 3.03 | up | 0.04041 |
| M86667 | 2410 | nucleosome assembly protein 1-like 1 | 3.03 | up | 0.04853 |
| X80198 | 3804 | steroidogenic acute regulatory protein related | 3.03 | up | 0.00044 |
| W44733 | 3516 | EST | 3.02 | up | 0.00097 |
| X63629 | 3759 | cadherin 3, P-cadherin (placental) | 3.02 | up | 0.01654 |
| AA427946 | 983 | dynein, axonemal, light polypeptide 4 | 3.01 | up | 0.00001 |
| R45698 | 2865 | EST | 3.01 | up | 0.04766 |
| W49661 | 3536 | FK506-binding protein 9 (63 kD) | 3.01 | up | 0.02259 |
| R06986 | 2775 | peptidylprolyl isomerase B (cyclophilin B) | 3.01 | up | 0.04418 |
| W72861 | 3583 | protein tyrosine phosphatase, receptor type, f polypeptide (PTPRF), interacting protein (liprin), alpha 3 | 3.01 | up | 0.00055 |
| AA278838 | 620 | EST | 3 | up | 0.02832 |
| U03891 | 3282 | phorbolin (similar to apolipoprotein B mRNA editing protein) | 3 | up | 0.00065 |

TABLE 6B

Down in Metastatics vs Normal Sample Set 2

| Fragment Name | SEQ ID: | Known Gene Name | Fold Change | Direction | Pvalue |
|---|---|---|---|---|---|
| N54417 | 2566 | fibrinogen, A alpha polypeptide | 99.28 | down | 0.00001 |
| N53031 | 2555 | UDP glycosyltransferase 2 family, polypeptide B4 | 97.58 | down | 0.00022 |
| M15656 | 2268 | aldolase B, fructose-bisphosphate | 96.66 | down | 0 |
| T73442 | 3212 | EST | 94.41 | down | 0 |
| T59148 | 3157 | carbamoyl-phosphate synthetase 1, mitochondrial | 88.89 | down | 0 |
| R49459 | 2881 | transferrin receptor 2 | 85.61 | down | 0.00048 |
| X55283 | 3731 | asialoglycoprotein receptor 2 | 84.99 | down | 0.00084 |
| L16883 | 2166 | cytochrome P450, subfamily IIC (mephenytoin 4-hydroxylase), polypeptide 9 | 84.71 | down | 0.00327 |
| T48039 | 3128 | protein C (inactivator of coagulation factors Va and VIIIa) | 84.39 | down | 0.00112 |
| T71373 | 3202 | EST | 83.08 | down | 0.00069 |
| H58692 | 1960 | formyltetrahydrofolate dehydrogenase | 81.41 | down | 0 |
| T46901 | 3122 | EST | 77.28 | down | 0.0006 |
| M81349 | 2404 | serum amyloid A4, constitutive | 76.15 | down | 0.00015 |
| R43174 | 2847 | paraoxonase 1 | 74.04 | down | 0.00038 |
| X65727 | 3765 | glutathione S-transferase A2,glutathione S-transferase A3 | 73.64 | down | 0 |
| M16594 | 2272 | glutathione S-transferase A2 | 73.21 | down | 0 |
| U22029 | 3326 | cytochrome P450, subfamily IIA (phenobarbital-inducible), polypeptide 7 | 71.98 | down | 0 |
| AA256367 | 579 | paraoxonase 3 | 70.33 | down | 0.00192 |
| K03192 | 2127 | cytochrome P450, subfamily IIA (phenobarbital-inducible), polypeptide 6 | 69.92 | down | 0 |
| AA035245 | 79 | aldehyde oxidase 1 | 69.82 | down | 0.00117 |
| N80129 | 2702 | metallothionein 1L | 66.48 | down | 0.00415 |
| R97419 | 3003 | cytochrome P450, subfamily VIIIB (sterol 12-alpha-hydroxylase), polypeptide 1 | 65.07 | down | 0.0039 |
| T83356 | 3231 | apolipoprotein H (beta-2-glycoprotein I) | 64.34 | down | 0.00802 |
| AA348922 | 758 | fatty-acid-Coenzyme A ligase, long-chain 1,fatty-acid-Coenzyme A ligase, long-chain 2 | 64.27 | down | 0.00002 |
| T83397 | 3232 | phytanoyl-CoA hydroxylase (Refsum disease) | 63.6 | down | 0 |
| R16098 | 2792 | EST | 63.41 | down | 0.00038 |
| R89811 | 2979 | HGF activator | 62.51 | down | 0.00148 |
| H57166 | 1955 | EST | 60.76 | down | 0.00007 |
| N33009 | 2491 | apolipoprotein E | 60.54 | down | 0.0093 |
| N54053 | 2560 | secreted phosphoprotein 2, 24kD | 60.39 | down | 0.00087 |
| T68878 | 3190 | carboxylesterase 1 (monocyte/macrophage serine esterase 1) | 60.35 | down | 0.00409 |
| R08564 | 2779 | plasminogen-like | 60.18 | down | 0.00091 |
| F10182 | 1812 | hepsin (transmembrane protease, serine 1) | 58.92 | down | 0.00837 |
| L25880 | 2184 | epoxide hydrolase 1, microsomal (xenobiotic) | 58.7 | down | 0.00013 |
| W88946 | 3636 | putative glycine-N-acyltransferase | 58.26 | down | 0 |
| N54429 | 2567 | EST | 57.81 | down | 0.00724 |
| M29873 | 2318 | cytochrome P450, subfamily IIB (phenobarbital-inducible) | 56.71 | down | 0.0054 |
| AA476324 | 1281 | EST | 55.22 | down | 0.00132 |
| R12472 | 2788 | EST | 55.18 | down | 0.00011 |
| AA453988 | 1160 | methionine adenosyltransferase I, alpha | 54.29 | down | 0.00381 |
| T56264 | 3148 | apolipoprotein C-II | 53.04 | down | 0.00938 |
| W92148 | 3647 | kininogen | 51.09 | down | 0.00376 |
| R01023 | 2751 | glucokinase (hexokinase 4) regulatory protein | 50.71 | down | 0.00321 |
| H80901 | 2005 | ficolin (collagen/fibrinogen domain-containing) 3 (Hakata antigen) | 50.61 | down | 0.00262 |
| D31628 | 1646 | 4-hydroxyphenylpyruvate dioxygenase | 50.48 | down | 0.00002 |
| AA401562 | 830 | EST | 50.45 | down | 0.00301 |
| K03192 | 2127 | cytochrome P450, subfamily IIA (phenobarbital-inducible), polypeptide 6 | 50.16 | down | 0 |
| T67931 | 3183 | fibrinogen, B beta polypeptide | 49.55 | down | 0 |
| M16974 | 2277 | complement component 8, alpha polypeptide | 49.47 | down | 0.00046 |
| M12963 | 2248 | alcohol dehydrogenase 1 (class I), alpha polypeptide,alcohol dehydrogenase 2 (class I), beta polypeptide,alcohol dehydrogenase 3 (class I), gamma polypeptide | 48.95 | down | 0.00104 |
| T73433 | 3211 | angiotensinogen | 48.3 | down | 0.00049 |
| AA009719 | 20 | peroxisomal membrane protein 2 (22kD) | 47.12 | down | 0.00008 |
| H94666 | 2045 | alpha-1-B glycoprotein | 47.03 | down | 0.01158 |
| T98676 | 3268 | EST | 46.94 | down | 0.0001 |
| T40936 | 3117 | EST | 46.92 | down | 0.00056 |
| R98073 | 3008 | EST | 46.87 | down | 0 |
| AA456311 | 1190 | EST | 46.81 | down | 0.001 |
| H91325 | 2029 | aldolase B, frutose-bisphosphate | 45.85 | down | 0.00505 |
| H74317 | 1997 | apolipoprotein A-II | 45.09 | down | 0.01982 |
| T61373 | 3162 | vitronectin (serum spreading factor, somatomedin B, complement S-protein) | 44.9 | down | 0.3172 |
| X16260 | 3707 | inter-alpha (globulin) inhibitor, H1 polypeptide | 44.65 | down | 0.00933 |
| AA421049 | 927 | activating transcription factor 5 | 44.41 | down | 0.00179 |
| M17262 | 2278 | coagulation factor II (thrombin) | 44.3 | down | 0.00345 |
| HG1827–HT1856 | | cytochrome P450, subfamily IIC (mephenytoin 4-hydroxylase), polypeptide 18,cytochrome P450, subfamily IIC (mephenytoin 4-hydroxylase), polypeptide 8 | 44.17 | down | 0.0003 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| AA417046 | 915 | fatty-acid-Coenzyme A ligase, very long-chain 1 | 44 | down | 0 |
| AA433946 | 1033 | EST | 43.74 | down | 0.00005 |
| T71012 | 3200 | fibrinogen, B beta polypeptide | 43.61 | down | 0.00743 |
| L11244 | 2155 | complement component 4-binding protein, beta | 43.33 | down | 0 |
| AA018867 | 39 | EST | 42.87 | down | 0.00002 |
| T23882 | 3084 | kininogen | 42.85 | down | 0.00641 |
| L00190 | 2130 | antithrombin III | 42.41 | down | 0.00012 |
| N68596 | 2635 | betaine-homocysteine methyltransferase | 40.99 | down | 0 |
| H94475 | 2043 | alpha-2-plasmin inhibitor | 40.92 | down | 0.00271 |
| AA085987 | 183 | UDP glycosyltransferase 1 | 40.87 | down | 0.00004 |
| M75106 | 2396 | carboxypeptidase B2 (plasma) | 40.63 | down | 0 |
| HG2841–HT2968 | | albumin | 40.5 | down | 0.001 |
| M58600 | 2362 | heparin cofactor II | 39.79 | down | 0.00034 |
| R37128 | 2826 | complement component 4A | 39.51 | down | 0.00364 |
| R93776 | 2992 | EST | 39.32 | down | 0.00176 |
| M61855 | 2371 | cytochrome P450, subfamily IIC (mephenytoin 4-hydroxylase), polypeptide 9 | 38.82 | down | 0.00023 |
| X13930 | 3697 | cytochrome P450, subfamily IIA (phenobarbital-inducible), polypeptide 6 | 38.52 | down | 0 |
| T95813 | 3261 | KIAA1051 protein | 38.38 | down | 0.00008 |
| X68679 | 3776 | complement factor H related 3,complement factor H-related 4 | 38.22 | down | 0.00036 |
| W20094 | 3476 | DKFZP586A0522 protein | 38.09 | down | 0.00188 |
| AA479148 | 1311 | EST | 38.05 | down | 0 |
| AA235310 | 496 | EST | 37.86 | down | 0.00091 |
| T68711 | 3187 | EST | 37.65 | down | 0.00036 |
| R40395 | 2840 | lecithin-cholesterol acyltransferase | 37.33 | down | 0.00032 |
| W28944 | 3493 | EST | 37.07 | down | 0.00205 |
| U50929 | 3379 | betaine-homocysteine methyltransferase | 36.91 | down | 0 |
| L04751 | 2138 | cytochrome P450, subfamily IVA, polypeptide 11 | 36.79 | down | 0.00004 |
| N76012 | 2693 | EST | 36.71 | down | 0.00598 |
| T69284 | 3195 | mannose-binding lectin (protein C) 2, soluble (opsonic defect) | 36.53 | down | 0 |
| R49602 | 2884 | EST | 36.5 | down | 0.00001 |
| X07618 | 3688 | cytochrome P450, subfamily IID (debrisoquine, sparteine, etc., -metabolising), polypeptide 7a (pseudogene) | 35.79 | down | 0.00065 |
| N22938 | 2452 | serum amyloid A4, constitutive | 35.39 | down | 0.00128 |
| AA621131 | 1513 | EST | 35.37 | down | 0 |
| D12620 | 1601 | cytochrome P450, subfamily IVF, polypeptide 2,cytochrome P450, subfamily IVF, polypeptide 3 (leukotriene B4 omega hydroxylase) | 35.09 | down | 0.00015 |
| N70358 | 2656 | growth hormone receptor | 34.35 | down | 0 |
| N70966 | 2662 | solute carrier family 10 (sodium/bile acid cotransporter family), member 1 | 34.06 | down | 0.0006 |
| T68855 | 3188 | EST | 34.04 | down | 0 |
| T69029 | 3193 | haptoglobin | 33.18 | down | 0.02825 |
| M33317 | 2338 | cytochrome P450, subfamily IIA (phenobarbital-inducible), polypeptide 7 | 32.63 | down | 0 |
| T48075 | 3129 | hemoglobin, alpha 1 | 32.56 | down | 0.00172 |
| M12272 | 2243 | alcohol dehydrogenase 1 (class I), alpha polypeptide,alcohol dehydrogenase 2 (class I), beta polypeptide,alcohol dehydrogenase 3 (class I), gamma polypeptide | 32.42 | down | 0.0034 |
| AA620556 | 1505 | EST | 32.4 | down | 0.00353 |
| T74542 | 3214 | UDP glycosyltransferase 2 family, polypeptide B10 | 32.36 | down | 0.00004 |
| T56281 | 3150 | RNA helicase-related protein | 32.34 | down | 0.00002 |
| W73601 | 3589 | EST | 32.25 | down | 0 |
| M11567 | 2239 | angiogenin, ribonuclease, RNase A family, 5 | 32.25 | down | 0.0001 |
| W86600 | 3625 | EST | 32.14 | down | 0 |
| AA039335 | 89 | coagulation factor XII (Hageman factor) | 32 | down | 0.0029 |
| T67705 | 3182 | asialoglycoprotein receptor 2 | 31.6 | down | 0.00705 |
| H89980 | 2026 | protein phosphatase 1, regulatory (inhibitor) subunit 5 | 31.13 | down | 0.00006 |
| H20543 | 1897 | DKFZP586B1621 protein | 31.03 | down | 0.00074 |
| H57060 | 1954 | EST | 30.98 | down | 0.01687 |
| W67564 | 3568 | nuclear receptor subfamily 0, group B, member 2 | 30.34 | down | 0 |
| N74422 | 2685 | EST | 30.32 | down | 0 |
| X07173 | 3687 | inter-alpha (globulin) inhibitor, H2 polypeptide | 30.3 | down | 0.00016 |
| T47778 | 3126 | fibrinogen, A alpha polypeptide | 30 | down | 0.01401 |
| X90579 | 3816 | EST | 29.82 | down | 0.00273 |
| T99636 | 3270 | complement component 3 | 29.6 | down | 0.00051 |
| Z20777 | 3863 | EST | 29.59 | down | 0.00044 |
| U56814 | 3392 | deoxyribonuclease I-like 3 | 29.43 | down | 0.00003 |
| M19828 | 2287 | apolipoprotein B (including Ag(x) antigen) | 29.37 | down | 0.00137 |
| R77628 | 2965 | insulin induced gene 1 | 29.23 | down | 0.00122 |
| AA452158 | 1141 | ras homolog gene family, member B | 28.96 | down | 0.00064 |
| K02402 | 2125 | coagulation factor IX (plasma thromboplastic component, Christmas disease, hemophilia B) | 28.81 | down | 0.00001 |
| T57140 | 3151 | paraoxonase 3 | 28.8 | down | 0 |
| T68873 | 3189 | metallothionein 1L | 28.72 | down | 0.02953 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| H95569 | 2051 | DKFZP586A0522 protein | 28.48 | down | 0.00139 |
| T56279 | 3149 | H factor (complement)-like 3 | 28.39 | down | 0.00016 |
| N66066 | 2612 | EST | 28.35 | down | 0.00055 |
| X07732 | 3690 | hepsin (transmembrane protease, serine 1) | 28.21 | down | 0 |
| AA253216 | 561 | EST | 28.18 | down | 0.00141 |
| W79046 | 3599 | peroxisomal D3,D2-enoyl-CoA isomerase | 27.9 | down | 0.00023 |
| U51010 | 3380 | nicotinamide N-methyltransferase | 27.79 | down | 0.00366 |
| H08102 | 1858 | breast cell glutaminase | 27.77 | down | 0.00032 |
| U70732 | 3414 | glutamic-pyruvate transaminase (alanine aminotransferase) | 27.63 | down | 0 |
| HG2730–HT2828 | | fibrinogen, A alpha polypeptide | 27.34 | down | 0.001 |
| D90282 | 1769 | carbamoyl-phosphate synthetase 1, mitochondrial | 27.29 | down | 0.00002 |
| X53595 | 3726 | apolipoprotein H (beta-2-glycoprotein I) | 27.28 | down | 0.0066 |
| AA599937 | 1458 | insulin-like growth factor-binding protein 4 | 26.92 | down | 0.00094 |
| L25878 | 2183 | epoxide hydrolase 1, microsomal (xenobiotic) | 26.84 | down | 0 |
| Z30425 | 3875 | nuclear receptor subfamily 1, group I, member 3 | 26.64 | down | 0 |
| X16260 | 3707 | inter-alpha (globulin) inhibitor, H1 polypeptide | 26.39 | down | 0.0004 |
| R92475 | 2986 | flavin containing monooxygenase 3 | 26.13 | down | 0 |
| T61649 | 3164 | superoxide dismutase 2, mitochondrial | 26.09 | down | 0.00734 |
| N63845 | 2604 | phytanoyl-CoA hydroxylase (Refsum disease) | 25.92 | down | 0.00084 |
| X03168 | 3671 | vitronectin (serum spreading factor, somatomedin B, complement S-protein) | 25.88 | down | 0.00911 |
| H81070 | 2006 | RNA helicase-related protein | 25.74 | down | 0.0126 |
| T61801 | 3166 | hemopexin | 25.7 | down | 0.01362 |
| L47726 | 2219 | phenylalanine hydroxylase | 25.63 | down | 0.00019 |
| N59550 | 2587 | EST | 25.56 | down | 0.00024 |
| X56411 | 3734 | alcohol dehydrogenase 4 (class II), pi polypeptide | 25.14 | down | 0.00144 |
| HG2730–HT2827 | | fibrinogen, A alpha polypeptide | 25.1 | down | 0 |
| AA448300 | 1116 | FXYD domain-containing ion transport regulator 1 (phospholemman) | 24.97 | down | 0.00001 |
| N39201 | 2509 | protease inhibitor 4 (kallistatin) | 24.91 | down | 0.00253 |
| M34276 | 2341 | plasminogen | 24.73 | down | 0.00031 |
| Z28339 | 3872 | aldo-keto reductase family 1, member D1 (delta 4-3-ketosteroid-5-beta-reductase) | 24.66 | down | 0 |
| W72044 | 3577 | insulin induced gene 1 | 24.58 | down | 0.00001 |
| AA232114 | 463 | epoxide hydrolase 2, cytoplasmic | 24.34 | down | 0.00007 |
| U06641 | 3286 | UDP glycosyltransferase 2 family, polypeptide B15 | 24.32 | down | 0.00001 |
| H93381 | 2036 | EST | 24.23 | down | 0 |
| S68287 | 3024 | aldo-keto reductase family 1, member C4 (chlordecone reductase; 3-alpha hydroxysteroid dehydrogenase, type I; dihydrodiol dehydrogenase 4) | 24.11 | down | 0 |
| F04611 | 1792 | EST | 23.96 | down | 0.00018 |
| M10058 | 2230 | asialoglycoprotein receptor 1 | 23.96 | down | 0 |
| L32179 | 2193 | arylacetamide deacetylase (esterase) | 23.83 | down | 0 |
| AA598419 | 1427 | translational inhibitor protein p14.5 | 23.6 | down | 0.00036 |
| F02028 | 1774 | EST | 23.48 | down | 0.00465 |
| N89302 | 2707 | HLA-B associated transcript-3 | 23.44 | down | 0.00192 |
| AA279676 | 630 | deoxyribonuclease I-like 3 | 23.35 | down | 0.00001 |
| U05861 | 3284 | aldo-keto reductase family 1, member C1 (dihydrodiol dehydrogenase 1; 20-alpha (3-alpha)-hydroxysteroid dehydrogenase) | 23.22 | down | 0.00002 |
| H09353 | 1866 | EST | 23.06 | down | 0.00094 |
| M93405 | 2423 | methylmalonate-semialdehyde dehydrogenase | 23.06 | down | 0 |
| S48983 | 3017 | serum amyloid A4, constitutive | 23.04 | down | 0.00022 |
| AA443936 | 1084 | EST | 22.96 | down | 0.00627 |
| N74025 | 2684 | deiodinase, iodothyronine, type I | 22.79 | down | 0 |
| M15517 | 2267 | EST | 22.76 | down | 0.03365 |
| M16973 | 2276 | complement component 8, beta polypeptide | 22.75 | down | 0.00001 |
| X86401 | 3812 | glycine amidinotransferase (L-arginine:glycine amidinotransferase) | 22.7 | down | 0 |
| D16626 | 1622 | histidine ammonia-lyase | 22.66 | down | 0 |
| J02843 | 2088 | cytochrome P450, subfamily IIE (ethanol-inducible) | 22.58 | down | 0.00935 |
| U22961 | 3329 | albumin | 22.22 | down | 0.01531 |
| AA486511 | 1349 | EST | 22.21 | down | 0.00113 |
| L48516 | 2220 | paraoxonase 3 | 22.21 | down | 0.00004 |
| M62486 | 2374 | complement component 4-binding protein, alpha | 22.08 | down | 0.00272 |
| D00003 | 1586 | cytochrome P450, subfamily IIIA (niphedipine oxidase), polypeptide 3 | 22.05 | down | 0.00059 |
| J03810 | 2099 | solute carrier family 2 (facilitated glucose transporter), member 2 | 21.99 | down | 0.00004 |
| AA219304 | 447 | alpha-2-macroglobulin | 21.97 | down | 0.00011 |
| R08615 | 2780 | homogentisate 1,2-dioxygenase (homogentisate oxidase) | 21.85 | down | 0.00026 |
| AA147646 | 317 | DKFZP586A0522 protein | 21.82 | down | 0 |
| AA292158 | 706 | EST | 21.79 | down | 0.00031 |
| D11835 | 1598 | low density lipoprotein receptor (familial hypercholesterolemia) | 21.76 | down | 0.00307 |
| T87174 | 3239 | EST | 21.71 | down | 0.00681 |
| M16961 | 2274 | alpha-2-HS-glycoprotein | 21.45 | down | 0.01175 |
| D78011 | 1717 | dihydropyrimidinase | 21.37 | down | 0.00003 |
| R98624 | 3012 | EST | 21.32 | down | 0 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| R65593 | 2934 | kynurenine 3-monooxygenase (kynurenine 3-hydroxylase) | 21.27 | down | 0.00007 |
| K02766 | 2126 | complement component 9 | 21.24 | down | 0 |
| AA171694 | 366 | ceruloplasmin (ferroxidase) | 21.23 | down | 0.00179 |
| T58775 | 3156 | small inducible cytokine subfamily A (Cys-Cys), member 16 | 21.18 | down | 0.00006 |
| N71542 | 2664 | kidney- and liver-specific gene | 21.05 | down | 0 |
| AA343142 | 751 | EST | 20.87 | down | 0.00003 |
| X12662 | 3694 | arginase, liver | 20.59 | down | 0 |
| R64131 | 2929 | EST | 20.58 | down | 0.01028 |
| M68516 | 2387 | protein C inhibitor (plasminogen activator inhibitor III) | 20.54 | down | 0 |
| L07765 | 2147 | carboxylesterase 1 (monocyte/macrophage serine esterase 1) | 20.53 | down | 0.00025 |
| D10040 | 1593 | fatty-acid-Coenzyme A ligase, long-chain 2 | 20.51 | down | 0 |
| D13243 | 1602 | pyruvate kinase, liver and RBC | 20.22 | down | 0 |
| X01038 | 3666 | apolipoprotein A-I,apolipoprotein C-III | 19.97 | down | 0.0275 |
| T78889 | 3220 | fibronectin 1 | 19.87 | down | 0.00912 |
| S95936 | 3040 | transferrin | 19.76 | down | 0.02009 |
| R59722 | 2915 | EST | 19.74 | down | 0.00016 |
| U08198 | 3291 | complement component 8, gamma polypeptide | 19.71 | down | 0 |
| AA148480 | 318 | flavin containing monooxygenase 5 | 19.64 | down | 0 |
| M83772 | 2408 | flavin containing monooxygenase 3 | 19.54 | down | 0 |
| X03350 | 3673 | alcohol dehydrogenase 2 (class I), beta polypeptide | 19.32 | down | 0.00001 |
| W86375 | 3623 | EST | 19.29 | down | 0.0061 |
| M76665 | 2397 | hydroxysteroid (11-beta) dehydrogenase 1 | 19.22 | down | 0.00004 |
| J02943 | 2090 | corticosteroid binding globulin | 18.98 | down | 0.00087 |
| T61389 | 3163 | haptoglobin | 18.95 | down | 0.04873 |
| J04093 | 2106 | UDP glycosyltransferase 1 | 18.92 | down | 0 |
| Y09616 | 3854 | carboxylesterase 2 (intestine, liver) | 18.78 | down | 0.00026 |
| Z40715 | 3920 | delta-6 fatty acid desaturase | 18.68 | down | 0.0007 |
| M13149 | 2250 | histidine-rich glycoprotein | 18.65 | down | 0.02974 |
| U32576 | 3346 | apolipoprotein C-IV | 18.59 | down | 0.00005 |
| X00129 | 3664 | retinol-binding protein 4, interstitial | 18.57 | down | 0.02378 |
| N69136 | 2644 | EST | 18.53 | down | 0.00366 |
| Z49269 | 3942 | small inducible cytokine subfamily A (Cys-Cys), member 14 | 18.46 | down | 0.00001 |
| M29874 | 2319 | cytochrome P450, subfamily IIB (phenobarbital-inducible) | 18.44 | down | 0.00081 |
| M11437 | 2238 | kininogen | 18.38 | down | 0.00006 |
| Y00317 | 3842 | UDP glycosyltransferase 2 family, polypeptide B4 | 18.34 | down | 0.00001 |
| L09229 | 2150 | fatty-acid-Coenzyme A ligase, long-chain 1,fatty-acid-Coenzyme A ligase, long-chain 2 | 18.34 | down | 0.00016 |
| U37055 | 3352 | macrophage stimulating 1 (hepatocyte growth factor-like),macrophage stimulating, pseudogene 9 | 18.28 | down | 0 |
| S68805 | 3025 | glycine amidinotransferase (L-arginine:glycine amidinotransferase) | 18.19 | down | 0.00083 |
| D49742 | 1668 | hyaluronan-binding protein 2 | 18.13 | down | 0.00012 |
| N49090 | 2532 | EST | 18 | down | 0.00501 |
| M20867 | 2291 | glutamate dehydrogenase 1 | 17.73 | down | 0.00002 |
| AA435985 | 1049 | EST | 17.7 | down | 0 |
| X95384 | 3830 | translational inhibitor protein p14.5 | 17.69 | down | 0.00048 |
| T51617 | 3137 | solute carrier family 22 (extraneuronal monoamine transporter), member 3 | 17.67 | down | 0.00018 |
| D59714 | 1700 | mitogen inducible 2 | 17.62 | down | 0.00014 |
| M11025 | 2235 | asialoglycoprotein receptor 2 | 17.56 | down | 0.00003 |
| M86873 | 2413 | plasminogen,plasminogen-like | 17.54 | down | 0 |
| AA292328 | 707 | activating transcription factor 5 | 17.51 | down | 0.00689 |
| HG1148–HT1148 | | EST | 17.51 | down | 0.00024 |
| D62518 | 1708 | EST | 17.49 | down | 0.00017 |
| AA424798 | 947 | EST | 17.45 | down | 0.00352 |
| L32140 | 2192 | afamin | 17.31 | down | 0.00003 |
| R02365 | 2754 | glucose-6-phosphatase, catalytic (glycogen storage disease type I, von Gierke disease) | 17.17 | down | 0.00124 |
| N54950 | 2572 | ketohexokinase (fructokinase) | 17.17 | down | 0.00078 |
| M10612 | 2232 | apolipoprotein C-II | 17.13 | down | 0.00746 |
| H30270 | 1915 | EST | 17.09 | down | 0.00001 |
| N73543 | 2674 | EST | 17 | down | 0.00003 |
| M20786 | 2290 | alpha-2-plasmin inhibitor | 16.95 | down | 0.00709 |
| U20530 | 3321 | secreted phosphoprotein 2, 24kD | 16.93 | down | 0 |
| Z39833 | 3910 | GTP-binding protein | 16.89 | down | 0.00034 |
| AA377087 | 771 | EST | 16.75 | down | 0.00002 |
| H47838 | 1936 | carboxypeptidase B2 (plasma) | 16.74 | down | 0.00002 |
| D00097 | 1588 | amyloid P component, serum | 16.72 | down | 0.00098 |
| AA236401 | 510 | EST | 16.71 | down | 0.00088 |
| T52813 | 3141 | putative lymphocyte G0/G1 switch gene | 16.71 | down | 0.03897 |
| W92713 | 3651 | EST | 16.55 | down | 0.00097 |
| H83109 | 2012 | EST | 16.55 | down | 0.00001 |
| T63490 | 3170 | EST | 16.54 | down | 0 |
| AA122345 | 238 | glutamate dehydrogenase 1 | 16.53 | down | 0.00004 |
| M11321 | 2237 | group-specific component (vitamin D binding protein) | 16.52 | down | 0.01416 |
| K02215 | 2124 | angiotensinogen | 16.51 | down | 0.00006 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| AA449267 | 1120 | EST | 16.44 | down | 0.00926 |
| N68974 | 2639 | EST | 16.44 | down | 0.00087 |
| R43799 | 2850 | EST | 16.35 | down | 0.00208 |
| N51773 | 2548 | EST | 16.32 | down | 0.0007 |
| L11005 | 2154 | aldehyde oxidase 1 | 16.3 | down | 0.00065 |
| N71935 | 2666 | multiple PDZ domain protein | 16.28 | down | 0 |
| M26393 | 2309 | acyl-Coenzyme A dehydrogenase, C-2 to C-3 short chain | 16.27 | down | 0.00007 |
| J05037 | 2116 | serine dehydratase | 16.24 | down | 0.00015 |
| M11437 | 2238 | kininogen | 16.19 | down | 0.02277 |
| T73739 | 3213 | alanine-glyoxylate aminotransferase (oxalosis I; hyperoxaluria I; glycolicaciduria; serine-pyruvate aminotransferase) | 16.18 | down | 0.00277 |
| AA404252 | 848 | lectin, mannose-binding, 1 | 16.15 | down | 0.00001 |
| M58569 | 2361 | EST | 16.15 | down | 0.00174 |
| J05428 | 2120 | UDP glycosyltransferase 2 family, polypeptide B7 | 16.14 | down | 0.00563 |
| AA194997 | 412 | EST | 16.12 | down | 0.00103 |
| X14690 | 3700 | pre-alpha (globulin) inhibitor, H3 polypeptide | 16.07 | down | 0.00438 |
| H77597 | 2000 | metallothionein 1H | 16.03 | down | 0.00675 |
| U08006 | 3289 | complement component 8, alpha polypeptide | 16 | down | 0.00111 |
| AA458946 | 1209 | EST | 15.88 | down | 0.00004 |
| M13699 | 2253 | ceruloplasmin (ferroxidase) | 15.85 | down | 0.00012 |
| M21642 | 2294 | antithrombin III | 15.82 | down | 0.01027 |
| W28824 | 3492 | EST | 15.8 | down | 0.00006 |
| H60595 | 1966 | progesterone binding protein | 15.8 | down | 0.01078 |
| R06746 | 2770 | EST | 15.77 | down | 0.00009 |
| AA236455 | 512 | EST | 15.71 | down | 0.00286 |
| AA253369 | 563 | EST | 15.59 | down | 0.00091 |
| AA479885 | 1318 | KIAA0843 protein | 15.57 | down | 0.00024 |
| AA455988 | 1184 | butyrobetaine (gamma), 2-oxoglutarate dioxygenase (gamma-butyrobetaine hydroxylase) | 15.54 | down | 0.00001 |
| AA381125 | 772 | EST | 15.48 | down | 0 |
| AA455403 | 1177 | EST | 15.46 | down | 0.01547 |
| U29953 | 3341 | pigment epithelium-derived factor | 15.33 | down | 0.00212 |
| AA456289 | 1189 | EST | 15.31 | down | 0.00004 |
| H93246 | 2035 | EST | 15.3 | down | 0.00233 |
| AA015768 | 34 | EST | 15.3 | down | 0.00008 |
| AA195656 | 418 | KIAA0977 protein | 15.29 | down | 0.00817 |
| M21642 | 2294 | antithrombin III | 15.23 | down | 0.02088 |
| X56692 | 3736 | C-reactive protein, pentraxin-related | 15.15 | down | 0.01884 |
| AA196287 | 420 | EST | 15.07 | down | 0.00001 |
| T48278 | 3131 | EST | 15.04 | down | 0.04751 |
| N66857 | 2619 | EST | 15.03 | down | 0.00005 |
| AA156565 | 344 | 4-nitrophenylphosphatase domain and non-neuronal SNAP25-like 1 | 15.01 | down | 0.01387 |
| N58326 | 2578 | EST | 14.97 | down | 0.00647 |
| W86431 | 3624 | protein C inhibitor (plasminogen activator inhibitor III) | 14.94 | down | 0.00152 |
| W79422 | 3601 | fumarylacetoacetate | 14.94 | down | 0.00059 |
| H58673 | 1959 | EST | 14.85 | down | 0.00005 |
| Y12711 | 3858 | progesterone binding protein | 14.83 | down | 0.00285 |
| N31741 | 2488 | serine hydroxymethyltransferase 1 (soluble) | 14.76 | down | 0.00001 |
| N57464 | 2575 | CCAAT/enhancer binding protein (C/EBP), delta | 14.69 | down | 0.00018 |
| X64877 | 3763 | H factor (complement)-like 3 | 14.6 | down | 0 |
| U24266 | 3330 | aldehyde dehydrogenase 4 (glutamate gamma-semialdehyde dehydrogenase; pyrroline-5-carboxylate dehydrogenase) | 14.54 | down | 0 |
| N91882 | 2719 | alpha2,3-sialyltransferase | 14.52 | down | 0.00024 |
| AA402224 | 836 | growth arrest and DNA-damage-inducible, gamma | 14.41 | down | 0.00012 |
| AA179004 | 377 | EST | 14.34 | down | 0.00008 |
| AA034030 | 75 | methylmalonyl Coenzyme A mutase | 14.32 | down | 0.00004 |
| M17262 | 2278 | coagulation factor II (thrombin) | 14.24 | down | 0.00028 |
| U48707 | 3370 | protein phosphatase 1, regulatory (inhibitor) subunit 1A | 14.22 | down | 0 |
| L35546 | 2203 | glutamate-cysteine ligase (gamma-glutamylcysteine synthetase), regulatory (30.8kD) | 14.18 | down | 0.00018 |
| T74608 | 3215 | hydroxyacid oxidase (glycolate oxidase) 1 | 14.03 | down | 0 |
| U95090 | 3463 | nephrosis 1, congenital, Finnish type (nephrin) | 14.01 | down | 0.00018 |
| AA092716 | 198 | HLA-B associated transcript-3 | 13.97 | down | 0.00009 |
| D20350 | 1624 | EST | 13.97 | down | 0.00057 |
| Z49878 | 3943 | guanidinoacetate N-methyltransferase | 13.96 | down | 0.00021 |
| HG1428–HT1428 | | hemoglobin, beta | 13.89 | down | 0.01109 |
| X53414 | 3725 | alanine-glyoxylate aminotransferase (oxalosis I; hyperoxaluria I; glycolicaciduria; serine-pyruvate aminotransferase) | 13.87 | down | 0.00003 |
| M57731 | 2359 | GRO2 oncogene | 13.87 | down | 0.0123 |
| Z48475 | 3940 | glucokinase (hexokinase 4) regulatory protein | 13.84 | down | 0 |
| W86075 | 3621 | EST | 13.83 | down | 0.00057 |
| N57934 | 2576 | formiminotransferase cyclodeaminase | 13.81 | down | 0.00171 |
| AF000573 | 1543 | homogentisate 1,2-dioxygenase (homogentisate oxidase) | 13.76 | down | 0.00002 |
| R36989 | 2825 | hypothetical protein, estradiol-induced | 13.7 | down | 0.00056 |
| | | macrophage stimulating 1 (hepatocyte growth factor- | | | |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| N78850 | 2698 | like),macrophage stimulating, pseudogene 9 | 13.69 | down | 0.00421 |
| X63359 | 3756 | UDP glycosyltransferase 2 family, polypeptide B10 | 13.66 | down | 0.00051 |
| N80129 | 2702 | metallothionein 1L | 13.6 | down | 0.00196 |
| T61256 | 3161 | ketohexokinase (fructokinase) | 13.59 | down | 0.00425 |
| X07618 | 3688 | cytochrome P450, subfamily IID (debrisoquine, sparteine, etc., - metabolising), polypeptide 7a (pseudogene) | 13.58 | down | 0 |
| HG2383–HT4824 |  | cystathionine-beta-synthase | 13.57 | down | 0.00035 |
| X52520 | 3720 | tyrosine aminotransferase | 13.51 | down | 0.00002 |
| X98337 | 3837 | complement factor H related 3,complement factor H-related 4 | 13.5 | down | 0.00001 |
| T17411 | 3077 | transthyretin (prealbumin, amyloidosis type I) | 13.49 | down | 0.00203 |
| D12620 | 1601 | cytochrome P450, subfamily IVF, polypeptide 2,cytochrome P450, subfamily IVF, polypeptide 3 (leukotriene B4 omega hydroxylase) | 13.45 | down | 0 |
| N75870 | 2692 | dual specificity phosphatase 1 | 13.41 | down | 0.00251 |
| U01120 | 3273 | glucose-6-phosphatase, catalytic (glycogen storage disease type I, von Gierke disease) | 13.41 | down | 0.00147 |
| T58756 | 3155 | EST | 13.39 | down | 0.00013 |
| AA470153 | 1275 | solute carrier family 21 (organic anion transporter), member 9 | 13.26 | down | 0.00315 |
| T40995 | 3118 | alcohol dehydrogenase 3 (class I), gamma polypeptide | 13.25 | down | 0.01531 |
| R92768 | 2988 | EST | 13.2 | down | 0.00001 |
| AA148923 | 321 | decidual protein induced by progesterone | 13.2 | down | 0.00257 |
| D38535 | 1654 | inter-alpha (globulin) inhibitor H4 (plasma Kallikrein-sensitive glycoprotein) | 13.2 | down | 0.01165 |
| L21893 | 2176 | solute carrier family 10 (sodium/bile acid cotransporter family), member 1 | 13.18 | down | 0.00155 |
| AA259064 | 602 | EST | 13.15 | down | 0.00001 |
| N73561 | 2675 | EST | 12.96 | down | 0.00011 |
| X59766 | 3746 | alpha-2-glycoprotein 1, zinc | 12.96 | down | 0.00043 |
| AA233152 | 467 | EST | 12.95 | down | 0 |
| X72177 | 3787 | complement component 6 | 12.94 | down | 0.00011 |
| Z40902 | 3923 | SEC14 (*S. cerevisiae*)-like 2 | 12.87 | down | 0.00001 |
| X95190 | 3829 | acyl-Coenzyme A oxidase 2, branched chain | 12.81 | down | 0 |
| R52822 | 2895 | EST | 12.79 | down | 0.00001 |
| W95041 | 3659 | EST | 12.79 | down | 0.00001 |
| X13334 | 3696 | CD14 antigen | 12.77 | down | 0.00887 |
| D14012 | 1612 | HGF activator | 12.75 | down | 0.0035 |
| L12760 | 2162 | phosphoenolpyruvate carboxykinase 1 (soluble) | 12.75 | down | 0.00035 |
| R08850 | 2781 | EST | 12.55 | down | 0.00009 |
| AA608546 | 1463 | EST | 12.52 | down | 0.00003 |
| AA398280 | 792 | EST | 12.43 | down | 0.00134 |
| J03910 | 2101 | EST | 12.42 | down | 0.01167 |
| AA599814 | 1456 | EST | 12.37 | down | 0.00002 |
| W87532 | 3631 | putative glycine-N-acyltransferase | 12.34 | down | 0.00014 |
| M14338 | 2260 | protein S (alpha) | 12.33 | down | 0 |
| X64877 | 3763 | H factor (complement)-like 3 | 12.33 | down | 0 |
| R80048 | 2971 | EST | 12.28 | down | 0.00128 |
| R06726 | 2769 | protease inhibitor 1 (anti-elastase), alpha-1-antitrypsin | 12.26 | down | 0.03905 |
| AA405832 | 866 | EST | 12.24 | down | 0.00441 |
| M29194 | 2315 | lipase, hepatic | 12.18 | down | 0.00012 |
| W58756 | 3551 | EST | 12.17 | down | 0.00087 |
| T24106 | 3088 | EST | 12.13 | down | 0.01687 |
| AA402656 | 841 | EST | 12.05 | down | 0.00001 |
| L11244 | 2155 | complement component 4-binding protein, beta | 12.03 | down | 0.0001 |
| M65134 | 2385 | complement component 5 | 12.01 | down | 0.00012 |
| HG3543–HT3739 |  | insulin-like growth factor 2 (somatomedin A) | 11.97 | down | 0.00221 |
| L34081 | 2199 | bile acid Coenzyme A: amino acid N-acyltransferase (glycine N-choloyltransferase) | 11.96 | down | 0.00008 |
| U77594 | 3427 | retinoic acid receptor responder (tazarotene induced) 2 | 11.95 | down | 0.00527 |
| AA400258 | 812 | EST | 11.89 | down | 0.00478 |
| AA402799 | 842 | EST | 11.81 | down | 0.00031 |
| M94065 | 2424 | dihydroorotate dehydrogenase | 11.78 | down | 0.00034 |
| U76376 | 3424 | harakiri, BCL2-interacting protein (contains only BH3 domain) | 11.77 | down | 0.00002 |
| AA090257 | 190 | superoxide dismutase 2, mitochondrial | 11.72 | down | 0.02072 |
| AA021623 | 43 | insulin induced gene 1 | 11.71 | down | 0.00094 |
| W70115 | 3573 | histidine ammonia-lyase | 11.65 | down | 0.0003 |
| M69177 | 2391 | monoamine oxidase B | 11.64 | down | 0.00001 |
| X14813 | 3702 | acetyl-Coenzyme A acyltransferase 1 (peroxisomal 3-oxoacyl-Coenzyme A thiolase) | 11.61 | down | 0.0002 |
| AA461444 | 1239 | EST | 11.56 | down | 0.00167 |
| R73816 | 2960 | EST | 11.53 | down | 0.00259 |
| U31449 | 3344 | transmembrane 4 superfamily member 4 | 11.53 | down | 0.00187 |
| H55759 | 1949 | EST | 11.52 | down | 0.00034 |
| U27460 | 3338 | UDP-glucose pyrophosphorylase 2 | 11.46 | down | 0.00088 |
| H29568 | 1914 | EST | 11.45 | down | 0.00058 |
| AA194833 | 411 | claudin 1 | 11.45 | down | 0.00034 |
| AA176233 | 376 | EST | 11.44 | down | 0.01856 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| M74587 | 2393 | insulin-like growth factor binding protein 1 | 11.42 | down | 0.00274 |
| AA436560 | 1055 | claudin 1 | 11.41 | down | 0.00756 |
| Z69923 | 3945 | HGF activator | 11.37 | down | 0.00053 |
| U56814 | 3392 | deoxyribonuclease I-like 3 | 11.36 | down | 0.00001 |
| AA236455 | 512 | EST | 11.35 | down | 0.02859 |
| U13061 | 3301 | sulfotransferase family 2A, dehydroepiandrosterone (DHEA)-preferring, member 1 | 11.32 | down | 0.00048 |
| D49357 | 1665 | methionine adenosyltransferase I, alpha | 11.28 | down | 0.00331 |
| X04085 | 3675 | catalase | 11.27 | down | 0.0002 |
| M31994 | 2332 | aldehyde dehydrogenase 1, soluble | 11.24 | down | 0.01192 |
| R10287 | 2784 | EST | 11.2 | down | 0.0003 |
| Z31357 | 3877 | cysteine dioxygenase, type I | 11.2 | down | 0.0001 |
| T86482 | 3237 | transferrin | 11.15 | down | 0.00006 |
| D00408 | 1589 | cytochrome P450, subfamily IIIA (niphedipine oxidase), polypeptide 3,cytochrome P450, subfamily IIIA (niphedipine oxidase), polypeptide 5,cytochrome P450, subfamily IIIA, polypeptide 7 | 11.1 | down | 0 |
| AA074885 | 161 | macrophage receptor with collagenous structure | 11.05 | down | 0.00786 |
| HG4533–HT4938 | | protease inhibitor 4 (kallistatin) | 11.01 | down | 0.00001 |
| H70554 | 1989 | EST | 10.99 | down | 0 |
| L38928 | 2209 | 5,10-methenyltetrahydrofolate synthetase (5-formyltetrahydrofolate cyclo-ligase) | 10.97 | down | 0.0267 |
| AA182568 | 388 | STAT induced STAT inhibitor-2 | 10.92 | down | 0.00099 |
| X01388 | 3667 | apolipoprotein C-III | 10.9 | down | 0.01246 |
| AA076326 | 170 | SEC14 (*S. cerevisiae*)-like 2 | 10.88 | down | 0.00616 |
| X06562 | 3683 | growth hormone receptor | 10.87 | down | 0.00001 |
| W89178 | 3638 | transferrin receptor 2 | 10.85 | down | 0.00116 |
| D13643 | 1609 | KIAA0018 gene product | 10.84 | down | 0.00058 |
| R62519 | 2925 | EST | 10.83 | down | 0.00243 |
| AA454159 | 1162 | EST | 10.81 | down | 0.00132 |
| R94674 | 2995 | EST | 10.76 | down | 0.00008 |
| H12593 | 1880 | zinc-finger protein 265 | 10.72 | down | 0.0056 |
| H61295 | 1968 | CD4 antigen (p55) | 10.71 | down | 0.00925 |
| AA489636 | 1370 | EST | 10.7 | down | 0 |
| D10511 | 1594 | acetyl-Coenzyme A acetyltransferase 1 (acetoacetyl Coenzyme A thiolase) | 10.68 | down | 0.0002 |
| M14091 | 2257 | thyroxin-binding globulin | 10.66 | down | 0.0024 |
| AA425294 | 952 | EST | 10.61 | down | 0.00083 |
| AA347674 | 753 | EST | 10.59 | down | 0.03716 |
| C20653 | 1578 | EST | 10.59 | down | 0.00001 |
| D31815 | 1648 | regucalcin (senescence marker protein-30) | 10.55 | down | 0.00037 |
| T51150 | 3136 | EST | 10.52 | down | 0.00377 |
| Y00451 | 3845 | aminolevulinate, delta-, synthase 1 | 10.52 | down | 0.00107 |
| N67893 | 2628 | EST | 10.48 | down | 0.00341 |
| T64575 | 3171 | EST | 10.46 | down | 0.00014 |
| AA150776 | 330 | EST | 10.45 | down | 0.00015 |
| R93714 | 2991 | fetuin B | 10.42 | down | 0.00043 |
| T72171 | 3205 | thyroxin-binding globulin | 10.41 | down | 0.00163 |
| S77410 | 3034 | angiotensin receptor 1 | 10.4 | down | 0 |
| N49595 | 2537 | EST | 10.39 | down | 0.00022 |
| M13143 | 2249 | kallikrein B plasma, (Fletcher factor) 1 | 10.39 | down | 0.00019 |
| W90455 | 3643 | alpha-2-macroglobulin | 10.35 | down | 0.00063 |
| H11739 | 1876 | glycine dehydrogenase (decarboxylating; glycine decarboxylase, glycine cleavage system protein P) | 10.33 | down | 0.00023 |
| T71776 | 3203 | EST | 10.3 | down | 0.00897 |
| AA454177 | 1164 | EST | 10.3 | down | 0.0008 |
| N73988 | 2682 | EST | 10.27 | down | 0.00083 |
| L27050 | 2186 | apolipoprotein F | 10.26 | down | 0.00026 |
| K02100 | 2123 | ornithine carbamoyltransferase | 10.24 | down | 0.00009 |
| AA236365 | 509 | 3-phosphoglycerate dehydrogenase | 10.23 | down | 0.00562 |
| AA010750 | 28 | calmodulin 1 (phosphorylase kinase, delta) | 10.22 | down | 0.00959 |
| R45656 | 2864 | EST | 10.21 | down | 0.00179 |
| X04325 | 3676 | gap junction protein, beta 1, 32kD (connexin 32, Charcot-Marie-Tooth neuropathy, X-linked) | 10.17 | down | 0.00061 |
| R06002 | 2762 | EST | 10.15 | down | 0.00003 |
| T82323 | 3230 | immunoglobulin superfamily, member 4 | 10.14 | down | 0 |
| AA017146 | 36 | EST | 10.1 | down | 0.00052 |
| U32989 | 3347 | tryptophan 2,3-dioxygenase | 10.07 | down | 0.02825 |
| AA035457 | 80 | EST | 10.06 | down | 0.00085 |
| N89738 | 2709 | EST | 10.06 | down | 0.00052 |
| N94930 | 2740 | multiple PDZ domain protein | 10.06 | down | 0.00226 |
| M93143 | 2422 | plasminogen-like | 10.06 | down | 0.00098 |
| AA448002 | 1113 | putative type II membrane protein | 10.05 | down | 0 |
| M11313 | 2236 | alpha-2-macroglobulin | 10.05 | down | 0.00014 |
| M23234 | 2299 | ATP-binding cassette, sub-family B (MDR/TAP), member 4 | 10.05 | down | 0 |
| W90128 | 3640 | X-box binding protein 1 | 10.04 | down | 0.00018 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| AA284795 | 678 | phosphatidylethanolamine N-methyltransferase | 10.03 | down | 0.00019 |
| T39897 | 3113 | androgen induced protein | 10 | down | 0.00466 |
| Y00318 | 3843 | I factor (complement) | 10 | down | 0.00019 |
| T51930 | 3138 | EST | 9.99 | down | 0.00066 |
| N64036 | 2606 | enoyl-Coenzyme A, hydratase/3-hydroxyacyl Coenzyme A dehydrogenase | 9.99 | down | 0.00125 |
| AA235873 | 505 | H factor (complement)-like 1,H factor 1 (complement) | 9.98 | down | 0.01667 |
| AA421561 | 933 | insulin-like growth factor 2 (somatomedin A) | 9.98 | down | 0.00007 |
| R31641 | 2813 | EST | 9.96 | down | 0.00011 |
| AA490670 | 1379 | EST | 9.96 | down | 0.00454 |
| N59543 | 2586 | PDZ domain containing 1 | 9.96 | down | 0.00052 |
| S70004 | 3028 | glycogen synthase 2 (liver) | 9.96 | down | 0.00001 |
| R08548 | 2778 | EST | 9.94 | down | 0.00326 |
| Z11793 | 3861 | selenoprotein P, plasma, 1 | 9.94 | down | 0.00021 |
| AA035638 | 82 | EST | 9.91 | down | 0.00541 |
| AA223902 | 450 | EST | 9.91 | down | 0.00003 |
| AA452855 | 1150 | lectin, mannose-binding, 1 | 9.88 | down | 0.00428 |
| AA400915 | 823 | EST | 9.84 | down | 0.00351 |
| M17466 | 2279 | coagulation factor XII (Hageman factor) | 9.76 | down | 0.00285 |
| W67147 | 3565 | deleted in liver cancer 1 | 9.74 | down | 0.00002 |
| H10779 | 1872 | methylenetetrahydrofolate dehydrogenase (NADP+ dependent), methenyltetrahydrofolate cyclohydrolase, formyltetrahydrofolate synthetase | 9.73 | down | 0.00035 |
| R98413 | 3011 | EST | 9.71 | down | 0.00007 |
| N51117 | 2543 | EST | 9.68 | down | 0.00081 |
| J04813 | 2114 | cytochrome P450, subfamily IIIA (niphedipine oxidase), polypeptide 5 | 9.67 | down | 0.0107 |
| R91503 | 2981 | ATP-binding cassette, sub-family C (CFTR/MRP), member 2 | 9.64 | down | 0.00584 |
| X02176 | 3669 | complement component 9 | 9.61 | down | 0.00004 |
| D85181 | 1750 | sterol-C5-desaturase (fungal ERG3, delta-5-desaturase)-like | 9.56 | down | 0.00005 |
| R99591 | 3015 | CD5 antigen-like (scavenger receptor cysteine rich family) | 9.52 | down | 0.00006 |
| H56584 | 1951 | 4-nitrophenylphosphatase domain and non-neuronal SNAP25-like 1 | 9.5 | down | 0 |
| H94247 | 2041 | 3-hydroxy-3-methylglutaryl-Coenzyme A synthase 2 (mitochondrial) | 9.49 | down | 0.02373 |
| D00003 | 1586 | cytochrome P450, subfamily IIIA (niphedipine oxidase), polypeptide 3 | 9.46 | down | 0.00001 |
| R67970 | 2939 | gamma-glutamyl carboxylase | 9.45 | down | 0.00212 |
| N24879 | 2459 | EST | 9.44 | down | 0.00008 |
| T86978 | 3238 | glutamate dehydrogenase 1 | 9.44 | down | 0.00006 |
| N23665 | 2454 | hydroxysteroid (17-beta) dehydrogenase 2 | 9.4 | down | 0.00055 |
| W42789 | 3512 | EST | 9.38 | down | 0.00059 |
| U02388 | 3277 | cytochrome P450, subfamily IVF, polypeptide 2 | 9.38 | down | 0.00001 |
| AA039616 | 90 | EST | 9.36 | down | 0.00009 |
| N73883 | 2681 | EST | 9.35 | down | 0 |
| X16349 | 3709 | sex hormone-binding globulin | 9.34 | down | 0.00007 |
| W61377 | 3559 | EST | 9.33 | down | 0.0012 |
| H38246 | 1917 | EST | 9.25 | down | 0.00157 |
| D16626 | 1622 | histidine ammonia-lyase | 9.25 | down | 0.00025 |
| W87606 | 3632 | protein Z, vitamin K-dependent plasma glycoprotein | 9.23 | down | 0.00085 |
| AA312946 | 731 | EST | 9.21 | down | 0.00106 |
| R98074 | 3009 | EST | 9.21 | down | 0.00048 |
| R64199 | 2932 | SEC22, vesicle trafficking protein (*S. cerevisiae*)-like 1 | 9.19 | down | 0.00387 |
| AA419608 | 925 | EST | 9.19 | down | 0.00005 |
| AA459690 | 1221 | EST | 9.18 | down | 0.00732 |
| N72695 | 2670 | EST | 9.18 | down | 0.00069 |
| U49082 | 3372 | transporter protein | 9.17 | down | 0.00088 |
| AA291323 | 699 | BCL2-interacting killer (apoptosis-inducing) | 9.15 | down | 0.00514 |
| M25079 | 2305 | hemoglobin, beta | 9.15 | down | 0.01399 |
| AA430028 | 1008 | EST | 9.14 | down | 0.00246 |
| W55903 | 3543 | adipose differentiation-related protein; adipophilin | 9.12 | down | 0.00459 |
| AA083812 | 175 | DKFZP566F123 protein | 9.11 | down | 0.00167 |
| R40899 | 2843 | glycine receptor, beta | 9.11 | down | 0.0009 |
| AA099391 | 207 | myosin, light polypeptide kinase | 9.07 | down | 0.00003 |
| AA287566 | 690 | KIAA0187 gene product | 9.07 | down | 0.00013 |
| AA233369 | 471 | histidine ammonia-lyase | 9.06 | down | 0.0008 |
| AA443658 | 1079 | transmembrane 7 superfamily member 2 | 9.06 | down | 0.00048 |
| M14218 | 2259 | argininosuccinate lyase | 9.03 | down | 0.00078 |
| W44745 | 3517 | EST | 9.02 | down | 0.00276 |
| AA479968 | 1321 | arylsulfatase A | 9.01 | down | 0.00224 |
| AA193204 | 402 | Arg/Abl-interacting protein ArgBP2 | 8.98 | down | 0.00861 |
| D14664 | 1616 | KIAA0022 gene product | 8.98 | down | 0.00001 |
| Y00317 | 3842 | UDP glycosyltransferase 2 family, polypeptide B4 | 8.97 | down | 0.00025 |
| AA480975 | 1322 | EST | 8.95 | down | 0.00259 |
| AA282061 | 652 | KIAA0962 protein | 8.95 | down | 0.01033 |
| R32490 | 2817 | EST | 8.95 | down | 0.00215 |
| R40492 | 2841 | EST | 8.89 | down | 0.00229 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| N67876 | 2627 | insulin-like growth factor 1 (somatomedin C) | 8.89 | down | 0.00042 |
| T72502 | 3207 | EST | 8.87 | down | 0.00009 |
| T58032 | 3152 | 3-hydroxyanthranilate 3,4-dioxygenase | 8.86 | down | 0.00023 |
| AA487503 | 1356 | EST | 8.85 | down | 0.00012 |
| N94367 | 2739 | EST | 8.79 | down | 0.01003 |
| C21130 | 1583 | EST | 8.79 | down | 0.00008 |
| Z84721 | 3950 | hemoglobin, zeta | 8.77 | down | 0.01446 |
| AA609537 | 1483 | hepatic leukemia factor | 8.76 | down | 0.00018 |
| AA489798 | 1373 | hypothetical protein, estradiol-induced | 8.75 | down | 0.00544 |
| N32071 | 2490 | EST | 8.75 | down | 0.00006 |
| AA236796 | 517 | follistatin | 8.74 | down | 0.00862 |
| M37400 | 2348 | glutamic-oxaloacetic transaminase 1, soluble (aspartate aminotransferase 1) | 8.7 | down | 0.0004 |
| T90520 | 3248 | EST | 8.67 | down | 0.00072 |
| H59136 | 1962 | EST | 8.64 | down | 0.00013 |
| T78433 | 3219 | glycogen synthase 2 (liver) | 8.62 | down | 0.00072 |
| N81025 | 2704 | EST | 8.61 | down | 0.00015 |
| T66189 | 3177 | glutaryl-Coenzyme A dehydrogenase | 8.61 | down | 0.00003 |
| AA405819 | 865 | KIAA0668 protein | 8.59 | down | 0.02034 |
| AA480991 | 1323 | EST | 8.59 | down | 0.00156 |
| AA488843 | 1362 | cornichon-like | 8.58 | down | 0.02131 |
| AA521292 | 1422 | EST | 8.58 | down | 0.00064 |
| AA598417 | 1426 | UDP-N-acetylglucosamine-2-epimerase/N-acetylmannosamine kinase | 8.56 | down | 0.01638 |
| AA010619 | 27 | EST | 8.55 | down | 0.00057 |
| H95978 | 2052 | EST | 8.55 | down | 0.00046 |
| AA477978 | 1294 | short-chain dehydrogenase/reductase 1 | 8.53 | down | 0.01651 |
| AA491001 | 1386 | EST | 8.52 | down | 0.01118 |
| J05158 | 2117 | carboxypeptidase N, polypeptide 2, 83kD | 8.52 | down | 0 |
| AA112101 | 222 | EST | 8.5 | down | 0.00004 |
| X17094 | 3714 | paired basic amino acid cleaving enzyme (furin, membrane associated receptor protein) | 8.5 | down | 0 |
| AA101235 | 214 | EST | 8.46 | down | 0.00822 |
| X54380 | 3727 | pregnancy-zone protein | 8.44 | down | 0.00059 |
| AA406126 | 869 | EST | 8.43 | down | 0.00569 |
| M96843 | 2434 | EST | 8.42 | down | 0.02394 |
| N99542 | 2746 | orosomucoid 1 | 8.41 | down | 0.00001 |
| AA428325 | 988 | EST | 8.36 | down | 0.00002 |
| AA430011 | 1006 | EST | 8.35 | down | 0.00729 |
| AA182030 | 387 | EST | 8.32 | down | 0.00018 |
| W61378 | 3560 | EST | 8.31 | down | 0 |
| W03796 | 3467 | EST | 8.3 | down | 0.0032 |
| X60673 | 3749 | adenylate kinase 3 | 8.3 | down | 0.00016 |
| F08817 | 1796 | EST | 8.29 | down | 0.0077 |
| X15422 | 3705 | mannose-binding lectin (protein C) 2, soluble (opsonic defect) | 8.29 | down | 0.00015 |
| AA398423 | 795 | EST | 8.26 | down | 0.00063 |
| AA412063 | 895 | EST | 8.26 | down | 0.00001 |
| AA458652 | 1202 | EST | 8.26 | down | 0.00001 |
| AA126722 | 251 | O-6-methylguanine-DNA methyltransferase | 8.26 | down | 0.002 |
| R96822 | 2999 | EST | 8.25 | down | 0.00008 |
| R38709 | 2832 | superoxide dismultase 2, mitochondrial | 8.23 | down | 0.01578 |
| AA397841 | 780 | EST | 8.21 | down | 0 |
| Z40259 | 3916 | EST | 8.18 | down | 0.00002 |
| AA125831 | 241 | myosin, light polypeptide kinase | 8.18 | down | 0.00039 |
| D49387 | 1666 | NADP dependent leukotriene b4 12-hydroxydehydrogenase | 8.17 | down | 0.00972 |
| M58286 | 2360 | tumor necrosis factor receptor superfamily, member 1A | 8.15 | down | 0.00037 |
| W26769 | 3482 | CGI-86 protein | 8.14 | down | 0.00204 |
| AA609519 | 1482 | EST | 8.13 | down | 0.00009 |
| F10276 | 1814 | dual specificity phosphatase 6 | 8.13 | down | 0.0001 |
| R10378 | 2785 | fibrinogen-like 1 | 8.13 | down | 0.00189 |
| AA257057 | 586 | EST | 8.11 | down | 0.00379 |
| D52097 | 1682 | prostatic binding protein | 8.1 | down | 0.00141 |
| X76717 | 3794 | metallothionein 1L | 8.09 | down | 0.00025 |
| AA447971 | 1110 | EST | 8.08 | down | 0.00035 |
| AA486410 | 1348 | aldehyde dehydrogenase 5 family, member A1 (succinate-semialdehyde dehydrogenase) | 8.08 | down | 0.00485 |
| N34804 | 2496 | DKFZP434J214 protein | 8.08 | down | 0.00028 |
| AA167565 | 362 | EST | 8.08 | down | 0.00046 |
| AA234095 | 478 | EST | 8.08 | down | 0.00394 |
| AA489629 | 1369 | EST | 8.08 | down | 0.00109 |
| AA412481 | 902 | EST | 8.07 | down | 0.00014 |
| N52271 | 2551 | LIM protein (similar to rat protein kinase C-binding enigma) | 8.06 | down | 0.00011 |
| N94146 | 2738 | EST | 8.05 | down | 0 |
| AA004521 | 8 | prostate cancer overexpressed gene 1 | 8.03 | down | 0.00027 |
| R49035 | 2876 | EST | 8.02 | down | 0.00991 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| M59815 | 2364 | complement component 4A | 8.02 | down | 0.00049 |
| HG3044–HT3742 | | fibronectin 1 | 8.02 | down | 0.02094 |
| AA007629 | 19 | EST | 8.01 | down | 0.00001 |
| W33167 | 3498 | EST | 8.01 | down | 0.00026 |
| H98771 | 2069 | BCL2/adenovirus E1B 19kD-interacting protein 3 | 8 | down | 0.0018 |
| AA450127 | 1132 | growth arrest and DNA-damage-inducible, beta | 7.98 | down | 0.00078 |
| AA609316 | 1481 | EGF-like-domain, multiple 5 | 7.97 | down | 0.00011 |
| W87454 | 3629 | homogentisate 1,2-dioxygenase (homogentisate oxidase) | 7.93 | down | 0.00149 |
| N63698 | 2603 | EST | 7.92 | down | 0.00001 |
| Z24725 | 3867 | mitogen inducible 2 | 7.9 | down | 0 |
| Z30425 | 3875 | nuclear receptor subfamily 1, group I, member 3 | 7.88 | down | 0.00006 |
| F03969 | 1785 | matrix metalloproteinase 2 (gelatinase A, 72kD gelatinase, 72kD type IV collagenase) | 7.87 | down | 0.00014 |
| X68733 | 3778 | alpha-1-antichymotrypsin | 7.87 | down | 0.03266 |
| AA599211 | 1445 | short-chain dehydrogenase/reductase 1 | 7.85 | down | 0.00911 |
| AA079758 | 174 | solute carrier family 25 (mitochondrial carrier; citrate transporter), member 1 | 7.83 | down | 0.00359 |
| AA398124 | 787 | growth factor receptor-bound protein 14 | 7.82 | down | 0.00009 |
| AA416873 | 908 | EST | 7.82 | down | 0.00005 |
| M61853 | 2369 | cytochrome P450, subfamily IIC (mephenytoin 4-hydroxylase), polypeptide 18 | 7.82 | down | 0.00024 |
| W95795 | 3662 | EST | 7.8 | down | 0.00359 |
| R69417 | 2941 | EST | 7.79 | down | 0.03795 |
| AA430044 | 1010 | EST | 7.78 | down | 0.00124 |
| AA460449 | 1228 | EST | 7.77 | down | 0.00011 |
| R73485 | 2957 | EST | 7.77 | down | 0.0009 |
| W20467 | 3479 | EST | 7.76 | down | 0.00008 |
| AA481432 | 1328 | fibronectin 1 | 7.76 | down | 0.0061 |
| L29433 | 2191 | coagulation factor X | 7.74 | down | 0.00244 |
| AA261954 | 604 | EST | 7.69 | down | 0.00334 |
| T16484 | 3070 | EST | 7.69 | down | 0.00805 |
| AA443272 | 1074 | EST | 7.68 | down | 0.00869 |
| AA282516 | 660 | 7-dehydrocholesterol reductase | 7.67 | down | 0.0008 |
| AA459668 | 1219 | 3-hydroxyisobutyryl-Coenzyme A hydrolase | 7.62 | down | 0.00225 |
| AA431773 | 1026 | EST | 7.61 | down | 0.00063 |
| X92720 | 3823 | phosphoenolpyruvate carboxykinase 2 (mitochondrial) | 7.6 | down | 0.00001 |
| AA142849 | 306 | EST | 7.59 | down | 0.00804 |
| W90766 | 3646 | EST | 7.58 | down | 0.00057 |
| N40320 | 2513 | EST | 7.56 | down | 0.01584 |
| AA410255 | 882 | EST | 7.56 | down | 0.00043 |
| T72906 | 3209 | EST | 7.56 | down | 0.00062 |
| M65292 | 2386 | H factor (complement)-like 1,H factor 1 (complement) | 7.56 | down | 0.01152 |
| R59221 | 2911 | progesterone binding protein | 7.54 | down | 0.00159 |
| N77326 | 2695 | EST | 7.51 | down | 0.00542 |
| AA400864 | 821 | EST | 7.51 | down | 0.02237 |
| HG2379–HT3996 | | serine hydroxymethyltransferase 1 (soluble) | 7.49 | down | 0.00093 |
| AA234634 | 486 | CCAAT/enhancer binding protein (C/EBP), delta | 7.48 | down | 0.03318 |
| AA435777 | 1047 | solute carrier family 25 (mitochondrial carrier; citrate transporter), member 1 | 7.48 | down | 0.00613 |
| W73889 | 3591 | tetranectin (plasminogen-binding protein) | 7.45 | down | 0.00091 |
| X67491 | 3773 | glutamate dehydrogenase 1 | 7.45 | down | 0.00019 |
| AA292773 | 713 | collagen, type XVIII, alpha 1 | 7.44 | down | 0.00158 |
| U95090 | 3463 | nephrosis 1, congenital, Finnish type (nephrin) | 7.44 | down | 0.00004 |
| M65131 | 2384 | methylmalonyl Coenzyme A mutase | 7.44 | down | 0.00004 |
| AA398892 | 800 | similar to yeast BET3 (S. cerevisiae) | 7.43 | down | 0.00038 |
| AA621274 | 1519 | EST | 7.43 | down | 0.00065 |
| T72268 | 3206 | B-factor, properdin | 7.43 | down | 0.01197 |
| AA010205 | 23 | EST | 7.41 | down | 0 |
| R32440 | 2816 | EST | 7.41 | down | 0.00159 |
| N63391 | 2599 | EST | 7.39 | down | 0.00565 |
| M22976 | 2297 | cytochrome b-5 | 7.39 | down | 0.02431 |
| U08854 | 3292 | UDP glycosyltransferase 2 family, polypeptide B15 | 7.38 | down | 0.00005 |
| M12712 | 2246 | protein C (inactivator of coagulation factors Va and VIIIa) | 7.37 | down | 0.01866 |
| AA256341 | 578 | EST | 7.37 | down | 0.00091 |
| AA256171 | 575 | EST | 7.34 | down | 0.04562 |
| AA436489 | 1053 | EST | 7.34 | down | 0.001 |
| AA099225 | 206 | EST | 7.33 | down | 0.00062 |
| T77729 | 3217 | pyruvate carboxylase | 7.29 | down | 0.00022 |
| AA191310 | 397 | protein phosphatase 2 (formerly 2A), regulatory subunit A (PR 65), beta isoform | 7.28 | down | 0 |
| AA497052 | 1408 | DKFZP727G051 protein | 7.28 | down | 0.01745 |
| W85847 | 3616 | EST | 7.28 | down | 0.00024 |
| AA344866 | 752 | complement component 8, gamma polypeptide | 7.28 | down | 0.00206 |
| L11931 | 2159 | serine hydroxymethyltransferase 1 (soluble) | 7.27 | down | 0.00041 |
| AA429904 | 1005 | EST | 7.26 | down | 0.00524 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| T23986 | 3085 | hydroxacyl glutathione hydrolase; glyoxalase 2 | 7.26 | down | 0.0062 |
| AA459420 | 1217 | EST | 7.25 | down | 0.0214 |
| W94942 | 3658 | dual specificity phosphatase 10 | 7.23 | down | 0.00137 |
| L00972 | 2133 | cystathionine-beta-synthase | 7.19 | down | 0.00008 |
| R48307 | 2869 | EST | 7.18 | down | 0.00007 |
| AA442334 | 1069 | EST | 7.15 | down | 0.00018 |
| AA243582 | 529 | hemoglobin, gamma A | 7.15 | down | 0.0021 |
| AA437235 | 1060 | EST | 7.15 | down | 0.01455 |
| N67378 | 2625 | KIAA1053 protein | 7.14 | down | 0 |
| AA047151 | 116 | EST | 7.13 | down | 0.00007 |
| R02572 | 2756 | fibronectin 1 | 7.1 | down | 0.00059 |
| M63509 | 2376 | glutathione S-transferase M1,glutathione S-transferase M2 (muscle),glutathione S-transferase M4 | 7.06 | down | 0.03887 |
| U49248 | 3373 | ATP-binding cassette, sub-family C (CFTR/MRP), member 2 | 7.06 | down | 0.00067 |
| D90042 | 1767 | N-acetyltransferase 2 (arylamine N-acetyltransferase) | 7.06 | down | 0 |
| T67231 | 3180 | succinate dehydrogenase complex, subunit D, integral membrane protein | 7.04 | down | 0.03554 |
| AA293327 | 716 | isocitrate dehydrogenase 1 (NADP+), soluble | 7.04 | down | 0.04377 |
| X02750 | 3670 | protein C (inactivator of coagulation factors Va and VIIIa) | 7.04 | down | 0.00079 |
| AA460661 | 1229 | EST | 7.02 | down | 0.00053 |
| W28798 | 3491 | phosphodiesterase 6A, cGMP-specific, rod, alpha | 7.01 | down | 0.00017 |
| AA428900 | 992 | EST | 7.01 | down | 0.00037 |
| R33146 | 2818 | EST | 7 | down | 0.00043 |
| AA404352 | 850 | EST | 7 | down | 0.00059 |
| L40401 | 2211 | putative protein | 6.97 | down | 0.00079 |
| M31627 | 2330 | X-box binding protein 1 | 6.97 | down | 0.00052 |
| AA608802 | 1470 | EST | 6.95 | down | 0.00263 |
| AA285053 | 681 | EST | 6.95 | down | 0.00125 |
| N59474 | 2583 | EST | 6.93 | down | 0.00337 |
| AA258567 | 597 | EST | 6.92 | down | 0.00096 |
| N91087 | 2716 | EST | 6.91 | down | 0.00109 |
| N81036 | 2705 | EST | 6.89 | down | 0.00276 |
| H73535 | 1996 | EST | 6.89 | down | 0.00202 |
| Y00339 | 3844 | carbonic anhydrase II | 6.89 | down | 0 |
| AA057678 | 143 | EST | 6.88 | down | 0.00078 |
| AA609934 | 1493 | EST | 6.84 | down | 0.00048 |
| AA342446 | 748 | insulin receptor | 6.83 | down | 0.00412 |
| H06935 | 1855 | electron-transferring-flavoprotein dehydrogenase | 6.82 | down | 0.00105 |
| H27442 | 1910 | erythrocyte membrane protein band 7.2 (stomatin) | 6.81 | down | 0.00083 |
| D79276 | 1722 | succinate-CoA ligase, GDP-forming, beta subunit | 6.8 | down | 0.00047 |
| AA609164 | 1480 | cytochrome b-561 | 6.8 | down | 0.02298 |
| W27023 | 3484 | neuroendocrine-specific protein C like (foocen) | 6.79 | down | 0.00805 |
| N78902 | 2699 | leptin receptor | 6.79 | down | 0.0041 |
| X95715 | 3832 | ATP-binding cassette, sub-family C (CFTR/MRP), member 6 | 6.78 | down | 0.00045 |
| T95515 | 3260 | KIAA0249 gene product | 6.77 | down | 0.0001 |
| H69138 | 1986 | v-Ki-ras2 Kirsten rat sarcoma 2 viral oncogene homolog | 6.76 | down | 0.00142 |
| U68233 | 3411 | nuclear receptor subfamily 1, group H, member 4 | 6.76 | down | 0.00022 |
| AA143019 | 309 | EST | 6.75 | down | 0.00109 |
| T71021 | 3201 | EST | 6.74 | down | 0.0017 |
| M91432 | 2419 | acyl-Coenzyme A dehydrogenase, C-4 to C-12 straight chain | 6.74 | down | 0.00008 |
| AA205724 | 426 | EST | 6.73 | down | 0.00027 |
| N59532 | 2584 | aminomethyltransferase (glycine cleavage system protein T) | 6.73 | down | 0.00005 |
| T63364 | 3169 | ficolin (collagen/fibrinogen domain-containing) 3 (Hakata antigen) | 6.72 | down | 0.00383 |
| AA044755 | 104 | EST | 6.7 | down | 0.01228 |
| D59554 | 1698 | EST | 6.7 | down | 0 |
| H66367 | 1977 | EST | 6.68 | down | 0.0001 |
| X68277 | 3774 | dual specificity phosphatase 1 | 6.68 | down | 0.0036 |
| R50008 | 2886 | 7-dehydrocholesterol reductase | 6.67 | down | 0.00409 |
| D20974 | 1581 | Vanin 1 | 6.66 | down | 0.00272 |
| R82074 | 2973 | syndecan 1 | 6.66 | down | 0.01336 |
| M14058 | 2256 | complement component 1, r subcomponent | 6.66 | down | 0.00229 |
| AA400979 | 825 | calcitonin receptor-like receptor activity modifying protein 3 | 6.65 | down | 0.01051 |
| U03056 | 3279 | hyaluronoglucosaminidase 1 | 6.64 | down | 0 |
| AA215919 | 443 | F-box protein 7 | 6.62 | down | 0.00921 |
| AA426304 | 962 | EST | 6.61 | down | 0.01092 |
| AA251114 | 539 | prostate cancer overexpressed gene 1 | 6.6 | down | 0.00039 |
| T60407 | 3160 | EST | 6.6 | down | 0.00167 |
| AA416890 | 909 | sphingomyelin phosphodiesterase 1, acid lysosomal (acid sphingomyelinase) | 6.6 | down | 0.00112 |
| AA235233 | 493 | EST | 6.59 | down | 0.00755 |
| H04854 | 1842 | interleukin 1 receptor accessory protein | 6.58 | down | 0.00007 |
| M16447 | 2270 | quinoid dihydropteridine reductase | 6.57 | down | 0.00015 |
| C20911 | 1580 | antithrombin III | 6.56 | down | 0.00175 |
| N70861 | 2660 | EST | 6.55 | down | 0.00001 |
| AA010360 | 24 | EST | 6.55 | down | 0.00027 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| D00632 | 1591 | glutathione peroxidase 3 (plasma) | 6.55 | down | 0.00121 |
| T69009 | 3191 | quinoid dihydropteridine reductase | 6.54 | down | 0.00145 |
| M13829 | 2254 | v-raf murine sarcoma 3611 viral oncogene homolog 1 | 6.52 | down | 0 |
| M72885 | 2392 | putative lymphocyte G0/G1 switch gene | 6.5 | down | 0.03461 |
| AA172372 | 370 | EST | 6.48 | down | 0.00344 |
| D14695 | 1618 | KIAA0025 gene product; MMS-inducible gene | 6.48 | down | 0 |
| AA253129 | 560 | F-box protein FBL11 | 6.47 | down | 0.00001 |
| T03651 | 3046 | tubulin, beta polypeptide | 6.47 | down | 0.00843 |
| M94065 | 2424 | dihydroorotate dehydrogenase | 6.47 | down | 0.00013 |
| M35410 | 2344 | insulin-like growth factor binding protein 2 (36kD) | 6.45 | down | 0.04517 |
| Z40305 | 3917 | EST | 6.45 | down | 0.00001 |
| D60856 | 1705 | UDP-glucose dehydrogenase | 6.45 | down | 0.01222 |
| AA195657 | 419 | EST | 6.44 | down | 0.00016 |
| H05985 | 1851 | hypothetical protein | 6.43 | down | 0.04887 |
| AA281440 | 644 | EST | 6.43 | down | 0.01246 |
| W26996 | 3483 | EST | 6.42 | down | 0.00005 |
| U90544 | 3453 | solute carrier family 17 (sodium phosphate), member 2 | 6.42 | down | 0.00023 |
| M64590 | 2381 | glycine dehydrogenase (decarboxylating; glycine decarboxylase, glycine cleavage system protein P) | 6.41 | down | 0.00002 |
| H68953 | 1985 | transferrin | 6.4 | down | 0.00132 |
| M20218 | 2288 | coagulation factor XI (plasma thromboplastin antecedent) | 6.4 | down | 0.00004 |
| U26173 | 3334 | nuclear factor, interleukin 3 regulated | 6.4 | down | 0.00001 |
| Z29481 | 3874 | 3-hydroxyanthranilate 3,4-dioxygenase | 6.39 | down | 0.00029 |
| AA410523 | 886 | EST | 6.37 | down | 0.03506 |
| AA447549 | 1101 | UDP-N-acteylglucosamine pyrophosphorylase 1; Sperm associated antigen 2 | 6.37 | down | 0.02815 |
| X85116 | 3811 | erythrocyte membrane protein band 7.2 (stomatin) | 6.37 | down | 0.00356 |
| W72079 | 3578 | EST | 6.36 | down | 0.00641 |
| AA621209 | 1516 | similar to Caenorhabditis elegans protein C42C1.9 | 6.34 | down | 0.00144 |
| W68721 | 3569 | cleft lip and palate associated transmembrane protein 1 | 6.32 | down | 0.00063 |
| R38185 | 2828 | EST | 6.31 | down | 0.0227 |
| H41084 | 1924 | EST | 6.28 | down | 0.01233 |
| AA426609 | 968 | EST | 6.28 | down | 0.00549 |
| H05974 | 1850 | EST | | | |
| X83618 | 3810 | 3-hydroxy-3-methylglutaryl-Coenzyme A synthase 2 (mitochondrial) | 6.27 | down | 0.02099 |
| AA431337 | 1020 | EST | 6.26 | down | 0.00053 |
| AA234817 | 490 | EST | 6.22 | down | 0.00099 |
| AA398102 | 786 | KIAA0429 gene product | 6.22 | down | 0.00396 |
| AA481670 | 1330 | retinal short-chain dehydrogenase/reductase retSDR2 | 6.2 | down | 0.0078 |
| AA608837 | 1472 | EST | 6.2 | down | 0.00006 |
| N64535 | 2609 | EST | 6.19 | down | 0.00106 |
| AA234527 | 483 | nuclear receptor subfamily 3, group C, member 1 | 6.19 | down | 0.00864 |
| M10942 | 2233 | metallothionein 1E (functional) | 6.19 | down | 0.00428 |
| W42996 | 3514 | EST | 6.18 | down | 0.00587 |
| Z47553 | 3936 | flavin containing monooxygenase 5 | 6.17 | down | 0.00011 |
| N36001 | 2503 | EST | 6.16 | down | 0.00222 |
| N27670 | 2473 | progesterone membrane binding protein | 6.15 | down | 0.00321 |
| N75203 | 2690 | EST | 6.15 | down | 0.00181 |
| R06271 | 2765 | EST | 6.14 | down | 0.00063 |
| R40946 | 2844 | crystallin, zeta (quinone reductase) | 6.14 | down | 0.00156 |
| U66674 | 3407 | ATP-binding cassette, sub-family C (CFTR/MRP), member 3 | 6.13 | down | 0.00127 |
| D82061 | 1741 | Ke6 gene, mouse, human homolog of | 6.1 | down | 0.00104 |
| R06977 | 2774 | glucokinase (hexokinase 4) regulatory protein | 6.1 | down | 0.00049 |
| W87781 | 3633 | EST | 6.1 | down | 0.00045 |
| M15465 | 2266 | pyruvate kinase, liver and RBC | 6.1 | down | 0.00069 |
| AA609773 | 1489 | EST | 6.09 | down | 0.01103 |
| AA197311 | 422 | intercellular adhesion molecule 1 (CD54), human rhinovirus receptor | 6.07 | down | 0.00053 |
| M13690 | 2252 | complement component 1 inhibitor (angioedema, hereditary) | 6.07 | down | 0.00045 |
| R48540 | 2872 | EST | 6.05 | down | 0.00086 |
| AA453770 | 1157 | EST | 6.04 | down | 0.00524 |
| AA455097 | 1172 | EST | 6.03 | down | 0.00419 |
| D82422 | 1745 | ferroportin 1; iron regulated gene 1 | 6.01 | down | 0.02351 |
| F13702 | 1826 | EST | 6.01 | down | 0.00064 |
| M83652 | 2407 | properdin P factor, complement | 6 | down | 0.00002 |
| L11708 | 2158 | hydroxysteroid (17-beta) dehydrogenase 2 | 5.99 | down | 0.01516 |
| H71861 | 1993 | glucan (1,4-alpha-), branching enzyme 1 (glycogen branching enzyme, Andersen disease, glycogen storage disease type IV) | 5.97 | down | 0.00007 |
| X97324 | 3836 | adipose differentiation-related protein; adipophilin | 5.97 | down | 0.04638 |
| AA157799 | 348 | aldo-keto reductase family 7, member A2 (aflatoxin aldehyde reductase) | 5.96 | down | 0 |
| M35590 | 2345 | small inducible cytokine A4 | 5.96 | down | 0.00604 |
| H02855 | 1832 | EST | 5.96 | down | 0.00458 |
| C16420 | 1576 | EST | 5.95 | down | 0.00119 |
| X07767 | 3691 | protein kinase, cAMP-dependent, catalytic, alpha | 5.94 | down | 0.00028 |
| AA045870 | 108 | EST | 5.93 | down | 0.00017 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| Z80345 | 3948 | acyl-Coenzyme A dehydrogenase, C-2 to C-3 short chain | 5.93 | down | 0.0024 |
| N93764 | 2736 | EST | 5.92 | down | 0.0109 |
| AA031543 | 68 | translocation protein 1 | 5.92 | down | 0.00405 |
| AA620667 | 1506 | protein tyrosine phosphatase type IVA, member 1 | 5.92 | down | 0.00206 |
| M59499 | 2363 | tissue factor pathway inhibitor (lipoprotein-associated coagulation inhibitor) | 5.92 | down | 0.0005 |
| X91148 | 3818 | microsomal triglyceride transfer protein (large polypeptide, 88kD) | 5.91 | down | 0.00045 |
| R09053 | 2782 | EST | 5.9 | down | 0.0002 |
| Z39476 | 3905 | EST | 5.9 | down | 0.00687 |
| AA233347 | 470 | zinc finger protein 216 | 5.9 | down | 0.0041 |
| M13232 | 2251 | coagulation factor VII (serum prothrombin conversion accelerator) | 5.9 | down | 0.00014 |
| T69384 | 3197 | period (Drosophila) homolog 1 | 5.88 | down | 0.01219 |
| D51279 | 1679 | ovarian granulosa cell protein (13kD) | 5.88 | down | 0.01271 |
| M64554 | 2380 | coagulation factor XIII, B polypeptide | 5.87 | down | 0.00011 |
| C02099 | 1560 | CGI-131 protein | 5.85 | down | 0.02377 |
| Y08409 | 3851 | thyroid hormone responsive SPOT14 (rat) homolog | 5.84 | down | 0.00455 |
| H99727 | 2080 | adipose differentiation-related protein; adipophilin | 5.83 | down | 0.04346 |
| L13278 | 2163 | crystallin, zeta (quinone reductase) | 5.83 | down | 0.0034 |
| S77356 | 3033 | EST | 5.83 | down | 0.00122 |
| M16474 | 2271 | butyrylcholinesterase | 5.82 | down | 0.00113 |
| U32576 | 3346 | apolipoprotein C-IV | 5.81 | down | 0.04343 |
| D37931 | 1650 | ribonuclease, RNase A family, 4 | 5.81 | down | 0.00836 |
| AA446587 | 1091 | EST | 5.8 | down | 0.00012 |
| R93908 | 2993 | EST | 5.8 | down | 0.02699 |
| AA086201 | 185 | EST | 5.8 | down | 0.00012 |
| AA164586 | 359 | estrogen receptor 1 | 5.8 | down | 0.00182 |
| AF007216 | 1550 | solute carrier family 4, sodium bicarbonate cotransporter, member 4 | 5.79 | down | 0.00005 |
| AA479498 | 1314 | EST | 5.78 | down | 0.01489 |
| AA424813 | 948 | EST | 5.77 | down | 0.00503 |
| H03348 | 1833 | claudin 1 | 5.77 | down | 0.0001 |
| R62173 | 2923 | UDP-glucose dehydrogenase | 5.76 | down | 0.0006 |
| Z39976 | 3912 | EST | 5.76 | down | 0.00012 |
| AA219039 | 446 | EST | 5.76 | down | 0.00053 |
| AA608751 | 1469 | EST | 5.76 | down | 0.01404 |
| T95064 | 3259 | EST | 5.75 | down | 0.00604 |
| H09364 | 1867 | succinate dehydrogenase complex, subunit A, flavoprotein (Fp) | 5.74 | down | 0.03125 |
| T90841 | 3250 | EST | 5.74 | down | 0.01876 |
| T03441 | 3043 | cytochrome b-561 | 5.74 | down | 0.02781 |
| AA424307 | 944 | EST | 5.73 | down | 0.0074 |
| AA398386 | 793 | EST | 5.71 | down | 0.00007 |
| R43910 | 2851 | EST | 5.71 | down | 0 |
| U12778 | 3300 | acyl-Coenzyme A dehydrogenase, short/branched chain | 5.68 | down | 0.00116 |
| AA255903 | 573 | CD39-like 4 | 5.67 | down | 0.01687 |
| AA252289 | 552 | quinolinate phosphoribosyltransferase (nicotinate-nucleotide pyrophosphorylase (carboxylating)) | 5.66 | down | 0.01389 |
| AA262766 | 609 | EST | 5.66 | down | 0.03832 |
| T64887 | 3172 | protein phosphatase 5, catalytic subunit | 5.66 | down | 0.00349 |
| D11802 | 1597 | angiotensinogen | 5.65 | down | 0.00009 |
| D45714 | 1664 | EST | 5.64 | down | 0.00384 |
| U70732 | 3414 | glutamic-pyruvate transaminase (alanine aminotransferase) | 5.64 | down | 0.00146 |
| H88675 | 2022 | EST | 5.63 | down | 0.00554 |
| AA442342 | 1070 | EST | 5.62 | down | 0.00052 |
| T79863 | 3225 | EST | 5.62 | down | 0.00074 |
| AA454733 | 1169 | EST | 5.61 | down | 0.01182 |
| W72972 | 3584 | EST | 5.61 | down | 0.00939 |
| N95495 | 2741 | EST | 5.61 | down | 0.00308 |
| J03764 | 2097 | plasminogen activator inhibitor, type I | 5.6 | down | 0.02196 |
| L07956 | 2148 | glucan (1,4-alpha-), branching enzyme 1 (glycogen branching enzyme, Andersen disease, glycogen storage disease type IV) | 5.6 | down | 0.00029 |
| AA090439 | 192 | ribosomal protein S6 | 5.58 | down | 0.00501 |
| AA419507 | 924 | EST | 5.58 | down | 0.00578 |
| AA236982 | 520 | sterol carrier protein 2 | 5.56 | down | 0.01542 |
| L35546 | 2203 | glutamate-cysteine ligase (gamma-glutamylcysteine synthetase), regulatory (30.8kD) | 5.56 | down | 0.0005 |
| M16967 | 2275 | coagulation factor V (proaccelerin, labile factor) | 5.56 | down | 0.00047 |
| AB002328 | 1536 | calcineurin binding protein 1 | 5.55 | down | 0.00016 |
| AA450281 | 1134 | EST | 5.55 | down | 0.00004 |
| W47175 | 3531 | 3-prime-phosphoadenosine 5-prime-phosphosulfate synthase 2 | 5.54 | down | 0.00914 |
| N52845 | 2553 | EST | 5.53 | down | 0.00088 |
| AA425782 | 956 | KIAA0874 protein | 5.52 | down | 0.03433 |
| R10684 | 2787 | EST | 5.51 | down | 0.00741 |
| AA436926 | 1059 | EST | 5.5 | down | 0.00984 |
| AA452598 | 1148 | genethonin 1 | 5.49 | down | 0.00163 |
| D11756 | 1596 | EST | 5.49 | down | 0.01272 |
| AA223335 | 449 | propionyl Coenzyme A carboxylase, beta polypeptide | 5.49 | down | 0.02761 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| D87436 | 1761 | KIAA0249 gene product | 5.49 | down | 0.00333 |
| J04080 | 2105 | complement component 1, s subcomponent | 5.48 | down | 0.0239 |
| X65962 | 3766 | cytochrome P450, subfamily IIC (mephenytoin 4-hydroxylase) | 5.47 | down | 0.00014 |
| AA443822 | 1082 | EST | 5.46 | down | 0.02538 |
| AA485089 | 1341 | EST | 5.46 | down | 0.00044 |
| AA032048 | 72 | EST | 5.45 | down | 0.00383 |
| AA400471 | 816 | EST | 5.45 | down | 0.0056 |
| AA490159 | 1374 | glucose-6-phosphatase, transport (glucose-6-phosphate) protein 1 | 5.44 | down | 0 |
| M12174 | 2242 | ras homolog gene family, member B | 5.44 | down | 0.0088 |
| U11313 | 3296 | sterol carrier protein 2 | 5.44 | down | 0.00187 |
| N65959 | 2611 | EST | 5.43 | down | 0.00044 |
| AA482594 | 1337 | EST | 5.42 | down | 0.00387 |
| AA455865 | 1180 | phosphatidylinositol glycan, class B | 5.41 | down | 0.00004 |
| N23761 | 2456 | DKFZP586G011 protein | 5.41 | down | 0.00448 |
| U49352 | 3374 | 2,4-dienoyl CoA reductase 1, mitochondrial | 5.41 | down | 0.02371 |
| R63545 | 2926 | EST | 5.4 | down | 0.00202 |
| AA258308 | 590 | EST | 5.4 | down | 0.00023 |
| R34362 | 2821 | KIAA0327 gene product | 5.4 | down | 0.04615 |
| AA621192 | 1515 | EST | 5.39 | down | 0.0016 |
| T69020 | 3192 | EST | 5.39 | down | 0.00383 |
| AA598679 | 1434 | EST | 5.37 | down | 0.00467 |
| R43365 | 2849 | EST | 5.37 | down | 0.00103 |
| AA455987 | 1183 | EST | 5.36 | down | 0.00029 |
| C01257 | 1554 | EST | 5.35 | down | 0.00608 |
| D31716 | 1647 | basic transcription element binding protein 1 | 5.35 | down | 0.00086 |
| L05779 | 2140 | epoxide hydrolase 2, cytoplasmic | 5.35 | down | 0.00006 |
| AA490775 | 1380 | UDP-N-acetylglucosamine-2-epimerase/N-acetylmannosamine kinase | 5.34 | down | 0.00118 |
| R15825 | 2791 | KIAA0946 protein; Huntingtin interacting protein H | 5.33 | down | 0.00391 |
| AA342771 | 749 | EST | 5.33 | down | 0.00331 |
| F10466 | 1820 | EST | 5.32 | down | 0.02494 |
| S72370 | 3029 | pyruvate carboxylase | 5.31 | down | 0.00075 |
| N27834 | 2474 | alpha2,3-sialyltransferase | 5.31 | down | 0.00039 |
| D31117 | 1640 | ribosome binding protein 1 (dog 180kD homolog) | 5.3 | down | 0.02749 |
| AA032005 | 71 | EST | 5.3 | down | 0.01202 |
| N48315 | 2526 | adaptor-related protein complex 2, mu 1 subunit | 5.3 | down | 0.0149 |
| T08879 | 3048 | cathepsin F | 5.29 | down | 0.0008 |
| X02160 | 3668 | insulin receptor | 5.29 | down | 0.0001 |
| Z24459 | 3866 | mature T-cell proliferation 1 | 5.29 | down | 0.00001 |
| AA236230 | 508 | EST | 5.28 | down | 0.01517 |
| AA258353 | 593 | EST | 5.28 | down | 0.00193 |
| N64017 | 2605 | EST | 5.27 | down | 0.00022 |
| X90999 | 3817 | hydroxyacyl glutathione hydrolase; glyoxalase 2 | 5.27 | down | 0.00047 |
| AA347717 | 754 | EST | 5.25 | down | 0.00207 |
| U19523 | 3319 | GTP cyclohydrolase 1 (dopa-responsive dystonia) | 5.25 | down | 0.00029 |
| J04449 | 2110 | cytochrome P450, subfamily IIIA (niphedipine oxidase), polypeptide 3 | 5.25 | down | 0.01583 |
| AA428150 | 985 | EST | 5.24 | down | 0.00167 |
| N20113 | 2438 | EST | 5.24 | down | 0.01346 |
| N70057 | 2653 | DNA segment on chromosome 6 (unique) 49 expressed sequence | 5.24 | down | 0.01178 |
| N62652 | 2592 | EST | 5.23 | down | 0.03006 |
| AA461057 | 1234 | nuclear localization signal deleted in velocardiofacial syndrome | 5.22 | down | 0.00051 |
| X04828 | 3680 | guanine nucleotide binding protein (G protein), alpha inhibiting activity polypeptide 2 | 5.22 | down | 0.01278 |
| AA044842 | 105 | Autosomal Highly Conserved Protein | 5.21 | down | 0.0009 |
| AA005358 | 14 | EST | 5.2 | down | 0.00318 |
| N25082 | 2462 | amplified in osteosarcoma | 5.19 | down | 0.00895 |
| Z39059 | 3896 | EST | 5.19 | down | 0.0014 |
| J04056 | 2104 | carbonyl reductase 1 | 5.19 | down | 0.00001 |
| U00115 | 3271 | B-cell CLL/lymphoma 6 (zinc finger protein 51) | 5.18 | down | 0.00045 |
| AA046674 | 112 | EST | 5.17 | down | 0.02561 |
| C20810 | 1579 | EST | 5.17 | down | 0.00614 |
| L38928 | 2209 | 5,10-methenyltetrahydrofolate synthetase (5-formyltetrahydrofolate cyclo-ligase) | 5.17 | down | 0.00726 |
| L76687 | 2227 | growth factor receptor-bound protein 14 | 5.16 | down | 0.00199 |
| AA456055 | 1185 | EST | 5.16 | down | 0.00158 |
| H14372 | 1883 | ATP-binding cassette, sub-family A (ABC1), member 5 | 5.16 | down | 0.00012 |
| H88359 | 2020 | nuclear factor (erytroid-derived 2)-like 2 | 5.16 | down | 0.01253 |
| U60205 | 3400 | sterol-C4-methyl oxidase-like | 5.16 | down | 0.00061 |
| N79778 | 2701 | extracellular matrix protein 2, female organ and adipocyte specific | 5.15 | down | 0.00286 |
| H54285 | 1947 | EST | 5.14 | down | 0.00426 |
| M99439 | 2437 | transducin-like enhancer of split 4, homolog of Drosophila E(sp1) | 5.14 | down | 0.00001 |
| AA094999 | 204 | zinc finger protein 216 | 5.12 | down | 0.0257 |
| AA114949 | 228 | UDP-N-acetylglucosamine pyrophosphorylase 1; Sperm associated antigen 2 | 5.12 | down | 0.01028 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| AA430666 | 1016 | EST | 5.12 | down | 0.00377 |
| AA149253 | 323 | EST | 5.12 | down | 0.00863 |
| R48732 | 2875 | EST | 5.12 | down | 0.00837 |
| L36033 | 2204 | stromal cell-derived factor 1 | 5.1 | down | 0.00603 |
| F10875 | 1824 | EST | 5.09 | down | 0.00004 |
| H98083 | 2067 | EST | 5.09 | down | 0.00025 |
| AA258350 | 592 | EST | 5.08 | down | 0.00035 |
| AA191014 | 396 | EST | 5.07 | down | 0.01455 |
| AA478441 | 1302 | cathepsin F | 5.07 | down | 0.00752 |
| AA599472 | 1451 | succinate-CoA ligase, GDP-forming, beta subunit | 5.07 | down | 0.00447 |
| D79687 | 1723 | KIAA1053 protein | 5.06 | down | 0.00047 |
| H93053 | 2034 | glutamate-cysteine ligase (gamma-glutamylcysteine synthetase), catalytic (72.8kD) | 5.06 | down | 0.01029 |
| W45560 | 3522 | EST | 5.06 | down | 0.00996 |
| AA443756 | 1080 | EST | 5.05 | down | 0.00341 |
| D51199 | 1677 | EST | 5.05 | down | 0.00192 |
| AA620343 | 1500 | EST | 5.04 | down | 0.00407 |
| T15482 | 3059 | EST | 5.04 | down | 0.00233 |
| H46001 | 1931 | EST | 5.03 | down | 0.00563 |
| R51831 | 2890 | EST | 5.03 | down | 0.00761 |
| W57821 | 3545 | EST | 5.03 | down | 0.00277 |
| W63728 | 3562 | EST | 5.03 | down | 0.00311 |
| AA609574 | 1485 | EST | 5.03 | down | 0 |
| N62523 | 2591 | hepatic leukemia factor | 5.02 | down | 0.00087 |
| AA449306 | 1122 | EST | 5.01 | down | 0.0006 |
| AA279533 | 627 | EST | 5.01 | down | 0.04448 |
| N67105 | 2623 | EST | 5.01 | down | 0.00176 |
| S74728 | 3032 | antiquitin 1 | 5.01 | down | 0.00008 |
| AA070091 | 153 | EST | 5 | down | 0 |
| AA292086 | 705 | EST | 5 | down | 0.00161 |
| R82837 | 2975 | KIAA0970 protein | 5 | down | 0.00181 |
| AA486567 | 1350 | EST | 5 | down | 0.00002 |
| H78628 | 2003 | EST | 4.98 | down | 0.00729 |
| AA416936 | 910 | 5-methyltetrahydrofolate-homocysteine methyltransferase reductase | 4.98 | down | 0.00632 |
| AA400934 | 824 | EST | 4.98 | down | 0.02013 |
| D31381 | 1644 | dynein, axonemal, light polypeptide 4 | 4.97 | down | 0.01806 |
| AA210850 | 431 | EST | 4.97 | down | 0.00735 |
| L41067 | 2213 | nuclear factor of activated T-cells, cytoplasmic 3 | 4.96 | down | 0.00473 |
| AA450114 | 1131 | EST | 4.96 | down | 0.01238 |
| X92744 | 3824 | defensin, beta 1 | 4.96 | down | 0.01804 |
| X07619 | 3689 | cytochrome P450, subfamily IID (debrisoquine, sparteine, etc., -metabolising), polypeptide 7a (pseudogene) | 4.96 | down | 0.00004 |
| AA406125 | 868 | EST | 4.95 | down | 0.01027 |
| M95767 | 2431 | chitobiase, di-N-acetyl- | 4.94 | down | 0.00004 |
| H03945 | 1835 | EST | 4.94 | down | 0.02603 |
| X96752 | 3834 | L-3-hydroxyacyl-Coenzyme A dehydrogenase, short chain | 4.94 | down | 0.00359 |
| AA282089 | 653 | EST | 4.93 | down | 0.00108 |
| AA463194 | 1244 | KIAA1037 protein | 4.92 | down | 0.01866 |
| W81053 | 3607 | EST | 4.91 | down | 0.00164 |
| R06764 | 2771 | apolipoprotein B (including Ag(x) antigen) | 4.91 | down | 0.00167 |
| X58528 | 3745 | ATP-binding cassette, sub-family D (ALD), member 3 | 4.91 | down | 0.00728 |
| AA425309 | 953 | nuclear factor I/B | 4.9 | down | 0.00466 |
| AA451836 | 1137 | EST | 4.9 | down | 0.01412 |
| H91456 | 2030 | nuclear receptor subfamily 1, group H, member 4 | 4.9 | down | 0.00255 |
| W86850 | 3628 | solute carrier family 25 (mitochondrial carrier; citrate transporter), member 1 | 4.9 | down | 0.03105 |
| S69232 | 3026 | electron-transferring-flavoprotein dehydrogenase | 4.9 | down | 0.00017 |
| X62822 | 3755 | sialyltransferase 1 (beta-galactoside alpha-2,6-sialytransferase) | 4.89 | down | 0.00274 |
| W60002 | 3552 | plastin 3 (T isoform) | 4.88 | down | 0.01694 |
| U51333 | 3382 | hexokinase 3 (white cell) | 4.88 | down | 0.00055 |
| R56094 | 2904 | EST | 4.87 | down | 0.00214 |
| AA314457 | 733 | synaptonemal complex protein 3 | 4.86 | down | 0.0013 |
| N90820 | 2714 | DKFZP566B1346 protein | 4.86 | down | 0.03008 |
| T98199 | 3266 | EST | 4.86 | down | 0.00431 |
| D61991 | 1706 | EST | 4.84 | down | 0.00005 |
| AA446342 | 1088 | seven in absentia (Drosophila) homolog 1 | 4.84 | down | 0.00015 |
| U53003 | 3387 | ES1 (zebrafish) protein, human homolog of | 4.84 | down | 0.00077 |
| D87466 | 1763 | KIAA0276 protein | 4.83 | down | 0.0007 |
| D45556 | 1663 | EST | 4.83 | down | 0.01044 |
| AA046747 | 114 | EST | 4.82 | down | 0.00022 |
| AA464188 | 1256 | EST | 4.82 | down | 0.03208 |
| N26184 | 2466 | MYLE protein | 4.82 | down | 0.00056 |
| AA056482 | 141 | EST | 4.82 | down | 0.00199 |
| AA370359 | 767 | KIAA0382 protein; leukemia-associated rho guanine nucleotide exchange factor (GEF) | 4.82 | down | 0.01077 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| N54311 | 2563 | EST | 4.82 | down | 0.00183 |
| L07077 | 2145 | enoyl-Coenzyme A, hydratase/3-hydroxyacyl Coenzyme A dehydrogenase | 4.82 | down | 0.00403 |
| U68494 | 3412 | EST | 4.82 | down | 0.00881 |
| M55513 | 2354 | potassium voltage-gated channel, shaker-related subfamily, member 5 | 4.81 | down | 0.02141 |
| W74158 | 3593 | EST | 4.81 | down | 0.00233 |
| D16294 | 1619 | acetyl-Coenzyme A acyltransferase 2 (mitochondrial 3-oxoacyl-Coenzyme A thiolase) | 4.81 | down | 0.03921 |
| X13227 | 3695 | D-amino-acid oxidase | 4.81 | down | 0.0002 |
| AA417373 | 917 | EST | 4.8 | down | 0.01342 |
| F09350 | 1801 | EST | 4.79 | down | 0.00088 |
| AA233837 | 474 | EST | 4.79 | down | 0.0034 |
| N29353 | 2476 | kynurenine 3-monooxygenase (kynurenine 3-hydroxylase) | 4.78 | down | 0.00019 |
| AA291749 | 703 | estrogen receptor 1 | 4.78 | down | 0.00059 |
| AA461303 | 1238 | DKFZP586D1519 protein | 4.77 | down | 0.0438 |
| AA490620 | 1378 | EST | 4.77 | down | 0.00201 |
| H94648 | 2044 | EST | 4.77 | down | 0.00266 |
| AA228119 | 462 | pre-B-cell colony-enhancing factor | 4.77 | down | 0.00031 |
| AA449327 | 1123 | EST | 4.77 | down | 0.01248 |
| X00351 | 3665 | actin, beta | 4.76 | down | 0.0003 |
| L05144 | 2139 | phosphoenolpyruvate carboxykinase 1 (soluble) | 4.76 | down | 0.02289 |
| N49214 | 2535 | EST | 4.74 | down | 0.00064 |
| N59089 | 2580 | EST | 4.74 | down | 0.00055 |
| M35590 | 2345 | small inducible cytokine A4 | 4.74 | down | 0.01225 |
| T41047 | 3119 | EST | 4.74 | down | 0.00015 |
| M55671 | 2355 | protein Z, vitamin K-dependent plasma glycoprotein | 4.74 | down | 0.00078 |
| AA400834 | 820 | EST | 4.73 | down | 0.01523 |
| X57025 | 3739 | insulin-like growth factor 1 (somatomedin C) | 4.72 | down | 0.00087 |
| AA432168 | 1031 | S-adenosylhomocysteine hydrolase-like 1 | 4.71 | down | 0.01377 |
| AA435753 | 1045 | EST | 4.71 | down | 0.00078 |
| AA227452 | 455 | EST | 4.7 | down | 0.02345 |
| T70087 | 3199 | EST | 4.7 | down | 0.00173 |
| AA477919 | 1293 | EST | 4.69 | down | 0.00141 |
| AA194075 | 406 | nuclear receptor coactivator 4 | 4.69 | down | 0.00862 |
| AA424672 | 946 | dermatopontin | 4.69 | down | 0.00843 |
| U03105 | 3280 | proline-rich protein with nuclear targeting signal | 4.69 | down | 0.00017 |
| X78992 | 3799 | butyrate response factor 2 (EGF-response factor 2) | 4.69 | down | 0.01995 |
| W45051 | 3518 | EST | 4.68 | down | 0.00433 |
| W80609 | 3603 | EST | 4.68 | down | 0.01729 |
| N53549 | 2558 | cytochrome P450, subfamily IIJ (arachidonic acid epoxygenase) polypeptide 2 | 4.68 | down | 0.00818 |
| F09578 | 1804 | core-binding factor, runt domain, alpha subunit 2; translocated to, 3 | 4.66 | down | 0.04463 |
| H98071 | 2066 | EST | 4.66 | down | 0.03722 |
| N59283 | 2582 | EST | 4.65 | down | 0.02343 |
| N72259 | 2669 | cornichon-like | 4.65 | down | 0.0054 |
| X59812 | 3747 | cytochrome P450, subfamily XXVIIA (steroid 27-hydroxylase, cerebrotendinous xanthomatosis), polypeptide 1 | 4.65 | down | 0.036 |
| X78706 | 3798 | carnitine acetyltransferase | 4.65 | down | 0.00442 |
| M31169 | 2325 | propionyl Coenzyme A carboxylase, beta polypeptide | 4.65 | down | 0.00467 |
| R22905 | 2800 | EST | 4.64 | down | 0.0043 |
| D80050 | 1726 | EST | 4.64 | down | 0.01001 |
| AA258813 | 600 | EST | 4.63 | down | 0.02395 |
| AA256666 | 583 | EST | 4.63 | down | 0.0018 |
| AA004905 | 11 | KIAA0937 protein | 4.63 | down | 0.00082 |
| M35590 | 2345 | small inducible cytokine A4 | 4.62 | down | 0.01268 |
| AA069768 | 151 | hevin | 4.62 | down | 0.00202 |
| AA419622 | 926 | EST | 4.62 | down | 0.00386 |
| M27492 | 2312 | interleukin 1 receptor, type I | 4.62 | down | 0.0082 |
| AA090434 | 191 | diaphanous (Drosophila, homolog) 1 | 4.61 | down | 0.01704 |
| AA233763 | 472 | EST | 4.61 | down | 0.00004 |
| AA151210 | 333 | EST | 4.61 | down | 0.00008 |
| M23263 | 2300 | androgen receptor (dihydrotestosterone receptor; testicular feminization; spinal and bulbar muscular atrophy; Kennedy disease) | 4.6 | down | 0.00005 |
| H40149 | 1921 | KIAA0937 protein | 4.59 | down | 0.00112 |
| U19495 | 3318 | stromal cell-derived factor 1 | 4.59 | down | 0.00011 |
| AA436690 | 1057 | EST | 4.58 | down | 0.00948 |
| N29319 | 2475 | EST | 4.58 | down | 0.00011 |
| R64144 | 2931 | cAMP responsive element binding protein-like 2 | 4.58 | down | 0.00495 |
| T73420 | 3210 | short-chain dehydrogenase/reductase 1 | 4.58 | down | 0.00656 |
| D87449 | 1762 | KIAA0260 protein | 4.58 | down | 0.00026 |
| D12485 | 1600 | phosphodiesterase I/nucleotide pyrophosphatase 1 (homologous to mouse Ly-41 antigen) | 4.57 | down | 0.00008 |
| AA211388 | 433 | EST | 4.56 | down | 0.02703 |
| AA133215 | 277 | calcitonin receptor-like receptor activity modifying protein 1 | 4.55 | down | 0.02092 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| AA425836 | 957 | EST | 4.55 | down | 0.00035 |
| N45307 | 2517 | EST | 4.55 | down | 0.00006 |
| M12625 | 2245 | lecithin-cholesterol acyltransferase | 4.55 | down | 0.01584 |
| AA348284 | 755 | EST | 4.54 | down | 0.00759 |
| H10661 | 1871 | EST | 4.54 | down | 0.00276 |
| AA485413 | 1344 | EST | 4.54 | down | 0.00137 |
| C21238 | 1584 | EST | 4.54 | down | 0.02074 |
| S72370 | 3029 | pyruvate carboxylase | 4.54 | down | 0.0001 |
| AA521290 | 1421 | EST | 4.53 | down | 0.0148 |
| R92737 | 2987 | EST | 4.53 | down | 0.04447 |
| AA250775 | 537 | EST | 4.52 | down | 0.01752 |
| AA052980 | 122 | EST | 4.52 | down | 0.023 |
| AA253459 | 566 | EST | 4.51 | down | 0.00419 |
| N47942 | 2522 | progesterone membrane binding protein | 4.51 | down | 0.00168 |
| T25506 | 3089 | EST | 4.51 | down | 0.00529 |
| R59325 | 2913 | EST | 4.48 | down | 0.00117 |
| U77396 | 3425 | LPS-induced TNF-alpha factor | 4.47 | down | 0.00108 |
| AA280413 | 638 | spleen focus forming virus (SFFV) proviral integration oncogene spi1 | 4.46 | down | 0.02062 |
| AA406231 | 873 | KIAA0381 protein | 4.46 | down | 0.04049 |
| AA452454 | 1144 | EST | 4.45 | down | 0.00179 |
| AA431462 | 1022 | EST | 4.45 | down | 0.00956 |
| U79303 | 3435 | protein predicted by clone 23882 | 4.45 | down | 0 |
| AA621796 | 1531 | kinesin family member 3B | 4.44 | down | 0.00032 |
| L76571 | 2226 | nuclear receptor subfamily 0, group B, member 2 | 4.44 | down | 0.00312 |
| D57823 | 1690 | Sec23 (*S. cerevisiae*) homolog A | 4.43 | down | 0 |
| AA398257 | 791 | 7-dehydrocholesterol reductase | 4.43 | down | 0.04169 |
| AA214542 | 438 | EST | 4.43 | down | 0.00601 |
| Z48199 | 3939 | syndecan 1 | 4.43 | down | 0.00408 |
| H88033 | 2019 | KIAA0733 protein | 4.42 | down | 0.02032 |
| W69675 | 3572 | EST | 4.42 | down | 0.00019 |
| C01409 | 1556 | EST | 4.41 | down | 0.01725 |
| R94662 | 2994 | heme-binding protein | 4.41 | down | 0.02301 |
| N70305 | 2654 | EST | 4.41 | down | 0.00078 |
| AA262033 | 606 | EST | 4.41 | down | 0.00054 |
| H57816 | 1957 | EST | 4.41 | down | 0.00206 |
| N48787 | 2530 | protease inhibitor 1 (anti-elastase), alpha-1-antitrypsin | 4.4 | down | 0.00292 |
| R44025 | 2853 | EST | 4.4 | down | 0.01325 |
| Z39622 | 3907 | EST | 4.4 | down | 0.00001 |
| N73468 | 2673 | protein S (alpha) | 4.4 | down | 0.00853 |
| R36228 | 2823 | EST | 4.39 | down | 0.00033 |
| T71978 | 3204 | EST | 4.39 | down | 0.0017 |
| AA437265 | 1061 | EST | 4.39 | down | 0.00826 |
| N93155 | 2728 | calmodulin 1 (phosphorylase kinase, delta) | 4.39 | down | 0.0002 |
| Z38161 | 3881 | EST | 4.38 | down | 0.0011 |
| H98910 | 2071 | EST | 4.38 | down | 0.00548 |
| N23730 | 2455 | v-fos FBJ murine osteosarcoma viral oncogene homolog | 4.38 | down | 0.04395 |
| T69164 | 3194 | EST | 4.38 | down | 0.00548 |
| M31667 | 2331 | cytochrome P450, subfamily I (aromatic compound-inducible), polypeptide 2 | 4.38 | down | 0.00078 |
| AA193297 | 404 | EST | 4.37 | down | 0.04676 |
| AA427783 | 979 | EST | 4.37 | down | 0.0004 |
| N22434 | 2450 | EST | 4.37 | down | 0.01725 |
| W37382 | 3501 | EST | 4.37 | down | 0.00677 |
| AA282971 | 665 | EST | 4.37 | down | 0.03822 |
| D11881 | 1599 | KIAA0962 protein | 4.37 | down | 0.01627 |
| F09979 | 1809 | EST | 4.36 | down | 0.02555 |
| W92771 | 3652 | glycine cleavage system protein H (aminomethyl carrier) | 4.36 | down | 0.0064 |
| AA437295 | 1062 | ribosomal protein L7a | 4.35 | down | 0.00347 |
| AA452559 | 1147 | EST | 4.35 | down | 0.00804 |
| W90583 | 3645 | EST | 4.35 | down | 0.00318 |
| T97234 | 3264 | EST | 4.34 | down | 0.00263 |
| U57721 | 3394 | kynureninase (L-kynurenine hydrolase) | 4.34 | down | 0.0197 |
| T85532 | 3235 | EST | 4.33 | down | 0.00591 |
| AA421244 | 932 | SH3-domain binding protein 5 (BTK-associated) | 4.32 | down | 0.007 |
| N25969 | 2465 | protein kinase, cAMP-dependent, regulatory, type I, alpha (tissue specific extinguisher 1) | 4.32 | down | 0.00304 |
| W73818 | 3590 | EST | 4.32 | down | 0.00385 |
| S90469 | 3039 | P450 (cytochrome) oxidoreductase | 4.32 | down | 0.0182 |
| AA258613 | 598 | EST | 4.31 | down | 0.0344 |
| AA001603 | 3 | EST | 4.31 | down | 0.00883 |
| AA258323 | 591 | EST | 4.31 | down | 0.00046 |
| D60769 | 1703 | KIAA0096 protein | 4.31 | down | 0.00142 |
| U34252 | 3349 | aldehyde dehydrogenase 9 (gamma-aminobutyraldehyde dehydrogenase, E3 isozyme) | 4.31 | down | 0.00613 |
| AA431480 | 1023 | EST | 4.3 | down | 0.00876 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| N39163 | 2508 | metallothionein 1L | 4.3 | down | 0.03917 |
| M35878 | 2346 | insulin-like growth factor binding protein 3 | 4.3 | down | 0.0027 |
| Z11559 | 3859 | iron-responsive element binding protein 1 | 4.3 | down | 0.00066 |
| AA454086 | 1161 | UDP-glucose dehydrogenase | 4.29 | down | 0.00981 |
| X59834 | 3748 | glutamate-ammonia ligase (glutamine synthase) | 4.29 | down | 0.00255 |
| W58540 | 3550 | KIAA1131 protein | 4.28 | down | 0.0184 |
| T81315 | 3226 | EST | 4.28 | down | 0.00187 |
| AA398445 | 796 | EST | 4.28 | down | 0.01764 |
| AA521306 | 1423 | EST | 4.27 | down | 0.00567 |
| R99909 | 3016 | EST | 4.27 | down | 0.00045 |
| AA460012 | 1224 | solute carrier family 22 (extraneuronal monoamine transporter), member 3 | 4.27 | down | 0.04975 |
| U46499 | 3364 | microsomal glutathione S-transferase 1 | 4.27 | down | 0.00244 |
| M83216 | 2406 | caldesmon 1 | 4.27 | down | 0.00037 |
| AA136079 | 297 | EST | 4.26 | down | 0.0057 |
| L40401 | 2211 | putative protein | 4.26 | down | 0.00194 |
| D31887 | 1649 | KIAA0062 protein | 4.26 | down | 0.00101 |
| M80482 | 2402 | paired basic amino acid cleaving system 4 | 4.26 | down | 0.00041 |
| N73461 | 2672 | EST | 4.25 | down | 0.00162 |
| M68895 | | alcohol dehydrogenase 6 (class V) | 4.25 | down | 0.00354 |
| U48296 | 3368 | protein tyrosine phosphatase type IVA, member 1 | 4.25 | down | 0.02037 |
| AA426330 | 963 | N-acylsphingosine amidohydrolase (acid ceramidase)-like | 4.24 | down | 0.00668 |
| Y10032 | 3855 | serum/glucocorticoid regulated kinase | 4.24 | down | 0.00148 |
| AA456147 | 1188 | general transcription factor IIIA | 4.23 | down | 0.00088 |
| AA456589 | 1194 | EST | 4.23 | down | 0.00102 |
| AA243495 | 528 | lectin, mannose-binding, 1 | 4.23 | down | 0.00179 |
| AA491000 | 1385 | EST | 4.23 | down | 0.02305 |
| AA133296 | 278 | EST | 4.23 | down | 0.00041 |
| AA299632 | 728 | EST | 4.23 | down | 0.00371 |
| T10322 | 3052 | dihydropyrimidinase-like 2 | 4.23 | down | 0.01527 |
| M96233 | 2432 | glutathione S-transferase M1,glutathione S-transferase M2 (muscle),glutathione S-transferase M4 | 4.23 | down | 0.04227 |
| N77606 | 2696 | EST | 4.22 | down | 0.00119 |
| Y10659 | 3856 | interleukin 13 receptor, alpha 1 | 4.22 | down | 0.00061 |
| AA150891 | 331 | EST | 4.22 | down | 0.01692 |
| AA203222 | 424 | FERM, RhoGEF (ARHGEF) and pleckstrin domain protein 1 (chondrocyte-derived) | 4.21 | down | 0.00745 |
| AB002311 | 1535 | PDZ domain containing guanine nucleotide exchange factor(GEF)1; RA(Ras/Rap1A-associating)-GEF | 4.21 | down | 0.00476 |
| AA428607 | 990 | ribosomal protein S5 pseudogene 1 | 4.21 | down | 0.04305 |
| AA417375 | 918 | EST | 4.21 | down | 0.00231 |
| AA504492 | 1414 | tubulin, alpha, ubiquitous | 4.21 | down | 0.00752 |
| N52985 | 2554 | nidogen (enactin) | 4.21 | down | 0.01385 |
| W81268 | 3609 | protein kinase, interferon-inducible double stranded RNA dependent | 4.2 | down | 0.00007 |
| H08054 | 1857 | EST | 4.2 | down | 0.0009 |
| AA193223 | 403 | EST | 4.2 | down | 0.02416 |
| T48980 | 3133 | calmodulin 1 (phosphorylase kinase, delta) | 4.2 | down | 0.0046 |
| X72012 | 3786 | endoglin (Osler-Rendu-Weber syndrome 1) | 4.2 | down | 0.005 |
| M95585 | 2429 | hepatic leukemia factor | 4.2 | down | 0.00212 |
| AA402006 | 834 | EST | 4.19 | down | 0.00094 |
| AA101632 | 217 | EST | 4.19 | down | 0.00023 |
| F10874 | 1823 | EST | 4.19 | down | 0.00025 |
| L00352 | 2131 | low density lipoprotein receptor (familial hypercholesterolemia) | 4.19 | down | 0.00352 |
| S67325 | 3023 | propionyl Coenzyme A carboxylase, beta polypeptide | 4.19 | down | 0.00151 |
| Z39406 | 3902 | nuclear receptor co-repressor 1 | 4.18 | down | 0.00439 |
| D00723 | 1592 | glycine cleavage system protein H (aminomethyl carrier) | 4.18 | down | 0.00543 |
| F13782 | 1827 | LIM binding domain 2 | 4.17 | down | 0.00109 |
| H90417 | 2028 | EST | 4.17 | down | 0.015 |
| W38407 | 3503 | EST | 4.17 | down | 0.00392 |
| AA135558 | 293 | peptidase D | 4.17 | down | 0.0068 |
| D31289 | 1642 | EST | 4.16 | down | 0.02166 |
| W88568 | 3635 | glycogenin 2 | 4.16 | down | 0.00111 |
| AA036662 | 83 | EST | 4.16 | down | 0.00235 |
| AA404500 | 852 | EST | 4.16 | down | 0.01375 |
| R05518 | 2761 | EST | 4.15 | down | 0.0125 |
| H91680 | 2032 | phosphorylase, glycogen; liver (Hers disease, glycogen storage disease type VI) | 4.15 | down | 0.00746 |
| D87075 | 1760 | solute carrier family 23 (nucleobase transporters), member 1 | 4.15 | down | 0.00067 |
| U90545 | 3454 | solute carrier family 17 (sodium phosphate), member 3 | 4.14 | down | 0.00005 |
| H11274 | 1874 | EST | 4.13 | down | 0.01478 |
| AA040087 | 92 | EST | 4.13 | down | 0.00123 |
| R34133 | 2820 | EST | 4.13 | down | 0.00008 |
| AA280130 | 636 | EST | 4.12 | down | 0.00114 |
| T15674 | 3060 | EST | 4.12 | down | 0.02111 |
| M62403 | 2373 | insulin-like growth factor-binding protein 4 | 4.12 | down | 0.00226 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| C01286 | 1555 | integral membrane protein 2B | 4.11 | down | 0.00292 |
| D62103 | 1707 | EST | 4.11 | down | 0.0263 |
| H69565 | 1987 | EST | 4.11 | down | 0.00002 |
| AA190816 | 395 | EST | 4.1 | down | 0.00037 |
| N66422 | 2615 | EST | 4.1 | down | 0.00237 |
| AA417078 | 916 | EST | 4.1 | down | 0.00414 |
| N21079 | 2440 | nucleolar cysteine-rich protein | 4.1 | down | 0.00028 |
| R87373 | 2977 | EST | 4.09 | down | 0.02253 |
| X58022 | 3744 | corticotropin releasing hormone-binding protein | 4.09 | down | 0.00076 |
| AA065173 | 148 | EST | 4.08 | down | 0.00377 |
| AA219653 | 448 | EST | 4.08 | down | 0.00607 |
| M96843 | 2434 | EST | 4.08 | down | 0.02912 |
| AA400251 | 811 | EST | 4.07 | down | 0.00032 |
| N91273 | 2717 | EST | 4.07 | down | 0.02965 |
| AA133439 | 279 | EST | 4.07 | down | 0.00022 |
| AA463729 | 1250 | EST | 4.07 | down | 0.00676 |
| R70790 | 2947 | EST | 4.07 | down | 0.02354 |
| AA279550 | 628 | Kruppel-like factor | 4.06 | down | 0.00957 |
| N36250 | 2505 | cellular repressor of E1A-stimulated genes | 4.06 | down | 0.00776 |
| N48674 | 2529 | EST | 4.06 | down | 0.00028 |
| AA255624 | 571 | EST | 4.06 | down | 0.00069 |
| L09717 | 2153 | lysosomal-associated membrane protein 2 | 4.06 | down | 0.00034 |
| HG2743–HT2845 | | caldesmon 1 | 4.06 | down | 0.00453 |
| AA188921 | 393 | similar to Caenorhabditis elegans protein C42C1.9 | 4.05 | down | 0.004 |
| AA191647 | 399 | ceruloplasmin (ferroxidase) | 4.05 | down | 0.00029 |
| AA084408 | 179 | EST | 4.05 | down | 0.00864 |
| AA418907 | 922 | cytochrome P450, subfamily 1 (aromatic compound-inducible), polypeptide 1 | 4.05 | down | 0.04276 |
| AA608807 | 1471 | inhibin, beta B (activin AB beta polypeptide) | 4.05 | down | 0.00568 |
| AA478416 | 1300 | EST | 4.04 | down | 0.00078 |
| M63967 | 2378 | aldehyde dehydrogenase 5 | 4.04 | down | 0.00058 |
| T68083 | 3184 | short-chain dehydrogenase/reductase 1 | 4.03 | down | 0.01593 |
| AA446666 | 1094 | EST | 4.03 | down | 0.02369 |
| AA465240 | 1270 | EST | 4.03 | down | 0.0046 |
| W46391 | 3524 | alpha integrin binding protein 63 | 4.03 | down | 0.01363 |
| W52821 | 3541 | leucine aminopeptidase | 4.02 | down | 0.03787 |
| AA135958 | 296 | EST | 4.02 | down | 0.00012 |
| AA609774 | 1490 | EST | 4.02 | down | 0.00424 |
| H96614 | 2054 | EST | 4.02 | down | 0.01565 |
| R32036 | 2815 | interleukin 1 receptor-like 1 | 4.02 | down | 0.00051 |
| R61740 | 2922 | EST | 4.02 | down | 0.00321 |
| L17128 | 2167 | gamma-glutamyl carboxylase | 4.02 | down | 0.00096 |
| AA348485 | 757 | KIAA0438 gene product | 4.01 | down | 0.04563 |
| AA151676 | 337 | peptidyl arginine deiminase, type II | 4.01 | down | 0.00911 |
| F04944 | 1795 | acyl-Coenzyme A oxidase | 4.01 | down | 0.00242 |
| D63160 | 1709 | ficolin (collagen/fibrinogen domain-containing lectin) 2 (hucolin) | 4.01 | down | 0.00391 |
| J03242 | 2092 | insulin-like growth factor 2 (somatomedin A) | 4.01 | down | 0.00042 |
| AA255546 | 569 | EST | 4 | down | 0.00301 |
| AA411764 | 891 | similar to APOBEC1 | 4 | down | 0.01491 |
| AA479488 | 1313 | S-adenosylhomocysteine hydrolase-like 1 | 4 | down | 0.0269 |
| R10138 | 2783 | EST | 4 | down | 0.00032 |
| T16478 | 3069 | EST | 4 | down | 0.01041 |
| H71169 | 1992 | putative protein similar to nessy (Drosophila) | 4 | down | 0.00709 |
| X76648 | 3793 | glutaredoxin (thioltransferase) | 4 | down | 0.00211 |
| AA428567 | 989 | EST | 3.99 | down | 0.00788 |
| N22404 | 2449 | EST | 3.99 | down | 0.01152 |
| T90037 | 3245 | EST | 3.99 | down | 0.0016 |
| AA452860 | 1151 | EST | 3.99 | down | 0.00831 |
| H83442 | 2013 | catechol-O-methyltransferase | 3.99 | down | 0.00594 |
| W85888 | 3619 | EST | 3.99 | down | 0.00697 |
| X05409 | 3681 | aldehyde dehydrogenase 2, mitochondrial | 3.99 | down | 0.01029 |
| R00296 | 2749 | EST | 3.98 | down | 0.04632 |
| T69728 | 3198 | heat shock 90kD protein 1, beta | 3.98 | down | 0.00786 |
| AA495820 | 1393 | EST | 3.98 | down | 0.00218 |
| AA400030 | 806 | EST | 3.98 | down | 0.00089 |
| N66130 | 2613 | progesterone membrane binding protein | 3.98 | down | 0.0106 |
| HG2379–HT3997 | | serine hydroxymethyltransferase 1 (soluble) | 3.98 | down | 0.00306 |
| R42241 | 2845 | EST | 3.97 | down | 0.00129 |
| AA449448 | 1125 | EST | 3.97 | down | 0.00103 |
| N53757 | 2559 | EST | 3.97 | down | 0.00255 |
| AA401376 | 829 | EST | 3.97 | down | 0.00797 |
| M29971 | 2320 | O-6-methylguanine-DNA methyltransferase | 3.97 | down | 0.00424 |
| AA281770 | 649 | seven in absentia (Drosophila) homolog 1 | 3.96 | down | 0.00094 |
| AA454184 | 1165 | EST | 3.96 | down | 0.04605 |
| AA255878 | 572 | KIAA0767 protein | 3.96 | down | 0.00592 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| R52800 | 2894 | EST | 3.96 | down | 0.00749 |
| M68840 | 2388 | monoamine oxidase A | 3.96 | down | 0.01396 |
| U16660 | 3312 | enoyl Coenzyme A hydratase 1, peroxisomal | 3.96 | down | 0.00002 |
| AA281677 | 648 | DKFZP564M2423 protein | 3.95 | down | 0.03606 |
| AA495758 | 1391 | EST | 3.94 | down | 0.00772 |
| W36290 | 3500 | Kreisler (mouse) maf-related leucine zipper homolog | 3.94 | down | 0.02718 |
| AA609011 | 1476 | EST | 3.94 | down | 0.0313 |
| T79758 | 3223 | EST | 3.94 | down | 0.00581 |
| W88985 | 3637 | KIAA0903 protein | 3.94 | down | 0.00295 |
| AA157112 | 345 | EST | 3.94 | down | 0.02571 |
| AA398422 | 794 | EST | 3.94 | down | 0.00388 |
| U78190 | 3430 | GTP cyclohydrolase 1 feedback regulatory protein | 3.94 | down | 0.034 |
| R98774 | 3013 | EST | 3.93 | down | 0.00001 |
| AA435824 | 1048 | EST | 3.93 | down | 0.02764 |
| AA609996 | 1495 | EST | 3.93 | down | 0.00988 |
| M55150 | 2352 | fumarylacetoacetate | 3.93 | down | 0.00213 |
| U50527 | 3377 | EST | 3.93 | down | 0.00123 |
| H11746 | 1877 | EST | 3.92 | down | 0.00012 |
| L09708 | 2152 | complement component 2 | 3.92 | down | 0.00693 |
| U20938 | 3323 | dihydropyrimidine dehydrogenase | 3.92 | down | 0.00053 |
| W63785 | 3564 | EST | 3.91 | down | 0.04089 |
| R31917 | 2814 | EST | 3.91 | down | 0.00071 |
| R96417 | 2997 | EST | 3.9 | down | 0.00019 |
| F02245 | 1776 | monoamine oxidase A | 3.9 | down | 0.02943 |
| F02345 | 1779 | EST | 3.9 | down | 0.0033 |
| AA252365 | 554 | EST | 3.9 | down | 0.01796 |
| C14963 | 1572 | nicotinamide nucleotide transhydrogenase | 3.9 | down | 0.0044 |
| T24055 | 3086 | ribosomal protein L26 | 3.9 | down | 0.00046 |
| AA599234 | 1447 | murine leukemia viral (bmi-1) oncogene homolog | 3.9 | down | 0.0068 |
| AA253043 | 559 | DKFZP586I1419 protein, | 3.89 | down | 0.00145 |
| Z40192 | 3915 | EST | 3.89 | down | 0.00223 |
| AA342301 | 746 | EST | 3.89 | down | 0.00038 |
| AA608729 | 1468 | EST | 3.89 | down | 0.01757 |
| AA234561 | 485 | EST | 3.88 | down | 0.02058 |
| H65650 | 1976 | EST | 3.88 | down | 0.0083 |
| N68730 | 2636 | EST | 3.88 | down | 0.00091 |
| T90492 | 3247 | EST | 3.88 | down | 0.00454 |
| M10943 | 2234 | metallothionein 1F (functional) | 3.88 | down | 0 |
| T68510 | 3186 | EST | 3.87 | down | 0.00617 |
| AA448282 | 1115 | EST | 3.87 | down | 0.00217 |
| H18997 | 1893 | F-box protein 21 | 3.87 | down | 0.00611 |
| AA251837 | 547 | EST | 3.87 | down | 0.00782 |
| AA342337 | 747 | EST | 3.87 | down | 0.0069 |
| L22548 | 2178 | collagen, type XVIII, alpha 1 | 3.87 | down | 0.0299 |
| J03805 | 2098 | protein phosphatase 2 (formerly 2A), catalytic subunit, beta isoform | 3.87 | down | 0.0116 |
| H87765 | 2017 | KIAA0626 gene product | 3.86 | down | 0.00131 |
| W94427 | 3656 | EST | 3.86 | down | 0.02649 |
| H97868 | 2064 | EST | 3.86 | down | 0.00362 |
| H97986 | 2065 | EST | 3.86 | down | 0.01534 |
| H18950 | 1892 | EST | 3.85 | down | 0.00162 |
| T10108 | 3049 | EST | 3.85 | down | 0.01155 |
| AA447977 | 1111 | EST | 3.84 | down | 0.00045 |
| T10264 | 3050 | EST | 3.84 | down | 0.00874 |
| Z11737 | 3860 | flavin containing monooxygenase 4 | 3.84 | down | 0.00043 |
| U49785 | 3375 | D-dopachrome tautomerase | 3.84 | down | 0.00044 |
| M30185 | 2321 | cholesteryl ester transfer protein, plasma | 3.83 | down | 0.0013 |
| W85765 | 3615 | EST | 3.83 | down | 0.00379 |
| D80218 | 1728 | brain acid-soluble protein 1 | 3.83 | down | 0.0137 |
| H68097 | 1982 | EST | 3.83 | down | 0.00797 |
| N49104 | 2533 | nuclear receptor interacting protein 1 | 3.83 | down | 0.00144 |
| D16350 | 1620 | SA (rat hypertension-associated) homolog | 3.83 | down | 0.00117 |
| Z31690 | 3878 | lipase A, lysosomal acid, cholesterol esterase (Wolman disease) | 3.83 | down | 0.00103 |
| AA056170 | 137 | EST | 3.82 | down | 0.0083 |
| AA093923 | 200 | EST | 3.82 | down | 0.03924 |
| U50196 | 3376 | adenosine kinase | 3.82 | down | 0.01425 |
| W20276 | 3477 | EST | 3.82 | down | 0.00033 |
| T82254 | 3228 | EST | 3.82 | down | 0.00091 |
| D45529 | 1662 | EST | 3.82 | down | 0.00193 |
| AA043501 | 98 | v-maf musculoaponeurotic fibrosarcoma (avian) oncogene homolog | 3.81 | down | 0.01304 |
| AA376875 | 770 | monoamine oxidase A | 3.8 | down | 0.02746 |
| AA430108 | 1013 | EST | 3.8 | down | 0.04484 |
| AA598746 | 1437 | EST | 3.8 | down | 0.02667 |
| AA046840 | 115 | CCAAT/enhancer binding protein (C/EBP), delta | 3.79 | down | 0.3319 |
| N21646 | 2445 | EST | 3.79 | down | 0.00079 |
| N66763 | 2618 | EST | 3.79 | down | 0.03015 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| R97798 | 3006 | EST | 3.79 | down | 0.00015 |
| U73514 | 3418 | hydroxyacyl-Coenzyme A dehydrogenase, type II | 3.79 | down | 0.01392 |
| HG2090–HT2152 | | CD163 antigen | 3.79 | down | 0.01078 |
| W45259 | 3519 | EST | 3.78 | down | 0.00069 |
| AA398221 | 790 | calcium/calmodulin-dependent protein kinase (CaM kinase) II beta | 3.78 | down | 0.00019 |
| AA449297 | 1121 | EST | 3.78 | down | 0.00039 |
| AA076249 | 169 | EST | 3.78 | down | 0.00029 |
| AA262349 | 607 | EST | 3.78 | down | 0.00043 |
| X75252 | 3790 | prostatic binding protein | 3.78 | down | 0.00231 |
| AA393961 | 777 | EST | 3.77 | down | 0.01029 |
| W86756 | 3627 | retinoid X receptor, alpha | 3.77 | down | 0.02472 |
| J03507 | 2095 | complement component 7 | 3.77 | down | 0.00184 |
| X52541 | 3721 | early growth response 1 | 3.77 | down | 0.00894 |
| N23817 | 2457 | EST | 3.76 | down | 0.00288 |
| T74884 | 3216 | EST | 3.76 | down | 0.0547 |
| X77548 | 3795 | nuclear receptor coactivator 4 | 3.76 | down | 0.00758 |
| F03200 | 1783 | EST | 3.75 | down | 0.01805 |
| R22196 | 2798 | EST | 3.75 | down | 0.02867 |
| R02371 | 2755 | EST | 3.75 | down | 0.00009 |
| M86826 | 2412 | insulin-like growth factor binding protein, acid labile subunit | 3.75 | down | 0.01157 |
| HG4322–HT4592 | | tubulin, beta polypeptide | 3.75 | down | 0.00554 |
| AA059489 | 145 | RGC32 protein | 3.74 | down | 0.00734 |
| AA010530 | 25 | EST | 3.74 | down | 0.0481 |
| D80312 | 1730 | EST | 3.74 | down | 0.01909 |
| AA426168 | 960 | KIAA0805 protein | 3.73 | down | 0.01477 |
| H51340 | 1941 | EST | 3.73 | down | 0.02643 |
| AA455367 | 1176 | DKFZP586F1018 protein | 3.73 | down | 0.00202 |
| AA481526 | 1329 | EST | 3.73 | down | 0.00002 |
| AA491001 | 1386 | EST | 3.73 | down | 0.01957 |
| D60670 | 1702 | EST | 3.73 | down | 0.00382 |
| N75072 | 2688 | EST | 3.73 | down | 0.00379 |
| R97302 | 3002 | EST | 3.73 | down | 0.01887 |
| AA410507 | 884 | EST | 3.73 | down | 0.01703 |
| W46404 | 3525 | EST | 3.73 | down | 0.00116 |
| AA459389 | 1216 | tyrosylprotein sulfotransferase 2 | 3.72 | down | 0.02252 |
| H16768 | 1887 | EST | 3.72 | down | 0.00688 |
| N54604 | 2569 | EST | 3.72 | down | 0.00741 |
| N62443 | 2589 | EST | 3.72 | down | 0.01717 |
| H49415 | 1938 | EST | 3.72 | down | 0.0005 |
| N40188 | 2512 | EST | 3.72 | down | 0.01771 |
| R05309 | 2758 | EST | 3.72 | down | 0.0008 |
| AA428006 | 984 | DKFZP564B167 protein | 3.71 | down | 0.02325 |
| AA463311 | 1248 | EST | 3.71 | down | 0.04902 |
| N30856 | 2484 | solute carrier family 19 (thiamine transporter), member 2 | 3.71 | down | 0.00393 |
| S62539 | 3021 | insulin receptor substrate 1 | 3.7 | down | 0.01307 |
| AA179387 | 379 | DKFZP434N126 protein | 3.7 | down | 0.01588 |
| AA235288 | 494 | PTPL1-associated RhoGAP 1 | 3.7 | down | 0.00643 |
| AA598926 | 1441 | EST | 3.7 | down | 0.00432 |
| AA099589 | 210 | GDP dissociation inhibitor 2 | 3.7 | down | 0.04069 |
| AA382975 | 773 | EST | 3.7 | down | 0.00131 |
| L15702 | 2165 | B-factor, properdin | 3.7 | down | 0.04693 |
| D13705 | 1610 | cytochrome P450, subfamily IVA, polypeptide 11 | 3.7 | down | 0.00038 |
| X14787 | 3701 | thrombospondin 1 | 3.69 | down | 0.01115 |
| AA125861 | 243 | EST | 3.69 | down | 0.01547 |
| AA460916 | 1233 | EST | 3.69 | down | 0.04841 |
| AA156336 | 341 | nuclear receptor co-repressor 1 | 3.69 | down | 0.01276 |
| H41280 | 1925 | EST | 3.68 | down | 0.00455 |
| R00843 | 2750 | fragile histidine triad gene | 3.68 | down | 0.03578 |
| Z39431 | 3904 | KIAA1086 protein | 3.68 | down | 0.0013 |
| AA426156 | 959 | EST | 3.67 | down | 0.00153 |
| Z11737 | 3860 | flavin containing monooxygenase 4 | 3.67 | down | 0.00632 |
| AA283758 | 670 | EST | 3.67 | down | 0.04293 |
| H66840 | 1978 | EST | 3.67 | down | 0.0143 |
| W87824 | 3634 | EST | 3.67 | down | 0.01559 |
| AA287122 | 686 | EST | 3.66 | down | 0.00161 |
| L76927 | 2228 | galactokinase 1 | 3.66 | down | 0.00999 |
| AA031548 | 69 | cell division cycle 42 (GTP-binding protein, 25kD) | 3.65 | down | 0.03029 |
| AA400259 | 813 | EST | 3.65 | down | 0.00476 |
| H25124 | 1903 | EST | 3.65 | down | 0.00004 |
| AA279802 | 631 | EST | 3.65 | down | 0.03366 |
| U27699 | 3339 | solute carrier family 6 (neurotransmitter transporter, betaine/GABA), member 12 | 3.65 | down | 0.00381 |
| C02460 | 1562 | EST | 3.64 | down | 0.02705 |
| Z29481 | 3874 | 3-hydroxyanthranilate 3,4-dioxygenase | 3.64 | down | 0.00096 |
| AA281545 | 645 | EST | 3.64 | down | 0.00002 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| AA235811 | 502 | EST | 3.64 | down | 0.01272 |
| D86062 | 1752 | ES1 (zebrafish) protein, human homolog of | 3.63 | down | 0.0001 |
| Z41042 | 3925 | EST | 3.63 | down | 0.00943 |
| N69299 | 2648 | EST | 3.63 | down | 0.03776 |
| AA044622 | 103 | EST | 3.62 | down | 0.03789 |
| AA393825 | 776 | EST | 3.62 | down | 0.0065 |
| D80217 | 1727 | H91620p protein | 3.61 | down | 0.01973 |
| N45232 | 2516 | EST | 3.61 | down | 0.01308 |
| U48959 | 3371 | myosin, light polypeptide kinase | 3.61 | down | 0.00084 |
| F09058 | 1799 | EST | 3.6 | down | 0.00595 |
| T90531 | 3249 | EST | 3.6 | down | 0.00301 |
| AA025930 | 52 | EST | 3.59 | down | 0.00372 |
| AA235765 | 501 | KIAA0214 gene product | 3.59 | down | 0.01148 |
| D80905 | 1735 | EST | 3.59 | down | 0.0007 |
| H99935 | 2085 | interleukin 6 signal transducer (gp130, oncostatin M receptor) | 3.59 | down | 0.00366 |
| AA242766 | 523 | EST | 3.58 | down | 0.0151 |
| AA441791 | 1065 | EST | 3.58 | down | 0.00357 |
| F10640 | 1821 | EST | 3.58 | down | 0.00152 |
| AA282886 | 663 | EST | 3.57 | down | 0.00049 |
| AA416723 | 906 | EST | 3.57 | down | 0.01042 |
| H98977 | 2073 | EST | 3.57 | down | 0.00298 |
| T33011 | 3103 | EST | 3.57 | down | 0.02486 |
| T41232 | 3121 | EST | 3.57 | down | 0.00846 |
| T91348 | 3253 | EST | 3.57 | down | 0.00011 |
| AA427778 | 978 | EST | 3.57 | down | 0.00368 |
| H04142 | 1836 | EST | 3.57 | down | 0.01906 |
| R40556 | 2842 | EST | 3.57 | down | 0.00184 |
| AA032250 | 73 | EST | 3.56 | down | 0.0009 |
| R21232 | 2797 | EST | 3.56 | down | 0.00246 |
| AA127444 | 252 | EST | 3.56 | down | 0.0291 |
| H40424 | 1922 | butyrate response factor 1 (EGF-response factor 1) | 3.56 | down | 0.04066 |
| W15528 | 3474 | EST | 3.56 | down | 0.00424 |
| Z39978 | 3913 | EST | 3.56 | down | 0.04051 |
| L76465 | 2224 | hydroxyprostaglandin dehydrogenase 15-(NAD) | 3.56 | down | 0.00688 |
| HG3417–HT3600 | | GTP cyclohydrolase 1 (dopa-responsive dystonia) | 3.56 | down | 0.00317 |
| R71491 | 2953 | EST | 3.55 | down | 0.01903 |
| AA040291 | 94 | KIAA0669 gene product | 3.55 | down | 0.00308 |
| N49902 | 2539 | EST | 3.55 | down | 0.00455 |
| N67009 | 2621 | prion protein (p27–30) (Creutzfeld-Jakob disease, Gerstmann-Strausler-Scheinker syndrome, fatal familial insomnia) | 3.55 | down | 0.00956 |
| H25551 | 1904 | EST | 3.54 | down | 0.00366 |
| R51309 | 2889 | KIAA1077 protein | 3.54 | down | 0.04112 |
| AA039806 | 91 | msh (Drosophila) homeo box homolog 1 (formerly homeo box 7) | 3.53 | down | 0.00114 |
| AA194146 | 407 | EST | 3.53 | down | 0.00352 |
| AA037357 | 85 | EST | 3.53 | down | 0.02129 |
| AA287550 | 689 | DKFZP434C171 protein | 3.53 | down | 0.00217 |
| AA094507 | 201 | EST | 3.52 | down | 0.04783 |
| AA496423 | 1399 | WW domain binding protein 2 | 3.52 | down | 0.01314 |
| AA421052 | 929 | branched chain alpha-ketoacid dehydrogenase kinase | 3.52 | down | 0.00869 |
| X94563 | 3828 | EST | 3.52 | down | 0.00928 |
| W07723 | 3470 | EST | 3.51 | down | 0.00026 |
| X52150 | 3719 | arylsulfatase A | 3.51 | down | 0.00113 |
| AA055992 | 136 | calumenin | 3.51 | down | 0.00604 |
| N64436 | 2608 | EST | 3.51 | down | 0.00441 |
| R26904 | 2804 | EST | 3.51 | down | 0.00058 |
| L29008 | 2189 | sorbitol dehydrogenase | 3.51 | down | 0.00825 |
| U79716 | 3436 | reelin | 3.51 | down | 0.00053 |
| AA435591 | 1038 | kinesin family member 3B | 3.5 | down | 0.0001 |
| R12579 | 2789 | EST | 3.5 | down | 0.00137 |
| AA428863 | 991 | EST | 3.5 | down | 0.01726 |
| AA400780 | 818 | EST | 3.5 | down | 0.00107 |
| U44111 | 3362 | histamine N-methyltransferase | 3.5 | down | 0.00942 |
| U46689 | 3365 | aldehyde dehydrogenase 10 (fatty aldehyde dehydrogenase) | 3.5 | down | 0.01292 |
| Y08374 | 3850 | chitinase 3-like 1 (cartilage glycoprotein-39) | 3.5 | down | 0.04208 |
| H42053 | 1927 | EST | 3.49 | down | 0.01057 |
| AA489061 | 1367 | EST | 3.49 | down | 0.00223 |
| AA400831 | 819 | EST | 3.49 | down | 0.00105 |
| L07033 | 2144 | 3-hydroxymethyl-3-methylglutaryl-Coenzyme A lyase (hydroxymethylglutaricaciduria) | 3.49 | down | 0 |
| AA056247 | 138 | EST | 3.48 | down | 0.03277 |
| AA496914 | 1401 | v-maf musculoaponeurotic fibrosarcoma (avian) oncogene homolog | 3.48 | down | 0.00361 |
| H13696 | 1882 | EST | 3.48 | down | 0.01796 |
| F08941 | 1798 | EST | 3.48 | down | 0.00428 |
| T91161 | 3252 | EST | 3.48 | down | 0.00002 |
| M60974 | 2368 | growth arrest and DNA-damage-inducible, alpha | 3.48 | down | 0.00209 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| AA069456 | 149 | KIAA0438 gene product | 3.47 | down | 0.02718 |
| AA218727 | 445 | EST | 3.47 | down | 0.00125 |
| H02848 | 1831 | TEK tyrosine kinase, endothelial (venous malformations, multiple cutaneous and mucosal) | 3.47 | down | 0.0089 |
| AA282238 | 656 | EST | 3.47 | down | 0.00677 |
| AA092596 | 197 | bone morphogenetic protein 6 | 3.46 | down | 0.02532 |
| U84569 | 3444 | chromosome 21 open reading frame 2 | 3.46 | down | 0.01844 |
| R52949 | 2896 | EST | 3.46 | down | 0.00395 |
| W85886 | 3618 | EST | 3.46 | down | 0.00814 |
| AA455896 | 1181 | glypican 1 | 3.46 | down | 0.00887 |
| N93155 | 2728 | calmodulin 1 (phosphorylase kinase, delta) | 3.46 | down | 0.00031 |
| N59231 | 2581 | pyruvate carboxylase | 3.45 | down | 0.02066 |
| W73194 | 3587 | dermatopontin | 3.45 | down | 0.02211 |
| N54511 | 2568 | KIAA0265 protein | 3.45 | down | 0.03362 |
| M14636 | 2262 | phosphorylase, glycogen; liver (Hers disease, glycogen storage disease type VI) | 3.45 | down | 0.00133 |
| M18533 | 2284 | dystrophin (muscular dystrophy, Duchenne and Becker types), includes DXS142, DXS164, DXS206, DXS230, DXS239, DXS268, DXS269, DXS270, DXS272 | 3.45 | down | 0.00313 |
| M81182 | 2403 | ATP-binding cassette, sub-family D (ALD), member 3 | 3.45 | down | 0.00499 |
| M23161 | 2298 | EST | 3.44 | down | 0.00733 |
| AA427819 | 980 | midline 2 | 3.44 | down | 0.00063 |
| AA430047 | 1011 | EST | 3.44 | down | 0.0016 |
| AA621235 | 1517 | EST | 3.44 | down | 0.0021 |
| AA451911 | 1139 | EST | 3.44 | down | 0.00221 |
| H89514 | 2023 | protein kinase, cAMP-dependent, catalytic, alpha | 3.44 | down | 0.00435 |
| AA017192 | 37 | EST | 3.43 | down | 0.04865 |
| AA235618 | 499 | EST | 3.43 | down | 0.02127 |
| H99393 | 2076 | endothelin receptor type B | 3.43 | down | 0.00093 |
| AF005039 | 1548 | secretory carrier membrane protein 3 | 3.42 | down | 0.04953 |
| AA234831 | 491 | EST | 3.42 | down | 0.00206 |
| AA620830 | 1509 | DKFZP564I122 protein | 3.42 | down | 0.02421 |
| N70005 | 2652 | EST | 3.42 | down | 0.04229 |
| T96969 | 3263 | EST | 3.42 | down | 0.00053 |
| AA279112 | 622 | EST | 3.42 | down | 0.01444 |
| H82966 | 2011 | apolipoprotein B (including Ag(x) antigen) | 3.42 | down | 0.00769 |
| AA505198 | 1419 | EST | 3.41 | down | 0.0343 |
| AA429478 | 998 | EST | 3.41 | down | 0.02599 |
| AA463195 | 1245 | EST | 3.41 | down | 0.00413 |
| AA476352 | 1284 | EST | 3.41 | down | 0.02233 |
| F02094 | 1775 | ecotropic viral integration site 5 | 3.41 | down | 0.00495 |
| H87144 | 2016 | EST | 3.41 | down | 0.00387 |
| U86529 | 3450 | glutathione S-transferase zeta 1 (maleylacetoacetate isomerase) | 3.41 | down | 0.0118 |
| N49113 | 2534 | EST | 3.4 | down | 0.00162 |
| AA127514 | 253 | EST | 3.4 | down | 0.00045 |
| N69216 | 2645 | EST | 3.4 | down | 0.00497 |
| J04031 | 2103 | methylenetetrahydrofolate dehydrogenase (NADP+ dependent), methenyltetrahydrofolate cyclohydrolase, formyltetrahydrofolate synthetase | 3.4 | down | 0.00786 |
| L49169 | 2221 | FBJ murine osteosarcoma viral oncogene homolog B | 3.4 | down | 0.01193 |
| M30269 | 2323 | nidogen (enactin) | 3.4 | down | 0.00026 |
| U21931 | 3325 | fructose-bisphosphatase 1 | 3.4 | down | 0.00709 |
| Y00097 | 3841 | annexin A6 | 3.4 | down | 0.00233 |
| AA047290 | 118 | EST | 3.39 | down | 0.00024 |
| AA250744 | 536 | EST | 3.39 | down | 0.01137 |
| H26763 | 1907 | EST | 3.39 | down | 0.04188 |
| M30185 | 2321 | cholesteryl ester transfer protein, plasma | 3.39 | down | 0.00089 |
| M25280 | 2306 | selectin L (lymphocyte adhesion molecule 1) | 3.39 | down | 0.004 |
| AA463946 | 1254 | pigment epithelium-derived factor | 3.38 | down | 0.0018 |
| AA279937 | 634 | EST | 3.38 | down | 0.02719 |
| AA426468 | 966 | EST | 3.38 | down | 0.0099 |
| J04621 | 2113 | syndecan 2 (heparan sulfate proteoglycan 1, cell surface-associated, fibroglycan) | 3.38 | down | 0.00275 |
| AA461458 | 1241 | EST | 3.37 | down | 0.02427 |
| R17762 | 2794 | EST | 3.37 | down | 0.01822 |
| R43166 | 2846 | EST | 3.37 | down | 0.00919 |
| R97711 | 3004 | EST | 3.37 | down | 0.00838 |
| AA112209 | 223 | acyl-Coenzyme A dehydrogenase, long chain | 3.37 | down | 0.00084 |
| M88163 | 2415 | SWI/SNF related, matrix associated, actin dependent regulator of chromatin, subfamily a, member 1 | 3.37 | down | 0.00098 |
| U02020 | 3276 | pre-B-cell colony-enhancing factor | 3.37 | down | 0.01112 |
| N48180 | 2525 | EST | 3.36 | down | 0.00543 |
| T16269 | 3066 | EST | 3.36 | down | 0.00282 |
| AA134549 | 288 | EST | 3.36 | down | 0.03438 |
| AA458923 | 1207 | EST | 3.36 | down | 0.00421 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| D80408 | 1731 | EST | 3.36 | down | 0.00102 |
| AA293485 | 718 | EST | 3.36 | down | 0.02799 |
| W31478 | 3495 | EST | 3.36 | down | 0.01511 |
| M59916 | 2365 | sphingomyelin phosphodiesterase 1, acid lysosomal (acid sphingomyelinase) | 3.36 | down | 0.0038 |
| M23263 | 2300 | androgen receptor (dihydrotestosterone receptor; testicular feminization; spinal and bulbar muscular atrophy; Kennedy disease) | 3.35 | down | 0.02551 |
| H83451 | 2014 | EST | 3.35 | down | 0.00498 |
| W90560 | 3644 | EST | 3.35 | down | 0.00388 |
| AA456326 | 1191 | EST | 3.35 | down | 0.00489 |
| Z38192 | 3882 | EST | 3.35 | down | 0.00184 |
| AA284721 | 677 | EST | 3.34 | down | 0.03296 |
| D59344 | 1695 | EST | 3.34 | down | 0.01337 |
| N47469 | 2521 | EST | 3.34 | down | 0.00329 |
| N22854 | 2451 | CASP2 and RIPK1 domain containing adaptor with death domain | 3.34 | down | 0.0084 |
| N54399 | 2565 | EST | 3.34 | down | 0.00048 |
| U82468 | 3441 | tubby like protein 1 | 3.34 | down | 0.0097 |
| AA460047 | 1226 | EST | 3.33 | down | 0.04011 |
| AA001604 | 4 | EST | 3.33 | down | 0.0215 |
| AA121140 | 235 | EST | 3.33 | down | 0.00058 |
| HG2743–HT2846 | | caldesmon 1 | 3.33 | down | 0.00135 |
| N51737 | 2546 | mitogen-activated protein kinase kinase kinase 12 | 3.32 | down | 0.00376 |
| AA430026 | 1007 | EST | 3.31 | down | 0.00786 |
| H06166 | 1854 | EST | 3.31 | down | 0.03778 |
| AA062744 | 147 | EST | 3.31 | down | 0.01909 |
| W81079 | 3608 | EST | 3.31 | down | 0.0167 |
| AA227480 | 456 | pim-2 oncogene | 3.31 | down | 0.02413 |
| AA463876 | 1252 | EST | 3.31 | down | 0.00109 |
| H09167 | 1860 | KIAA0195 gene product | 3.31 | down | 0.00313 |
| H98822 | 2070 | EST | 3.31 | down | 0.00174 |
| R92458 | 2985 | hemoglobin, gamma G | 3.31 | down | 0.00763 |
| AA453917 | 1159 | EST | 3.3 | down | 0.01896 |
| M61854 | 2370 | cytochrome P450, subfamily IIC (mephenytoin 4-hydroxylase) | 3.3 | down | 0.04185 |
| AA281796 | 650 | mannose-P-dolichol utilitzation defect 1 | 3.3 | down | 0.04108 |
| F09353 | 1802 | solute carrier family 5 (inositol transporters), member 3 | 3.3 | down | 0.02841 |
| N27563 | 2472 | EST | 3.3 | down | 0.00021 |
| R01081 | 2752 | EST | 3.3 | down | 0.00839 |
| H25836 | 1905 | tumor necrosis factor (ligand) superfamily, member 10 | 3.3 | down | 0.03125 |
| AA452549 | 1146 | platelet-derived growth factor receptor, alpha polypeptide | 3.3 | down | 0.04155 |
| U28833 | 3340 | Down syndrome candidate region 1 | 3.3 | down | 0.00306 |
| T23680 | 3083 | calcium channel, voltage-dependent, gamma subunit 3 | 3.29 | down | 0.0003 |
| AA429038 | 995 | EST | 3.29 | down | 0.00927 |
| AA490882 | 1381 | EST | 3.29 | down | 0.00319 |
| AA460128 | 1227 | similar to S. pombe dim1+ | 3.28 | down | 0.01299 |
| AA496053 | 1396 | EST | 3.28 | down | 0.00095 |
| T52564 | 3140 | EST | 3.28 | down | 0.01506 |
| T55547 | 3147 | EST | 3.28 | down | 0.00047 |
| Z38777 | 3892 | nuclear receptor binding factor-2 | 3.28 | down | 0.022 |
| AA235507 | 498 | golgi autoantigen, golgin subfamily a, 5 | 3.28 | down | 0.00249 |
| X83416 | 3808 | prion protein (p27–30) (Creutzfeld-Jakob disease, Gerstmann-Strausler-Scheinker syndrome, fatal familial insomnia) | 3.28 | down | 0.00221 |
| H04242 | 1837 | RAB5B, member RAS oncogene family | 3.27 | down | 0.04826 |
| N52322 | 2552 | EST | 3.27 | down | 0.00933 |
| H63251 | 1972 | KIAA0606 protein; SCN Circadian Oscillatory Protein (SCOP) | 3.27 | down | 0.02455 |
| AA281930 | 651 | core-binding factor, runt domain, alpha subunit 2; translocated to, 3 | 3.27 | down | 0.02329 |
| X02160 | 3668 | insulin receptor | 3.27 | down | 0.0007 |
| C15871 | 1575 | EST | 3.26 | down | 0.00046 |
| AA447617 | 1103 | EST | 3.26 | down | 0.04687 |
| AA464603 | 1260 | EST | 3.26 | down | 0.0007 |
| Z39818 | 3909 | EST | 3.26 | down | 0.00089 |
| Z84718 | 3949 | EST | 3.26 | down | 0.02252 |
| AA598675 | 1433 | EST | 3.25 | down | 0.03934 |
| N93191 | 2729 | EST | 3.25 | down | 0.00232 |
| H09959 | 1869 | choline kinase | 3.25 | down | 0.00225 |
| H79820 | 2004 | EST | 3.25 | down | 0.01466 |
| AA070090 | 152 | EST | 3.24 | down | 0.00804 |
| AA406435 | 877 | EST | 3.24 | down | 0.00941 |
| W60186 | 3554 | EST | 3.24 | down | 0.00228 |
| H67094 | 1979 | EST | 3.24 | down | 0.00075 |
| R39234 | 2834 | EST | 3.24 | down | 0.0412 |
| T54160 | 3144 | EST | 3.24 | down | 0.00168 |
| T72629 | 3208 | EST | 3.24 | down | 0.00556 |
| W87480 | 3630 | STAT induced STAT inhibitor-2 | 3.24 | down | 0.01063 |
| Z14093 | 3862 | branched chain keto acid dehydrogenase E1, alpha polypeptide (maple syrup urine disease) | 3.24 | down | 0.00301 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| N54792 | 2570 | cytidine monophosphate-N-acetylneuraminic acid hydroxylase (CMP-N-acetylneuraminate monooxygenase) | 3.23 | down | 0.0099 |
| AA076238 | 168 | EST | 3.23 | down | 0.00395 |
| AA088698 | 188 | EST | 3.23 | down | 0.02543 |
| AA281591 | 646 | EST | 3.23 | down | 0.00895 |
| N67096 | 2622 | EST | 3.23 | down | 0.00446 |
| U51903 | 3386 | IQ motif containing GTPase activating protein 2 | 3.23 | down | 0.00242 |
| AA436880 | 1058 | EST | 3.22 | down | 0.00699 |
| H26417 | 1906 | EST | 3.22 | down | 0.03672 |
| N53352 | 2557 | EST | 3.22 | down | 0.00416 |
| AA447740 | 1106 | EST | 3.22 | down | 0.02518 |
| HG3510–HT3704 | | nuclear receptor subfamily 2, group F, member 1 | 3.22 | down | 0.00034 |
| HG3431–HT3616 | | decorin | 3.22 | down | 0.01941 |
| AA443993 | 1086 | EST | 3.21 | down | 0.02948 |
| T65972 | 3176 | EST | 3.21 | down | 0.04847 |
| S52028 | 3018 | cystathionase (cystathionine gamma-lyase) | 3.21 | down | 0.00476 |
| M33318 | 2339 | cytochrome P450, subfamily IIA (phenobarbital-inducible), polypeptide 6 | 3.21 | down | 0.01621 |
| AA348466 | 756 | regulator of G-protein signalling 5 | 3.2 | down | 0.00571 |
| AA459293 | 1213 | EST | 3.2 | down | 0.0001 |
| H27330 | 1909 | EST | 3.2 | down | 0.00067 |
| AA046457 | 111 | EST | 3.2 | down | 0.00513 |
| AA234916 | 492 | EST | 3.2 | down | 0.00799 |
| R10662 | 2786 | mutL (E. coli) homolog 1 (colon cancer, nonpolyposis type 2) | 3.2 | down | 0.0005 |
| H46990 | 1933 | cytochrome P450, subfamily IIE (ethanol-inducible) | 3.2 | down | 0.00095 |
| U01824 | 3275 | solute carrier family 1 (glial high affinity gluamate transporter), member 2 | 3.2 | down | 0.00021 |
| X61123 | 3750 | B-cell translocation gene 1, anti-proliferative | 3.2 | down | 0.00796 |
| H10482 | 1870 | EST | 3.19 | down | 0.01611 |
| U82108 | 3440 | solute carrier family 9 (sodium/hydrogen exchanger), isoform 3 regulatory factor 2 | 3.19 | down | 0.01545 |
| AA084668 | 180 | ubiquitin-like 3 | 3.19 | down | 0.0419 |
| H12257 | 1879 | EST | 3.19 | down | 0.0069 |
| N74558 | 2686 | EST | 3.19 | down | 0.00247 |
| R69031 | 2940 | EST | 3.19 | down | 0.00798 |
| AA191488 | 398 | solute carrier family 31 (copper transporters), member 1 | 3.19 | down | 0.00013 |
| U67963 | 3409 | lysophospholipase-like | 3.19 | down | 0.00029 |
| M24283 | 2303 | intercellular adhesion molecule 1 (CD54), human rhinovirus receptor | 3.19 | down | 0.04985 |
| AA157520 | 347 | EST | 3.18 | down | 0.00516 |
| AA418098 | 920 | cAMP responsive element binding protein-like 2 | 3.18 | down | 0.03824 |
| AA005202 | 12 | retinol-binding protein 4, interstitial | 3.18 | down | 0.00106 |
| AA227901 | 459 | SEC24 (S. cerevisiae) related gene family, member B | 3.18 | down | 0.00397 |
| H40534 | 1923 | EST | 3.18 | down | 0.01381 |
| AA236942 | 519 | EST | 3.18 | down | 0 |
| D16481 | 1621 | hydroxyacyl-Coenzyme A dehydrogenase/3-ketoacyl-Coenzyme A thiolase/enoyl-Coenzyme A hydratase (trifunctional protein), beta subunit | 3.18 | down | 0.00695 |
| D31225 | 1641 | EST | 3.17 | down | 0.01073 |
| H95358 | 2049 | EST | 3.17 | down | 0.00182 |
| H89893 | 2025 | EST | 3.17 | down | 0.00658 |
| N48602 | 2528 | EST | 3.17 | down | 0.02913 |
| T86464 | 3236 | EST | 3.17 | down | 0.00498 |
| AA125856 | 242 | EST | 3.17 | down | 0.01545 |
| H93562 | 2038 | proline synthetase co-transcribed (bacterial homolog) | 3.17 | down | 0.00113 |
| Y10659 | 3856 | interleukin 13 receptor, alpha 1 | 3.17 | down | 0.00095 |
| X67235 | 3770 | hematopoietically expressed homeobox | 3.17 | down | 0.0045 |
| AA004231 | 7 | EST | 3.16 | down | 0.03067 |
| F04335 | 1787 | EST | 3.16 | down | 0.0058 |
| T10822 | 3054 | EST | 3.16 | down | 0.00635 |
| T79842 | 3224 | EST | 3.16 | down | 0.03159 |
| AA180356 | 382 | EST | 3.16 | down | 0.00917 |
| AA207123 | 430 | immunoglobulin superfamily, member 3 | 3.16 | down | 0.00328 |
| AA397914 | 783 | EST | 3.16 | down | 0.00336 |
| AA599954 | 1459 | cell cycle progression 8 protein | 3.15 | down | 0.00021 |
| H06063 | 1852 | chondroitin sulfate proteoglycan 3 (neurocan) | 3.15 | down | 0.00599 |
| W61000 | 3557 | EST | 3.15 | down | 0.03143 |
| J02888 | 2089 | NAD(P)H menadione oxidoreductase 2, dioxin-inducible | 3.15 | down | 0.02385 |
| U62389 | 3401 | isocitrate dehydrogenase 1 (NADP+), soluble | 3.15 | down | 0.03949 |
| X04729 | 3679 | plasminogen activator inhibitor, type 1 | 3.15 | down | 0.01337 |
| N45998 | 2519 | EST | 3.14 | down | 0.00337 |
| R54416 | 2900 | EST | 3.14 | down | 0.00236 |
| AA446651 | 1093 | EST | 3.14 | down | 0.01902 |
| AA608671 | 1466 | EST | 3.14 | down | 0.04543 |
| W51951 | 3539 | dCMP deaminase | 3.14 | down | 0.01691 |
| AA101055 | 213 | leptin receptor | 3.14 | down | 0.0071 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| J04615 | 2112 | SNRPN upstream reading frame | 3.14 | down | 0.02928 |
| M20902 | 2292 | apolipoprotein C-I | 3.14 | down | 0.0389 |
| L77567 | 2229 | solute carrier family 25 (mitochondrial carrier; citrate transporter), member 1 | 3.14 | down | 0.04095 |
| AA487161 | 1353 | ubiquilin 2 | 3.13 | down | 0.00023 |
| H19504 | 1895 | EST | 3.13 | down | 0.04948 |
| N27524 | 2471 | EST | 3.13 | down | 0.00216 |
| N31952 | 2489 | EST | 3.13 | down | 0.01481 |
| N25193 | 2463 | EST | 3.13 | down | 0.01955 |
| N63688 | 2602 | EST | 3.13 | down | 0.002 |
| N99866 | 2747 | EST | 3.13 | down | 0.04148 |
| AA452915 | 1152 | EST | 3.13 | down | 0.00561 |
| AA477119 | 1289 | EST | 3.13 | down | 0.0338 |
| U25182 | 3332 | thioredoxin peroxidase (antioxidant enzyme) | 3.13 | down | 0.02543 |
| U79294 | 3434 | Phosphatidic acid phosphatase type 2b | 3.13 | down | 0.00129 |
| X17025 | 3712 | isopentenyl-diphosphate delta isomerase | 3.13 | down | 0.0043 |
| L38490 | 2207 | ADP-ribosylation factor 4-like | 3.13 | down | 0.01306 |
| AA402095 | 835 | EST | 3.12 | down | 0.01412 |
| AA479132 | 1309 | EST | 3.12 | down | 0.00876 |
| R67751 | 2938 | EST | 3.12 | down | 0.00319 |
| AA490214 | 1376 | EST | 3.12 | down | 0.02382 |
| H09594 | 1868 | EST | 3.12 | down | 0.00231 |
| H59141 | 1963 | EST | 3.12 | down | 0.00293 |
| T23430 | 3079 | EST | 3.12 | down | 0.00949 |
| T82259 | 3229 | EST | 3.12 | down | 0.01122 |
| Z38435 | 3887 | ribosomal protein L21 | 3.12 | down | 0.03617 |
| AA074891 | 162 | EST | 3.12 | down | 0.01897 |
| AA476346 | 1283 | EST | 3.12 | down | 0.01067 |
| H05072 | 1843 | EST | 3.12 | down | 0.01248 |
| AA405907 | 867 | EST | 3.12 | down | 0 |
| N79435 | 2700 | chromosome 15 open reading frame 3 | 3.12 | down | 0.00861 |
| R44761 | 2857 | aryl hydrocarbon receptor nuclear translocator | 3.12 | down | 0.02663 |
| D13814 | 1611 | angiotensin receptor 1,angiotensin receptor 1B | 3.12 | down | 0.00101 |
| X95876 | 3833 | G protein-coupled receptor 9 | 3.12 | down | 0.001 |
| AA298180 | 726 | EST | 3.11 | down | 0.00747 |
| W35309 | 3499 | EST | 3.11 | down | 0.029 |
| AA243595 | 530 | EST | 3.11 | down | 0.008 |
| AA280791 | 640 | eukaryotic translation initiation factor 5 | 3.11 | down | 0.03339 |
| T68426 | 3185 | CD81 antigen (target of antiproliferative antibody 1) | 3.11 | down | 0.01634 |
| AA401343 | 828 | EST | 3.11 | down | 0.01929 |
| AA454170 | 1163 | EST | 3.11 | down | 0.03 |
| M30257 | 2322 | vascular cell adhesion molecule 1 | 3.11 | down | 0.00064 |
| H67840 | 1980 | EST | 3.1 | down | 0.00528 |
| AA455962 | 1182 | EST | 3.1 | down | 0.03905 |
| AA609576 | 1486 | EST | 3.1 | down | 0.00266 |
| H06144 | 1853 | EST | 3.1 | down | 0.00745 |
| H47391 | 1935 | EST | 3.1 | down | 0.03807 |
| N31598 | 2487 | EST | 3.1 | down | 0.00203 |
| N95585 | 2742 | EST | 3.1 | down | 0.0083 |
| AA457377 | 1201 | EST | 3.1 | down | 0.00549 |
| HG3998–HT4268 | | glycerol-3-phosphate dehydrogenase 1 (soluble) | 3.1 | down | 0.00523 |
| AA247453 | 533 | EST | 3.09 | down | 0.0015 |
| AA284558 | 674 | Nck, Ash and phospholipase C binding protein | 3.09 | down | 0.00027 |
| U06863 | 3287 | follistatin-like 1 | 3.09 | down | 0.00091 |
| AA282179 | 655 | EST | 3.09 | down | 0.01693 |
| AA621430 | 1525 | doublecortex; lissencephaly, X-linked (doublecortin) | 3.09 | down | 0.00024 |
| H82838 | 1971 | EST | 3.09 | down | 0.03201 |
| W67199 | 3566 | EST | 3.09 | down | 0.01528 |
| AA400246 | 810 | mitogen-activated protein kinase-activated protein kinase 2 | 3.09 | down | 0.00476 |
| AA412034 | 894 | EST | 3.09 | down | 0.02309 |
| AA443934 | 1083 | GTP-binding protein Rho7 | 3.09 | down | 0.00214 |
| AA456687 | 1197 | EST | 3.08 | down | 0.01189 |
| R80573 | 2972 | EST | 3.08 | down | 0.02126 |
| R82229 | 2974 | phosphatidylserine decarboxylase | 3.08 | down | 0.03455 |
| W52581 | 3540 | CD36 antigen (collagen type I receptor, thrombospondin receptor)-like 2 (lysosomal integral membrane protein II) | 3.08 | down | 0.00091 |
| N90584 | 2713 | EST | 3.08 | down | 0.02602 |
| AA126059 | 246 | EST | 3.08 | down | 0.00706 |
| AA485326 | 1342 | ATP-binding cassette, sub-family D (ALD), member 4 | 3.08 | down | 0.00415 |
| N21550 | 2443 | EST | 3.08 | down | 0.00006 |
| AA412184 | 898 | EST | 3.08 | down | 0.00012 |
| AA416740 | 907 | EST | 3.08 | down | 0.01592 |
| U73682 | 3419 | meningioma expressed antigen 6 (coiled-coil proline-rich) | 3.08 | down | 0.01249 |
| M16750 | 2273 | pim-1 oncogene | 3.08 | down | 0.01811 |
| Z26491 | 3870 | catechol-O-methyltransferase | 3.08 | down | 0.00877 |

TABLE 6B-continued

Down in Metastatics vs Normal Sample Set 2

| Fragment Name | SEQ ID: | Known Gene Name | Fold Change | Direction | Pvalue |
|---|---|---|---|---|---|
| D58231 | 1692 | ubiquitin-like 3 | 3.07 | down | 0.0002 |
| T94862 | 3257 | EST | 3.07 | down | 0.01417 |
| N34441 | 2495 | EST | 3.07 | down | 0.00186 |
| T16175 | 3063 | protein tyrosine phosphatase, non-receptor type substrate 1 | 3.07 | down | 0.01007 |
| H39119 | 1919 | EST | 3.06 | down | 0.03349 |
| R56602 | 2906 | Ig superfamily protein | 3.06 | down | 0.02464 |
| T49061 | 3134 | EST | 3.06 | down | 0.00768 |
| N68993 | 2640 | EST | 3.06 | down | 0.00867 |
| U36922 | 3351 | EST | 3.06 | down | 0.01388 |
| U69141 | 3413 | glutaryl-Coenzyme A dehydrogenase | 3.06 | down | 0.00053 |
| AA253455 | 565 | EST | 3.05 | down | 0.00533 |
| AA338512 | 742 | EST | 3.05 | down | 0.03427 |
| AA487606 | 1358 | EST | 3.05 | down | 0.00291 |
| R02752 | 2757 | EST | 3.05 | down | 0.00362 |
| M12529 | 2244 | apolipoprotein E | 3.05 | down | 0.03776 |
| T30341 | 3100 | EST | 3.04 | down | 0.04567 |
| AA047187 | 117 | EST | 3.04 | down | 0.04306 |
| R07637 | 2777 | EST | 3.04 | down | 0.00118 |
| R51256 | 2888 | EST | 3.04 | down | 0.00286 |
| W42483 | 3507 | EST | 3.04 | down | 0.02518 |
| X87344 | 3814 | EST | 3.04 | down | 0.02779 |
| AA040270 | 93 | EST | 3.03 | down | 0.01367 |
| R05490 | 2760 | SEC24 (*S. cerevisiae*) related gene family, member B | 3.03 | down | 0.00317 |
| N93246 | 2730 | EST | 3.03 | down | 0.00049 |
| L20965 | 2175 | phosphodiesterase 4A, cAMP-specific (dunce (Drosophila)-homolog phosphodiesterase E2) | 3.02 | down | 0.01177 |
| H57850 | 1958 | protein phosphatase 2 (formerly 2A), regulatory subunit A (PR 65), beta isoform | 3.02 | down | 0.00123 |
| W61319 | 3558 | EST | 3.02 | down | 0.00031 |
| AA599526 | 1453 | cartilage associated protein | 3.02 | down | 0.00043 |
| AA609572 | 1484 | EST | 3.02 | down | 0.01534 |
| AA490890 | 1382 | EST | 3.02 | down | 0.00007 |
| X76105 | 3791 | death-associated protein | 3.02 | down | 0.00944 |
| M92843 | 2420 | zinc finger protein homologous to Zfp-36 in mouse | 3.02 | down | 0.04958 |
| D01686 | 1557 | EST | 3.01 | down | 0.00048 |
| T92950 | 3255 | EST | 3.01 | down | 0.00497 |
| AA349836 | 760 | EST | 3.01 | down | 0.00911 |
| AA401151 | 827 | lysozyme (renal amyloidosis) | 3.01 | down | 0.0051 |
| AA459256 | 1212 | lectin, mannose-binding, 1 | 3.01 | down | 0.00094 |
| AA215585 | 442 | nucix (nucleoside diphosphate linked moiety X)-type motif 3 | 3 | down | 0.03027 |
| AA292711 | 711 | EST | 3 | down | 0.01053 |
| AA410181 | 881 | EST | 3 | down | 0.00268 |
| W70313 | 3575 | EST | 3 | down | 0.00643 |

TABLE 7A

Up in HCC vs Normal Sample Set 2

| Fragment Name | SEQ ID: | Known Gene Name | Fold Change | Direction | Pvalue |
|---|---|---|---|---|---|
| N33920 | 2492 | diubiquitin | 50.29 | up | 0 |
| Y00705 | 3847 | serine protease inhibitor, Kazal type 1 | 28.88 | up | 0.00003 |
| AA398908 | 801 | EST | 20.72 | up | 0.00114 |
| AA099404 | 208 | EST | 20.22 | up | 0 |
| AA610116 | 1499 | tetraspan NET-6 potein | 16.35 | up | 0.00249 |
| N26904 | 2468 | EST | 15.38 | up | 0.00077 |
| R91819 | 2983 | EST | 12.81 | up | 0.00037 |
| AA505133 | 1417 | solute carrier family 2 (facilitated glucose transporter), member 3 | 12.21 | up | 0.00169 |
| AA405791 | 864 | EST | 11.79 | up | 0.00587 |
| N59536 | 2585 | EST | 11.68 | up | 0.00484 |
| AA055896 | 135 | collagen, type V, alpha 1 | 10.87 | up | 0.00907 |
| H99879 | 2084 | EST | 10.81 | up | 0.001 |
| L47125 | 2218 | glypican 3 | 10.69 | up | 0.04129 |
| AA430032 | 1009 | pituitary tumor-transforming 1 | 10.67 | up | 0.00052 |
| Z37987 | 3879 | glypican 3 | 10.66 | up | 0.02304 |
| J03464 | 2094 | collagen, type I, alpha 2 | 10.37 | up | 0.00979 |
| W45320 | 3520 | KRAB-associated protein 1 | 10.05 | up | 0.00002 |
| M94250 | 2425 | midkine (neurite growth-promoting factor 2) | 9.86 | up | 0.02104 |
| AA428172 | 986 | Notch (Drosophila) homolog 3 | 9.63 | up | 0.00195 |
| AA620881 | 1510 | trinucleotide repeat containing 3 | 9.49 | up | 0.00062 |
| AA142857 | 307 | EST | 9.48 | up | 0.00376 |

TABLE 7A-continued

Up in HCC vs Normal Sample Set 2

| Fragment Name | SEQ ID: | Known Gene Name | Fold Change | Direction | Pvalue |
|---|---|---|---|---|---|
| D51276 | 1678 | leukemia-associated phosphoprotein p18 (stathmin) | 9.42 | up | 0.00015 |
| AA156187 | 339 | ATP synthase, H + transporting, mitochondrial F0 complex, subunit b, isoform 1 | 9.38 | up | 0.02007 |
| D31094 | 1639 | G8 protein | 9.37 | up | 0.0048 |
| AA148977 | 322 | EST | 9.3 | up | 0.00002 |
| F08876 | 1797 | EST | 9.06 | up | 0 |
| AA232837 | 465 | EST | 8.85 | up | 0.0048 |
| AA429472 | 997 | DKFZP434P106 protein | 8.78 | up | 0.00063 |
| T24068 | 3087 | EST | 8.65 | up | 0.00118 |
| AA149889 | 326 | neighbor of A-kinase anchoring protein 95 | 8.55 | up | 0.00224 |
| AA398926 | 802 | EST | 8.25 | up | 0.00066 |
| C01766 | 1559 | EST | 8.18 | up | 0.00505 |
| N36432 | 2506 | erythrocyte membrane protein band 4.1-like 2 | 7.95 | up | 0.00067 |
| AA452724 | 1149 | programmed cell death 5 | 7.7 | up | 0.00085 |
| AA401965 | 833 | tumor suppressor deleted in oral cancer-related 1 | 7.58 | up | 0.00089 |
| AA620553 | 1504 | flap structure-specific endonuclease 1 | 7.56 | up | 0.00101 |
| AA024658 | 47 | ribosomal protein S19 | 7.55 | up | 0.00592 |
| AA136269 | 298 | EST | 7.5 | up | 0.00014 |
| H78211 | 2001 | EST | 7.5 | up | 0.02674 |
| AA393139 | 775 | geminin | 7.44 | up | 0.00888 |
| AA251792 | 546 | fatty-acid-Coenzyme A ligase, long-chain 4 | 7.44 | up | 0.00285 |
| AA417030 | 914 | EST | 7.35 | up | 0.00555 |
| AA394258 | 779 | RD RNA-binding protein | 7.27 | up | 0.00054 |
| AA292765 | 712 | ZW10 interactor | 7.24 | up | 0.00498 |
| T16226 | 3065 | EST | 7.23 | up | 0.00119 |
| H08863 | 1859 | hypothetical protein | 7.18 | up | 0.02102 |
| M12125 | 2241 | tropomyosin 2 (beta) | 7.13 | up | 0.0004 |
| R96924 | 3000 | EST | 7.04 | up | 0.00012 |
| AA243133 | 525 | serine/threonine kinase 15 | 7.03 | up | 0.00005 |
| R06986 | 2775 | peptidylprolyl isomerase B (cylophilin B) | 7.03 | up | 0.00628 |
| N93299 | 2731 | nuclear receptor co-repressor 1 | 6.99 | up | 0.0371 |
| Z39682 | 3908 | KIAA0954 protein | 6.96 | up | 0.01966 |
| D26129 | 1635 | ribonuclease, RNase A family, 1 (pancreatic) | 6.9 | up | 0.00008 |
| AA280734 | 639 | KIAA0618 gene product | 6.83 | up | 0.001 |
| T58607 | 3154 | EST | 6.83 | up | 0.03711 |
| H97013 | 2059 | ephrin-A4 | 6.8 | up | 0.00023 |
| AA283182 | 668 | EST | 6.78 | up | 0.01784 |
| M57710 | 2357 | lectin, galactoside-binding, soluble, 3 (galectin 3) | 6.76 | up | 0.00103 |
| AA434418 | 1036 | KIAA1115 protein | 6.75 | up | 0.0032 |
| AA263032 | 614 | ATP synthase, H + transporting, mitochondrial F0 complex, subunit b, isoform 1 | 6.73 | up | 0.04478 |
| AA173755 | 374 | EST | 6.73 | up | 0.00666 |
| AA421951 | 936 | EST | 6.69 | up | 0.00013 |
| W31906 | 3496 | secretagogin | 6.62 | up | 0.00926 |
| AA148885 | 320 | minichromosome maintenance deficient (S. cerevisiae) 4 | 6.59 | up | 0.00112 |
| AA159025 | 353 | EST | 6.58 | up | 0.01946 |
| R44617 | 2856 | MyoD family inhibitor | 6.54 | up | 0.02505 |
| W94885 | 3657 | EST | 6.53 | up | 0 |
| L29218 | 2190 | CDC-like kinase 2 | 6.51 | up | 0.00019 |
| H99473 | 2077 | regulator of nonsense transcripts 1 | 6.51 | up | 0.00025 |
| AA258421 | 595 | hypothetical protein | 6.5 | up | 0.00559 |
| AA454830 | 1170 | DKFZP586M2123 protein | 6.48 | up | 0.00555 |
| R45994 | 2866 | EST | 6.48 | up | 0.00358 |
| AA335191 | 741 | creatine kinase, brain | 6.47 | up | 0.01462 |
| T95057 | 3258 | EST | 6.46 | up | 0.00613 |
| AA011209 | 30 | melanoma-associated antigen recognised by T lymphocytes | 6.45 | up | 0.00088 |
| N73808 | 2678 | EST | 6.44 | up | 0.00352 |
| N62126 | 2588 | EST | 6.42 | up | 0.00109 |
| AA454908 | 1171 | KIAA0144 gene product | 6.39 | up | 0.01863 |
| W80852 | 3606 | KDEL (Lys-Asp-Glu-Leu) endoplasmic reticulum protein retention receptor 3 | 6.37 | up | 0.00005 |
| AA043111 | 97 | EST | 6.36 | up | 0.0005 |
| AA446242 | 1087 | EST | 6.3 | up | 0.00169 |
| F04320 | 1786 | replication factor C (activator 1) 4 (37 kD) | 6.29 | up | 0.00042 |
| H94471 | 2042 | occludin | 6.26 | up | 0.00379 |
| AA284945 | 680 | EST | 6.25 | up | 0.0002 |
| J00231 | 2087 | immunoglobulin heavy constant gamma 3 (G3m marker) | 6.23 | up | 0.00177 |
| AA258131 | 587 | putative GTP-binding protein similar to RAY/RAB1C | 6.23 | up | 0.00931 |
| AA291139 | 695 | EST | 6.22 | up | 0.03491 |
| AA459254 | 1211 | EST | 6.22 | up | 0.00001 |
| H10933 | 1873 | EST | 6.18 | up | 0.00003 |
| R48594 | 2874 | EST | 6.15 | up | 0.03831 |
| AA204927 | 425 | tropomyosin 1 (alpha) | 6.11 | up | 0.0014 |
| AA405098 | 855 | EST | 6.09 | up | 0.01224 |
| T47032 | 3123 | partner of RAC1 (arfaptin 2) | 6.09 | up | 0.00019 |
| W81654 | 3613 | SRY (sex determining region Y)-box 13 | 6.06 | up | 0.00127 |
| R79246 | 2968 | melanoma adhesion molecule | 6.06 | up | 0.00057 |

TABLE 7A-continued

Up in HCC vs Normal Sample Set 2

| Fragment Name | SEQ ID: | Known Gene Name | Fold Change | Direction | Pvalue |
|---|---|---|---|---|---|
| R70801 | 2949 | EST | 6.06 | up | 0.00291 |
| D59355 | 1696 | cytoskeleton-associated protein 1 | 6.05 | up | 0.0015 |
| X05610 | 3682 | collagen, type IV, alpha 2 | 6.04 | up | 0.00062 |
| F01831 | 1773 | EST | 5.95 | up | 0.00532 |
| D59553 | 1697 | golgin-67 | 5.95 | up | 0.00169 |
| Z74616 | 3947 | collagen, type I, alpha 2 | 5.95 | up | 0.02212 |
| AA181705 | 385 | EST | 5.9 | up | 0.00023 |
| C01721 | 1558 | phospholipase C, beta 3, neighbor pseudogene | 5.89 | up | 0.0383 |
| T16550 | 3071 | vacuolar protein sorting 45B (yeast homolog) | 5.88 | up | 0.00004 |
| AA282247 | 657 | EST | 5.88 | up | 0.01112 |
| N54841 | 2571 | EST | 5.87 | up | 0.02752 |
| M31303 | 2327 | leukemia-associated phosphoprotein p18 (stathmin) | 5.86 | up | 0.00071 |
| H05084 | 1844 | EST | 5.85 | up | 0.0059 |
| H27188 | 1908 | collagen-binding protein 2 (colligen 2) | 5.84 | up | 0.01826 |
| AA496981 | 1404 | v-erb-b2 avian erythroblastic leukemia viral oncogene homolog 3 | 5.82 | up | 0.00521 |
| H59617 | 1964 | EST | 5.81 | up | 0.0115 |
| W42957 | 3513 | calmodulin 2 (phosphorylase kinase, delta) | 5.79 | up | 0.03669 |
| AA282343 | 658 | purine-rich element binding protein B | 5.78 | up | 0.00128 |
| AA455239 | 1174 | chromosome-associated polypeptide C | 5.78 | up | 0.00003 |
| AA234096 | 479 | EST | 5.75 | up | 0.01169 |
| U45285 | 3363 | T-cell, immune regulator 1 | 5.75 | up | 0.00006 |
| AA504512 | 1415 | KIAA0943 protein | 5.72 | up | 0.00384 |
| AA443602 | 1078 | EST | 5.71 | up | 0.00736 |
| AA092129 | 194 | EST | 5.67 | up | 0.00011 |
| F02807 | 1781 | KIAA0838 protein | 5.67 | up | 0.02064 |
| N80703 | 2703 | EST | 5.65 | up | 0.0001 |
| AA235448 | 497 | EST | 5.62 | up | 0.00077 |
| AA449073 | 1117 | EST | 5.61 | up | 0.01214 |
| T47325 | 3124 | EST | 5.6 | up | 0.02923 |
| AA135153 | 291 | EST | 5.58 | up | 0.00327 |
| D00596 | 1590 | thymidylate synthetase | 5.58 | up | 0.0098 |
| N72116 | 2667 | solute carrier family 11 (proton-coupled divalent metal ion transporters), member 2 | 5.57 | up | 0.00709 |
| T03580 | 3045 | pyruvate kinase, muscle | 5.57 | up | 0.01344 |
| R07172 | 2776 | EST | 5.54 | up | 0.01322 |
| W78057 | 3597 | EST | 5.53 | up | 0.01231 |
| R72886 | 2955 | KIAA0422 protein | 5.5 | up | 0.00091 |
| AA458878 | 1204 | EST | 5.49 | up | 0.00977 |
| D55716 | 1686 | minichromosome maintenance deficient (*S. cerevisiae*) 7 | 5.48 | up | 0.00003 |
| W26716 | 3481 | non-histone chromosome protein 2 (*S. cerevisiae*)-like 1 | 5.47 | up | 0.00146 |
| AA134052 | 285 | Rab geranylgeranyltransferase, alpha subunit | 5.47 | up | 0.00982 |
| Z74615 | 3946 | collagen, type I, alpha 1 | 5.47 | up | 0.00283 |
| AA410469 | 883 | EST | 5.45 | up | 0.00068 |
| R44793 | 2858 | EST | 5.4 | up | 0.00329 |
| AA133666 | 283 | cysteine-rich protein 2 | 5.35 | up | 0.00433 |
| W02041 | 3465 | EST | 5.34 | up | 0.00027 |
| U75285 | 3421 | apoptosis inhibitor 4 (survivin) | 5.32 | up | 0.01127 |
| AA416970 | 912 | Mad4 homolog | 5.3 | up | 0.00418 |
| AA102489 | 219 | EST | 5.28 | up | 0.02122 |
| T89703 | 3243 | EST | 5.27 | up | 0.00019 |
| N69263 | 2647 | EST | 5.26 | up | 0.0276 |
| T62918 | 3168 | EST | 5.25 | up | 0.00687 |
| AA226932 | 453 | DKFZP564F0923 protein | 5.25 | up | 0.00612 |
| AA007507 | 18 | KIAA1080 protein; Golgi-associated, gamma-adaptin ear containing, ARF-binding protein 2 | 5.23 | up | 0.00159 |
| AA133527 | 281 | EST | 5.23 | up | 0.00037 |
| AA249819 | 535 | EST | 5.22 | up | 0.00049 |
| T15852 | 3061 | EST | 5.21 | up | 0.00642 |
| R39191 | 2833 | KIAA1020 protein | 5.18 | up | 0.03185 |
| M86752 | 2411 | stress-induced-phosphoprotein 1 (Hsp70/Hsp90-organizing protein) | 5.15 | up | 0.02881 |
| T17066 | 3074 | SET domain, bifurcated, 1 | 5.14 | up | 0.00073 |
| W46846 | 3529 | EST | 5.11 | up | 0.00025 |
| F02254 | 1777 | Fas-activated serine/threonine kinase | 5.1 | up | 0.00329 |
| W86748 | 3626 | EST | 5.09 | up | 0.01882 |
| T53590 | 3143 | cytochrome P450, subfamily XIA (cholesterol side chain cleavage) | 5.09 | up | 0.00002 |
| H41529 | 1926 | EST | 5.06 | up | 0.03309 |
| AA608897 | 1473 | EST | 5.05 | up | 0.01782 |
| AA491188 | 1387 | solute carrier family 2 (facilitated glucose transporter), member 3 | 5.04 | up | 0.02291 |
| AA026356 | 57 | EST | 5.04 | up | 0.02483 |
| W46634 | 3527 | EST | 5.03 | up | 0.02152 |
| AA460909 | 1232 | EST | 5.02 | up | 0.01354 |
| AA421562 | 934 | anterior gradient 2 (*Xenopus laevis*) homolog | 5.02 | up | 0.02818 |
| AA027833 | 59 | EST | 5.02 | up | 0.01123 |
| AA435748 | 1044 | EST | 5.01 | up | 0.01812 |
| R44839 | 2860 | i-beta-1,3-N-acetylglucosaminyltransferase | 5 | up | 0.01812 |

TABLE 7A-continued

Up in HCC vs Normal Sample Set 2

| Fragment Name | SEQ ID: | Known Gene Name | Fold Change | Direction | Pvalue |
|---|---|---|---|---|---|
| T67053 | 3179 | EST | 5 | up | 0.01846 |
| AA470156 | 1276 | EST | 4.99 | up | 0.0206 |
| R70005 | 2943 | EST | 4.98 | up | 0.00007 |
| W80763 | 3605 | EST | 4.98 | up | 0.01026 |
| T33508 | 3105 | phosphatidylinositol-4-phosphate 5-kinase, type II, beta | 4.96 | up | 0.00064 |
| AA442054 | 1067 | phospholipase C, gamma 1 (formerly subtype 148) | 4.94 | up | 0.04102 |
| H28333 | 1912 | melanoma adhesion molecule | 4.94 | up | 0.00166 |
| R49476 | 2882 | EST | 4.93 | up | 0.00763 |
| AA291168 | 696 | EST | 4.93 | up | 0.01633 |
| AA410962 | 887 | peroxisome proliferative activated receptor, delta | 4.91 | up | 0.0044 |
| N93798 | 2737 | protein tyrosine phosphatase type IVA, member 3 | 4.91 | up | 0.00245 |
| W85875 | 3617 | EST | 4.91 | up | 0.01198 |
| AA089997 | 189 | EST | 4.9 | up | 0.0241 |
| AA482319 | 1335 | putative type II membrane protein | 4.9 | up | 0.00028 |
| AA037433 | 86 | EST | 4.9 | up | 0.0194 |
| W79773 | 3602 | EST | 4.89 | up | 0.00034 |
| AA188378 | 392 | EST | 4.88 | up | 0.01653 |
| AA252060 | 550 | EST | 4.88 | up | 0.00169 |
| F01538 | 1771 | RAP1, GTPase activating protein 1 | 4.88 | up | 0.00292 |
| R06251 | 2763 | tumor protein D52-like 2 | 4.88 | up | 0.03097 |
| T90190 | 3246 | H1 histone family, member 2 | 4.88 | up | 0.00555 |
| AA281599 | 647 | EST | 4.87 | up | 0.00248 |
| T88814 | 3241 | EST | 4.87 | up | 0.00001 |
| W92608 | 3650 | BAI1-associated protein 3 | 4.84 | up | 0.00599 |
| AA477549 | 1291 | T-cell, immune regulator 1 | 4.84 | up | 0.04096 |
| W73038 | 3585 | EST | 4.83 | up | 0.00902 |
| S78187 | 3035 | cell division cycle 25B | 4.83 | up | 0.00547 |
| N54067 | 2561 | mitogen-activated protein kinase kinase kinase kinase 4 | 4.82 | up | 0.00229 |
| W60097 | 3553 | DEAD/H (Asp-Glu-Ala-Asp/His) box polypeptide, Y chromosome | 4.82 | up | 0.04903 |
| AA215299 | 439 | U6 snRNA-associated Sm-like protein LSm7 | 4.81 | up | 0.00119 |
| AA497018 | 1406 | adenylate cyclase 1 (brain) | 4.81 | up | 0.00352 |
| AA115735 | 230 | EST | 4.8 | up | 0.02671 |
| C14051 | 1565 | phosphoprotein enriched in astrocytes 15 | 4.79 | up | 0.00548 |
| H09271 | 1862 | EST | 4.78 | up | 0.00072 |
| AA482104 | 1332 | non-metastatic cells 3, protein expressed in | 4.78 | up | 0.00135 |
| AA283832 | 672 | EST | 4.77 | up | 0.00156 |
| AA464963 | 1265 | EST | 4.77 | up | 0.00086 |
| R48447 | 2870 | EST | 4.76 | up | 0.00533 |
| AA251299 | 541 | KIAA0014 gene product | 4.74 | up | 0.0252 |
| H64493 | 1973 | immunoglobulin heavy constant gamma 3 (G3m marker) | 4.74 | up | 0.00751 |
| M60784 | 2366 | small nuclear ribonucleoprotein polypeptide A | 4.74 | up | 0.00001 |
| AA146849 | 313 | target of myb1 (chicken) homolog | 4.72 | up | 0.00326 |
| AA179787 | 380 | polyglutamine binding protein 1 | 4.71 | up | 0.00725 |
| AA430474 | 1015 | EST | 4.69 | up | 0.00007 |
| Z38462 | 3889 | KIAA0938 protein | 4.69 | up | 0.0142 |
| AA489712 | 1372 | EST | 4.69 | up | 0.00587 |
| R52649 | 2893 | EST | 4.69 | up | 0.00135 |
| AA424487 | 945 | EST | 4.68 | up | 0.0013 |
| D82558 | 1746 | novel centrosomal protein RanBPM | 4.67 | up | 0.00458 |
| X99920 | 3840 | S100 calcium-binding protein A13 | 4.66 | up | 0.00113 |
| M35252 | 2343 | transmembrane 4 superfamily member 3 | 4.65 | up | 0.04128 |
| U73377 | 3416 | SHC (Src homology 2 domain-containing) transforming protein 1 | 4.64 | up | 0.00081 |
| X57129 | 3740 | H1 histone family, member 2 | 4.63 | up | 0.00663 |
| L28821 | 2188 | mannosidase, alpha, class 2A, member 2 | 4.63 | up | 0.00876 |
| AA431571 | 1024 | EST | 4.62 | up | 0.0174 |
| C14098 | 1566 | EST | 4.62 | up | 0.01654 |
| R96527 | 2998 | KIAA0253 protein | 4.62 | up | 0.00702 |
| AA451877 | 1138 | EST | 4.6 | up | 0.04045 |
| T33489 | 3104 | EST | 4.6 | up | 0.00285 |
| M27830 | 2314 | EST | 4.6 | up | 0.04719 |
| AA621242 | 1518 | hypothetical protein, peptidylprolyl isomerase B (cyclophilin B) | 4.59 | up | 0.00081 |
| M87339 | 2414 | replication factor C (activator 1) 4 (37 kD) | 4.59 | up | 0.00116 |
| H46486 | 1932 | nesca protein | 4.57 | up | 0.00749 |
| AA262477 | 608 | ribonuclease HI, large subunit | 4.57 | up | 0.00724 |
| AA194730 | 410 | EST | 4.57 | up | 0.00801 |
| R49708 | 2885 | EST | 4.56 | up | 0.03767 |
| T34377 | 3110 | potassium voltage-gated channel, shaker-related subfamily, beta member 2 | 4.55 | up | 0.00041 |
| AA424029 | 943 | EST | 4.54 | up | 0.02721 |
| AA151435 | 336 | EST | 4.52 | up | 0.01134 |
| AA086232 | 186 | kangai 1 (suppression of tumorigenicity 6, prostate; CD82 antigen (R2 leukocyte antigen, antigen detected by monoclonal and antibody IA4)) | 4.52 | up | 0.00452 |
| AA280840 | 641 | casein kinase 1, gamma 2 | 4.51 | up | 0.0186 |
| AA127741 | 256 | EST | 4.49 | up | 0.0463 |
| H86072 | 2015 | EST | 4.49 | up | 0.01301 |

TABLE 7A-continued

Up in HCC vs Normal Sample Set 2

| Fragment Name | SEQ ID: | Known Gene Name | Fold Change | Direction | Pvalue |
|---|---|---|---|---|---|
| AA482224 | 1334 | putative type II membrane protein | 4.47 | up | 0.0001 |
| U47025 | 3367 | phosphorylase, glycogen; brain | 4.47 | up | 0.00037 |
| T30214 | 3098 | EST | 4.46 | up | 0.03654 |
| W70336 | 3576 | EST | 4.46 | up | 0.00023 |
| AA251769 | 544 | EST | 4.45 | up | 0.01431 |
| L17131 | 2168 | high-mobility group (nonhistone chromosomal) protein isoforms I and Y | 4.45 | up | 0.03141 |
| AA001504 | 2 | EST | 4.44 | up | 0.03077 |
| AA215379 | 440 | EST | 4.44 | up | 0.01675 |
| H99587 | 2079 | EST | 4.44 | up | 0.00532 |
| AA487218 | 1355 | EST | 4.43 | up | 0.03198 |
| N75541 | 2691 | EST | 4.43 | up | 0.01059 |
| N73865 | 2680 | EST | 4.43 | up | 0.00177 |
| L25876 | 2182 | cyclin-dependent kinase inhibitor 3 (CDK2-associated dual specificity phosphatase) | 4.43 | up | 0.00082 |
| AB002373 | 1538 | KIAA0375 gene product | 4.41 | up | 0.00795 |
| H57709 | 1956 | ribosomal protein L31 | 4.41 | up | 0.00091 |
| F13809 | 1828 | tropomyosin 1 (alpha) | 4.4 | up | 0.01221 |
| T79477 | 3222 | death-associated protein 6 | 4.4 | up | 0.00074 |
| AA156460 | 343 | EST | 4.39 | up | 0.01223 |
| AA171760 | 367 | EST | 4.39 | up | 0.04582 |
| AA423827 | 941 | chromosome 22 open reading frame 3 | 4.39 | up | 0.00345 |
| W28362 | 3487 | KIAA0974 protein | 4.38 | up | 0.00322 |
| W69302 | 3570 | EST | 4.37 | up | 0.00165 |
| AA236672 | 515 | EST | 4.37 | up | 0.00385 |
| AA043959 | 101 | tropomyosin 4 | 4.37 | up | 0.01641 |
| AA070827 | 157 | EST | 4.37 | up | 0.02617 |
| W42627 | 3508 | EST | 4.37 | up | 0.00021 |
| D82226 | 1742 | proteasome (prosome, macropain) 26S subunit, ATPase, 4 | 4.35 | up | 0.00184 |
| L33930 | 2198 | CD24 antigen (small cell lung carcinoma cluster 4 antigen) | 4.35 | up | 0.03968 |
| AA218663 | 444 | acid-inducible phosphoprotein | 4.34 | up | 0.00161 |
| D59570 | 1699 | EST | 4.34 | up | 0.00487 |
| D60811 | 1704 | EST | 4.34 | up | 0.00217 |
| H70739 | 1991 | EST | 4.34 | up | 0.00106 |
| H97677 | 2062 | EST | 4.34 | up | 0.00753 |
| R92449 | 2984 | KIAA0323 protein | 4.34 | up | 0.00104 |
| R61374 | 2920 | EST | 4.33 | up | 0.01489 |
| N68241 | 2633 | EST | 4.32 | up | 0.00532 |
| AA430048 | 1012 | KIAA0160 protein | 4.32 | up | 0.00279 |
| AA235289 | 495 | RAP2A, member of RAS oncogene family | 4.31 | up | 0.00135 |
| N91773 | 2718 | lysyl oxidase | 4.31 | up | 0.00302 |
| AA429539 | 999 | EST | 4.3 | up | 0.01035 |
| AA399251 | 804 | EST | 4.3 | up | 0.01578 |
| AA461063 | 1235 | EST | 4.3 | up | 0.00074 |
| W86214 | 3622 | EST | 4.3 | up | 0.00194 |
| M19267 | 2286 | tropomyosin 1 (alpha) | 4.3 | up | 0.00893 |
| AA416973 | 913 | EST | 4.29 | up | 0.00155 |
| T16206 | 3064 | EST | 4.29 | up | 0.00868 |
| AA252627 | 556 | chaperonin containing TCP1, subunit 6A (zeta 1), homeo box B5 | 4.28 | up | 0.00363 |
| W60486 | 3555 | EST | 4.27 | up | 0.0046 |
| AA478017 | 1295 | zyxin | 4.25 | up | 0.01223 |
| M37583 | 2349 | H2A histone family, member Z | 4.25 | up | 0.00135 |
| T55196 | 3146 | EST | 4.24 | up | 0.00046 |
| AA454597 | 1166 | EST | 4.23 | up | 0.00917 |
| T03749 | 3047 | KIAA1089 protein | 4.23 | up | 0.00776 |
| AA256688 | 584 | EST | 4.23 | up | 0.03094 |
| T16983 | 3073 | cleavage and polyadenylation specific factor 4, 30 kD subunit | 4.23 | up | 0.0106 |
| AA398205 | 789 | EST | 4.22 | up | 0.00059 |
| AA488432 | 1361 | phosphoserine phosphatase | 4.2 | up | 0.00128 |
| R05316 | 2759 | EST | 4.2 | up | 0.00011 |
| AA136547 | 302 | EST | 4.19 | up | 0.00098 |
| AA112679 | 224 | EST | 4.19 | up | 0.00572 |
| R39390 | 2836 | EST | 4.18 | up | 0.0004 |
| D83783 | 1748 | trinucleotide repeat containing 11 (THR-associated protein, 230 kDa subunit | 4.16 | up | 0.00055 |
| AA291786 | 704 | FE65-LIKE 2 | 4.15 | up | 0.00362 |
| AA291659 | 702 | EST | 4.15 | up | 0.00019 |
| H88674 | 2021 | collagen, type I, alpha 2 | 4.15 | up | 0.02664 |
| AA488892 | 1364 | EST | 4.14 | up | 0.04766 |
| F01568 | 1772 | EST | 4.13 | up | 0.00084 |
| F04444 | 1788 | EST | 4.13 | up | 0.00944 |
| N70481 | 2657 | EST | 4.13 | up | 0.0099 |
| AA102837 | 221 | EST | 4.13 | up | 0.0067 |
| AA365742 | 765 | tetraspan NET-6 protein | 4.12 | up | 0.00255 |
| R71395 | 2951 | EST | 4.12 | up | 0.03719 |
| AA447574 | 1102 | EST | 4.12 | up | 0.00779 |

TABLE 7A-continued

Up in HCC vs Normal Sample Set 2

| Fragment Name | SEQ ID: | Known Gene Name | Fold Change | Direction | Pvalue |
|---|---|---|---|---|---|
| AA400184 | 809 | KIAA0907 protein | 4.11 | up | 0.01123 |
| AA211483 | 435 | EST | 4.11 | up | 0.0365 |
| AA037058 | 84 | laminin, gamma 1 (formerly LAMB2) | 4.11 | up | 0.02264 |
| W44557 | 3515 | chromosome 1 open reading frame 2 | 4.1 | up | 0.00433 |
| T62521 | 3167 | EST | 4.1 | up | 0.00392 |
| D38073 | 1651 | minichromosome maintenance deficient (*S. cerevisiae*) 3 | 4.1 | up | 0.01195 |
| N92948 | 2725 | nuclear phosphoprotein similar to *S. cerevisiae* PWP1 | 4.09 | up | 0.0019 |
| AA464414 | 1258 | EST | 4.08 | up | 0.02299 |
| AA142858 | 308 | EST | 4.07 | up | 0.0022 |
| AA610089 | 1498 | U4/U6-associated RNA splicing factor | 4.07 | up | 0.00361 |
| Z39200 | 3899 | EST | 4.07 | up | 0.00075 |
| AA443802 | 1081 | EST | 4.07 | up | 0.01546 |
| AA453783 | 1158 | EST | 4.07 | up | 0.00786 |
| AA053680 | 130 | high-mobility group protein 2-like 1 | 4.07 | up | 0.03144 |
| L03411 | 2134 | RD RNA-binding protein | 4.06 | up | 0.00467 |
| AA405505 | 860 | RNA helicase family | 4.05 | up | 0.00747 |
| AA293420 | 717 | EST | 4.05 | up | 0.01189 |
| AA400643 | 817 | GAS2-related on chromosome 22 | 4.04 | up | 0.03751 |
| AA609008 | 1475 | EST | 4.04 | up | 0.00002 |
| N56935 | 2574 | EST | 4.04 | up | 0.00797 |
| AA446581 | 1090 | DKFZP564P0462 protein | 4.04 | up | 0.00479 |
| H52937 | 1944 | roundabout (axon guidance receptor, Drosophila) homolog 1 | 4.02 | up | 0.00163 |
| D42040 | 1657 | female sterile homeotic-related gene 1 (mouse homolog) | 4.02 | up | 0.00389 |
| W04550 | 3469 | EST | 4.01 | up | 0.00349 |
| AA460665 | 1230 | EST | 4.01 | up | 0.01866 |
| AA463254 | 1247 | histone deacetylase 3 | 4.01 | up | 0.01856 |
| U85625 | 3447 | ribonuclease 6 precursor | 4 | up | 0.01664 |
| T77733 | 3218 | tubulin, gamma 1 | 4 | up | 0.00526 |
| AA464043 | 1255 | EST | 3.99 | up | 0.00056 |
| N69390 | 2649 | EST | 3.99 | up | 0.00016 |
| X54941 | 3729 | CDC28 protein kinase 1 | 3.99 | up | 0.0016 |
| HG2259-HT2348 | | tubulin, alpha 1 (testis specific), tubulin, alpha, ubiquitous | 3.99 | up | 0.00945 |
| AA425852 | 958 | EST | 3.98 | up | 0.02796 |
| D84557 | 1749 | minichromosome maintenance deficient (mis5, *S. pombe*) 6 | 3.97 | up | 0.0017 |
| AA338760 | 744 | EST | 3.96 | up | 0.01307 |
| R45569 | 2863 | DKFZP547E1010 protein | 3.96 | up | 0.00259 |
| X17567 | 3716 | small nuclear ribonucleoprotein polypeptides B and B1 | 3.96 | up | 0.00317 |
| M68864 | 2389 | ORF | 3.95 | up | 0.00144 |
| X53331 | 3724 | matrix Gla protein | 3.95 | up | 0.0151 |
| AA258614 | 599 | EST | 3.94 | up | 0.0048 |
| T65957 | 3175 | ribosomal protein S3A | 3.94 | up | 0.04187 |
| AA435665 | 1040 | EST | 3.94 | up | 0.00274 |
| M32977 | 2336 | vascular endothelial growth factor | 3.93 | up | 0.04917 |
| F10199 | 1813 | EST | 3.93 | up | 0.03209 |
| AA256606 | 581 | EST | 3.92 | up | 0.03087 |
| R61557 | 2921 | KIAA0100 gene product | 3.9 | up | 0.00292 |
| T33859 | 3108 | KIAA0365 gene product | 3.9 | up | 0.0019 |
| U18018 | 3316 | ets variant gene 4 (E1A enhancer-binding protein, E1AF) | 3.9 | up | 0.0403 |
| T78922 | 3221 | stem cell growth factor; lymphocyte secreted C-type lectin | 3.89 | up | 0.00604 |
| D63478 | 1711 | KIAA0144 gene product | 3.89 | up | 0.00253 |
| AA320369 | 735 | chromosome 19 open reading frame 3 | 3.88 | up | 0.00452 |
| AA598405 | 1424 | membrane interacting protein of RGS16 | 3.87 | up | 0.00649 |
| AA127444 | 252 | EST | 3.87 | up | 0.01751 |
| AA465000 | 1266 | EST | 3.86 | up | 0.00431 |
| D80420 | 1732 | ubiquinol-cytochrome c reductase hinge protein | 3.86 | up | 0.00412 |
| T10698 | 3053 | EST | 3.86 | up | 0.00195 |
| X74801 | 3788 | chaperonin containing TCP1, subunit 3 (gamma) | 3.86 | up | 0.00453 |
| AA451680 | 1136 | hepatocellular carcinoma associated protein; breast cancer associated gene 1 | 3.85 | up | 0.0018 |
| L76191 | 2222 | interleukin-1 receptor-associated kinase 1 | 3.85 | up | 0.00152 |
| N68018 | 2630 | TBP-associated factor 172 | 3.84 | up | 0.00277 |
| AA132032 | 271 | trinucleotide repeat containing 1 | 3.84 | up | 0.01136 |
| N67815 | 2626 | EST | 3.84 | up | 0.00439 |
| D14657 | 1615 | KIAA0101 gene product | 3.84 | up | 0.02048 |
| AA478422 | 1301 | unc-51 (C. elegans)-like kinase 1 | 3.83 | up | 0.00116 |
| AA485060 | 1339 | EST | 3.83 | up | 0.03172 |
| AA101272 | 215 | EST | 3.83 | up | 0.0386 |
| AA425852 | 958 | EST | 3.82 | up | 0.0395 |
| L29218 | 2190 | CDC-like kinase 2 | 3.82 | up | 0.00035 |
| AA485431 | 1345 | EST | 3.81 | up | 0.00441 |
| AA233897 | 476 | EST | 3.8 | up | 0.02145 |
| R26744 | 2803 | midline 1 (Opitz/BBB syndrome) | 3.8 | up | 0.00266 |
| AA160775 | 355 | BCL2-antagonist of cell death | 3.8 | up | 0.01145 |
| X54942 | 3730 | CDC28 protein kinase 2 | 3.8 | up | 0.0035 |
| T03438 | 3042 | EST | 3.79 | up | 0.02042 |

TABLE 7A-continued

Up in HCC vs Normal Sample Set 2

| Fragment Name | SEQ ID: | Known Gene Name | Fold Change | Direction | Pvalue |
|---|---|---|---|---|---|
| AA182001 | 386 | EST | 3.78 | up | 0.04446 |
| N70678 | 2659 | TAR (HIV) RNA-binding protein 1 | 3.78 | up | 0.02858 |
| L25444 | 2181 | TATA box binding protein (TBP)-associated factor, RNA polymerase II, E, 70/85 kD | 3.78 | up | 0.00011 |
| AA086071 | 184 | chromosome-associated polypeptide C | 3.77 | up | 0.01993 |
| AA278768 | 617 | EST | 3.77 | up | 0.03239 |
| Z39379 | 3900 | EST | 3.77 | up | 0.00513 |
| J03040 | 2091 | secreted protein, acidic, cysteine-rich (osteonectin) | 3.77 | up | 0.00594 |
| AA449431 | 1124 | translation initiation factor IF2 | 3.76 | up | 0.00571 |
| T26471 | 3093 | EST | 3.76 | up | 0.0165 |
| AA262957 | 612 | EST | 3.76 | up | 0.00157 |
| N47956 | 2523 | eukaryotic translation initiation factor 3, subunit 3 (gamma, 40 kD) | 3.76 | up | 0.00968 |
| AA478300 | 1298 | CD39-like 2 | 3.75 | up | 0.00152 |
| C14756 | 1570 | MLN51 protein | 3.75 | up | 0.0226 |
| N73705 | 2676 | EST | 3.75 | up | 0.01762 |
| AA046103 | 109 | EST | 3.75 | up | 0.02893 |
| AA076138 | 167 | H2A histone family, member Y | 3.75 | up | 0.01442 |
| AA129757 | 264 | EST | 3.75 | up | 0.0166 |
| H99877 | 2083 | exportin, tRNA (nuclear export receptor for tRNAs) | 3.75 | up | 0.00302 |
| AA488074 | 1360 | cell division cycle 42 (GTP-binding protein, 25 kD) | 3.74 | up | 0.01887 |
| H00540 | 1829 | EST | 3.74 | up | 0.00234 |
| AA173430 | 371 | EST | 3.74 | up | 0.01159 |
| N29742 | 2480 | EST | 3.74 | up | 0.00104 |
| AA402272 | 837 | EST | 3.73 | up | 0.02336 |
| AA404560 | 853 | O-linked N-acetylglucosamine (GlcNAc) transferase (UDP-N-acetylgluosamine:polypeptide-N-acetylglucosaminyl transferase) | 3.73 | up | 0.0143 |
| N21648 | 2446 | MpV17 transgene, murine homolog, glomerulosclerosis | 3.73 | up | 0.00071 |
| H56345 | 1950 | EST | 3.73 | up | 0.00853 |
| R76782 | 2962 | O-linked N-acetylglucosamine (GlcNAc) transferase (UDP-N-acetylglucosamine:polypeptide-N-acetylgluosaminyl transferase) | 3.73 | up | 0.00094 |
| J05614 | 2122 | EST | 3.73 | up | 0.03419 |
| AA461476 | 1243 | EST | 3.72 | up | 0.00744 |
| AA255486 | 568 | EST | 3.72 | up | 0.00154 |
| AA423841 | 942 | EST | 3.71 | up | 0.01481 |
| AA491295 | 1390 | calcium/calmodulin-dependent protein kinase kinase 2, beta | 3.71 | up | 0.0103 |
| Z38299 | 3884 | EST | 3.71 | up | 0.0036 |
| AA600153 | 1460 | DEK oncogene (DNA binding) | 3.71 | up | 0.02967 |
| AA609080 | 1478 | EST | 3.71 | up | 0.0306 |
| AA010065 | 22 | CDC28 protein kinase 2 | 3.71 | up | 0.00432 |
| D31417 | 1645 | secreted protein of unknown funtion | 3.69 | up | 0.0004 |
| AA018346 | 38 | EST | 3.69 | up | 0.04582 |
| N69252 | 2646 | ferritin, light polypeptide | 3.69 | up | 0.04116 |
| Z23090 | 3865 | heat shock 27 kD protein 1 | 3.69 | up | 0.00628 |
| AA402968 | 844 | EST | 3.68 | up | 0.00123 |
| N98464 | 2743 | EST | 3.68 | up | 0.03007 |
| AA165526 | 360 | 3-prime-phosphoadenosine 5-prime-phosphosulfate synthase 1 | 3.68 | up | 0.00021 |
| W46286 | 3523 | EST | 3.68 | up | 0.00311 |
| M21259 | 2293 | small nuclear ribonucleoprotein polypeptide E | 3.68 | up | 0.00415 |
| U91930 | 3459 | adaptor-related protein complex 3, delta 1 subunit | 3.68 | up | 0.00009 |
| F09788 | 1808 | procollagen-proline. 2-oxoglutarate 4-dioxygenase (proline 4-hydroxylase), alpha polypeptide II | 3.67 | up | 0.01682 |
| AA291137 | 694 | EST | 3.67 | up | 0.03243 |
| H68794 | 1984 | EST | 3.67 | up | 0.00327 |
| N73762 | 2677 | EST | 3.67 | up | 0.00796 |
| R56095 | 2905 | EST | 3.67 | up | 0.0158 |
| R77451 | 2963 | EST | 3.67 | up | 0.00078 |
| N52168 | 2550 | EST | 3.66 | up | 0.00127 |
| AA456852 | 1199 | suppressor of white apricot homolog 2 | 3.66 | up | 0.00614 |
| X83425 | 3809 | Lutheran blood group (Auberger b antigen included) | 3.66 | up | 0.02661 |
| H47357 | 1934 | EST | 3.65 | up | 0.03799 |
| AA292788 | 714 | EST | 3.65 | up | 0.01765 |
| U51586 | 3385 | siah binding protein 1; FBP interacting repressor; pyrimidine tract binding splicing factor; Ro ribonucleoprotein-binding protein 1 | 3.65 | up | 0.00403 |
| X56494 | 3735 | pyruvate kinase, muscle | 3.65 | up | 0.04795 |
| F10453 | 1819 | EST | 3.64 | up | 0.01878 |
| T23465 | 3080 | EST | 3.64 | up | 0.00265 |
| Z24727 | 3868 | tropomyosin 1 (alpha) | 3.64 | up | 0.00388 |
| X57809 | 3743 | immunoglobulin lambda locus | 3.64 | up | 0.02655 |
| AA040465 | 95 | EST | 3.63 | up | 0.01806 |
| T16652 | 3072 | BCS1 (yeast homolog)-like | 3.63 | up | 0.00434 |
| AA037766 | 87 | EST | 3.63 | up | 0.0328 |
| AA227541 | 457 | NS1-binding protein | 3.6 | up | 0.02801 |
| AA313213 | 732 | flotillin 1 | 3.59 | up | 0.00878 |
| AA251909 | 549 | EST | 3.59 | up | 0.01129 |

TABLE 7A-continued

Up in HCC vs Normal Sample Set 2

| Fragment Name | SEQ ID: | Known Gene Name | Fold Change | Direction | Pvalue |
|---|---|---|---|---|---|
| AA487856 | 1359 | KIAA0676 protein | 3.59 | up | 0.01408 |
| M63573 | 2377 | peptidylprolyl isomerase B (cyclophilin B) | 3.59 | up | 0.00916 |
| M94345 | 2426 | capping protein (acetin filament), gelsolin-like | 3.59 | up | 0.04508 |
| AF003521 | 1545 | jagged 2 | 3.58 | up | 0.00299 |
| AA489091 | 1368 | EST | 3.58 | up | 0.0002 |
| W49791 | 3538 | plasminogen activator, tissue | 3.58 | up | 0.02438 |
| W90146 | 3641 | EST | 3.58 | up | 0.00322 |
| Z39429 | 3903 | EST | 3.58 | up | 0.00416 |
| X06700 | 3685 | collagen, type III, alpha 1 (Ehlers-Danlos syndrome type IV, autosomal dominant) | 3.58 | up | 0.02964 |
| W79421 | 3600 | EST | 3.57 | up | 0.00895 |
| X64364 | 3761 | basigin | 3.57 | up | 0.00902 |
| Z21507 | 3864 | eukaryotic translation elongation factor 1 delta (guanine nucleotide exchange protein) | 3.57 | up | 0.01898 |
| U62392 | 3402 | zinc finger protein 193 | 3.56 | up | 0.0407 |
| AA135871 | 294 | EST | 3.56 | up | 0.01718 |
| W72276 | 3580 | EST | 3.56 | up | 0.0476 |
| D63486 | 1712 | KIAA0152 gene product | 3.56 | up | 0.00063 |
| AA258182 | 589 | EST | 3.55 | up | 0.01198 |
| AA179845 | 381 | EST | 3.55 | up | 0.02484 |
| AA599850 | 1457 | EST | 3.55 | up | 0.03215 |
| D13640 | 1608 | KIAA0015 gene product | 3.55 | up | 0.00347 |
| U66661 | 3405 | gamma-aminobutyric acid (GABA) A receptor, epsilon | 3.55 | up | 0.0045 |
| R73569 | 2959 | EST | 3.54 | up | 0.01962 |
| Z40006 | 3914 | EST | 3.54 | up | 0.00156 |
| AA400896 | 822 | EST | 3.54 | up | 0.00889 |
| N98758 | 2744 | EST | 3.54 | up | 0.02609 |
| M27830 | 2314 | EST | 3.54 | up | 0.00777 |
| U90551 | 3456 | H2A histone family, member L | 3.54 | up | 0.01523 |
| M55998 | 2356 | collagen, type I, alpha 1 | 3.54 | up | 0.01449 |
| AA485697 | 1346 | EST | 3.53 | up | 0.03566 |
| H07873 | 1856 | EST | 3.53 | up | 0.0391 |
| R06254 | 2764 | tumor protein D52-like 2 | 3.53 | up | 0.04865 |
| R27016 | 2805 | myristoylated alanine-rich protein kinase C substrate (MARCKS, 80K-L) | 3.53 | up | 0.03056 |
| U26727 | 3336 | cyclin-dependent kinase inhibtor 2A (melanoma, p16, inhibits CDK4) | 3.53 | up | 0.02913 |
| D81608 | 1740 | polymerase (RNA) II (DNA directed) polypeptide K (7.0 kD) | 3.52 | up | 0.00437 |
| R22565 | 2799 | EST | 3.52 | up | 0.04352 |
| T17353 | 3076 | EST | 3.52 | up | 0.02085 |
| AA409212 | 1375 | H2A histone family, member Y | 3.52 | up | 0.02202 |
| R66469 | 2936 | pleckstrin and Sec7 domain protein | 3.52 | up | 0.0272 |
| AA464722 | 1263 | DKFZP566C243 protein | 3.51 | up | 0.00101 |
| H97012 | 2058 | EST | 3.51 | up | 0.03505 |
| T23426 | 3078 | EST | 3.51 | up | 0.00674 |
| AA399264 | 805 | EST | 3.51 | up | 0.00327 |
| H99774 | 2081 | EST | 3.51 | up | 0.00009 |
| W94281 | 3655 | integral membrane protein 2C | 3.51 | up | 0.01689 |
| X54667 | 3728 | cystatin S,cystatin SN | 3.51 | up | 0.00187 |
| AA278817 | 618 | EST | 3.5 | up | 0.01159 |
| AA489707 | 1371 | EST | 3.5 | up | 0.03208 |
| T59668 | 3159 | lysyl oxidase | 3.5 | up | 0.00083 |
| AA598447 | 1428 | exportin, tRNA (nuclear export receptor for tRNAs) | 3.5 | up | 0.01201 |
| H91632 | 2031 | EST | 3.5 | up | 0.03688 |
| N51771 | 2547 | KIAA0652 gene product | 3.5 | up | 0.00028 |
| R33498 | 2819 | EST | 3.5 | up | 0.03336 |
| AA621409 | 1524 | putative type II membrane protein | 3.5 | up | 0.00462 |
| L04270 | 2135 | lymphotoxin beta receptor (TNFR superfamily, member 3 | 3.5 | up | 0.01547 |
| AA243173 | 526 | EST | 3.49 | up | 0.0401 |
| AA442763 | 1072 | cyclin B2 | 3.49 | up | 0.04176 |
| AA235868 | 504 | nuclear transcription factor Y, beta | 3.49 | up | 0.01897 |
| T26646 | 3096 | X-ray repair complementing defective repair in Chinese hamster cells 1 | 3.49 | up | 0.02482 |
| M34309 | 2342 | v-erb-b2 avian erythroblastic leukemia viral oncogene homolog 3 | 3.49 | up | 0.00191 |
| N35913 | 2502 | EST | 3.48 | up | 0.0016 |
| M26576 | 2310 | EST | 3.48 | up | 0.00062 |
| Y08302 | 3849 | dual specificity phosphatase 9 | 3.48 | up | 0.00787 |
| Z39191 | 3898 | EST | 3.47 | up | 0.00756 |
| N21407 | 2442 | EST | 3.47 | up | 0.01037 |
| M55210 | 2353 | laminin, gamma 1 (formerly LAMB2) | 3.47 | up | 0.02551 |
| AA236150 | 507 | 3-prime-phosphoadenosine 5-prime-phosphosulfate synthase 1 | 3.46 | up | 0.0008 |
| R48473 | 2871 | EST | 3.46 | up | 0.01196 |
| N99944 | 2748 | EST | 3.46 | up | 0.00104 |
| AA598648 | 1432 | SWI/SNF related, matrix associated, actin dependent regulator of chromatin) subfamily a, member 4 | 3.46 | up | 0.00293 |
| C00358 | 1552 | nucleolar protein 3 (apoptosis repressor with CARD domain) | 3.45 | up | 0.00985 |
| AA464251 | 1257 | EST | 3.45 | up | 0.02229 |
| AA598712 | 1436 | EST | 3.45 | up | 0.00005 |

TABLE 7A-continued

Up in HCC vs Normal Sample Set 2

| Fragment Name | SEQ ID: | Known Gene Name | Fold Change | Direction | Pvalue |
|---|---|---|---|---|---|
| AA620461 | 1501 | EST | 3.45 | up | 0.01146 |
| R91753 | 2982 | EST | 3.45 | up | 0.02391 |
| Z41349 | 3928 | EST | 3.45 | up | 0.01503 |
| N39237 | 2510 | EST | 3.45 | up | 0.02481 |
| HG4074-HT4344 | | flap structure-specific endonuclease 1 | 3.45 | up | 0.01695 |
| U24704 | 3331 | proteasome (prosome, macropain) 26S subunit, non-ATPase, 4 | 3.45 | up | 0.00037 |
| X87212 | 3813 | cathepsin C | 3.45 | up | 0.02486 |
| AA094752 | 203 | hypothetical 43.2 Kd protein | 3.44 | up | 0.04445 |
| AA471384 | 1278 | divalent cation tolerant protein CUTA | 3.44 | up | 0.01161 |
| AA443271 | 1073 | KIAA0546 protein | 3.44 | up | 0.00324 |
| R62456 | 2924 | EST | 3.44 | up | 0.00285 |
| R70532 | 2946 | EST | 3.44 | up | 0.02186 |
| T51972 | 3139 | EST | 3.44 | up | 0.00406 |
| AA122386 | 239 | collagen, type V, alpha 2 | 3.44 | up | 0.02566 |
| AA496715 | 1400 | spectrin SH3 domain binding protein 1 | 3.44 | up | 0.00069 |
| H65042 | 1975 | EST | 3.44 | up | 0.0006 |
| AA024776 | 48 | EST | 3.44 | up | 0.00334 |
| X62153 | 3751 | minichromosome maintenance deficient (*S. cerevisiae*) 3 | 3.44 | up | 0.00704 |
| D30946 | 1638 | kinesin family member 3B | 3.43 | up | 0.01458 |
| AA384184 | 774 | DKFZP586B0519 protein | 3.42 | up | 0.01222 |
| AA461282 | 1237 | dihydropyrimidinase-like 2 | 3.42 | up | 0.02014 |
| AA417884 | 919 | cyclin-dependent kinase inhibitor 2C (p18, inhibits CDK4) | 3.42 | up | 0.02997 |
| W46947 | 3530 | EST | 3.42 | up | 0.04665 |
| AA479139 | 1310 | acid phosphatase 1, soluble | 3.42 | up | 0.01853 |
| AA412301 | 899 | EST | 3.42 | up | 0.0129 |
| AA116036 | 233 | chromosome 20 open reading frame 1 | 3.41 | up | 0.00089 |
| AA370163 | 766 | EST | 3.41 | up | 0.00134 |
| AA598831 | 1440 | EST | 3.41 | up | 0.00452 |
| R31607 | 2812 | EST | 3.41 | up | 0.00163 |
| R27296 | 2806 | EST | 3.41 | up | 0.00309 |
| R52161 | 2892 | EST | 3.41 | up | 0.00053 |
| X66899 | 3769 | Ewing sarcoma breakpoint region 1 | 3.41 | up | 0.03777 |
| AA187579 | 390 | MCT-1 protein | 3.4 | up | 0.02455 |
| AA459542 | 1218 | regulatory factor X-associated ankyrin-containing protein | 3.4 | up | 0.00841 |
| AA227145 | 454 | EST | 3.4 | up | 0.03422 |
| AA406216 | 871 | EST | 3.4 | up | 0.00529 |
| AA443316 | 1075 | v-Ha-ras Harvey rat sarcoma viral oncogene homolog | 3.4 | up | 0.00133 |
| H99489 | 2078 | quiescin Q6 | 3.4 | up | 0.02682 |
| L11669 | 2157 | tetracycline transporter-like protein | 3.4 | up | 0.02062 |
| L76568 | 2225 | excision repair cross-complementing rodent repair deficiency, complementation group 4 | 3.4 | up | 0.0172 |
| AA424881 | 949 | EST | 3.39 | up | 0.03546 |
| N51855 | 2549 | ADP-ribosyltransferase (NAD+; poly (ADP-ribose) polymerase)-like 3 | 3.39 | up | 0.00115 |
| R43952 | 2852 | homeo box B5 | 3.39 | up | 0.04829 |
| T23516 | 3082 | 3-phosphoglycerate dehydrogenase | 3.39 | up | 0.00551 |
| F10290 | 1815 | EST | 3.39 | up | 0.02392 |
| H62474 | 1970 | EST | 3.39 | up | 0.04173 |
| M57730 | 2358 | ephrin-A1 | 3.39 | up | 0.00199 |
| X62534 | 3752 | high-mobility group (nonhistone chromosomal) protein 2 | 3.39 | up | 0.0186 |
| Z38444 | 3888 | KIAA0923 protein | 3.38 | up | 0.02918 |
| R70253 | 2944 | EST | 3.38 | up | 0.03125 |
| D28589 | 1637 | EST | 3.38 | up | 0.01144 |
| AA173597 | 373 | EST | 3.37 | up | 0.03622 |
| AA456583 | 1193 | PL6 protein | 3.37 | up | 0.00139 |
| AA621535 | 1527 | FE65-LIKE 2 | 3.37 | up | 0.0167 |
| AA029288 | 65 | EST | 3.36 | up | 0.04908 |
| AA207103 | 429 | EST | 3.36 | up | 0.00131 |
| AA286911 | 684 | EST | 3.36 | up | 0.00037 |
| T33625 | 3107 | EST | 3.36 | up | 0.04096 |
| AA052941 | 121 | EST | 3.36 | up | 0.00088 |
| R15740 | 2790 | carbohydrate (keratan sulfate Gal-6) sulfotransferase 1 | 3.36 | up | 0.00268 |
| T33619 | 3106 | EST | 3.36 | up | 0.01283 |
| M14483 | 2261 | prothymosin, alpha (gene sequence 28) | 3.36 | up | 0.00033 |
| AA488872 | 1363 | EST | 3.35 | up | 0.03191 |
| W80730 | 3604 | EST | 3.35 | up | 0.01526 |
| AA115562 | 229 | EST | 3.35 | up | 0.00283 |
| AA620779 | 1508 | golgin-67 | 3.35 | up | 0.00297 |
| C14835 | 1571 | EST | 3.35 | up | 0.0316 |
| AA442155 | 1068 | transforming acidic coiled-coil containing protein 3 | 3.35 | up | 0.00344 |
| AA449828 | 1130 | EST | 3.35 | up | 0.01609 |
| X69910 | 3784 | transmembrane protein (63 kD), endoplasmic reticulum/Golgi intermediate compartment | 3.35 | up | 0.00898 |
| AA421213 | 931 | Lsm3 protein | 3.34 | up | 0.00198 |
| AA456646 | 1196 | EST | 3.34 | up | 0.0309 |

TABLE 7A-continued

Up in HCC vs Normal Sample Set 2

| Fragment Name | SEQ ID: | Known Gene Name | Fold Change | Direction | Pvalue |
|---|---|---|---|---|---|
| W84447 | 3614 | EST | 3.34 | up | 0.00986 |
| AA479881 | 1317 | EST | 3.34 | up | 0.03289 |
| D51072 | 1674 | biliverdin reductase A | 3.34 | up | 0.0254 |
| U55206 | 3391 | gamma-glutamyl hydrolase (conjugase, folylpolygammaglutamyl hydrolase) | 3.34 | up | 0.00315 |
| X04347 | 3677 | heterogeneous nuclear ribonucleoprotein A1 | 3.34 | up | 0.00123 |
| AA451992 | 1140 | HSPC039 protein | 3.33 | up | 0.01696 |
| D82277 | 1743 | LDL induced EC protein | 3.33 | up | 0.00355 |
| AA426521 | 967 | Sjogren's syndrome nuclear autoantigen 1 | 3.33 | up | 0.01163 |
| AA128407 | 259 | EST | 3.33 | up | 0.02298 |
| AA046745 | 113 | Wolf-Hirschhorn syndrome candidate 1 | 3.33 | up | 0.00648 |
| AA521149 | 1420 | EST | 3.33 | up | 0.00211 |
| AA608668 | 1465 | erythrocyte membrane protein band 4.1-like 2 | 3.33 | up | 0.02014 |
| H99261 | 2074 | EST | 3.33 | up | 0.00319 |
| W63608 | 3561 | EST | 3.33 | up | 0.02443 |
| AA456415 | 1192 | KIAA0537 gene product | 3.32 | up | 0.00155 |
| AA479096 | 1308 | EST | 3.32 | up | 0.00118 |
| T97679 | 3265 | EST | 3.32 | up | 0.01566 |
| N48790 | 2531 | EST | 3.32 | up | 0.00654 |
| T81393 | 3227 | HMT1 (hnRNP methyltransferase, S. cerevisiae)-like 1 | 3.32 | up | 0.0023 |
| U73379 | 3417 | ubiquitin carrier protein E2-C | 3.32 | up | 0.00808 |
| AA071387 | 158 | jumping translocation breakpoint | 3.31 | up | 0.0001 |
| AA504413 | 1413 | EST | 3.31 | up | 0.00036 |
| AA429572 | 1000 | ribosomal protein S6 | 3.31 | up | 0.02144 |
| R49395 | 2880 | EST | 3.31 | up | 0.00867 |
| R53109 | 2898 | dimethylarginine dimethylaminohydrolase 2 | 3.31 | up | 0.02406 |
| AA485084 | 1340 | EST | 3.31 | up | 0.01232 |
| AA136864 | 304 | zinc finger protein homologous to Zfp-36 in mouse | 3.31 | up | 0.00346 |
| D31294 | 1643 | EST | 3.3 | up | 0.004 |
| AA398141 | 788 | EST | 3.3 | up | 0.00211 |
| AA465093 | 1267 | TIA1 cytotoxic granule-associated RNA-binding protein | 3.3 | up | 0.01314 |
| H16251 | 1886 | EST | 3.3 | up | 0.03286 |
| AA620761 | 1507 | EST | 3.3 | up | 0.00285 |
| AA053662 | 129 | EST | 3.3 | up | 0.00558 |
| M27830 | 2314 | EST | 3.3 | up | 0.02453 |
| AF004022 | 1546 | serine/threonine kinase 12 | 3.29 | up | 0.00841 |
| AA476944 | 1288 | EST | 3.29 | up | 0.00189 |
| AA452167 | 1142 | EST | 3.29 | up | 0.03337 |
| T17339 | 3075 | EST | 3.29 | up | 0.00669 |
| AA291644 | 701 | EST | 3.28 | up | 0.00033 |
| Z47727 | 3937 | polymerase (RNA) II (DNA directed) polypeptide K (7.0 kD) | 3.28 | up | 0.00317 |
| AA242757 | 522 | EST | 3.27 | up | 0.00286 |
| AA458890 | 1206 | EST | 3.27 | up | 0.00079 |
| R49482 | 2883 | EST | 3.27 | up | 0.0161 |
| W42778 | 3510 | EST | 3.27 | up | 0.02411 |
| AA022623 | 44 | EST | 3.27 | up | 0.01556 |
| AA435662 | 1039 | EST | 3.27 | up | 0.0433 |
| AA284565 | 675 | EST | 3.27 | up | 0.0362 |
| N34825 | 2497 | DKFZP434P106 protein | 3.27 | up | 0.01334 |
| H65030 | 1974 | phospholipase A2, group VII (platelet-activating factor acetylhydrolase, plasma) | 3.26 | up | 0.02278 |
| Z40883 | 3921 | EST | 3.26 | up | 0.01863 |
| AA621530 | 1526 | EST | 3.26 | up | 0.00298 |
| AA091752 | 193 | purine-rich element binding protein B | 3.25 | up | 0.01419 |
| AA092290 | 195 | EST | 3.25 | up | 0.01616 |
| AA478971 | 1306 | disabled (Drosophila) homolog 2 (mitogen-responsive phosphoprotein) | 3.25 | up | 0.02698 |
| AA610073 | 1497 | EST | 3.25 | up | 0.00859 |
| AA251230 | 540 | EST | 3.25 | up | 0.01417 |
| N64374 | 2607 | KIAA0537 gene product | 3.25 | up | 0.01652 |
| W69468 | 3571 | EST | 3.25 | up | 0.00055 |
| AA426374 | 964 | tubulin, alpha 2 | 3.25 | up | 0.04346 |
| D21063 | 1628 | minichromosome maintenance deficient (S. cerevisiae) 2 (mitotin) | 3.25 | up | 0.03558 |
| AA598589 | 1431 | EST | 3.24 | up | 0.00432 |
| R16144 | 2793 | EST | 3.24 | up | 0.0087 |
| AA195067 | 414 | GTPase activating protein-like | 3.24 | up | 0.00606 |
| W42788 | 3511 | deoxynucleotidyltransferase, terminal | 3.24 | up | 0.02261 |
| U90426 | 3452 | nuclear RNA helicase, DECD variant of DEAD box family | 3.24 | up | 0.00035 |
| AA279418 | 626 | EST | 3.23 | up | 0.02054 |
| F04479 | 1789 | KIAA1067 protein | 3.23 | up | 0.04522 |
| T94452 | 3256 | EST | 3.23 | up | 0.02245 |
| W47206 | 3532 | EST | 3.23 | up | 0.01931 |
| AA074162 | 159 | superkiller viralicidic activity 2 (S. cerevisiae homolog)-like | 3.23 | up | 0.00642 |
| AA406384 | 875 | KIAA0670 protein/acinus | 3.23 | up | 0.00486 |
| L06797 | 2143 | chemokine (C-X-C motif), receptor 4 (fusin) | 3.23 | up | 0.04782 |
| T99312 | 3269 | EST | 3.22 | up | 0.00084 |
| R54614 | 2901 | EST | 3.22 | up | 0.00334 |

TABLE 7A-continued

Up in HCC vs Normal Sample Set 2

| Fragment Name | SEQ ID: | Known Gene Name | Fold Change | Direction | Pvalue |
|---|---|---|---|---|---|
| D38305 | 1652 | transducer of ERBB2, 1 | 3.22 | up | 0.0215 |
| AA495857 | 1394 | EST | 3.21 | up | 0.02243 |
| W28366 | 3488 | EST | 3.21 | up | 0.01007 |
| AA465342 | 1271 | EST | 3.21 | up | 0.01378 |
| M97856 | 2435 | nuclear autoantigenic sperm protein (histone-binding) | 3.21 | up | 0.00444 |
| T10316 | 3051 | EST | 3.2 | up | 0.04794 |
| AA429470 | 996 | EST | 3.2 | up | 0.0153 |
| AA047704 | 120 | EST | 3.2 | up | 0.0029 |
| AA132514 | 272 | EST | 3.2 | up | 0.00876 |
| X14487 | 3699 | keratin 10 (epidermolytic hyperkeratosis; keratosis palmaris et plantaris) | 3.19 | up | 0.01268 |
| AA167708 | 363 | EST | 3.19 | up | 0.01871 |
| AA431719 | 1025 | EST | 3.19 | up | 0.00294 |
| AA070485 | 156 | interleukin 13 receptor, alpha 1 | 3.19 | up | 0.03465 |
| T47969 | 3127 | ceroid-lipofuscinosis, neuronal 3, juvenile (Batten, Spielmeyer-Vogt disease) | 3.19 | up | 0.02283 |
| M91083 | 2418 | chromosome 11 open reading frame 13 | 3.19 | up | 0.00243 |
| AA476754 | 1287 | EST | 3.18 | up | 0.01696 |
| AA046410 | 110 | EST | 3.18 | up | 0.00797 |
| AA131220 | 267 | EST | 3.18 | up | 0.00974 |
| H73484 | 1995 | ferritin, heavy polypeptide 1 | 3.18 | up | 0.00432 |
| M61916 | 2372 | laminin, beta 1 | 3.18 | up | 0.01171 |
| AA453628 | 1154 | EST | 3.18 | up | 0.00849 |
| AA465218 | 1268 | DKFZP586M1523 protein | 3.17 | up | 0.00357 |
| N31597 | 2486 | DKFZP564G2022 protein | 3.17 | up | 0.03017 |
| AA021549 | 42 | EST | 3.17 | up | 0.00158 |
| AA025166 | 50 | fusion, derived from t(12;16) malignant liposarcoma | 3.17 | up | 0.00009 |
| AA252524 | 555 | EST | 3.17 | up | 0.00686 |
| W46810 | 3528 | HMT1 (hnRNP methyltransferase, S. cerevisiae)-like 2 | 3.17 | up | 0.03434 |
| AA045365 | 106 | EST | 3.17 | up | 0.0149 |
| D57317 | 1688 | activated RNA polymerase II transcription cofactor 4 | 3.17 | up | 0.00464 |
| D80710 | 1734 | integral type I protein | 3.17 | up | 0.04549 |
| AA296994 | 724 | seven transmembrane domain protein | 3.16 | up | 0.0076 |
| AA256131 | 574 | glycophosphatidylinositol anchor attachment 1 | 3.16 | up | 0.00011 |
| AA282571 | 662 | FSHD region gene 1 | 3.16 | up | 0.01355 |
| AA321833 | 736 | EST | 3.16 | up | 0.00523 |
| AA430675 | 1019 | Fanconi anemia, complementation group G | 3.16 | up | 0.01007 |
| AA235853 | 503 | CGI-96 protein | 3.16 | up | 0.00744 |
| N93316 | 2732 | EST | 3.16 | up | 0.01262 |
| R51908 | 2891 | EST | 3.16 | up | 0.0083 |
| AA136474 | 301 | Meis (mouse) homolog 2 | 3.15 | up | 0.02837 |
| AA463934 | 1253 | splicing factor 3b, subunit 4, 49 kD | 3.15 | up | 0.00952 |
| W56642 | 3544 | EST | 3.15 | up | 0.00654 |
| AA070206 | 155 | EST | 3.15 | up | 0.03914 |
| AA251428 | 542 | DKFZP586I2223 protein | 3.15 | up | 0.01223 |
| AA253011 | 558 | KIAA0713 protein | 3.15 | up | 0.00035 |
| AA258387 | 594 | EST | 3.15 | up | 0.02028 |
| AA621146 | 1514 | MUF1 protein | 3.15 | up | 0.02116 |
| N69879 | 2650 | drebrin 1 | 3.15 | up | 0.01659 |
| AA047379 | 119 | karyopherin (importin) beta 1 | 3.15 | up | 0.01572 |
| AA398563 | 797 | EST | 3.14 | up | 0.01895 |
| AA478415 | 1299 | EST | 3.14 | up | 0.0483 |
| U18321 | 3317 | death associated protein 3 | 3.14 | up | 0.00833 |
| AA482319 | 1335 | putative type II membrane protein | 3.13 | up | 0.00071 |
| AA086412 | 187 | DEAD/H (Asp-Glu-Ala-Asp/His) box polypeptide 16 | 3.13 | up | 0.00327 |
| AA256268 | 576 | EST | 3.13 | up | 0.03874 |
| AA450247 | 1133 | EST | 3.13 | up | 0.00531 |
| AA621752 | 1529 | 26S proteasome-associated pad1 homolog | 3.13 | up | 0.01571 |
| D20899 | 1626 | EST | 3.13 | up | 0.02128 |
| H89987 | 2027 | ATP-binding cassette, sub-family C (CFTR/MRP), member 5 | 3.13 | up | 0.01194 |
| N90238 | 2711 | EST | 3.13 | up | 0.02492 |
| R39610 | 2837 | calpain, large polypeptide L2 | 3.13 | up | 0.01863 |
| X14850 | 3703 | H2A histone family, member X | 3.13 | up | 0.01523 |
| Y08999 | 3852 | actin related protein 2/3 complex, subunit 1A (41 kD) | 3.13 | up | 0.02376 |
| HG2994-HT4850 | | elastin (supravalvular aortic stenosis, Williams-Beuren syndrome) | 3.13 | up | 0.01206 |
| AA446570 | 1089 | EST | 3.12 | up | 0.02228 |
| D13636 | 1606 | general transcription factor IIIC, polypeptide 2 (beta subunit, 110 kD) | 3.12 | up | 0.00022 |
| L34587 | 2200 | transcription elongation factor B (SIII), polypeptide 1 (15 kD, elongin C) | 3.12 | up | 0.00946 |
| S67070 | 3022 | heat shock 27 kD protein 2 | 3.12 | up | 0.01688 |
| U59321 | 3397 | DEAD/H (Asp-Glu-Ala-Asp/His) box polypeptide 17 (72 kD) | 3.12 | up | 0.02469 |
| AA429825 | 1003 | DKFZP566B023 protein | 3.11 | up | 0.01857 |
| W49743 | 3537 | EST | 3.11 | up | 0.01121 |
| N69084 | 2642 | EST | 3.11 | up | 0.0094 |
| AA236412 | 511 | EST | 3.1 | up | 0.04463 |
| W02695 | 3466 | EST | 3.1 | up | 0.04745 |
| AA285132 | 682 | apoptotic protease activating factor | 3.1 | up | 0.00844 |

TABLE 7A-continued

Up in HCC vs Normal Sample Set 2

| Fragment Name | SEQ ID: | Known Gene Name | Fold Change | Direction | Pvalue |
|---|---|---|---|---|---|
| AA621367 | 1523 | EST | 3.1 | up | 0.00066 |
| H48459 | 1937 | KIAA0186 gene product | 3.1 | up | 0.02325 |
| N53067 | 2556 | DKFZP547E1010 protein | 3.1 | up | 0.00101 |
| X92896 | 3826 | DNA segment on chromosome X (unique) 9879 expressed sequence | 3.1 | up | 0.0405 |
| AA005262 | 13 | EST | 3.09 | up | 0.0064 |
| AA430154 | 1014 | EST | 3.09 | up | 0.04401 |
| AA433947 | 1034 | EST | 3.09 | up | 0.00253 |
| AA599808 | 1455 | EST | 3.09 | up | 0.00726 |
| Z38431 | 3886 | EST | 3.09 | up | 0.0083 |
| AA405544 | 861 | EST | 3.09 | up | 0.04146 |
| AA446970 | 1098 | EST | 3.09 | up | 0.01627 |
| D80917 | 1736 | KIAA0670 protein/acinus | 3.09 | up | 0.00168 |
| W72187 | 3579 | EST | 3.09 | up | 0.00134 |
| AA478615 | 1305 | H1 histone family, member X | 3.09 | up | 0.0499 |
| W15495 | 3473 | chromosome 21 open reading frame 5 | 3.09 | up | 0.00491 |
| W58247 | 3548 | kinesin family member 4 | 3.08 | up | 0.00048 |
| AA428204 | 987 | cofactor required for Sp1 transcriptional activation, subunit 6 (77 kD) | 3.08 | up | 0.00313 |
| AA481060 | 1326 | EST | 3.08 | up | 0.00029 |
| AA481420 | 1327 | EST | 3.08 | up | 0.0206 |
| AA505141 | 1418 | EST | 3.08 | up | 0.02327 |
| T41078 | 3120 | bromodomain adjacent to zinc finger domain, 2B | 3.08 | up | 0.03426 |
| N29484 | 2477 | EST | 3.08 | up | 0.04834 |
| R60512 | 2917 | KIAA0191 protein | 3.08 | up | 0.00856 |
| AA011679 | 32 | EST | 3.08 | up | 0.03649 |
| AA427734 | 977 | cholinergic receptor, nicotinic, epsilon polypeptide | 3.08 | up | 0.04796 |
| D86957 | 1754 | KIAA0202 protein | 3.08 | up | 0.02949 |
| M86667 | 2410 | nucleosome assembly protein 1-like 1 | 3.08 | up | 0.00473 |
| AA031814 | 70 | KIAA0958 protein | 3.07 | up | 0.00681 |
| AA236904 | 518 | EST | 3.07 | up | 0.01503 |
| D80946 | 1737 | SFRS protein kinase 1 | 3.07 | up | 0.00986 |
| W42674 | 3509 | EST | 3.07 | up | 0.0261 |
| W74536 | 3595 | advanced glycosylation end product-specific receptor | 3.07 | up | 0.00251 |
| AA435681 | 1041 | EST | 3.07 | up | 0.01166 |
| AA599469 | 1450 | EST | 3.07 | up | 0.04154 |
| D13370 | 1603 | APEX nuclease (multifunctional DNA repair enzyme) | 3.07 | up | 0.00857 |
| HG4297-HT4567 | | activated RNA polymerase II transcription cofactor 4 | 3.07 | up | 0.00787 |
| M93036 | 2421 | membrane component, chromosomal 4, surface marker (35 kD glycoprotein) | 3.07 | up | 0.04199 |
| U30825 | 3342 | splicing factor, arginine/serine-rich 9 | 3.07 | up | 0.01928 |
| H67964 | 1981 | EST | 3.06 | up | 0.02707 |
| AA194998 | 413 | purinergic receptor (family A group 5) | 3.06 | up | 0.04752 |
| AA435769 | 1046 | EST | 3.06 | up | 0.00615 |
| AA464423 | 1259 | EST | 3.06 | up | 0.01416 |
| AA251766 | 543 | EST | 3.06 | up | 0.0098 |
| AA256524 | 580 | AD022 protein | 3.06 | up | 0.00626 |
| AA412720 | 905 | EST | 3.06 | up | 0.02153 |
| H11320 | 1875 | SUMO-1 activating enzyme subunit 2 | 3.06 | up | 0.00167 |
| R28636 | 2808 | UDP-Gal:betaGlcNAc beta 1,4- galactosyltransferase, polypeptide 3 | 3.06 | up | 0.03678 |
| T40439 | 3114 | small nuclear ribonucleoprotein polypeptide B" | 3.06 | up | 0.02842 |
| X79536 | 3801 | heterogeneous nuclear ribonucleoprotein A1 | 3.06 | up | 0.00449 |
| H09241 | 1861 | EST | 3.05 | up | 0.01487 |
| AA425544 | 955 | eukaryotic translation initiation factor 2B, subunit 2 (beta, 39 kD) | 3.05 | up | 0.0346 |
| F02863 | 1782 | EST | 3.05 | up | 0.03504 |
| AA477316 | 1290 | calumenin | 3.05 | up | 0.00608 |
| W58081 | 3547 | neuroendocrine-specific protein C like (foocen) | 3.05 | up | 0.03767 |
| AA293868 | 721 | EST | 3.04 | up | 0.0054 |
| AA125808 | 240 | EST | 3.04 | up | 0.02112 |
| AA236532 | 513 | EST | 3.04 | up | 0.03747 |
| Z41747 | 3933 | succinate dehydrogenase complex, subunit A, flavoprotein (Fp) | 3.04 | up | 0.01336 |
| AA598829 | 1439 | heterogeneous nuclear ribonucleoprotein U (scaffold attachment factor A) | 3.04 | up | 0.00967 |
| Y00764 | 3848 | ubiquinol-cytochrome c reductase hinge protein | 3.04 | up | 0.01294 |
| N42272 | 2514 | EST | 3.03 | up | 0.0017 |
| AA284720 | 676 | EST | 3.03 | up | 0.00252 |
| R46079 | 2867 | EST | 3.03 | up | 0.00755 |
| H96850 | 2055 | dolichyl-diphosphooligosaccharide-protein glycosyltransferase | 3.03 | up | 0.00679 |
| AA426291 | 961 | EST | 3.03 | up | 0.00365 |
| H99364 | 2075 | chloride channel 7 | 3.03 | up | 0.01727 |
| R06400 | 2767 | EST | 3.03 | up | 0.03266 |
| R20817 | 2796 | ubiquitin-conjugating enzyme E2A (RAD6 homolog) | 3.03 | up | 0.01091 |
| D86977 | 1757 | KIAA0224 gene product | 3.03 | up | 0.00053 |
| AA442400 | 1071 | hepatitis B virus x-interacting protein (9.6 kD) | 3.02 | up | 0.04037 |
| AA055892 | 134 | EST | 3.02 | up | 0.04984 |
| W04507 | 3468 | prefoldin 4 | 3.02 | up | 0.04091 |
| Z38904 | 3893 | EST | 3.02 | up | 0.00814 |
| AA252355 | 553 | EST | 3.02 | up | 0.00715 |

TABLE 7A-continued

Up in HCC vs Normal Sample Set 2

| Fragment Name | SEQ ID: | Known Gene Name | Fold Change | Direction | Pvalue |
|---|---|---|---|---|---|
| AA293589 | 719 | zinc finger protein | 3.02 | up | 0.01809 |
| AA453656 | 1155 | EST | 3.02 | up | 0.00958 |
| U68142 | 3410 | RAB2, member RAS oncogene family-like | 3.02 | up | 0.0296 |
| U90904 | 3457 | EST | 3.02 | up | 0.00381 |
| J04029 | 2102 | keratin 10 (epidermolytic hyperkeratosis; keratosis palmaris et plantaris) | 3.02 | up | 0.00032 |
| AA598749 | 1438 | EST | 3.01 | up | 0.03714 |
| F10741 | 1822 | KIAA0622 protein | 3.01 | up | 0.03079 |
| AA365708 | 764 | microfibrillar-associated protein 1 | 3.01 | up | 0.02372 |
| AA426447 | 965 | EST | 3.01 | up | 0.02414 |
| W57931 | 3546 | EST | 3.01 | up | 0.02661 |
| AA181580 | 383 | karyopherin (importin) beta 1 | 3.01 | up | 0.0125 |
| H27897 | 1911 | hypothetical protein | 3.01 | up | 0.00174 |
| N51590 | 2545 | EST | 3.01 | up | 0.04345 |
| R46337 | 2868 | secretory carrier membrane protein 3 | 3.01 | up | 0.00374 |
| T66935 | 3178 | EST | 3.01 | up | 0.00123 |
| AA173505 | 372 | EST | 3 | up | 0.01736 |
| AA476473 | 1285 | EST | 3 | up | 0.01324 |
| AA448252 | 1114 | EST | 3 | up | 0.00256 |
| W95841 | 3663 | EST | 3 | up | 0.00466 |

TABLE 7B

Down in HCC 2 vs Normal Sample Set 2

| Fragment Name | SEQ ID: | Known Gene Name | Fold Change | Direction | Pvalue |
|---|---|---|---|---|---|
| H81070 | 2006 | RNA helicase-related protein | 39.64 | down | 0.00002 |
| AA007395 | 17 | alcohol dehydrogenase 4 (class II), pi polypeptide | 37.78 | down | 0.00939 |
| T68711 | 3187 | EST | 35.98 | down | 0.0003 |
| T48075 | 3129 | hemoglobin, alpha 1 | 35.75 | down | 0.00471 |
| N80129 | 2702 | metallothionein 1L | 26.87 | down | 0.00999 |
| AA010605 | 26 | 4-hydroxyphenylpyruvate dioxygenase | 25.52 | down | 0.00855 |
| W88946 | 3636 | putative glycine-N-acyltransferase | 25.28 | down | 0.00221 |
| T48278 | 3131 | EST | 24.1 | down | 0.00595 |
| T95813 | 3261 | KIAA1051 protein | 20.36 | down | 0.01361 |
| H58692 | 1960 | formyltetrahydrofolate dehydrogenase | 20.18 | down | 0.00485 |
| R97419 | 3003 | cytochrome P450, subfamily VIIIB (sterol 12-alpha-hydroxylase), polypeptide 1 | 19.3 | down | 0.00807 |
| H80901 | 2005 | ficolin (collagen/fibrinogen domain-containing) 3 (Hakata antigen) | 18.59 | down | 0 |
| J03910 | 2101 | EST | 18.13 | down | 0.00119 |
| M29873 | 2318 | cytochrome P450, subfamily IIB (phenobarbital-inducible) | 17.92 | down | 0.01469 |
| U56814 | 3392 | deoxyribonuclease I-like 3 | 17.69 | down | 0.00007 |
| T67931 | 3183 | fibrinogen, B beta polypeptide | 17.25 | down | 0.00128 |
| T58756 | 3155 | EST | 16.61 | down | 0 |
| R49602 | 2884 | EST | 16.17 | down | 0.00279 |
| T69305 | 3196 | EST | 15.87 | down | 0.02258 |
| Z20777 | 3863 | EST | 15.73 | down | 0.00147 |
| H58673 | 1959 | EST | 15.49 | down | 0.00002 |
| T56281 | 3150 | RNA helicase-related protein | 14.64 | down | 0.00027 |
| K03192 | 2127 | cytochrome P450, subfamily IIA (phenobarbital-inducible), polypeptide 6 | 14.19 | down | 0.0307 |
| AA448002 | 1113 | putative type II membrane protein | 14.14 | down | 0 |
| T68873 | 3189 | metallothionein 1L | 13.68 | down | 0.00593 |
| R89811 | 2979 | HGF activator | 13.29 | down | 0.00148 |
| M14777 | 2263 | glutathione S-transferase A2, glutathione S-transferase A3 | 13.23 | down | 0.03224 |
| D31628 | 1646 | 4-hydroxyphenylpyruvate dioxygenase | 13.18 | down | 0.02064 |
| H20543 | 1897 | DKFZP586B1621 protein | 13.06 | down | 0.00218 |
| W81552 | 3612 | EST | 12.97 | down | 0.00244 |
| N54053 | 2560 | secreted phosphoprotein 2, 24 kD | 12.87 | down | 0.01821 |
| R40395 | 2840 | lecithin-cholesterol acyltransferase | 12.85 | down | 0.01334 |
| H08102 | 1858 | breast cell glutaminase | 12.85 | down | 0.0424 |
| AA455988 | 1184 | butyrobetaine (gamma), 2-oxoglutarate dioxygenase (gamma-butyrobetaine hydroxylase) | 12.51 | down | 0 |
| R12472 | 2788 | EST | 12.09 | down | 0.02379 |
| U22029 | 3326 | cytochrome P450, subfamily IIA (phenobarbital-inducible), polypeptide 7 | 11.85 | down | 0.03538 |

TABLE 7B-continued

Down in HCC 2 vs Normal Sample Set 2

| Fragment Name | SEQ ID: | Known Gene Name | Fold Change | Direction | Pvalue |
|---|---|---|---|---|---|
| AA446864 | 1095 | EST | 11.57 | down | 0.0001 |
| N80129 | 2702 | metallothionein 1L | 11.48 | down | 0.00167 |
| M33317 | 2338 | cytochrome P450, subfamily IIA (phenobarbital-inducible), polypeptide 7 fatty-acid-Coenzyme A ligase, long-chain 1, fatty-acid-Coenzyme A ligase, | 11.47 | down | 0.02611 |
| AA348922 | 758 | long-chain 2 | 11.4 | down | 0.00848 |
| T98676 | 3268 | EST | 11.15 | down | 0.0323 |
| M81349 | 2404 | serum amyloid A4, constitutive | 10.97 | down | 0.01946 |
| AA074885 | 161 | macrophage receptor with collagenous structure | 10.88 | down | 0.00087 |
| M16974 | 2277 | complement component 8, alpha polypeptide | 10.85 | down | 0.02313 |
| N70966 | 2662 | solute carrier family 10 (sodium/bile acid cotransporter family), member 1 | 10.8 | down | 0.02894 |
| AA279676 | 630 | deoxyribonuclease I-like 3 | 10.52 | down | 0.00181 |
| N68596 | 2635 | betaine-homocysteine methyltransferase | 10.46 | down | 0.01971 |
| AA433946 | 1033 | EST | 10.24 | down | 0.00663 |
| W72382 | 3581 | oxidative 3 alpha hydroxysteroid dehydrogenase; retinol dehydrogenase | 9.89 | down | 0.03091 |
| X56411 | 3734 | alcohol dehydrogenase 4 (class II), pi polypeptide | 9.87 | down | 0.01416 |
| D00003 | 1586 | cytochrome P450, subfamily IIIA (niphedipine oxidase), polypeptide 3 | 9.46 | down | 0.00001 |
| AA448300 | 1116 | FXYD domain-containing ion transport regulator 1 (phospholemman) | 9.27 | down | 0.00108 |
| H77597 | 2000 | metallothionein 1H | 9.01 | down | 0.00022 |
| HG1428-HT1428 | | hemoglobin, beta | 8.98 | down | 0.02071 |
| R08564 | 2779 | plasminogen-like | 8.77 | down | 0.01284 |
| T51150 | 3136 | EST | 8.65 | down | 0.00553 |
| H93381 | 2036 | EST | 8.62 | down | 0.01271 |
| N58009 | 2577 | formiminotransferase cyclodeaminase | 8.52 | down | 0.01808 |
| AA417046 | 915 | fatty-acid-Coenzyme A ligase, very long-chain 1 | 8.49 | down | 0.02476 |
| T57140 | 3151 | paraoxonase 3 | 8.47 | down | 0.01048 |
| N70358 | 2656 | growth hormone receptor | 8.47 | down | 0.00816 |
| AA256367 | 579 | paraoxonase 3 | 8.37 | down | 0.02326 |
| R98073 | 3008 | EST | 8.37 | down | 0.01436 |
| N74025 | 2684 | deiodinase, iodothyronine, type I | 8.18 | down | 0.01363 |
| N51117 | 2543 | EST | 8.17 | down | 0.00105 |
| M29874 | 2319 | cytochrome P450, subfamily IIB (phenobarbital-inducible) | 8.13 | down | 0.01064 |
| L04751 | 2138 | cytochrome P450, subfamily IVA, polypeptide 11 | 8.13 | down | 0.02065 |
| X13930 | 3697 | cytochrome P450, subfamily IIA (phenobarbital-inducible), polypeptide 6 | 8.1 | down | 0.0219 |
| U50929 | 3379 | betaine-homocysteine methyltransferase | 8.04 | down | 0.0188 |
| Z28339 | 3872 | aldo-keto reductase family 1, member D1 (delta 4-3-ketosteroid-5-beta-reductase) | 8.03 | down | 0.00853 |
| T83397 | 3232 | phytanoyl-CoA hydroxylase (Refsum disease) | 8.03 | down | 0.02173 |
| K03192 | 2127 | cytochrome P450, subfamily IIA (phenobarbital-inducible), polypeptide 6 | 8.02 | down | 0.03483 |
| AA401562 | 830 | EST | 7.97 | down | 0.00527 |
| AA035245 | 79 | aldehyde oxidase 1 | 7.79 | down | 0.02387 |
| M94065 | 2424 | dihydroorotate dehydrogenase | 7.87 | down | 0.0011 |
| AA453988 | 1160 | methionine adenosyltransferase I, alpha | 7.78 | down | 0.02695 |
| X54380 | 3727 | pregnancy-zone protein | 7.71 | down | 0.00069 |
| H57060 | 1954 | EST | 7.57 | down | 0.00875 |
| R99591 | 3015 | CD5 antigen-like (scavenger receptor cysteine rich family) | 7.41 | down | 0.00043 |
| Z84721 | 3950 | hemoglobin, zeta | 7.39 | down | 0.01921 |
| D14012 | 1612 | HGF activator | 7.27 | down | 0.00145 |
| Z49269 | 3942 | small inducible cytokine subfamily A (Cys-Cys), member 14 | 7.24 | down | 0.01047 |
| T74542 | 3214 | UDP glycosyltransferase 2 family, polypeptide B10 | 7.19 | down | 0.011 |
| AA235310 | 496 | EST | 7.08 | down | 0.04056 |
| R73816 | 2960 | EST | 7.05 | down | 0.01287 |
| AA287566 | 690 | KIAA0187 gene product | 6.99 | down | 0.00023 |
| N51773 | 2548 | EST | 6.92 | down | 0.01839 |
| W28944 | 3493 | EST | 6.9 | down | 0.01014 |
| N54429 | 2567 | EST | 6.85 | down | 0.03334 |
| N63845 | 2604 | phytanoyl-CoA hydroxylase (Refsum disease) | 6.82 | down | 0.00369 |
| D00003 | 1586 | cytochrome P450, subfamily IIIA (niphedipine oxidase), polypeptide 3 | 6.8 | down | 0.01328 |
| AA236455 | 512 | EST | 6.73 | down | 0.02418 |
| K02402 | 2125 | coagulation factor IX (plasma thromboplastic component, Christmas disease, hemophilia B) | 6.64 | down | 0.04082 |
| H59136 | 1962 | EST | 6.63 | down | 0.00033 |
| AA057678 | 143 | EST | 6.63 | down | 0.00089 |
| X16349 | 3709 | sex hormone-binding globulin | 6.61 | down | 0.00008 |

TABLE 7B-continued

Down in HCC 2 vs Normal Sample Set 2

| Fragment Name | SEQ ID: | Known Gene Name | Fold Change | Direction | Pvalue |
|---|---|---|---|---|---|
| R65593 | 2934 | kynurenine 3-monooxygenase (kynurenine 3-hydroxylase) | 6.6 | down | 0.01982 |
| AA099225 | 206 | EST | 6.59 | down | 0.00064 |
| N54950 | 2572 | ketohexokinase (fructokinase) | 6.47 | down | 0.0223 |
| N54417 | 2566 | fibrinogen, A alpha polypeptide | 6.47 | down | 0.00733 |
| R92475 | 2986 | flavin containing monooxygenase 3 | 6.46 | down | 0.02269 |
| R69417 | 2941 | EST | 6.43 | down | 0.00778 |
| R40492 | 2841 | EST | 6.4 | down | 0.00527 |
| U06641 | 3286 | UDP glycosyltransferase 2 family, polypeptide B15 | 6.37 | down | 0.01594 |
| AA599937 | 1458 | insulin-like growth factor-binding protein 4 | 6.31 | down | 0.0477 |
| T63364 | 3169 | ficolin (collagen/fibrinogen domain-containing) 3 (Hakata antigen) | 6.27 | down | 0.00455 |
| AA490620 | 1378 | EST | 6.25 | down | 0.03613 |
| R59722 | 2915 | EST | 6.24 | down | 0.02361 |
| M10943 | 2234 | metallothionein 1F (functional) | 6.23 | down | 0.00007 |
| X95190 | 3829 | acyl-Coenzyme A oxidase 2, branched chain | 6.22 | down | 0.00162 |
| AA232114 | 463 | epoxide hydrolase 2, cytoplasmic | 6.18 | down | 0.00231 |
| J02843 | 2088 | cytochrome P450, subfamily IIE (ethanol-inducible) | 6.18 | down | 0.01308 |
| AA150776 | 330 | EST | 6.17 | down | 0.00004 |
| T51617 | 3137 | solute carrier family 22 (extraneuronal monoamine transporter), member 3 | 6.16 | down | 0.04198 |
| N64036 | 2606 | enoyl-Coenzyme A, hydratase/3-hydroxyacyl Coenzyme A dehydrogenase | 6.12 | down | 0.00476 |
| T74608 | 3215 | hydroxyacid oxidase (glycolate oxidase) 1 | 6.1 | down | 0.00249 |
| M76665 | 2397 | hydroxysteroid (11-beta) dehydrogenase 1 | 6.06 | down | 0.01317 |
| L12760 | 2162 | phosphoenolpyruvate carboxykinase 1 (soluble) | 6.06 | down | 0.01005 |
| W86075 | 3621 | EST | 6.04 | down | 0.01486 |
| D12620 | 1601 | cytochrome P450, subfamily IVF, polypeptide 2, cytochrome P450, subfamily IVE, polypeptide 3 (leukotriene B4 omega hydroxylase) | 6.03 | down | 0.03947 |
| M83652 | 2407 | properdin P factor, complement | 6 | down | 0.00002 |
| D62518 | 1708 | EST | 5.96 | down | 0.00027 |
| L16883 | 2166 | cytochrome P450, subfamily IIC (mephenytoin 4-hydroxylase), polypeptide 9 | 5.85 | down | 0.04368 |
| AA233152 | 467 | EST | 5.8 | down | 0.00272 |
| AA343142 | 751 | EST | 5.79 | down | 0.02747 |
| U56814 | 3392 | deoxyribonuclease I-like 3 | 5.75 | down | 0.00152 |
| T78433 | 3219 | glycogen synthase 2 (liver) | 5.74 | down | 0.00949 |
| AA454733 | 1169 | EST | 5.73 | down | 0.00748 |
| AA010205 | 23 | EST | 5.71 | down | 0.00014 |
| AA284795 | 678 | phosphatidylethanolamine N-methyltransferase | 5.7 | down | 0.00004 |
| N31741 | 2488 | serine hydroxymethyltransferase 1 (soluble) | 5.66 | down | 0.00212 |
| X76717 | 3794 | metallothionein 1L | 5.64 | down | 0.00215 |
| W55903 | 3543 | adipose differentiation-related protein; adipophilin | 5.64 | down | 0.00014 |
| AA253369 | 563 | EST | 5.64 | down | 0.00478 |
| D13243 | 1602 | pyruvate kinase, liver and RBC | 5.58 | down | 0.04029 |
| AA007629 | 19 | EST | 5.56 | down | 0.00005 |
| R93776 | 2992 | EST | 5.55 | down | 0.00084 |
| D78011 | 1717 | dihydropyrimidinase | 5.54 | down | 0.0312 |
| AA005358 | 14 | EST | 5.51 | down | 0.00059 |
| R77628 | 2965 | insulin induced gene 1 | 5.51 | down | 0.0404 |
| W87532 | 3631 | putative glycine-N-acyltransferase | 5.5 | down | 0.00739 |
| AA460661 | 1229 | EST | 5.46 | down | 0.00151 |
| M16594 | 2272 | glutathione S-transferase A2 | 5.42 | down | 0.03813 |
| T52813 | 3141 | putative lymphocyte G0/G1 switch gene | 5.4 | down | 0.02021 |
| L32140 | 2192 | afamin | 5.39 | down | 0.02767 |
| AA039335 | 89 | coagulation factor XII (Hageman factor) | 5.33 | down | 0.03807 |
| U20530 | 3321 | secreted phosphoprotein 2, 24 kD | 5.31 | down | 0.01119 |
| AA236401 | 510 | EST | 5.31 | down | 0.01787 |
| AA478298 | 1297 | adipose specific 2 | 5.29 | down | 0.00943 |
| AA010619 | 27 | EST | 5.28 | down | 0.002 |
| AA609519 | 1482 | EST | 5.23 | down | 0.00068 |
| L21893 | 2176 | solute carrier family 10 (sodium/bile acid cotransporter family), member 1 | 5.23 | down | 0.03367 |
| AA287122 | 686 | EST | 5.21 | down | 0.00523 |
| AA608837 | 1472 | EST | 5.15 | down | 0.00005 |
| M83772 | 2408 | flavin containing monooxygenase 3 | 5.14 | down | 0.02023 |
| S70004 | 3028 | glycogen synthase 2 (liver) | 5.13 | down | 0.00183 |
| AA172372 | 370 | EST | 5.12 | down | 0.00032 |
| AA090439 | 192 | ribosomal protein S6 | 5.11 | down | 0.01108 |
| AA236455 | 512 | EST | 5.1 | down | 0.00307 |
| J04449 | 2110 | cytochrome P450, subfamily IIIA (niphedipine oxidase), polypeptide 3 | 5.07 | down | 0.01733 |
| AA291749 | 703 | estrogen receptor 1 | 5.06 | down | 0.00044 |
| S68287 | 3024 | aldo-keto reductase family 1, member C4 | 5.04 | down | 0.02895 |

TABLE 7B-continued

Down in HCC 2 vs Normal Sample Set 2

| Fragment Name | SEQ ID: | Known Gene Name | Fold Change | Direction | Pvalue |
|---|---|---|---|---|---|
| | | (chlordecone reductase; 3-alpha hydroxysteroid dehydrogenase, type I; dihydrodiol dehydrogenase 4) | | | |
| AA458652 | 1202 | EST | 5.03 | down | 0.00065 |
| K02766 | 2126 | complement component 9 | 5.03 | down | 0.0433 |
| AA297532 | 725 | EST | 5.01 | down | 0.00745 |
| H29568 | 1914 | EST | 5 | down | 0.00426 |
| AA285053 | 681 | EST | 5 | down | 0.00718 |
| Z40902 | 3923 | SEC14 (*S. cerevisiae*)-like 2 | 4.97 | down | 0.04672 |
| T72906 | 3209 | EST | 4.91 | down | 0.00512 |
| N22938 | 2452 | serum amyloid A4, constitutive | 4.91 | down | 0.01918 |
| R79750 | 2970 | EST | 4.89 | down | 0.00695 |
| AA609537 | 1483 | hepatic leukemia factor | 4.88 | down | 0.00118 |
| N57464 | 2575 | CCAAT/enhancer binding protein (C/EBP), delta | 4.87 | down | 0.00111 |
| AA196287 | 420 | EST | 4.86 | down | 0.01656 |
| J05428 | 2120 | UDP glycosyltransferase 2 family, polypeptide B7 | 4.86 | down | 0.03414 |
| D49357 | 1665 | methionine adenosyltransferase I, alpha | 4.85 | down | 0.04435 |
| R40899 | 2843 | glycine receptor, beta | 4.84 | down | 0.02369 |
| AA480991 | 1323 | EST | 4.83 | down | 0.03498 |
| M99439 | 2437 | transducin-like enhancer of split 4, homolog of Drosophila E(sp1) | 4.82 | down | 0.00121 |
| X06562 | 3683 | growth hormone receptor | 4.8 | down | 0.00507 |
| AA426640 | 969 | small inducible cytokine subfamily B (Cys-X-Cys), member 14 (BRAK) | 4.8 | down | 0.00539 |
| AA194997 | 412 | EST | 4.8 | down | 0.00153 |
| N39201 | 2509 | protease inhibitor 4 (kallistatin) | 4.79 | down | 0.02015 |
| T16484 | 3070 | EST | 4.78 | down | 0.00009 |
| N59550 | 2587 | EST | 4.78 | down | 0.02924 |
| AA046747 | 114 | EST | 4.77 | down | 0.00023 |
| T72502 | 3207 | EST | 4.74 | down | 0.00404 |
| AA085987 | 183 | UDP glycosyltransferase 1 | 4.74 | down | 0.03035 |
| D12620 | 1601 | cytochrome P450, subfamily IVF, polypeptide 2, cytochrome P450, subfamily IVF, polypeptide 3 (leukotriene B4 omega hydroxylase) | 4.7 | down | 0.04091 |
| U51010 | 3380 | nicotinamide N-methyltransferase | 4.69 | down | 0.03099 |
| N67105 | 2623 | EST | 4.69 | down | 0.00194 |
| R93714 | 2991 | fetuin B | 4.65 | down | 0.03704 |
| AA076383 | 171 | EST | 4.65 | down | 0.00593 |
| N73543 | 2674 | EST | 4.64 | down | 0.03981 |
| Y00317 | 3842 | UDP glycosyltransferase 2 family, polypeptide B4 | 4.63 | down | 0.02986 |
| U95090 | 3463 | nephrosis 1, congenital, Finnish type (nephrin) | 4.63 | down | 0.01595 |
| T40936 | 3117 | EST | 4.62 | down | 0.02844 |
| AA477119 | 1289 | EST | 4.62 | down | 0.00072 |
| HG2841-HT2968 | | albumin | 4.62 | down | 0.00552 |
| AA377087 | 771 | EST | 4.61 | down | 0.01616 |
| Z48475 | 3940 | glucokinase (hexokinase 4) regulatory protein | 4.6 | down | 0.01693 |
| R94674 | 2995 | EST | 4.58 | down | 0.0047 |
| N52322 | 2552 | EST | 4.58 | down | 0.02077 |
| AA621131 | 1513 | EST | 4.57 | down | 0.03867 |
| R01023 | 2751 | glucokinase (hexokinase 4) regulatory protein | 4.56 | down | 0.04036 |
| L09229 | 2150 | fatty-acid-Coenzyme A ligase, long-chain 1, fatty-acid-Coenzyme A ligase, long-chain 2 | 4.5 | down | 0.01347 |
| N29764 | 2481 | EST | 4.48 | down | 0.013 |
| Z40259 | 3916 | EST | 4.47 | down | 0.00093 |
| M31667 | 2331 | cytochrome P450, subfamily I (aromatic compound-inducible), polypeptide 2 | 4.47 | down | 0.01116 |
| W26996 | 3483 | EST | 4.46 | down | 0.00734 |
| U02388 | 3277 | cytochrome P450, subfamily IVF, polypeptide 2 | 4.4 | down | 0.00761 |
| W67147 | 3565 | deleted in liver cancer 1 | 4.37 | down | 0.00069 |
| H55759 | 1949 | EST | 4.36 | down | 0.0398 |
| AA112101 | 222 | EST | 4.36 | down | 0.03175 |
| D79276 | 1722 | succinate-CoA ligase, GDP-forming, beta subunit | 4.34 | down | 0.00836 |
| R66002 | 2935 | EST | 4.33 | down | 0.00789 |
| N66066 | 2612 | EST | 4.33 | down | 0.0184 |
| AA398892 | 800 | similar to yeast BET3 (*S. cerevisiae*) | 4.33 | down | 0.01326 |
| C20653 | 1578 | EST | 4.32 | down | 0.00718 |
| R22905 | 2800 | EST | 4.31 | down | 0.01744 |
| M25079 | 2305 | hemoglobin, beta | 4.31 | down | 0.01567 |
| N39163 | 2508 | metallothionein 1L | 4.3 | down | 0.03917 |
| M26393 | 2309 | acyl-Coenzyme A dehydrogenase, C-2 to C-3 short chain | 4.3 | down | 0.02294 |
| H02855 | 1832 | EST | 4.29 | down | 0.0138 |
| X90579 | 3816 | EST | 4.26 | down | 0.04759 |
| X63359 | 3756 | UDP glycosyltransferase 2 family, polypeptide B10 | 4.26 | down | 0.01725 |
| X72177 | 3787 | complement component 6 | 4.25 | down | 0.01598 |
| W95041 | 3659 | EST | 4.22 | down | 0.01005 |

TABLE 7B-continued

Down in HCC 2 vs Normal Sample Set 2

| Fragment Name | SEQ ID: | Known Gene Name | Fold Change | Direction | Pvalue |
|---|---|---|---|---|---|
| AA223902 | 450 | EST | 4.22 | down | 0.01315 |
| AA435746 | 1043 | GTPase activating protein-like | 4.21 | down | 0.03192 |
| T68878 | 3190 | carboxylesterase 1 (monocyte/macrophage serine esterase 1) | 4.18 | down | 0.02474 |
| AA100026 | 211 | EST | 4.18 | down | 0.00567 |
| L27050 | 2186 | apolipoprotein F | 4.18 | down | 0.04901 |
| D10040 | 1593 | fatty-acid-Coenzyme A ligase, long-chain 2 | 4.15 | down | 0.02947 |
| AA253216 | 561 | EST | 4.14 | down | 0.0014 |
| H93246 | 2035 | EST | 4.14 | down | 0.00058 |
| AA258350 | 592 | EST | 4.1 | down | 0.02962 |
| X58022 | 3744 | corticotropin releasing hormone-binding protein | 4.09 | down | 0.00076 |
| Z40305 | 3917 | EST | 4.09 | down | 0.00096 |
| AA599814 | 1456 | EST | 4.09 | down | 0.00235 |
| AA428325 | 988 | EST | 4.09 | down | 0.02486 |
| T61649 | 3164 | superoxide dismutase 2, mitochondrial | 4.08 | down | 0.0389 |
| D11756 | 1596 | EST | 4.08 | down | 0.02972 |
| N77326 | 2695 | EST | 4.08 | down | 0.00768 |
| X67491 | 3773 | glutamate dehydrogenase 1 | 4.06 | down | 0.00273 |
| W28414 | 3489 | EST | 4.06 | down | 0.00083 |
| T98199 | 3266 | EST | 4.05 | down | 0.00753 |
| M10942 | 2233 | metallothionein 1E (functional) | 4.05 | down | 0.01412 |
| H06935 | 1855 | electron-transferring-flavoprotein dehydrogenase | 4.04 | down | 0.01498 |
| AA129390 | 262 | EST | 4.03 | down | 0.00128 |
| W87781 | 3633 | EST | 4.02 | down | 0.00284 |
| AA621209 | 1516 | similar to Caenorhabditis elegans protein C42C1.9 | 4.01 | down | 0.00563 |
| L05144 | 2139 | phosphoenolpyruvate carboxykinase 1 (soluble) | 4 | down | 0.021 |
| N34804 | 2496 | DKFZP434J214 protein | 3.97 | down | 0.0175 |
| U08006 | 3289 | complement component 8, alpha polypeptide | 3.96 | down | 0.04272 |
| Z69923 | 3945 | HGF activator | 3.95 | down | 0.00012 |
| H87765 | 2017 | KIAA0626 gene product | 3.94 | down | 0.00123 |
| R43799 | 2850 | EST | 3.93 | down | 0.005 |
| C02460 | 1562 | EST | 3.92 | down | 0.03073 |
| H99727 | 2080 | adipose differentiation-related protein; adipophilin | 3.91 | down | 0.00325 |
| AA486511 | 1349 | EST | 3.9 | down | 0.01409 |
| AA477919 | 1293 | EST | 3.9 | down | 0.00265 |
| M63967 | 2378 | aldehyde dehydrogenase 5 | 3.88 | down | 0.00274 |
| W44745 | 3517 | EST | 3.87 | down | 0.01051 |
| N63391 | 2599 | EST | 3.87 | down | 0.02935 |
| L00389 | 2132 | cytochrome P450, subfamily I (aromatic compound-inducible), polypeptide 2 | 3.87 | down | 0.00844 |
| W63728 | 3562 | EST | 3.86 | down | 0.00288 |
| AA435985 | 1049 | EST | 3.86 | down | 0.01713 |
| AA151676 | 337 | peptidyl arginine deiminase, type II | 3.85 | down | 0.00875 |
| AA076326 | 170 | SEC14 (S. cerevisiae)-like 2 | 3.85 | down | 0.0349 |
| X02176 | 3669 | complement component 9 | 3.84 | down | 0.01793 |
| AA039616 | 90 | EST | 3.84 | down | 0.00997 |
| HG2730-HT2827 | | fibrinogen, A alpha polypeptide | 3.84 | down | 0.00795 |
| H66367 | 1977 | EST | 3.84 | down | 0.00133 |
| M30185 | 2321 | cholesteryl ester transfer protein, plasma | 3.82 | down | 0.00131 |
| AA167565 | 362 | EST | 3.81 | down | 0.04057 |
| HG2379-HT3996 | | serine hydroxymethyltransferase 1 (soluble) | 3.81 | down | 0.01837 |
| D90042 | 1767 | N-acetyltransferase 2 (arylamine N-acetyltransferase) | 3.79 | down | 0.00697 |
| X16260 | 3707 | inter-alpha (globulin) inhibitor, H1 polypeptide | 3.76 | down | 0.00291 |
| AA122345 | 238 | glutamate dehydrogenase 1 | 3.75 | down | 0.01058 |
| M86826 | 2412 | insulin-like growth factor binding protein, acid labile subunit | 3.75 | down | 0.01157 |
| L11931 | 2159 | serine hydroxymethyltransferase 1 (soluble) | 3.74 | down | 0.0056 |
| AA460012 | 1224 | solute carrier family 22 (extraneuronal monoamine transporter), member 3 | 3.73 | down | 0.0313 |
| X97324 | 3836 | adipose differentiation-related protein; adipophilin | 3.72 | down | 0.00202 |
| D63160 | 1709 | ficolin (collagen/fibrinogen domain-containing lectin) 2 (hucolin) | 3.72 | down | 0.00312 |
| W86600 | 3625 | EST | 3.67 | down | 0.04208 |
| N52271 | 2551 | LIM protein (similar to rat protein kinase C-binding enigma) | 3.67 | down | 0.01102 |
| AA402224 | 836 | growth arrest and DNA-damage-inducible, gamma | 3.66 | down | 0.0033 |
| N91087 | 2716 | EST | 3.66 | down | 0.00725 |
| C02386 | 1561 | hypothetical protein | 3.66 | down | 0.00673 |
| U27699 | 3339 | solute carrier family 6 (neurotransmitter transporter, betaine/GABA), member 12 | 3.65 | down | 0.00381 |
| U08021 | 3290 | nicotinamide N-methyltransferase | 3.63 | down | 0.03762 |
| HG2730-HT2828 | | fibrinogen, A alpha polypeptide | 3.62 | down | 0.01013 |
| R80048 | 2971 | EST | 3.61 | down | 0.01209 |

TABLE 7B-continued

Down in HCC 2 vs Normal Sample Set 2

| Fragment Name | SEQ ID: | Known Gene Name | Fold Change | Direction | Pvalue |
|---|---|---|---|---|---|
| M94065 | 2424 | dihydroorotate dehydrogenase | 3.61 | down | 0.00229 |
| J03810 | 2099 | solute carrier family 2 (facilitated glucose transporter), member 2 | 3.6 | down | 0.02376 |
| D00408 | 1589 | cytochrome P450, subfamily IIIA (niphedipine oxidase), polypeptide 3, cytochrome P450, subfamily IIIA (niphedipine oxidase), polypeptide 5, cytochrome P450, subfamily IIIA, polypeptide 7 | 3.58 | down | 0.02048 |
| C20810 | 1579 | EST | 3.57 | down | 0.02116 |
| T61256 | 3161 | ketohexokinase (fructokinase) | 3.56 | down | 0.04957 |
| AA164586 | 359 | estrogen receptor 1 | 3.56 | down | 0.01231 |
| S77356 | 3033 | EST | 3.55 | down | 0.03874 |
| X14813 | 3702 | acetyl-Coenzyme A acyltransferase 1 (peroxisomal 3-oxoacyl-Coenzyme A thiolase) | 3.53 | down | 0.00059 |
| AA460449 | 1228 | EST | 3.53 | down | 0.01247 |
| N99542 | 2746 | orosomucoid 1 | 3.53 | down | 0.00607 |
| W07723 | 3470 | EST | 3.51 | down | 0.00026 |
| F02245 | 1776 | monoamine oxidase A | 3.51 | down | 0.01692 |
| AA182030 | 387 | EST | 3.51 | down | 0.0403 |
| W45560 | 3522 | EST | 3.48 | down | 0.0179 |
| W73818 | 3590 | EST | 3.47 | down | 0.00927 |
| AA455367 | 1176 | DKFZP586F1018 protein | 3.47 | down | 0.00138 |
| T87174 | 3239 | EST | 3.46 | down | 0.00026 |
| AA282061 | 652 | KIAA0962 protein | 3.46 | down | 0.00698 |
| AA233837 | 474 | EST | 3.46 | down | 0.01365 |
| W73601 | 3589 | EST | 3.45 | down | 0.01382 |
| R09053 | 2782 | EST | 3.45 | down | 0.03074 |
| AA142849 | 306 | EST | 3.45 | down | 0.03495 |
| M61854 | 2370 | cytochrome P450, subfamily IIC (mephenytoin 4-hydroxylase) | 3.45 | down | 0.02949 |
| AA376875 | 770 | monoamine oxidase A | 3.45 | down | 0.00105 |
| N29353 | 2476 | kynurenine 3-monooxygenase (kynurenine 3-hydroxylase) | 3.44 | down | 0.01212 |
| N22404 | 2449 | EST | 3.44 | down | 0.02267 |
| AA608802 | 1470 | EST | 3.44 | down | 0.01709 |
| T40995 | 3118 | alcohol dehydrogenase 3 (class I), gamma polypeptide | 3.42 | down | 0.00957 |
| AA035457 | 80 | EST | 3.41 | down | 0.00968 |
| AA401376 | 829 | EST | 3.39 | down | 0.01403 |
| AA018922 | 40 | core promoter element binding protein | 3.39 | down | 0.01801 |
| N65959 | 2611 | EST | 3.38 | down | 0.00785 |
| AA188921 | 393 | similar to Caenorhabditis elegans protein C42C1.9 | 3.38 | down | 0.00862 |
| Z41042 | 3925 | EST | 3.37 | down | 0.00703 |
| H27330 | 1909 | EST | 3.37 | down | 0.01318 |
| AA450127 | 1132 | growth arrest and DNA-damage-inducible, beta | 3.37 | down | 0.00647 |
| J05158 | 2117 | carboxypeptidase N, polypeptide 2, 83 kD | 3.37 | down | 0.01156 |
| N90584 | 2713 | EST | 3.36 | down | 0.01561 |
| F03969 | 1785 | matrix metalloproteinase 2 (gelatinase A, 72 kD gelatinase, 72 kD type IV collagenase) | 3.36 | down | 0.01685 |
| M95585 | 2429 | hepatic leukemia factor | 3.36 | down | 0.00492 |
| HG4533-HT4938 | | protease inhibitor 4 (kallistatin) | 3.35 | down | 0.01605 |
| X06985 | 3686 | heme oxygenase (decycling) 1 | 3.34 | down | 0.00045 |
| H66840 | 1978 | EST | 3.34 | down | 0.01884 |
| M72885 | 2392 | putative lymphocyte G0/G1 switch gene | 3.34 | down | 0.02943 |
| W28798 | 3491 | phosphodiesterase 6A, cGMP-specific, rod, alpha | 3.33 | down | 0.00222 |
| T47778 | 3126 | fibrinogen, A alpha polypeptide | 3.33 | down | 0.00637 |
| AA599472 | 1451 | succinate-CoA ligase, GDP-forming, beta subunit | 3.31 | down | 0.02619 |
| AA084668 | 180 | ubiquitin-like 3 | 3.31 | down | 0.02055 |
| M30185 | 2321 | cholesteryl ester transfer protein, plasma | 3.31 | down | 0.00109 |
| L00352 | 2131 | low density lipoprotein receptor (familial hypercholesterolemia) | 3.3 | down | 0.03487 |
| D13705 | 1610 | cytochrome P450, subfamily IVA, polypeptide 11 | 3.3 | down | 0.0051 |
| Z31690 | 3878 | lipase A, lysosomal acid, cholesterol esterase (Wolman disease) | 3.29 | down | 0.00161 |
| AA450114 | 1131 | EST | 3.29 | down | 0.01171 |
| AA282886 | 663 | EST | 3.29 | down | 0.00025 |
| AA397841 | 780 | EST | 3.29 | down | 0.00825 |
| N57934 | 2576 | formiminotransferase cyclodeaminase | 3.28 | down | 0.01555 |
| J04093 | 2106 | UDP glycosyltransferase 1 | 3.28 | down | 0.02286 |
| X64177 | 3760 | metallothionein 1H | 3.26 | down | 0.03928 |
| T10264 | 3050 | EST | 3.26 | down | 0.01718 |
| C21130 | 1583 | EST | 3.24 | down | 0.03355 |
| AA070191 | 154 | EST | 3.24 | down | 0.00216 |
| H62212 | 1969 | telomeric repeat binding factor 2 | 3.23 | down | 0.00513 |
| X13227 | 3695 | D-amino-acid oxidase | 3.22 | down | 0.01753 |
| Z80345 | 3948 | acyl-Coenzyme A dehydrogenase, C-2 to C-3 short chain | 3.21 | down | 0.04734 |

TABLE 7B-continued

Down in HCC 2 vs Normal Sample Set 2

| Fragment Name | SEQ ID: | Known Gene Name | Fold Change | Direction | Pvalue |
|---|---|---|---|---|---|
| M68895 | | alcohol dehydrogenase 6 (class V) | 3.21 | down | 0.02095 |
| AA400177 | 808 | EST | 3.21 | down | 0.03901 |
| H09317 | 1864 | EST | 3.2 | down | 0.00914 |
| T68510 | 3186 | EST | 3.19 | down | 0.01504 |
| AA465233 | 1269 | succinate-CoA ligase, GDP-forming, beta subunit | 3.19 | down | 0.00036 |
| AA461444 | 1239 | EST | 3.19 | down | 0.02844 |
| AA147646 | 317 | DKFZP586A0522 protein | 3.19 | down | 0.00508 |
| D78725 | 1720 | KIAA0914 gene product | 3.19 | down | 0.01083 |
| U65932 | 3404 | extracellular matrix protein 1 | 3.18 | down | 0.00575 |
| U21931 | 3325 | fructose-bisphosphatase 1 | 3.17 | down | 0.0143 |
| T64575 | 3171 | EST | 3.16 | down | 0.01855 |
| M57731 | 2359 | GRO2 oncogene | 3.16 | down | 0.02204 |
| F02028 | 1774 | EST | 3.15 | down | 0.00902 |
| T41232 | 3121 | EST | 3.14 | down | 0.02012 |
| AA210850 | 431 | EST | 3.12 | down | 0.00288 |
| W72044 | 3577 | insulin induced gene 1 | 3.1 | down | 0.03445 |
| M68840 | 2388 | monoamine oxidase A | 3.1 | down | 0.01953 |
| H57816 | 1957 | EST | 3.09 | down | 0.01327 |
| H10779 | 1872 | methylenetetrahydrofolate dehydrogenase (NADP + dependent). methenyltetrahydrofolate cyclohydrolase, formyltetrahydrofolate synthetase | 3.09 | down | 0.0496 |
| M93405 | 2423 | methylmalonate-semialdehyde dehydrogenase | 3.09 | down | 0.03285 |
| T41047 | 3119 | EST | 3.08 | down | 0.00553 |
| AA157799 | 348 | aldo-keto reductase family 7, member A2 (aflatoxin aldehyde reductase) | 3.08 | down | 0.00207 |
| M34276 | 2341 | plasminogen | 3.08 | down | 0.02754 |
| H05704 | 1848 | EST | 3.07 | down | 0.00363 |
| AA069696 | 150 | EST | 3.07 | down | 0.01569 |
| M16750 | 2273 | pim-1 oncogene | 3.07 | down | 0.02391 |
| AA056482 | 141 | EST | 3.06 | down | 0.01313 |
| AA046457 | 111 | EST | 3.05 | down | 0.02078 |
| M13143 | 2249 | kallikrein B plasma, (Fletcher factor) 1 | 3.04 | down | 0.008 |
| U50196 | 3376 | adenosine kinase | 3.03 | down | 0.00975 |
| AA090257 | 190 | superoxide dismutase 2, mitochondrial | 3.03 | down | 0.02774 |
| N49902 | 2539 | EST | 3.02 | down | 0.00951 |
| AA442334 | 1069 | EST | 3.02 | down | 0.01936 |
| D45529 | 1662 | EST | 3.01 | down | 0.03105 |
| AA404487 | 851 | EST | 3.01 | down | 0.0059 |

TABLE 8A

Genes and ESTs expressed only in HCC2 vs Normal2

| Fragment Name | SEQ ID: | Known Gene Name | fold change in hcc set 2 | p value | hcc sample set 2: Mean | hcc sample set 2: Median | hcc sample set 2: Std Dev | normal set 2: Mean | normal set 2: Median | normal set 2: Std Dev |
|---|---|---|---|---|---|---|---|---|---|---|
| AA093497 | 199 | DEK oncogene (DNA binding) | #N/A | #N/A | 180.58 | 107.64 | 165.71 | 52.11 | 48.84 | 26.51 |
| AA248283 | 534 | EST | #N/A | #N/A | 67.18 | 45.86 | 55.18 | 21.63 | 18.96 | 11.71 |
| AA291456 | 700 | EST | #N/A | #N/A | 828.34 | 830.24 | 196.63 | 671.21 | 509.58 | 629.13 |
| AA400643 | 817 | GAS2-related on chromosome 22 | 4.04 | 0.03751 | 118.72 | 123.18 | 137.15 | -43.6 | -33.96 | 60.39 |
| AA421079 | 930 | EST | #N/A | #N/A | 37.17 | 34.26 | 18.5 | 15.27 | 16.75 | 15.28 |
| AA428172 | 986 | Notch (Drosophila) homolog 3 | 9.63 | 0.00195 | 335.57 | 374.9 | 231.52 | -9.64 | -15.61 | 56.16 |
| AA464043 | 1255 | EST | 3.99 | 0.00056 | 116.97 | 115.99 | 53.49 | 14.27 | 10.06 | 25.86 |
| H19562 | 1896 | PTD010 protein | #N/A | #N/A | 522.13 | 432.65 | 256.94 | 393.61 | 326.53 | 182.71 |
| L08044 | 2149 | trefoil factor 3 (intestinal) | #N/A | #N/A | 214.6 | 108.17 | 238.79 | 107.82 | 58.55 | 184.16 |
| L29218 | 2190 | CDC-like kinase 2 | 6.51 | 0.00019 | 219.64 | 237.35 | 104.29 | 6.53 | -10.03 | 59.8 |
| L37747 | 2206 | lamin B1 | #N/A | #N/A | 43.42 | 28.65 | 37.33 | 5.97 | 5.1 | 7.57 |
| N34257 | 2494 | EST | #N/A | #N/A | 20.76 | 21.48 | 19.54 | -1.84 | -2.74 | 8.53 |
| R50692 | 2887 | KIAA0476 gene product | #N/A | #N/A | 197.89 | 187.87 | 101.08 | 148.53 | 151.12 | 63.03 |
| R60368 | 2916 | EST | #N/A | #N/A | 29.68 | 28.93 | 31.9 | -28.29 | -26.44 | 41.68 |
| R66475 | 2937 | EST | #N/A | #N/A | 45.68 | 32.34 | 34.37 | 7.64 | 8.26 | 6.3 |
| T34377 | 3110 | potassium voltage-gated channel, shaker-related subfamily, beta member 2 | 4.55 | 0.00041 | 113.59 | 120.58 | 51.65 | 6.87 | 11.17 | 25.69 |
| U75968 | 3422 | DEAD/H (Asp-Glu-Ala-Asp/His) box polypeptide 11 (S.cerevisiae CHL1-like helicase) | #N/A | #N/A | 187.33 | 200.16 | 90.35 | 115.5 | 102.24 | 77.72 |
| W21426 | 3480 | KIAA0806 gene product | #N/A | #N/A | 63.36 | 64.93 | 20.23 | 45.59 | 40.39 | 19.89 |
| W28696 | 3490 | EST | #N/A | #N/A | 14.7 | 20.64 | 17.12 | 4.28 | 4.33 | 2.47 |
| X57129 | 3740 | H1 histone family, member 2 | 4.63 | 0.00663 | 137.13 | 137.75 | 87.31 | 8.38 | 5.39 | 28.3 |
| AA024658 | 47 | ribosomal protein S19 | 7.55 | 0.00592 | 278.11 | 120.83 | 373.3 | 7.62 | 5.03 | 10.68 |
| AA029288 | 65 | EST | 3.36 | 0.04908 | 134.53 | 56.15 | 209.69 | 4.09 | 3.35 | 8.39 |
| AA037828 | 88 | KIAA0614 protein | #N/A | #N/A | 53.61 | 46.86 | 41.68 | 13.32 | 10.65 | 11.96 |
| AA040465 | 95 | EST | 3.63 | 0.01806 | 229.8 | 210.67 | 180.94 | 47.15 | 45.53 | 5.48 |
| AA053660 | 128 | EST | #N/A | #N/A | 543.66 | 223.47 | 685.44 | 95.24 | 79.97 | 42.99 |
| AA136332 | 299 | cAMP responsive element binding protein 3 (luman) | #N/A | #N/A | 49.04 | 33.07 | 31.07 | -18.27 | -20.23 | 13.05 |
| AA149530 | 324 | interferon regulatory factor 3 | #N/A | #N/A | 32.94 | 23.12 | 34.23 | 4.21 | 5.38 | 8.53 |
| AA149586 | 325 | EST | #N/A | #N/A | 24.99 | 26.6 | 34.37 | 5.26 | 9.11 | 23.41 |
| AA206023 | 427 | EST | #N/A | #N/A | 154.13 | 170.36 | 85.33 | 108.57 | 111.76 | 58.39 |
| AA234530 | 484 | N-ethylmaleimide-sensitive factor | #N/A | #N/A | 143.67 | 135.48 | 82.59 | 51.33 | 42.9 | 35.02 |
| AA251909 | 549 | EST | 3.59 | 0.01129 | 92.19 | 79.34 | 72.73 | 8.88 | 11.22 | 8.27 |
| AA262030 | 605 | EST | #N/A | #N/A | 119.75 | 89.66 | 103.84 | 31.51 | 32.91 | 14.46 |
| AA262477 | 608 | ribonuclease H1, large subunit | 4.57 | 0.00724 | 242.42 | 199.5 | 182.26 | 44.51 | 36.87 | 22.37 |
| AA283759 | 671 | EST | #N/A | #N/A | 91.82 | 76.73 | 42.28 | 46.87 | 45.86 | 21.54 |
| AA291644 | 701 | EST | 3.28 | 0.00033 | 114.73 | 117.29 | 44.59 | 32.77 | 30.24 | 21.1 |
| AA338760 | 744 | EST | 3.96 | 0.01307 | 129.77 | 130.26 | 87.27 | 14.91 | 21.91 | 26.96 |
| AA398205 | 789 | EST | 4.22 | 0.00059 | 125.4 | 107.84 | 63.85 | 15.01 | 7.37 | 26.26 |
| AA401965 | 833 | tumor suppressor deleted in oral cancer-related 1 | 7.58 | 0.00089 | 932.74 | 924.02 | 593.69 | 120.58 | 93.29 | 109.41 |
| AA402272 | 837 | EST | 3.73 | 0.02336 | 348.91 | 340 | 230.15 | 99.7 | 92.28 | 80.27 |
| AA404597 | 854 | EST | #N/A | #N/A | 609.98 | 525.02 | 371.31 | 379.26 | 336.33 | 167.43 |

TABLE 8A-continued

Genes and ESTs expressed only in HCC2 vs Normal2

| Fragment Name | SEQ ID: | Known Gene Name | fold change in hcc set 2 | p value | hcc sample set 2: Mean | hcc sample set 2: Median | hcc sample set 2: Std Dev | normal set 2: Mean | normal set 2: Median | normal set 2: Std Dev |
|---|---|---|---|---|---|---|---|---|---|---|
| AA417030 | 914 | EST | 7.35 | 0.00555 | 200.3 | 168.21 | 135.63 | 6.42 | 7.5 | 7.77 |
| AA423820 | 940 | EST | #N/A | #N/A | 111.38 | 111.23 | 120.84 | 41.9 | 21.93 | 44.58 |
| AA425852 | 958 | EST | 3.82 | 0.0395 | 131.52 | 95.35 | 166.76 | 7.02 | 5.22 | 4.75 |
| AA430032 | 1009 | pituitary tumor-transforming 1 | 10.67 | 0.00052 | 377.69 | 320.44 | 294.49 | 26.8 | 15.31 | 35.24 |
| AA430673 | 1017 | EST | #N/A | #N/A | 45.74 | 34.15 | 44.8 | -1.21 | 3.63 | 15.26 |
| AA443321 | 1076 | EST | #N/A | #N/A | 33.93 | 32.89 | 11.76 | 10.79 | 9.65 | 7.26 |
| AA443941 | 1085 | tumor suppressing subtransferable candidate 1 | #N/A | #N/A | 97.74 | 103.38 | 47.48 | 31.09 | 34.9 | 16.61 |
| AA447223 | 1100 | EST | #N/A | #N/A | 31.66 | 18.91 | 31.1 | 4.45 | 3.74 | 6.5 |
| AA449431 | 1124 | translation initiation factor IF2 | 3.76 | 0.00571 | 94.41 | 95.64 | 54.08 | 17.4 | 16.96 | 5.38 |
| AA454597 | 1166 | EST | 4.23 | 0.00917 | 342.59 | 311.81 | 207.71 | 66.6 | 57.29 | 23.41 |
| AA458882 | 1205 | EST | #N/A | #N/A | 93.56 | 52.28 | 98.72 | 24.97 | 22.52 | 17.66 |
| AA458934 | 1208 | EST | #N/A | #N/A | 33.6 | 28.19 | 29.02 | 7.1 | 7.91 | 4.22 |
| AA465342 | 1271 | EST | 3.21 | 0.01378 | 131.07 | 109.99 | 95.4 | 30.07 | 33.06 | 23.97 |
| AA477561 | 1292 | EST | #N/A | #N/A | 146.3 | 127.03 | 97.99 | 63.83 | 76.56 | 37.87 |
| AA491295 | 1390 | calcium/calmodulin-dependent protein kinase kinase 2, beta | 3.71 | 0.0103 | 180.61 | 173.47 | 118.85 | 46.95 | 31.51 | 65.56 |
| AA608545 | 1462 | RAD51 (S. cerevisiae) homolog (E. coli RecA homolog) | #N/A | #N/A | 70.5 | 57.51 | 53.36 | 7.76 | 8.92 | 6.17 |
| AA620553 | 1504 | flap structure-specific endonuclease 1 | 7.56 | 0.00101 | 262.87 | 232.63 | 201.66 | 14.44 | 4.85 | 38.53 |
| AA621325 | 1522 | HNK-1 sulfotransferase | #N/A | #N/A | 74.57 | 70.64 | 46.61 | 27.23 | 25.89 | 16.03 |
| AA621780 | 1530 | CGI-96 protein | #N/A | #N/A | 81.72 | 92.23 | 49.69 | 12.06 | 11.27 | 19.2 |
| F02807 | 1781 | KIAA0838 protein | 5.67 | 0.02064 | 260.02 | 219.01 | 229.96 | 20.93 | 16.66 | 22.24 |
| F04444 | 1788 | EST | 4.13 | 0.00944 | 371.21 | 360.5 | 186.45 | 119.68 | 121.27 | 109.82 |
| F04524 | 1790 | stomatin-like protein 1 | #N/A | #N/A | 117.77 | 135.65 | 68.29 | 46.56 | 44.53 | 33.75 |
| F08876 | 1797 | EST | 9.06 | 0 | 209.64 | 201.85 | 53.21 | -22.5 | -20.17 | 37.21 |
| F10161 | 1811 | EST | #N/A | #N/A | 50.78 | 46.73 | 32.42 | 15.4 | 14.78 | 11.87 |
| F10453 | 1819 | EST | 3.64 | 0.01878 | 135.07 | 138.53 | 85.7 | 27.28 | 14.2 | 54.04 |
| H04649 | 1838 | EST | #N/A | #N/A | 180.25 | 158.18 | 164.34 | 50.86 | 41.2 | 33.9 |
| H04793 | 1840 | DKFZP434F091 protein | #N/A | #N/A | 23.18 | 20 | 41.25 | -14.45 | -20.45 | 29 |
| H59617 | 1964 | EST | 5.81 | 0.0115 | 212.68 | 209.19 | 157.42 | 19.24 | 21.65 | 16.88 |
| H97012 | 2058 | EST | 3.51 | 0.03505 | 171.34 | 138.12 | 170.68 | 27.69 | 38.46 | 36.08 |
| H98657 | 2068 | EST | #N/A | #N/A | 141.17 | 131.42 | 69.63 | 111.2 | 84.74 | 128.92 |
| N23319 | 2453 | EST | #N/A | #N/A | 70.62 | 66.39 | 49.4 | 13.74 | 8.56 | 21.62 |
| N23868 | 2458 | EST | #N/A | #N/A | 79.69 | 81.67 | 56.06 | 20.52 | 20.19 | 11.48 |
| N45224 | 2515 | EST | #N/A | #N/A | 349.73 | 360.67 | 164.87 | 215.49 | 223.16 | 151.06 |
| N48595 | 2527 | EST | #N/A | #N/A | 85.77 | 67.62 | 51.78 | 28.84 | 29.38 | 8.3 |
| N75541 | 2691 | EST | 4.43 | 0.01059 | 182.83 | 131.35 | 183.41 | 34.1 | 15.82 | 56.07 |
| N90273 | 2712 | ras homolog gene family, member H | #N/A | #N/A | 105.53 | 96.01 | 41.89 | 68.92 | 59.56 | 35.69 |
| N93465 | 2734 | EST | #N/A | #N/A | 803.68 | 716.56 | 385.5 | 624.57 | 694.14 | 306.11 |
| R39191 | 2833 | KIAA1020 protein | 5.18 | 0.03185 | 331.72 | 80.62 | 590.96 | 17.46 | 18.33 | 16.04 |
| R44793 | 2858 | EST | 5.4 | 0.00329 | 155.86 | 121.83 | 125.26 | 10.1 | 7.86 | 16.54 |
| R44817 | 2859 | EST | #N/A | #N/A | 594.46 | 602.82 | 206.15 | 255.91 | 249.29 | 69.09 |
| R44896 | 2861 | KIAA0665 gene product | #N/A | #N/A | 67.08 | 57.13 | 34.18 | 19.1 | 20.75 | 23.04 |
| R64137 | 2930 | EST | #N/A | #N/A | 31.25 | 24.23 | 21 | 2.9 | 2.65 | 6.94 |
| R71395 | 2951 | EST | 4.12 | 0.03719 | 166.03 | 99.42 | 190.98 | 14.99 | 12.28 | 14.58 |

TABLE 8A-continued

Genes and ESTs expressed only in HCC2 vs Normal2

| Fragment Name | SEQ ID: | Known Gene Name | fold change in hcc set 2 | p value | hcc sample set 2: Mean | hcc sample set 2: Median | hcc sample set 2: Std Dev | normal set 2: Mean | normal set 2: Median | normal set 2: Std Dev |
|---|---|---|---|---|---|---|---|---|---|---|
| R72087 | 2954 | EST | #N/A | #N/A | 262.11 | 302.11 | 95 | 201.97 | 183.76 | 83.41 |
| R91819 | 2983 | EST | 12.81 | 0.00037 | 467.79 | 364.2 | 426.16 | 11.34 | 9.35 | 36.49 |
| T03749 | 3047 | KIAA1089 protein | 4.23 | 0.00776 | 103 | 97.55 | 74.34 | -5.18 | -6.08 | 13.69 |
| T25744 | 3091 | EST | #N/A | #N/A | 72.74 | 73.3 | 37.84 | 15.56 | 12.65 | 13.18 |
| T62918 | 3168 | EST | 5.25 | 0.00687 | 136.22 | 142.37 | 83.63 | -12.41 | -6.89 | 17.59 |
| T89731 | 3244 | EST | #N/A | #N/A | 63.59 | 65.07 | 20.47 | 5.75 | 3.83 | 11.8 |
| W32176 | 3497 | zinc metalloproteinase, STE24 (yeast, homolog) | #N/A | #N/A | 550.53 | 614.92 | 234.79 | 290.18 | 277.95 | 129.45 |
| W47388 | 3533 | rab6 GTPase activating protein (GAP and centrosome-associated) | #N/A | #N/A | 97.33 | 71 | 59.73 | 43.93 | 36.52 | 48.34 |
| W78057 | 3597 | EST | 5.53 | 0.01231 | 265.23 | 222.35 | 199.24 | 29.21 | 29.9 | 34.33 |
| W80763 | 3605 | EST | 4.98 | 0.01026 | 147.37 | 138.37 | 122.38 | 16.84 | 15.48 | 9.22 |
| W90146 | 3641 | EST | 3.58 | 0.00322 | 82.11 | 69.02 | 47.2 | 9.93 | 8.63 | 6.49 |
| Z38299 | 3884 | EST | 3.71 | 0.0036 | 140.86 | 127.16 | 96.62 | 30.48 | 25.94 | 23.34 |
| Z38404 | 3885 | EST | #N/A | #N/A | 59.77 | 56.71 | 37.29 | 29.82 | 30.16 | 9 |
| Z38462 | 3889 | KIAA0938 protein | 4.69 | 0.0142 | 137.19 | 116.11 | 116.16 | -0.86 | 0.53 | 7.64 |
| Z38688 | 3890 | EST | #N/A | #N/A | 49.85 | 46.83 | 42.25 | 21.38 | 13.4 | 29.47 |
| Z38729 | 3891 | EST | #N/A | #N/A | 77.67 | 57.81 | 60.7 | -2.4 | -5.01 | 46.96 |
| Z40556 | 3918 | CGI-96 protein | 3.17 | 0.00158 | 176.19 | 76.96 | 285.02 | 59.62 | 55.07 | 16.66 |
| AA021549 | 42 | EST | #N/A | #N/A | 100.01 | 83.02 | 44.39 | 31.74 | 20.12 | 36.74 |
| AA026670 | 56 | tyrosyl-tRNA synthetase | #N/A | #N/A | 269.96 | 261.31 | 191.51 | 76.85 | 76.68 | 45.22 |
| AA055896 | 135 | collagen, type V, alpha 1 | 10.87 | 0.00907 | 414.16 | 454.82 | 330.75 | -3.14 | -5.8 | 33.88 |
| AA112979 | 225 | vaccinia related kinase 1 | #N/A | #N/A | 37.93 | 31.05 | 16.86 | 8.54 | 8.02 | 2.59 |
| AA134063 | 286 | EST | #N/A | #N/A | 25.71 | 13.84 | 34.35 | -5.21 | -6.17 | 6 |
| AA150053 | 327 | EST | #N/A | #N/A | 270.14 | 248.87 | 144.92 | 101.87 | 88.37 | 73.73 |
| AA206914 | 428 | EST | #N/A | #N/A | 89.35 | 94.1 | 46.27 | 66.34 | 69.2 | 26.35 |
| AA243133 | 525 | serine/threonine kinase 15 | 7.03 | 0.00005 | 147.5 | 162.28 | 43.03 | 9.69 | 12.1 | 9.8 |
| AA243466 | 527 | EST | #N/A | #N/A | 61.94 | 42.38 | 37.6 | 13.66 | 13.42 | 9.63 |
| AA243598 | 531 | EST | #N/A | #N/A | 60.15 | 62.79 | 32.67 | 11.41 | 13.18 | 13.43 |
| AA252147 | 551 | EST | #N/A | #N/A | 95.91 | 56.69 | 122.31 | 3.65 | -0.82 | 22.5 |
| AA255566 | 570 | EST | #N/A | #N/A | 64.28 | 50.15 | 52.25 | 16.18 | 14.38 | 13.17 |
| AA279667 | 629 | EST | #N/A | #N/A | 184.99 | 102.43 | 289.71 | 8.06 | 7.61 | 23.78 |
| AA279943 | 635 | EST | #N/A | #N/A | 137.05 | 63.54 | 232.2 | -4.7 | -5.33 | 11.18 |
| AA290594 | 691 | EST | #N/A | #N/A | 59.19 | 56.31 | 23.84 | 21.4 | 18.8 | 23.98 |
| AA290776 | 693 | EST | #N/A | #N/A | 524.07 | 516.6 | 88.67 | 441.83 | 355.04 | 245.84 |
| AA292765 | 712 | ZW10 interactor | 7.24 | 0.00498 | 202.52 | 192.15 | 142.78 | 11.33 | 18.29 | 13.27 |
| AA398908 | 801 | EST | 20.72 | 0.00114 | 629.56 | 433.87 | 551.97 | -174.29 | -216.08 | 104.42 |
| AA405098 | 855 | EST | 6.09 | 0.01224 | 221.56 | 130.95 | 237.73 | -4.35 | -8.44 | 30.78 |
| AA406542 | 878 | EST | #N/A | #N/A | 179.08 | 84.98 | 218.93 | -1.99 | 1.49 | 12.75 |
| AA435738 | 1042 | EST | #N/A | #N/A | 80.97 | 82 | 30.96 | 50.41 | 51.29 | 33.08 |
| AA443585 | 1077 | EST | #N/A | #N/A | 200.3 | 136.72 | 140.42 | 118.18 | 97.38 | 102.71 |
| AA446596 | 1092 | Ts translation elongation factor, mitochondrial | #N/A | #N/A | 103.35 | 97.42 | 153.31 | 72.58 | 70.64 | 154.24 |
| AA447777 | 1107 | EST | #N/A | #N/A | 258.37 | 212.57 | 171.93 | 133.78 | 116.63 | 56.34 |
| AA453757 | 1156 | EST | #N/A | #N/A | 128.41 | 118.8 | 40.54 | 65.66 | 70.33 | 40.45 |
| AA459254 | 1211 | EST | 6.22 | 0.00001 | 309.74 | 308.36 | 112.62 | 51.84 | 43.51 | 37.57 |

TABLE 8A-continued

Genes and ESTs expressed only in HCC2 vs Normal2

| Fragment Name | SEQ ID: | Known Gene Name | fold change in hcc set 2 | p value | hcc sample set 2: Mean | hcc sample set 2: Median | hcc sample set 2: Std Dev | normal set 2: Mean | normal set 2: Median | normal set 2: Std Dev |
|---|---|---|---|---|---|---|---|---|---|---|
| AA459673 | 1220 | chromosome-associated polypeptide C | #N/A | #N/A | 32.11 | 31.27 | 15.41 | 8.91 | 6.74 | 8.86 |
| AA476333 | 1282 | EST | #N/A | #N/A | 52.26 | 34.54 | 55.5 | 9.04 | 14.67 | 24.04 |
| AA496993 | 1405 | EST | #N/A | #N/A | 91.01 | 73.62 | 80.93 | 24.83 | 12.83 | 29.07 |
| AA504512 | 1415 | KIAA0943 protein | 5.72 | 0.00384 | 316.32 | 322.55 | 180.22 | 65.48 | 28.37 | 93.94 |
| AA609132 | 1479 | EST | #N/A | #N/A | 67.33 | 42.61 | 65.11 | 29.14 | 23.25 | 53.79 |
| AA609942 | 1494 | EST | #N/A | #N/A | 89.98 | 66.8 | 71.4 | 15.89 | 14.41 | 25.58 |
| F02254 | 1777 | Fas-activated serine/threonine kinase | 5.1 | 0.00329 | 376.8 | 341.06 | 145.28 | 90 | 72.97 | 135.39 |
| H48459 | 1937 | KIAA0186 gene product | 3.1 | 0.02325 | 71.21 | 49.95 | 87.89 | −29.4 | −30.17 | 6.19 |
| H87790 | 2018 | EST | #N/A | #N/A | 284.91 | 287.54 | 145.66 | 466.07 | 547.34 | 192.71 |
| N34017 | 2493 | EST | #N/A | #N/A | 39.35 | 37.49 | 4.67 | 5.47 | 7.05 | 10.01 |
| N35493 | 2501 | EST | #N/A | #N/A | 73.6 | 80.62 | 31.24 | 19.03 | 18.75 | 17 |
| N63604 | 2600 | EST | #N/A | #N/A | 47.18 | 32.72 | 35 | 16.51 | 14.36 | 10.5 |
| N63646 | 2601 | EST | #N/A | #N/A | 479.9 | 367.24 | 240.56 | 182.22 | 137.95 | 90.9 |
| N69014 | 2641 | SRY (sex-determining region Y)-box 22 | #N/A | #N/A | 193.21 | 174.83 | 48.23 | 116.34 | 129.47 | 50.74 |
| N69879 | 2650 | drebrin 1 | 3.15 | 0.01659 | 88.78 | 84.86 | 61.76 | 3.69 | −2.94 | 21.49 |
| N69983 | 2651 | EST | #N/A | #N/A | 93.25 | 96.86 | 49.82 | 76.2 | 93.14 | 54.92 |
| N70330 | 2655 | EST | #N/A | #N/A | 108.39 | 69.74 | 105.54 | 33.78 | 27.33 | 16.47 |
| N74018 | 2683 | EST | #N/A | #N/A | 22.65 | 25.34 | 10.26 | 2.34 | 1.47 | 10.41 |
| N89670 | 2708 | EST | #N/A | #N/A | 65.03 | 59.18 | 66.58 | 3.16 | −1.81 | 43.32 |
| N93000 | 2726 | EST | #N/A | #N/A | 77.68 | 64.15 | 45.06 | 17.65 | 18.66 | 10.91 |
| N99944 | 2748 | EST | 3.46 | 0.00104 | 211.02 | 200.61 | 102.49 | 60.05 | 50.12 | 29.73 |
| R97176 | 3001 | EST | #N/A | #N/A | 143.07 | 152.08 | 86.96 | 53.41 | 58.26 | 38.91 |
| T16226 | 3065 | EST | 7.23 | 0.00119 | 323.53 | 312.1 | 209.59 | 33.87 | 22.78 | 38.68 |
| T32108 | 3102 | EST | #N/A | #N/A | 180.81 | 165.53 | 68.41 | 148.09 | 152.11 | 92.06 |
| W15275 | 3471 | EST | #N/A | #N/A | 33.62 | 31.78 | 35.23 | 30.09 | 24.85 | 43.25 |
| W31906 | 3496 | secretagogin | 6.62 | 0.00926 | 474.89 | 174.52 | 605.68 | 42.41 | 30.95 | 47.65 |
| W46286 | 3523 | EST | 3.68 | 0.00311 | 154.73 | 166.08 | 72.64 | 23.51 | 22.85 | 61.89 |
| W60097 | 3553 | DEAD/H (Asp-Glu-Ala-Asp/His) box polypeptide, Y chromosome | 4.82 | 0.04903 | 235.42 | 265.15 | 189.13 | 35.34 | 11.72 | 84.5 |
| W80852 | 3606 | KDEL (Lys-Asp-Glu-Leu) endoplasmic reticulum protein retention receptor 3 | 6.37 | 0.00005 | 184.61 | 159.98 | 100.74 | 11.16 | 11.92 | 36.06 |
| AA046745 | 113 | Wolf-Hirschhorn syndrome candidate 1 | 3.33 | 0.00648 | 73.04 | 72.71 | 48.97 | 10.59 | 12.02 | 7.33 |
| AA052941 | 121 | EST | 3.36 | 0.00088 | 100.81 | 106.86 | 44.56 | 25.66 | 25.65 | 13.62 |
| AA058589 | 144 | EST | #N/A | #N/A | 44.63 | 51.66 | 34.1 | −9.37 | −10.9 | 8.66 |
| AA126561 | 249 | EST | #N/A | #N/A | 51.44 | 44.19 | 31.6 | 7.16 | 7.73 | 8.55 |
| AA146849 | 313 | target of myb1 (chicken) homolog | 4.72 | 0.00326 | 398.05 | 341.23 | 244.73 | 98.86 | 106.97 | 86.19 |
| AA149889 | 326 | neighbor of A-kinase anchoring protein 95 | 8.55 | 0.00224 | 240.81 | 312.86 | 143.89 | −0.24 | 8.25 | 29.83 |
| AA283711 | 669 | ubiquitin carrier protein | #N/A | #N/A | 382.91 | 380.33 | 210.95 | 221.7 | 203.51 | 93.54 |
| AA284153 | 673 | EST | #N/A | #N/A | 117.98 | 127.81 | 72.86 | 53.98 | 43.58 | 32.17 |
| AA335191 | 741 | creatine kinase, brain | 6.47 | 0.01462 | 512.64 | 199.99 | 673.92 | 43.84 | 33.21 | 43.52 |
| AA402642 | 840 | TNF receptor-associated factor 1 | #N/A | #N/A | 137.67 | 59.13 | 211.07 | 35.93 | 19.15 | 31.32 |
| AA427460 | 972 | ATP-binding cassette, sub-family F (GCN20), member 2 | #N/A | #N/A | 190.92 | 187.57 | 78.83 | 92.5 | 83.63 | 49.3 |
| AA431429 | 1021 | EST | #N/A | #N/A | 25.39 | 21.98 | 9.32 | 5.32 | 4.23 | 4.43 |
| AA443316 | 1075 | v-Ha-ras Harvey rat sarcoma viral oncogene homolog | 3.4 | 0.00133 | 138.89 | 124.06 | 70.22 | 40.07 | 41.12 | 32.54 |

TABLE 8A-continued

Genes and ESTs expressed only in HCC2 vs Normal2

| Fragment Name | SEQ ID: | Known Gene Name | fold change in hcc set 2 | p value | hcc sample set 2: Mean | hcc sample set 2: Median | hcc sample set 2: Std Dev | normal set 2: Mean | normal set 2: Median | normal set 2: Std Dev |
|---|---|---|---|---|---|---|---|---|---|---|
| AA476260 | 1280 | EST | #N/A | #N/A | 61.23 | 69.49 | 40.45 | −32.66 | −15.85 | 56.91 |
| AA487058 | 1352 | ubiquitin-conjugating enzyme E2L 3 | #N/A | #N/A | 245.56 | 225.48 | 137.4 | 315.7 | 232.85 | 213.47 |
| AA521149 | 1420 | EST | 3.33 | 0.00211 | 113.43 | 106.74 | 60.79 | 28.44 | 29.54 | 18.61 |
| AA599244 | 1448 | KIAA0530 protein | #N/A | #N/A | 53.83 | 48.84 | 25.7 | 7.71 | 6.06 | 7.11 |
| AA599850 | 1457 | EST | 3.55 | 0.03215 | 122.91 | 75.32 | 123.52 | −1.23 | −2.33 | 31.86 |
| AA621530 | 1526 | EST | 3.26 | 0.00298 | 78.73 | 75.43 | 40.45 | 12.46 | 15.12 | 13.43 |
| AA621644 | 1528 | EST | #N/A | #N/A | 83.13 | 88.29 | 43.19 | 71.19 | 66.84 | 29.87 |
| C15078 | 1573 | EST | #N/A | #N/A | 121.71 | 98.25 | 100.16 | 26.22 | 31.14 | 60.2 |
| D80710 | 1734 | integral type I protein | 3.17 | 0.04549 | 153.76 | 74.74 | 166.28 | 22.95 | 28.29 | 24.59 |
| D80948 | 1738 | EST | #N/A | #N/A | 70.05 | 77.71 | 32.11 | 41.25 | 43.53 | 17.46 |
| D81048 | 1739 | EST | #N/A | #N/A | 150.18 | 149.32 | 51.77 | 86.08 | 85.08 | 39.11 |
| F04320 | 1786 | replication factor C (activator 1) 4 (37kD) | 6.29 | 0.00042 | 156.76 | 122.53 | 109.02 | 14.92 | 17.26 | 9.79 |
| H14617 | 1884 | EST | #N/A | #N/A | 143.86 | 147.93 | 66.03 | 133.9 | 150.35 | 53.38 |
| H26763 | 1907 | EST | 3.67 | 0.00327 | 408.05 | 321.65 | 219.8 | 409.85 | 391.85 | 155.84 |
| H68794 | 1984 | EST | 7.5 | 0.02674 | 215.75 | 176.78 | 110.42 | 65.56 | 54 | 51.09 |
| H78211 | 2001 | EST | #N/A | #N/A | 285.43 | 307.06 | 261.02 | −115.95 | −129.18 | 70.22 |
| H95566 | 2050 | EST | #N/A | #N/A | 136.58 | 143.31 | 26.27 | 74.11 | 89.04 | 126.61 |
| H99870 | 2082 | EST | 6.48 | 0.00358 | 92.81 | 94.93 | 33.98 | 53.96 | 61.17 | 29.86 |
| N62487 | 2590 | EST | 3.38 | 0.03125 | 56.6 | 52.26 | 33.75 | 13.89 | 16.02 | 8.53 |
| N67815 | 2626 | EST | 3.84 | 0.00439 | 351.55 | 356.17 | 99.35 | 104.07 | 151.77 | 86.01 |
| N69084 | 2642 | EST | 3.11 | 0.0094 | 233.32 | 208.16 | 169.31 | 72.13 | 67.7 | 49.99 |
| N73278 | 2671 | tumor protein D52-like 2 | #N/A | #N/A | 77.72 | 71.59 | 49.4 | 25.36 | 19.22 | 26.85 |
| R06251 | 2763 | carbohydrate (keratan sulfate Gal-6) sulfotransferase 1 | 4.88 | 0.03097 | 466.88 | 341.39 | 380.43 | 74.25 | 66.72 | 64.11 |
| R15740 | 2790 | EST | 3.36 | 0.00268 | 117.43 | 100.03 | 64.73 | 31.77 | 21.3 | 33.53 |
| R24507 | 2801 | EST | #N/A | #N/A | 31.61 | 16.41 | 30.69 | 3 | 3.45 | 5.62 |
| R27296 | 2806 | EST | 3.41 | 0.00309 | 77.08 | 67.51 | 39.42 | 8.27 | 11.07 | 7.26 |
| R30931 | 2809 | EST | #N/A | #N/A | 54.19 | 57.09 | 29.34 | 17.58 | 13.67 | 14.21 |
| R45994 | 2866 | EST | 6.48 | 0.00358 | 730.52 | 598.82 | 420.14 | 145.88 | 160.69 | 163.03 |
| R70253 | 2944 | EST | 3.38 | 0.03125 | 99.7 | 88.01 | 87.93 | −9.59 | −0.47 | 30.83 |
| R72886 | 2955 | KIAA0422 protein | 5.5 | 0.00091 | 564.05 | 473.4 | 207.71 | 126.66 | 121.18 | 116.07 |
| R96924 | 3000 | EST | 7.04 | 0.00012 | 336.8 | 329 | 106.3 | 51.01 | 52.94 | 54.09 |
| T15852 | 3061 | EST | 5.21 | 0.00642 | 168.18 | 134.42 | 120.18 | −7.59 | 7.36 | 51.48 |
| T16983 | 3073 | cleavage and polyadenylation specific factor 4, 30kD subunit | 4.23 | 0.0106 | 262.26 | 268.2 | 155.86 | 65.64 | 45.67 | 74.28 |
| T33865 | 3109 | RNA (guanine-7-) methyltransferase | #N/A | #N/A | 29.73 | 32.86 | 22.11 | −0.26 | 2.33 | 8.15 |
| T66935 | 3178 | EST | 3.01 | 0.00123 | 181.34 | 189.67 | 61.49 | 66.8 | 52.94 | 42.32 |
| T95057 | 3258 | EST | 6.46 | 0.00613 | 229.11 | 188.71 | 174.46 | 7.13 | 15.37 | 37.2 |
| W45320 | 3520 | KRAB-associated protein 1 | 10.05 | 0.00002 | 365.22 | 345.46 | 124.13 | −2.52 | 25.03 | 112.32 |
| AF006041 | 1549 | death-associated protein 6 | #N/A | #N/A | 174.22 | 170.16 | 37.64 | 74.91 | 58.55 | 50.31 |
| D00596 | 1590 | thymidylate synthetase | 5.58 | 0.0098 | 200.17 | 128.11 | 170.5 | 20.16 | 20.43 | 12.43 |
| D38491 | 1653 | KIAA0117 protein | #N/A | #N/A | 47.67 | 52.03 | 21.01 | 20.77 | 20.88 | 17.43 |
| D63486 | 1712 | KIAA0152 gene product | 3.56 | 0.00063 | 277.42 | 248.24 | 99.25 | 84.6 | 95.61 | 45.48 |
| D84557 | 1749 | minichromosome maintenance deficient (mis5, S.pombe) 6 | 3.97 | 0.0017 | 184.48 | 132.11 | 125.74 | 37.22 | 43.12 | 28.15 |
| D86957 | 1754 | KIAA0202 protein | 3.08 | 0.02949 | 91.22 | 73.14 | 89.89 | 14.7 | 12.7 | 6.29 |

TABLE 8A-continued

Genes and ESTs expressed only in HCC2 vs Normal2

| Fragment Name | SEQ ID: | Known Gene Name | fold change in hcc set 2 | p value | hcc sample set 2: Mean | hcc sample set 2: Median | hcc sample set 2: Std Dev | normal set 2: Mean | normal set 2: Median | normal set 2: Std Dev |
|---|---|---|---|---|---|---|---|---|---|---|
| D86972 | 1755 | KIAA0218 gene product | #N/A | #N/A | 68.56 | 66.54 | 32.32 | 34.58 | 32.05 | 21.82 |
| D90097 | 1768 | amylase, alpha 2B; pancreatic | #N/A | #N/A | 41.19 | 37.49 | 21.85 | 6.55 | 11.44 | 15.06 |
| L29218 | 2190 | CDC-like kinase 2 | 3.82 | 0.00035 | 155.42 | 142.58 | 76.28 | 35.11 | 41.27 | 26.41 |
| L38696 | 2208 | RNA-binding protein (autoantigenic) | #N/A | #N/A | 127.32 | 114.91 | 62.34 | 60.18 | 58.55 | 24.77 |
| M11749 | 2240 | Thy-1 cell surface antigen | #N/A | #N/A | 83.1 | 65.86 | 64.52 | 26.05 | 28.95 | 20.56 |
| M25753 | 2308 | cyclin B1 | #N/A | #N/A | 44.14 | 30.96 | 40.36 | -0.8 | 3.03 | 15.35 |
| M32334 | 2333 | intercellular adhesion molecule 2 | #N/A | #N/A | 95.04 | 92.33 | 67.51 | 42.19 | 41.31 | 27.33 |
| M55210 | 2353 | laminin, gamma 1 (formerly LAMB2) | 3.47 | 0.02551 | 137.63 | 115.85 | 102.71 | 27.07 | 29.17 | 12.36 |
| M61916 | 2372 | laminin, beta 1 | 3.18 | 0.01171 | 75.1 | 67.4 | 61.41 | 7.19 | 7.98 | 8.99 |
| M86752 | 2411 | stress-induced-phosphoprotein 1 (Hsp70/Hsp90-organizing protein) | 5.15 | 0.02881 | 216.51 | 248.21 | 192.98 | 8.67 | 20.63 | 39.03 |
| M87339 | 2414 | replication factor C (activator 1) 4 (37kD) | 4.59 | 0.00116 | 110.39 | 82.61 | 79.29 | 4.26 | 9.92 | 16.79 |
| M94250 | 2425 | midkine (neurite growth-promoting factor 2) | 9.86 | 0.02104 | 690.32 | 193.74 | 1414.43 | -155.4 | -175.43 | 101.89 |
| S72904 | 3030 | cytosolic ovarian carcinoma antigen 1 | #N/A | #N/A | 29.33 | 29.21 | 18.34 | 11.53 | 12.85 | 7.55 |
| S78187 | 3035 | cell division cycle 25B | 4.83 | 0.0047 | 143.52 | 115.3 | 109.13 | 3.36 | -1.2 | 26.9 |
| S78569 | 3036 | laminin, alpha 4 | #N/A | #N/A | 25.79 | 26.91 | 21.66 | 6.3 | 7.6 | 9.38 |
| U38847 | 3356 | TAR (HIV) RNA-binding protein 1 | #N/A | #N/A | 83.43 | 70.23 | 66.3 | 15.7 | 17.43 | 10.2 |
| U51477 | 3383 | diacylglycerol kinase, zeta (104kD) | #N/A | #N/A | 73.85 | 61.64 | 31.81 | 36.35 | 36.29 | 23.02 |
| U59321 | 3397 | DEAD/H (Asp-Glu-Ala-Asp/His) box polypeptide 17 (72kD) | 3.12 | 0.02469 | 84.5 | 98.2 | 70.13 | 3.1 | -1.83 | 19.73 |
| U66661 | 3405 | gamma-aminobutyric acid (GABA) A receptor, epsilon | 3.55 | 0.0045 | 97.79 | 83.66 | 61.79 | 16.58 | 14.81 | 11.96 |
| U93237 | 3461 | multiple endocrine neoplasia I | #N/A | #N/A | 84.78 | 93.3 | 24.25 | 45.63 | 45.39 | 17.66 |
| X92106 | 3819 | bleomycin hydrolase | #N/A | #N/A | 56.15 | 48.48 | 36.93 | 4.73 | 3.77 | 11.78 |
| X92762 | 3825 | tafazzin (cardiomyopathy, dilated 3A (X-linked); endocardial fibroelastosis 2; Barth syndrome) | #N/A | #N/A | 82.96 | 83.94 | 15.05 | 23.4 | 33.5 | 24.15 |
| Y09216 | 3853 | dual-specificity tyrosine-(Y)-phosphorylation regulated kinase 2 | #N/A | #N/A | 47.87 | 47.61 | 18.08 | 18.99 | 22.48 | 13.31 |
| M69013 | 2390 | guanine nucleotide binding protein (G protein), alpha 11 (Gq class) | #N/A | #N/A | 86.89 | 70.61 | 47.65 | 38.18 | 47.33 | 23.06 |
| AD000092 | 1542 | RAD23 (S.cerevisiae) homolog A | #N/A | #N/A | 97.12 | 98.23 | 25.66 | 37.18 | 32.35 | 28.04 |
| X04654 | 3678 | small nuclear ribonucleoprotein 70kD polypeptide (RNP antigen) | #N/A | #N/A | 122.45 | 134.9 | 49.51 | 42.22 | 41.24 | 17.18 |
| M31211 | 2326 | myosin, light polypeptide 1, alkali; skeletal, fast | #N/A | #N/A | 60.22 | 49.75 | 54.83 | -2.19 | -4.38 | 11.56 |
| U50648 | 3378 | protein kinase, interferon-inducible double stranded RNA dependent | #N/A | #N/A | 214.34 | 192.86 | 122.38 | 105.38 | 92.58 | 43.12 |
| M74715 | 2394 | iduronidase, alpha-L- | #N/A | #N/A | 122.69 | 121.95 | 72.58 | 41.88 | 24.48 | 43.99 |
| U41767 | 3359 | a disintegrin and metalloproteinase domain 15 (metargidin) | #N/A | #N/A | 196.76 | 147.11 | 113.93 | 83.03 | 66.93 | 68.33 |
| M12125 | 2241 | tropomyosin 2 (beta) | 7.13 | 0.0004 | 174.25 | 183.97 | 95.24 | 13.01 | 16.33 | 11.64 |
| U20499 | 3320 | sulfotransferase family 1A, phenol-preferring, member 3 | #N/A | #N/A | 141.35 | 126.33 | 135.57 | 48.34 | 54.37 | 24.69 |

TABLE 8B

Genes and ESTs expressed only in Normal2 vs HCC2

| Fragment Name | SEQ ID: | Known Gene Name | hcc fold change | p value | hcc sample set 2: Mean | hcc sample set 2: Median | hcc sample set 2: Std Dev | normal set 2: Mean | normal set 2: Median | normal set 2: Std Dev |
|---|---|---|---|---|---|---|---|---|---|---|
| H66367 | 1977 | EST | 3.84 | 0.00133 | 37.14 | 35.15 | 26.61 | 155.38 | 149.31 | 70.77 |
| H72650 | 1994 | EST | #N/A | #N/A | 78.97 | 93.74 | 40.9 | 122 | 125 | 42.24 |
| M30185 | 2321 | cholesteryl ester transfer protein, plasma | 3.82 | 0.00131 | −15.66 | −12.63 | 23.86 | 93.07 | 86.04 | 61.35 |
| N99542 | 2746 | orosomucoid 1 | 3.53 | 0.00607 | 61.09 | 67.97 | 39.3 | 226.06 | 187.68 | 146.11 |
| T68083 | 3184 | short-chain dehydrogenase/reductase 1 | #N/A | #N/A | 96.34 | 59.71 | 104.53 | 263.22 | 280.22 | 136.48 |
| Z48475 | 3940 | glucokinase (hexokinase 4) regulatory protein | 4.6 | 0.01693 | 65.99 | 51.37 | 146.72 | 305.23 | 239.52 | 155.98 |
| AA046747 | 114 | EST | 4.77 | 0.00023 | −0.57 | 3.68 | 23.81 | 113.78 | 88.54 | 66.41 |
| AA253410 | 564 | EST | #N/A | #N/A | 3.66 | 1.48 | 10.67 | 49.37 | 26.82 | 45.2 |
| AA281796 | 650 | mannose-P-dolichol utilization defect 1 | #N/A | #N/A | 95.74 | 105.86 | 45.46 | 170.88 | 165.02 | 41.87 |
| AA287566 | 690 | KIAA0187 gene product | 6.99 | 0.00023 | 18.67 | 14.05 | 35.71 | 246.24 | 201.66 | 228.64 |
| AA404248 | 847 | EST | #N/A | #N/A | 24.05 | 30.59 | 15.83 | 40.92 | 35.06 | 17.49 |
| AA448002 | 1113 | putative type II membrane protein | 14.14 | 0 | 39.9 | 38.99 | 13.33 | 594.13 | 528.63 | 282.58 |
| AA487576 | 1357 | EST | #N/A | #N/A | 11.67 | 2.42 | 27.75 | 26.05 | 25.27 | 11.13 |
| AA621235 | 1517 | EST | #N/A | #N/A | 65.79 | 68.63 | 35.33 | 114.75 | 113.36 | 65.35 |
| F09979 | 1809 | EST | #N/A | #N/A | 61.21 | 6.31 | 128.69 | 226.47 | 116.41 | 288.21 |
| H57056 | 1953 | EST | #N/A | #N/A | −1.79 | −7.37 | 11.38 | 35.07 | 38.32 | 17.88 |
| H58673 | 1959 | EST | 15.49 | 0.00002 | 34.96 | 26.37 | 38.53 | 652.47 | 677.55 | 376.36 |
| H59136 | 1962 | EST | 6.63 | 0.00033 | 33.12 | 21.17 | 42.92 | 250.23 | 229.94 | 129.12 |
| H87765 | 2017 | KIAA0626 gene product | 3.94 | 0.00123 | 10.11 | 10.07 | 4.23 | 94.26 | 93.78 | 60.64 |
| N22404 | 2449 | EST | 3.44 | 0.02267 | 56.69 | 35.82 | 73.26 | 193.63 | 130.09 | 162.83 |
| N34919 | 2498 | EST | #N/A | #N/A | 19.32 | 19.72 | 14.37 | 52.96 | 44.23 | 24.23 |
| N54604 | 2569 | EST | #N/A | #N/A | 45.27 | 14.34 | 81.45 | 133.06 | 119.1 | 109.95 |
| N65959 | 2611 | EST | 3.38 | 0.00785 | 37.8 | 28.94 | 31.45 | 142.87 | 149.26 | 79.26 |
| N74624 | 2687 | collectin sub-family member 10 (C-type lectin) | #N/A | #N/A | 39.43 | 35.17 | 24.21 | 71.81 | 62.09 | 43.57 |
| R09053 | 2782 | EST | 3.45 | 0.03074 | 64.12 | 36.33 | 102.03 | 186.87 | 204.61 | 113.19 |
| R73816 | 2960 | EST | 7.05 | 0.01287 | 35.12 | 13.76 | 100.6 | 462.31 | 374.67 | 450.91 |
| T58756 | 3155 | EST | 16.61 | 0 | −1.02 | 1.06 | 24.36 | 390.04 | 386.76 | 164.41 |
| W48860 | 3534 | EST | #N/A | #N/A | 37.25 | 31.7 | 27.5 | 52.69 | 41.31 | 21.1 |
| W90018 | 3639 | EST | #N/A | #N/A | 21.51 | 1.31 | 56.9 | 59.32 | 53.19 | 41.68 |
| AA010205 | 23 | potassium voltage-gated channel, shaker-related subfamily, beta member 1, | 5.71 | 0.00014 | 26.95 | 20.06 | 32.19 | 187.55 | 154.99 | 92.13 |
| AA013095 | 33 | macrophage receptor with collagenous structure | #N/A | #N/A | 5.12 | 7.9 | 12.98 | 18.56 | 15.83 | 8.24 |
| AA074885 | 161 | EST | 10.88 | 0.00087 | 35.67 | 58.01 | 44.34 | 652.03 | 761.74 | 300.57 |
| AA09225 | 206 | EST | 6.59 | 0.00064 | 10.9 | 9.75 | 15.11 | 212.68 | 163.45 | 194.31 |
| AA282541 | 661 | CD5 antigen-like (scavenger receptor cysteine rich family) | #N/A | #N/A | 17.21 | 11.75 | 13.38 | 31.31 | 29.9 | 13.53 |
| R99591 | 3015 | EST | 7.41 | 0.00043 | 124.14 | 139.76 | 50.35 | 1035.39 | 904.92 | 691.83 |
| T68711 | 3187 | X-prolyl aminopeptidase (aminopeptidase P) | 35.98 | 0.0003 | 29.03 | −33.95 | 176.15 | 1388.67 | 1074.67 | 890.91 |

TABLE 8B-continued

Genes and ESTs expressed only in Normal2 vs HCC2

| Fragment Name | SEQ ID: | Known Gene Name | hcc fold change | p value | hcc sample set 2: Mean | hcc sample set 2: Median | hcc sample set 2: Std Dev | normal set 2: Mean | normal set 2: Median | normal set 2: Std Dev |
|---|---|---|---|---|---|---|---|---|---|---|
| W78093 | 3598 | 2, membrane-bound | #N/A | #N/A | 408.58 | 397.88 | 102.27 | 518.77 | 518.8 | 211.32 |
| W85890 | 3620 | EST | #N/A | #N/A | 60.91 | 60.47 | 23.73 | 70.98 | 66.52 | 24.66 |
| AA285053 | 681 | EST | 5 | 0.00718 | 36.49 | 20.15 | 49.24 | 238.16 | 242.27 | 169.12 |
| AA460661 | 1229 | EST | 5.46 | 0.00151 | 20.05 | 8.57 | 39.04 | 184.62 | 198.21 | 108.17 |
| F10380 | 1816 | butyrobetaine (gamma), 2-oxoglutarate dioxygenase (gamma-butyrobetaine hydroxylase) | #N/A | #N/A | 43.64 | 47.09 | 18.15 | 106.49 | 93.71 | 83.35 |
| N67105 | 2623 | EST | 4.69 | 0.00194 | 12.46 | 10.45 | 12.64 | 143.36 | 102.9 | 121.4 |
| N69114 | 2643 | nuclear receptor subfamily 1, group I, member 3 | #N/A | #N/A | 12.69 | 5.95 | 15.01 | 72.29 | 73.28 | 57.34 |
| M63967 | 2378 | aldehyde dehydrogenase 5 | 3.88 | 0.00274 | 40.43 | 30.04 | 29.05 | 164.38 | 178.74 | 87.39 |
| X54380 | 3727 | pregnancy-zone protein | 7.71 | 0.00069 | 15.11 | 8.07 | 27.07 | 274.41 | 255.4 | 203.47 |
| Z49269 | 3942 | small inducible cytokine subfamily A (Cys-Cys), member 14 | 7.24 | 0.01047 | 138.63 | 66.95 | 201.93 | 526.13 | 532.29 | 166.67 |
| M10943 | 2234 | metallothionein 1F (functional) | 6.23 | 0.00007 | 35.67 | 28.76 | 22.4 | 217.65 | 186.71 | 86.73 |

TABLE 9A

Genes and ESTs expressed only in Metastatic Liver Tumor vs Normal2

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| AA009913 | 21 | diptheria toxin resistance protein required for diphthamide biosynthesis (Saccharomyces)-like 2 | #N/A | #N/A | 69.53 | 81.03 | 27.69 | 16.81 | 18.22 | 13.51 |
| AA127712 | 255 | EST | 6.59 | 0.03706 | 332.45 | 208.85 | 296.68 | −29.54 | −28.71 | 104.37 |
| AA253330 | 562 | adaptor-related protein complex 1, gamma 1 subunit | 3.87 | 0.00708 | 219.95 | 186.12 | 141.92 | 47.32 | 51.59 | 30.28 |
| AA291456 | 700 | EST | 3.96 | 0.03633 | 1808.4 | 1273.75 | 1481.84 | 671.21 | 509.58 | 629.13 |
| AA295819 | 722 | EST | 8 | 0.01793 | 230.14 | 251.43 | 146.89 | −14.93 | −20.8 | 19.72 |
| AA372630 | 769 | differentially expressed in hematopoietic lineages | 25.49 | 0.01743 | 2094.32 | 436.62 | 3873.61 | 6.67 | 4.87 | 7.16 |
| AA384184 | 774 | DKFZP586B0519 protein | 3.38 | 0.01209 | 476.17 | 411.64 | 148.86 | 181.02 | 188.54 | 135.4 |
| AA427468 | 973 | claudin 4 | 84.43 | 0 | 5646.4 | 5344.98 | 1581.19 | 72.58 | 64.85 | 87.74 |
| AA454908 | 1171 | KIAA0144 gene product | 9.3 | 0.00539 | 320.03 | 253.32 | 238.5 | −33.7 | −46.73 | 73.56 |
| AB002304 | 1534 | KIAA0306 protein | #N/A | #N/A | 584.5 | 621.94 | 136.64 | 313.99 | 298.88 | 88.6 |
| AB002349 | 1537 | KIAA0351 gene product | #N/A | #N/A | 65.63 | 52.11 | 32.26 | 49.37 | 46.52 | 37.93 |
| AF003521 | 1545 | jagged 2 | 11.26 | 0.00008 | 426 | 330.95 | 309.91 | 15.48 | −3.6 | 91.81 |
| C00808 | 1553 | EST | #N/A | #N/A | 122.57 | 118.32 | 53.36 | 91.65 | 87.87 | 32.51 |
| C14228 | 1567 | EST | #N/A | #N/A | 39.93 | 33.15 | 13.59 | −0.51 | 2.85 | 8.61 |
| D83783 | 1748 | trinucleotide repeat containing 11 (THR-associated protein, 230 kDa subunit) | 6.55 | 0.00176 | 236.64 | 156.39 | 216.64 | 23.23 | 19.65 | 27.84 |
| D88154 | 1766 | villin-like | 4.18 | 0.00051 | 117.8 | 129.16 | 47.7 | 23.85 | 18.99 | 17.79 |
| H43286 | 1929 | gamma-aminobutyric acid (GABA) B receptor, 1 | 5.02 | 0.01972 | 377.04 | 222.91 | 315.96 | 57.02 | 63.58 | 24.25 |
| H53657 | 1945 | adenylate cyclase 3 | 3.98 | 0.0045 | 140.07 | 111.99 | 74.77 | 31.33 | 31.74 | 15.29 |
| L08044 | 2149 | trefoil factor 3 (intestinal) | 21.42 | 0.01674 | 2956.22 | 1618.2 | 3127.19 | 107.82 | 58.55 | 184.16 |
| M94891 | 2428 | pregnancy specific beta-1-glycoprotein 4, pregnancy specific beta-1-glycoprotein 7 | #N/A | #N/A | 221.09 | 197.74 | 80.32 | 178.23 | 166.98 | 61.33 |
| R56678 | 2907 | EST | 3.81 | 0.02242 | 98.37 | 78.38 | 75.74 | 2.67 | 5 | 5.82 |
| R69700 | 2942 | EST | 6.71 | 0.0021 | 387.34 | 393.81 | 94.86 | 79.33 | 57.85 | 129.97 |
| R76363 | 2961 | EST | #N/A | #N/A | 47.81 | 38.04 | 24.76 | 12.67 | 16.94 | 13.17 |
| U75968 | 3422 | DEAD/H (Asp-Glu-Ala-Asp/His) box polypeptide 11 (S.cerevisiae CHL1-like helicase) | #N/A | #N/A | 195.48 | 155.37 | 89.8 | 115.5 | 102.24 | 77.72 |
| W95348 | 3660 | HSPC113 protein | 10.89 | 0.01065 | 555.52 | 492.63 | 563.86 | 26.59 | 29.36 | 21.03 |
| AA007160 | 16 | EST | 6 | 0.01035 | 171.32 | 175.07 | 138.03 | 9.1 | 8.6 | 12.54 |
| AA024482 | 45 | DKFZP434G032 protein | #N/A | #N/A | 207.37 | 118.58 | 230.63 | −1.3 | −3.13 | 13.6 |
| AA040465 | 95 | EST | 3.25 | 0.00146 | 161.91 | 125.35 | 72.19 | 47.15 | 45.53 | 5.48 |
| AA053660 | 128 | EST | 15.98 | 0.00003 | 1573.49 | 1340 | 820.5 | 95.24 | 79.97 | 42.99 |
| AA100719 | 212 | carcinoembryonic antigen-related cell adhesion molecule 6 (non-specific cross reacting antigen) | 50.88 | 0.00081 | 1405.2 | 1264.79 | 1137.97 | −17.03 | −22.23 | 16.43 |
| AA115979 | 232 | mitotic spindle coiled-coil related protein | #N/A | #N/A | 74.58 | 89.38 | 66.52 | 22.91 | 13.67 | 29.42 |
| AA134968 | 289 | EST | 12.11 | 0.00079 | 322.34 | 208.47 | 256.66 | 10.04 | 7.96 | 15.53 |
| AA179787 | 380 | polyglutamine binding protein 1 | 6.44 | 0.00206 | 191.33 | 171.71 | 138.9 | −11.56 | −12.46 | 42.46 |
| AA227926 | 460 | EST | 6.81 | 0.01701 | 228.91 | 120.1 | 243.92 | 16.24 | 14.21 | 6.86 |
| AA235707 | 500 | EST | 9.17 | 0.00005 | 189.42 | 161.88 | 57.05 | −18.19 | −19.06 | 14.8 |
| AA236533 | 514 | ecotropic viral integration site 1 | 4.01 | 0.02882 | 106.15 | 76.05 | 78.18 | −16.45 | −14.04 | 8.52 |
| AA243173 | 526 | EST | 8.75 | 0.00003 | 384.86 | 482.53 | 162.08 | 41.66 | 40.74 | 27.31 |

TABLE 9A-continued

Genes and ESTs expressed only in Metastatic Liver Tumor vs Normal2

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| AA262943 | 611 | EST | 13.42 | 0.00234 | 430.7 | 207.29 | 511.01 | -1.08 | -6.93 | 19.06 |
| AA281214 | 643 | neuroblastoma-amplified protein | #N/A | #N/A | 130.98 | 133.63 | 68.42 | 69.89 | 53.91 | 39.31 |
| AA282505 | 659 | EST | #N/A | #N/A | 461.54 | 478.83 | 622.39 | -41.45 | -17 | 98.17 |
| AA292931 | 715 | EST | 3.97 | 0.00067 | 230.65 | 260.43 | 79.42 | 57.32 | 61.89 | 18.62 |
| AA372018 | 768 | EST | 14.3 | 0.00178 | 363.44 | 220.03 | 261.04 | -2.44 | -3.09 | 8.36 |
| AA394121 | 778 | laminin receptor 1 (67kD, ribosomal protein SA) | 23.78 | 0.00099 | 788.51 | 677.33 | 612.74 | 0.21 | -8.38 | 31.59 |
| AA399226 | 803 | tight junction protein 3 (zona occludens 3) | 3.59 | 0.02002 | 89.54 | 78.97 | 63.98 | -5.01 | -6.48 | 11.33 |
| AA401965 | 833 | tumor suppressor deleted in oral cancer-related 1 | #N/A | #N/A | 384.12 | 271.95 | 444.06 | 120.58 | 93.29 | 109.41 |
| AA404597 | 854 | EST | #N/A | #N/A | 624.37 | 495.56 | 274.8 | 379.26 | 336.33 | 167.43 |
| AA410469 | 883 | EST | 6.3 | 0.00103 | 337.03 | 250.11 | 264.1 | 50.51 | 42.79 | 60.18 |
| AA419217 | 923 | DKFZP586E1422 protein | 6.77 | 0.00045 | 276.53 | 215.37 | 172.25 | 36.93 | 36.7 | 21.88 |
| AA424881 | 949 | EST | 6.3 | 0.00556 | 158.13 | 155.45 | 82.63 | -16.85 | -22.15 | 20.49 |
| AA425852 | 958 | EST | 4.8 | 0.03874 | 149.8 | 125.7 | 128.03 | 7.02 | 5.22 | 4.75 |
| AA430674 | 1018 | EST | 15.11 | 0.00293 | 454.82 | 306.15 | 378.36 | -71.57 | -82.03 | 59.56 |
| AA442763 | 1072 | cyclin B2 | 5.09 | 0.02168 | 136.16 | 109.91 | 91.52 | -14.64 | -15.1 | 13.08 |
| AA443941 | 1085 | tumor suppressing subtransferable candidate 1 | 3.57 | 0.01685 | 137.02 | 138.22 | 83.35 | 31.09 | 34.9 | 16.61 |
| AA449456 | 1126 | EST | 6.29 | 0.00087 | 847.4 | 775.81 | 377.99 | 160.93 | 178.76 | 112.71 |
| AA451877 | 1138 | EST | 8.63 | 0.00489 | 239.55 | 157.3 | 244.02 | -27.28 | -27.59 | 18.28 |
| AA454597 | 1166 | EST | 3.63 | 0.0067 | 268.15 | 274.94 | 167.72 | 66.6 | 57.29 | 23.41 |
| AA457235 | 1200 | EST | #N/A | #N/A | 481.26 | 138.32 | 573.73 | 11.06 | 17.32 | 15.26 |
| AA460666 | 1231 | EST | #N/A | #N/A | 56.19 | 58.13 | 26.29 | -24.55 | -17.23 | 20.98 |
| AA463861 | 1251 | EST | 24.79 | 0.00096 | 672.22 | 311.71 | 641.54 | -22.02 | -20.04 | 16.5 |
| AA464962 | 1264 | EST | #N/A | #N/A | 61.02 | 56.4 | 30.98 | 20.99 | 14.37 | 19.64 |
| AA465342 | 1271 | EST | #N/A | #N/A | 113.36 | 100.15 | 87.62 | 30.07 | 33.06 | 23.97 |
| AA465660 | 1273 | LIM domain binding 1 | #N/A | #N/A | 171.26 | 118.15 | 103.39 | 124.59 | 105.93 | 56.71 |
| AA476749 | 1286 | tumor necrosis factor receptor superfamily, member 12 (translocating chain-association membrane protein) | #N/A | #N/A | 53.23 | 44.04 | 18.16 | 25.5 | 29.62 | 11.96 |
| AA477561 | 1292 | EST | #N/A | #N/A | 160.87 | 104.95 | 133.7 | 63.83 | 76.56 | 37.87 |
| AA482546 | 1336 | KIAA0124 protein | 4.41 | 0.00604 | 181.72 | 113.91 | 140.73 | 38.26 | 30.26 | 32.72 |
| AA609795 | 1492 | EST | #N/A | #N/A | 74.38 | 34 | 77.76 | -41.44 | -45.5 | 28.82 |
| AA621277 | 1520 | EST | 3.81 | 0.00194 | 81.18 | 74.81 | 30.84 | -0.15 | 1.98 | 12.84 |
| F09788 | 1808 | procollagen-proline, 2-oxoglutarate 4-dioxygenase (proline 4-hydroxylase), alpha polypeptide II | 4.14 | 0.00003 | 104.92 | 112.31 | 27.67 | 19.92 | 20.29 | 13.83 |
| H09281 | 1863 | EST | 6 | 0.00966 | 147.11 | 187.25 | 71.67 | -2.97 | -0.54 | 11.7 |
| H59617 | 1964 | EST | 3.3 | 0.04588 | 116.07 | 71.39 | 101 | 19.24 | 21.65 | 16.88 |
| H98657 | 2068 | KIAA0124 protein | #N/A | #N/A | 179.15 | 192.17 | 32.25 | 111.2 | 84.74 | 128.92 |
| N22015 | 2447 | EST | 46.61 | 0.00025 | 1225.51 | 887.65 | 1106.3 | -5.3 | -6.84 | 18.82 |
| N35376 | 2500 | EST | #N/A | #N/A | 39.01 | 35.99 | 19.81 | 28.53 | 29.44 | 8.2 |
| N63165 | 2597 | EST | #N/A | #N/A | 68.04 | 62.1 | 44.7 | 30.07 | 26.23 | 13.84 |
| N64616 | 2610 | EST | 3.11 | 0.0074 | 68.89 | 75.8 | 32.12 | -0.83 | 9.77 | 28.69 |
| N66951 | 2620 | EST | 5.54 | 0.02442 | 451.16 | 432.45 | 381.81 | 59.83 | 75.27 | 32.75 |
| N72116 | 2667 | solute carrier family 11 (proton-coupled divalent metal ion transporters), member 2 | 9.01 | 0.00051 | 338.43 | 314.06 | 196.66 | 32.57 | 29.68 | 20.1 |

TABLE 9A-continued

Genes and ESTs expressed only in Metastatic Liver Tumor vs Normal2

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| N92659 | 2720 | EST | #N/A | #N/A | 31.19 | 37.23 | 14.14 | 5.91 | 4.05 | 5.63 |
| R06866 | 2773 | EST | 5.18 | 0.00187 | 148.48 | 114.86 | 102.01 | 18.26 | 15.16 | 17.11 |
| R26744 | 2803 | midline 1 (Opitz/BBB syndrome) | 4.32 | 0.00532 | 112.54 | 90 | 76.53 | -0.2 | -3.06 | 24.42 |
| R36109 | 2822 | EST | #N/A | #N/A | 47.54 | 48.43 | 19.9 | 25.67 | 20.25 | 34.73 |
| R38511 | 2831 | protein similar to E.coli yhdg and R. capsulatus nifR3 | 5.19 | 0.00015 | 131.5 | 147.54 | 44.02 | 21.3 | 23.75 | 9.22 |
| R39191 | 2833 | KIAA1020 protein | 4.69 | 0.00456 | 130.93 | 145.31 | 62.13 | 17.46 | 18.33 | 16.04 |
| R40057 | 2838 | prominin (mouse)-like 1 | #N/A | #N/A | 47.6 | 46.28 | 36.57 | 0.83 | -0.8 | 7.91 |
| R44817 | 2859 | EST | #N/A | #N/A | 600.1 | 550.42 | 309.14 | 255.91 | 249.29 | 69.09 |
| R49047 | 2877 | Fc fragment of IgG, low affinity IIIa, receptor for (CD16) | #N/A | #N/A | 44.49 | 36.71 | 14.37 | 15.43 | 14.16 | 14.13 |
| R54935 | 2902 | ubiquitin specific protease 7 (herpes virus-associated) | #N/A | #N/A | 75.76 | 81.15 | 31.57 | 17.77 | 14 | 18.86 |
| R55470 | 2903 | EST | 3.59 | 0.00515 | 256.38 | 225.69 | 138.22 | 75.29 | 73.42 | 53.04 |
| R59093 | 2910 | EST | #N/A | #N/A | 57.79 | 33.48 | 73.58 | 12.26 | 10.21 | 7.73 |
| R63925 | 2928 | EST | #N/A | #N/A | 70.52 | 60.93 | 15.36 | 49.82 | 52.73 | 13.77 |
| R71395 | 2951 | EST | 10.42 | 0.00422 | 318.75 | 274.93 | 227.75 | 14.99 | 12.28 | 14.58 |
| R85266 | 2976 | EST | #N/A | #N/A | 53.4 | 54.53 | 25.44 | 48.68 | 39.83 | 33.9 |
| R91819 | 2983 | EST | 8.95 | 0.00009 | 263.33 | 219.91 | 135.67 | 11.34 | 9.35 | 36.49 |
| T03438 | 3042 | EST | 8.18 | 0.00032 | 300.09 | 229.6 | 218.02 | 31.03 | 28.88 | 15.86 |
| T03541 | 3044 | EST | #N/A | #N/A | 455.39 | 418.21 | 288.45 | 155.27 | 155.62 | 50.93 |
| T25744 | 3091 | EST | #N/A | #N/A | 79.78 | 68.72 | 52.01 | 15.56 | 12.65 | 13.18 |
| T53404 | 3142 | EST | 10.68 | 0.00582 | 654.13 | 475.25 | 687.49 | 48.3 | 0.6 | 93.06 |
| T91116 | 3251 | EST | 4.01 | 0.02721 | 133.54 | 61.72 | 126.12 | 16.62 | 11.42 | 13.64 |
| T96060 | 3262 | EST | #N/A | #N/A | 910.76 | 225.75 | 1282.67 | 67.92 | 70.44 | 91.72 |
| W02695 | 3466 | EST | #N/A | #N/A | 129.58 | 99.52 | 100.52 | 30.69 | 33.06 | 16.14 |
| W67251 | 3567 | EST | 6.13 | 0.01463 | 204.71 | 182.17 | 127.82 | 21.77 | 23.88 | 12.17 |
| W78057 | 3597 | EST | 9.06 | 0.0034 | 397.29 | 374.78 | 305.93 | 29.21 | 29.9 | 34.33 |
| W90146 | 3641 | EST | 6.23 | 0.01558 | 170.66 | 147.78 | 126.32 | 9.93 | 8.63 | 6.49 |
| W92449 | 3649 | EST | 31.67 | 0.00011 | 715.17 | 491.5 | 459.71 | -40.13 | -40.74 | 17.76 |
| Z39191 | 3898 | EST | 8.84 | 0.00011 | 442.36 | 371.88 | 228.18 | 46.98 | 49.3 | 33.31 |
| Z39569 | 3906 | EST | #N/A | #N/A | 166.55 | 125.78 | 217.77 | -9.57 | -12.15 | 17.32 |
| Z41415 | 3930 | EST | #N/A | #N/A | 199.73 | 88.96 | 271.2 | 10.38 | 6.64 | 11.47 |
| AA026030 | 53 | EST | 11.01 | 0.01649 | 566.65 | 284.32 | 828.01 | 3.02 | 4.66 | 40.87 |
| AA026270 | 56 | tyrosyl-tRNA synthetase | #N/A | #N/A | 201.1 | 224.51 | 50.82 | 76.85 | 76.68 | 45.22 |
| AA043944 | 100 | EST | #N/A | #N/A | 52.9 | 29.13 | 46.43 | 3.69 | 3.15 | 7.26 |
| AA053102 | 125 | cadherin 17, LI cadherin (liver-intestine) | 26.63 | 0.01745 | 1053.43 | 972.71 | 785.51 | 4.92 | 4.94 | 9.04 |
| AA053248 | 126 | EST | 7.01 | 0.00003 | 2234.44 | 1595.15 | 1053.3 | 341.06 | 304.8 | 189.89 |
| AA055896 | 135 | collagen, type V, alpha 1 | 18.16 | 0.00146 | 540.67 | 538.43 | 382 | -3.14 | -5.8 | 33.88 |
| AA084343 | 178 | EST | #N/A | #N/A | 133.86 | 126.19 | 19.99 | 84.58 | 76.82 | 41.45 |
| AA112979 | 225 | vaccinia related kinase 1 | #N/A | #N/A | 25.08 | 24.98 | 13.02 | 8.54 | 8.02 | 2.59 |
| AA126041 | 244 | EST | #N/A | #N/A | 42.91 | 33.83 | 16.2 | 26.42 | 28.92 | 9.81 |
| AA128553 | 260 | amyloid beta (A4) precursor protein (protease nexin-II, Alzheimer disease) | #N/A | #N/A | 87.35 | 102.82 | 24.17 | 114.91 | 108.16 | 30.28 |
| AA150053 | 327 | EST | 3.71 | 0.00102 | 309.61 | 304.16 | 82.48 | 101.87 | 88.37 | 73.73 |
| AA151428 | 335 | matrix metalloproteinase 23B | 7.15 | 0.00056 | 174.77 | 131.66 | 104.51 | 3.23 | 10.67 | 24.39 |

TABLE 9A-continued

Genes and ESTs expressed only in Metastatic Liver Tumor vs Normal2

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| AA156243 | 340 | serine protease, umbilical endothelium | 41.44 | 0.00139 | 1255.4 | 547.15 | 1189.26 | 9.32 | 11.44 | 9.39 |
| AA159525 | 354 | EST | 49.39 | 0.00062 | 1309.05 | 1107.08 | 965.67 | -32.72 | -28.32 | 20.11 |
| AA161043 | 356 | tetraspan 1 | 18.8 | 0.00015 | 1477.19 | 932.02 | 1467.59 | 70.82 | 58.62 | 42.88 |
| AA171760 | 367 | EST | 17.86 | 0 | 645.43 | 578.38 | 312.37 | 28.03 | 16.24 | 57.21 |
| AA179845 | 381 | EST | 5.77 | 0.01414 | 280.06 | 335.41 | 172.62 | 37.43 | 37.69 | 14.87 |
| AA181600 | 384 | EST | 5.38 | 0.03316 | 166.88 | 94.16 | 153.49 | -40.51 | -47.81 | 24.34 |
| AA196790 | 421 | EST | 7.64 | 0.00287 | 239.45 | 275.18 | 142.37 | 22.91 | 26.8 | 10.54 |
| AA211483 | 435 | EST | 44.07 | 0.00175 | 1300.23 | 1303.61 | 1051.58 | -29.25 | -34.99 | 17.49 |
| AA232508 | 464 | EST | #N/A | #N/A | 464 | 533.98 | 266.87 | 170.48 | 156.89 | 104.75 |
| AA233290 | 469 | general transcription factor IIIC, polypeptide I (alpha subunit, 220kD) | 23.72 | 0.00018 | 607.06 | 420.34 | 366.53 | -3.47 | 1.73 | 30.91 |
| AA234096 | 479 | EST | #N/A | #N/A | 56.54 | 43.91 | 22.15 | 28.32 | 31.59 | 25.36 |
| AA234346 | 480 | EST | #N/A | #N/A | 36.98 | 39.47 | 12.81 | 6.21 | 6.79 | 19.99 |
| AA234362 | 481 | EST | 3.89 | 0.03524 | 116.26 | 75.37 | 105.77 | -1.86 | -4.2 | 16.67 |
| AA234365 | 482 | survival of motor neuron protein interacting protein 1 | #N/A | #N/A | 56.37 | 42.6 | 34.73 | 12.96 | 16.93 | 12.99 |
| AA234706 | 488 | EST | #N/A | #N/A | 68.33 | 53.21 | 21.55 | 49.66 | 39.76 | 42.06 |
| AA253473 | 567 | EST | 15.23 | 0.00171 | 375.2 | 435.68 | 216.18 | -4.38 | -3.19 | 12.35 |
| AA255566 | 570 | EST | #N/A | #N/A | 63.43 | 65.2 | 30.17 | 16.18 | 14.38 | 13.17 |
| AA256642 | 582 | EST | 11.17 | 0.00035 | 266.31 | 275.43 | 135.85 | 0.78 | -1.34 | 15.74 |
| AA292765 | 712 | EST | 7.14 | 0.02623 | 230.83 | 166.72 | 232.16 | 11.33 | 18.29 | 13.27 |
| AA331393 | 739 | ZW10 interactor | 16.73 | 0.00848 | 600.02 | 315.98 | 598.52 | 5.08 | 3.88 | 9.43 |
| AA349792 | 759 | mutY (E. coli) homolog | #N/A | #N/A | 525.17 | 553.97 | 245.2 | 221.5 | 212.24 | 98.86 |
| AA398908 | 801 | EST | 38.69 | 0.01089 | 1678.58 | 1796.68 | 1500.48 | -174.29 | -216.08 | 104.42 |
| AA405715 | 862 | hypothetical protein | 4.68 | 0.00898 | 152.23 | 138.92 | 96.78 | 24.47 | 27.3 | 11.75 |
| AA406542 | 878 | EST | 8.27 | 0.00724 | 230.18 | 170.94 | 206.8 | -1.99 | 1.49 | 12.75 |
| AA421562 | 934 | anterior gradient 2 (Xenopus laevis) homolog | 56.3 | 0.0041 | 2556.78 | 792 | 3323.39 | 14.22 | 15.72 | 6.54 |
| AA424487 | 945 | EST | 38.41 | 0.00002 | 2689.32 | 1863.02 | 1900.51 | 67.92 | 61.95 | 46.24 |
| AA425279 | 951 | quiescin Q6 | 6.15 | 0.00083 | 221.93 | 181.8 | 167.44 | 18.33 | 22.33 | 44.81 |
| AA425401 | 954 | serine/threonine kinase 24 (Ste20, yeast homolog) | 3.22 | 0.00625 | 246.6 | 166.4 | 175.99 | 76.4 | 78.33 | 43.72 |
| AA429009 | 994 | serine protease inhibitor, Kunitz type 1 | 30.04 | 0.00001 | 1010.32 | 1100.19 | 472.23 | -2.97 | -24.67 | 62.21 |
| AA436616 | 1056 | EST | 3.18 | 0.04402 | 79.96 | 91.35 | 62.83 | -0.73 | 3.24 | 15.36 |
| AA447687 | 1104 | EST | 11.42 | 0.00362 | 306.28 | 178.65 | 244.12 | -16.27 | -14.45 | 8.55 |
| AA447991 | 1112 | EST | 4.99 | 0.00173 | 279.79 | 234.63 | 161.24 | 64.49 | 40.73 | 53.34 |
| AA459254 | 1211 | EST | 5.36 | 0.0259 | 403.69 | 194.85 | 401.21 | 51.84 | 43.51 | 37.57 |
| AA478556 | 1303 | EST | #N/A | #N/A | 172.35 | 135.55 | 120.49 | 143.25 | 134.62 | 109.1 |
| AA491208 | 1388 | chromosome 6 open reading frame 1 | 9.88 | #N/A | 159.88 | 143.86 | 80.49 | 123.37 | 131.81 | 47.97 |
| AA599585 | 1454 | EST | #N/A | #N/A | 66.17 | 48.91 | 48.12 | -12.47 | -17.55 | 21.82 |
| C21248 | 1585 | pituitary tumor-transforming 1 | 3.85 | 0.00456 | 100.24 | 96.81 | 47.17 | -1.7 | -11.27 | 28.49 |
| D20906 | 1627 | EST | 5.18 | 0.02189 | 210.11 | 151.67 | 185.24 | 14.87 | 11.71 | 27.2 |
| F02330 | 1778 | EST | #N/A | #N/A | 199.08 | 170.47 | 83.95 | 178.42 | 195.54 | 58.6 |
| F03811 | 1784 | KIAA0440 protein | #N/A | #N/A | 638.66 | 598.46 | 142.63 | 235.37 | 232.6 | 47.16 |
| F04531 | 1791 | Kell blood group precursor (McLeod phenotype) | 7.79 | 0.03205 | 311.05 | 366.72 | 262.03 | 16.22 | 20.65 | 13.52 |
| F09394 | 1803 | KIAA0715 protein | 22.89 | 0.01753 | 865.39 | 696.47 | 631.83 | -49.72 | -50.25 | 35.81 |
| H43646 | 1930 | H2A histone family, member Y | 4.6 | 0.00147 | 413.02 | 424.34 | 219.27 | 92.12 | 91.3 | 52.41 |

TABLE 9A-continued

Genes and ESTs expressed only in Metastatic Liver Tumor vs Normal2

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| N49284 | 2536 | v-myb avian myeloblastosis viral oncogene homolog | 11.82 | 0.01981 | 510.82 | 523.45 | 423.41 | −36.17 | −50.08 | 50.71 |
| N54265 | 2562 | EST | #N/A | #N/A | 45.56 | 44.98 | 19.91 | 17.71 | 26.43 | 25.36 |
| N62675 | 2593 | DEAD/H (Asp-Glu-Ala-Asp/His) box polypeptide 16 | 3.61 | 0.04034 | 109.44 | 104.65 | 108.08 | 6.49 | 15.91 | 35.18 |
| N73846 | 2679 | EST | 3.27 | 0.00012 | 78.37 | 79.7 | 20.06 | 14.43 | 14.3 | 17.21 |
| N89670 | 2708 | EST | 4.26 | 0.00002 | 115.98 | 108.4 | 29.79 | 3.16 | −1.81 | 43.32 |
| N93798 | 2737 | protein tyrosine phosphatase type IVA, member 3 | 4.65 | 0.00118 | 557.51 | 523.56 | 229.03 | 139.69 | 122.61 | 84.93 |
| R33498 | 2819 | EST | 41.34 | 0.00001 | 1839.74 | 1920.41 | 1082.84 | 46.45 | 33.01 | 43.64 |
| R44479 | 2854 | KIAA0552 gene product | 4.14 | 0.0181 | 97.01 | 105.95 | 60.51 | 7.08 | 5.99 | 7.62 |
| R92994 | 2989 | matrix metalloproteinase 12 (macrophage elastase) | 11.05 | 0.00248 | 312.14 | 252.62 | 248.32 | 11.43 | 6.64 | 11.52 |
| R95966 | 2996 | EST | 11.22 | 0.00682 | 482.68 | 436.3 | 446.39 | −106.64 | −160.75 | 127.91 |
| T30222 | 3099 | EST | #N/A | #N/A | 35.41 | 34.75 | 27.14 | 8.47 | 9.56 | 17.71 |
| T32108 | 3102 | EST | 6.96 | 0.00723 | 1095.16 | 593.52 | 923.47 | 148.09 | 152.11 | 92.06 |
| T89601 | 3242 | EST | #N/A | #N/A | 839.07 | 747.51 | 231.92 | 410.07 | 342.22 | 200.88 |
| W46451 | 3526 | leukemia inhibitory factor (cholinergic differentiation factor) | #N/A | #N/A | 125.95 | 76.95 | 88.42 | 36.63 | 40.09 | 21.06 |
| W60968 | 3556 | EST | #N/A | #N/A | 125.7 | 144.72 | 48.22 | 51.99 | 55.29 | 21.11 |
| W93726 | 3653 | protease inhibitor 5 (maspin) | 16.48 | 0.00014 | 355.41 | 304.26 | 149.69 | −14.2 | −14.8 | 10.59 |
| W95477 | 3661 | EST | 26.51 | 0.00161 | 941.08 | 566.6 | 1130.33 | 17.15 | 18.75 | 12.83 |
| AA011134 | 29 | EST | 28.79 | 0.00602 | 1157.47 | 566.78 | 1448.16 | −72.57 | −51.2 | 69.3 |
| AA035540 | 81 | glutamate-cysteine ligase (gamma-glutamylcysteine synthetase), regulatory (30.8kD) | #N/A | #N/A | 39.84 | 34.37 | 13.29 | 13.59 | 12.27 | 8.96 |
| AA053033 | 124 | EST | 7.83 | 0.00379 | 212.61 | 135.28 | 160.82 | 3.41 | −1.28 | 19.74 |
| AA055805 | 132 | EST | 42.83 | 0.00142 | 1270.03 | 1026.97 | 1179.12 | −11.11 | −10.85 | 20.27 |
| AA055811 | 133 | glycoprotein A33 (transmembrane) | 6.86 | 0.02152 | 236.18 | 196.53 | 171.06 | 14.84 | 17.82 | 17.5 |
| AA131162 | 266 | EST | 4.68 | 0.00042 | 117.43 | 123.78 | 39.05 | 11.86 | 13.57 | 19.83 |
| AA157857 | 350 | keratin 19 | #N/A | #N/A | 2728.74 | 2917.98 | 1076.95 | −13.21 | −14.4 | 15.84 |
| AA252994 | 557 | apoptosis inhibitor 4 (survivin) | 3.55 | 0.00075 | 152.63 | 140.53 | 31.01 | 50.23 | 40.59 | 35.61 |
| AA258836 | 601 | WW domain binding protein 4 (formin binding protein 21) | #N/A | #N/A | 41.9 | 44.58 | 13.6 | 26.08 | 23.64 | 10.4 |
| AA291259 | 697 | putative G protein-coupled receptor | #N/A | #N/A | 112.28 | 45.1 | 113.44 | 1.53 | 1.88 | 6.06 |
| AA335191 | 741 | creatine kinase, brain | 47.35 | 0.00419 | 3540.65 | 3971.43 | 3135.19 | 43.84 | 33.21 | 43.52 |
| AA422086 | 938 | EST | 10.71 | 0.03418 | 828.27 | 598.22 | 800.79 | 39.48 | 34.98 | 23.29 |
| AA422150 | 939 | cytochrome P540 family member predicted from ESTs | 17.14 | 0.00108 | 664.26 | 609.99 | 475.91 | 28.76 | 27.53 | 22.47 |
| AA427460 | 972 | ATP-binding cassette, sub-family F (GCN20), member 2 | #N/A | #N/A | 215.08 | 135.22 | 216.95 | 92.5 | 83.63 | 49.3 |
| AA427636 | 976 | EST | 19.23 | 0.00145 | 511.98 | 500.83 | 299.69 | 6.19 | 3.7 | 15.84 |
| AA429890 | 1004 | cisplatin resistance associated | 12.51 | 0.00053 | 1225.72 | 590.09 | 992.47 | 90.02 | 67.23 | 59.35 |
| AA443316 | 1075 | v-Ha-ras Harvey rat sarcoma viral oncogene homolog | 4.13 | 0.01729 | 191.06 | 173.3 | 113.42 | 40.07 | 41.12 | 32.54 |
| AA599244 | 1448 | KIAA0530 protein | 3.39 | 0.01246 | 77.48 | 78.85 | 37.98 | 7.71 | 6.06 | 7.11 |

TABLE 9A-continued

Genes and ESTs expressed only in Metastatic Liver Tumor vs Normal2

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| AA609013 | 1477 | dipeptidase 1 (renal) | 10.17 | 0.00109 | 1185.55 | 1222.89 | 634.13 | 114.31 | 98.91 | 75.22 |
| AA620497 | 1503 | EST | #N/A | #N/A | 147.72 | 165.83 | 66.02 | 95.91 | 76.7 | 80.33 |
| AA620995 | 1512 | EST | 3.74 | 0.03414 | 100.71 | 80.15 | 101.95 | 3.5 | 1.8 | 3.77 |
| C15078 | 1573 | EST | #N/A | #N/A | 115.08 | 73.82 | 91.34 | 26.22 | 31.14 | 60.2 |
| D80710 | 1734 | integral type I protein | 7.08 | 0.00213 | 253.6 | 303.7 | 149.08 | 22.95 | 28.29 | 24.59 |
| D80948 | 1738 | EST | #N/A | #N/A | 82.4 | 67.39 | 42.83 | 41.25 | 43.53 | 17.46 |
| F04320 | 1786 | replication factor C (activator 1) 4 (37kD) | 3.63 | 0.01119 | 90.37 | 115.96 | 49.41 | 14.92 | 17.26 | 9.79 |
| H03629 | 1834 | desmin | #N/A | #N/A | 52.19 | 58.52 | 35.47 | −1.96 | −2.94 | 8.58 |
| H11760 | 1878 | EST | #N/A | #N/A | 70.59 | 62.53 | 58.16 | 9.96 | 8.19 | 11.54 |
| H24269 | 1902 | E74-like factor 4 (ets domain transcription factor) | #N/A | #N/A | 51.79 | 47.58 | 24.25 | 15.19 | 16.8 | 12.36 |
| H57709 | 1956 | ribosomal protein L31 | #N/A | #N/A | 47.56 | 34.17 | 56.68 | 4.55 | 2.44 | 52.46 |
| H58873 | 1961 | solute carrier family 2 (facilitated glucose transporter), member 1 | 57.98 | 0.00063 | 4996.66 | 4603.55 | 4107.24 | 69.89 | 70.74 | 58.94 |
| H78211 | 2001 | EST | 6.73 | 0.02488 | 211.51 | 183.81 | 208.45 | −115.95 | −129.18 | 70.22 |
| N54395 | 2564 | EST | #N/A | #N/A | 49.95 | 46.84 | 48.26 | −16.14 | −17.71 | 6.65 |
| N92734 | 2721 | EST | #N/A | #N/A | 45.63 | 39.49 | 14.19 | 27.31 | 25.45 | 10.41 |
| R06251 | 2763 | tumor protein D52-like 2 | 5.57 | 0.00037 | 343.86 | 381.79 | 95.11 | 74.25 | 66.72 | 64.11 |
| R27296 | 2806 | EST | #N/A | #N/A | 41.82 | 39.83 | 32.72 | 8.27 | 11.07 | 7.26 |
| R36947 | 2824 | calcium channel, voltage-dependent, beta 3 subunit | 4.11 | 0.00006 | 101.82 | 109.62 | 28.57 | −0.61 | 0.94 | 37.6 |
| R96924 | 3000 | EST | 6.18 | 0.03417 | 451.59 | 490.51 | 339.66 | 51.01 | 52.94 | 54.09 |
| T15473 | 3057 | muscle specific gene | 5.81 | 0.02404 | 189.25 | 139.11 | 184.39 | −5.65 | −10.77 | 15.89 |
| T16983 | 3073 | cleavage and polyadenylation specific factor 4, 30kD subunit | 5.23 | 0.00075 | 268.21 | 300.53 | 81.43 | 65.64 | 45.67 | 74.28 |
| T30193 | 3097 | protease, serine, 8 (prostasin) | 8.39 | 0.00043 | 1912.22 | 1228.46 | 1739.5 | 214.88 | 175.57 | 127.28 |
| T47601 | 3125 | EST | 4.05 | 0.00878 | 199.79 | 219.84 | 62.16 | 84.5 | 28.33 | 122.16 |
| T66935 | 3178 | EST | 3.97 | 0.00188 | 253.93 | 230.32 | 129.66 | 66.8 | 52.94 | 42.32 |
| W73189 | 3586 | EphB2 | 3.69 | 0.02909 | 113.63 | 144.75 | 67.73 | 20.7 | 23.2 | 15.44 |
| D13435 | 1605 | phosphatidylinositol glycan, class F | #N/A | #N/A | 80.8 | 88.58 | 41.56 | 34.85 | 41.76 | 18.11 |
| D14520 | 1613 | basic transcription element binding protein 2 | 4.93 | 0.00004 | 151.12 | 135.19 | 57.24 | 25.67 | 17.28 | 25.67 |
| D21063 | 1628 | minichromosome maintenance deficient (S. cerevisiae) 2 (mitotin) | 3.83 | 0.00983 | 91.18 | 55.12 | 60.89 | −51.33 | −62.63 | 28.4 |
| D50914 | 1673 | KIAA0124 protein | 4.74 | 0.00752 | 116.55 | 91.64 | 89.27 | −17.4 | −17.86 | 16.97 |
| 063486 | 1712 | KIAA0152 gene product | 6.33 | 0.00078 | 543.91 | 676.55 | 287.16 | 84.6 | 95.61 | 45.48 |
| D63880 | 1715 | KIAA0159 gene product | 4.26 | 0.00253 | 93.03 | 103.26 | 41.4 | −2.12 | −4.45 | 9.38 |
| D79992 | 1724 | KIAA0170 gene product | #N/A | #N/A | 35.23 | 42.16 | 14.88 | 22 | 18.09 | 11.9 |
| D79997 | 1725 | KIAA0175 gene product | #N/A | #N/A | 55.25 | 42.49 | 53.87 | 8.57 | 6.15 | 13.07 |
| D83735 | 1747 | calponin 2 | 10.42 | 0.00001 | 486.85 | 436.55 | 172.25 | 42.54 | 43.06 | 57.58 |
| D84557 | 1749 | minichromosome maintenance deficient (mis5, S. pombe) 6 | #N/A | #N/A | 142.92 | 125.75 | 102.81 | 37.22 | 43.12 | 28.15 |
| D87073 | 1759 | zinc finger protein 142 (clone pHZ-49) | #N/A | #N/A | 40.84 | 34.37 | 13.36 | 33.34 | 33.07 | 21.13 |
| J04469 | 2111 | creatine kinase, mitochondrial 1 (ubiquitous) | 7.9 | 0.00705 | 212.04 | 143.89 | 162.12 | −17.21 | −18.81 | 12.68 |
| J05257 | 2118 | dipeptidase 1 (renal) | 12.02 | 0.02099 | 429.91 | 300.76 | 352.56 | −21.05 | −21.78 | 30.67 |
| J05272 | 2119 | IMP (inosine monophosphate) dehydrogenase 1 | #N/A | #N/A | 269.89 | 205 | 173.64 | 126.69 | 106.27 | 82.73 |

TABLE 9A-continued

Genes and ESTs expressed only in Metastatic Liver Tumor vs Normal2

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| L07597 | 2146 | ribosomal protein S6 kinase, 90kD, polypeptide 1 | #N/A | #N/A | 36.09 | 29.39 | 44.43 | -12.04 | -10.72 | 11.97 |
| L11669 | 2157 | tetracycline transporter-like protein | 6.75 | 0.00101 | 218.77 | 261.77 | 115.8 | 26.26 | 25.92 | 17.48 |
| L23808 | 2179 | matrix metalloproteinase 12 (macrophage elastase) | 6.18 | 0.02195 | 175.24 | 161.83 | 132.75 | -9.99 | -8.2 | 8.11 |
| L35035 | 2201 | ribose 5-phosphate isomerase A (ribose 5-phosphate epimerase) | #N/A | #N/A | 64.36 | 69.69 | 40.9 | 11.52 | 12.58 | 6.43 |
| L35545 | 2202 | endothelial cell protein C/activated protein C receptor | #N/A | #N/A | 66.65 | 55.46 | 68.13 | 7.75 | 5.68 | 11.48 |
| L38696 | 2208 | RNA-binding protein (autoantigenic) | 3.7 | 0.00093 | 230.48 | 161.69 | 118.85 | 60.18 | 58.55 | 24.77 |
| L41351 | 2214 | protease, serine, 8 (prostasin) | 6.34 | 0.01132 | 214.13 | 104.95 | 189.28 | 10.88 | 9.6 | 22.68 |
| M15205 | 2265 | thymidine kinase 1, soluble | 3.75 | 0.00159 | 153.15 | 150.31 | 66.27 | 41.98 | 35.02 | 29.02 |
| M18728 | 2285 | carcinoembryonic antigen-related cell adhesion molecule 6 (non-specific cross reacting antigen) | 44.82 | 0.00291 | 1390.62 | 1362.73 | 1031.01 | -9.17 | -13.17 | 11.83 |
| M25629 | 2307 | kallikrein 1, renal/pancreas/salivary | #N/A | #N/A | 47.43 | 40.22 | 29.15 | -2.42 | 2.12 | 15.6 |
| M27826 | 2313 | endogenous retroviral protease | 26.36 | 0.00342 | 993.89 | 833.56 | 816.33 | 5.88 | 7.04 | 32.2 |
| M29540 | 2317 | carcinoembryonic antigen-related cell adhesion molecule 5 | 36.57 | 0.0116 | 1516.55 | 1083.69 | 1372.55 | -1.09 | -3.15 | 11.75 |
| M87339 | 2414 | replication factor C (activator 1) 4 (37kD) | 4.07 | 0.00316 | 93.72 | 78.1 | 56.58 | 4.26 | 9.92 | 16.79 |
| M94250 | 2425 | midkine (neurite growth-promoting factor 2) | 10.39 | 0.01818 | 442.2 | 188.32 | 624.9 | -155.4 | -175.43 | 101.89 |
| M94345 | 2426 | capping protein (actin filament), gelsolin-like | 22.38 | 0.00003 | 503.47 | 539.15 | 179.05 | -7.51 | -10.35 | 22.75 |
| M94362 | 2427 | lamin B2 | #N/A | #N/A | 175.16 | 154.32 | 75.52 | 79.2 | 81.73 | 34.64 |
| M95623 | 2430 | hydroxymethylbilane synthase | #N/A | #N/A | 67.65 | 72.44 | 22.29 | 6.67 | 0.88 | 24.92 |
| S78187 | 3035 | cell division cycle 25B | 8.07 | 0.00009 | 198.51 | 218.04 | 74.52 | 3.36 | -1.2 | 26.9 |
| U01062 | 3272 | inositol 1,4,5-triphosphate receptor, type 3 | 7.41 | 0 | 160.46 | 164.36 | 23.91 | -16.8 | -26.61 | 26.44 |
| U01147 | 3274 | active BCR-related gene | 3.22 | 0.00103 | 97.43 | 84.12 | 41.43 | 27.15 | 22.94 | 17 |
| U03398 | 3281 | tumor necrosis factor (ligand) superfamily, member 9 | #N/A | #N/A | 116.17 | 88.07 | 59.5 | 115.08 | 92.7 | 93.14 |
| U04313 | 3283 | protease inhibitor 5 (maspin) | 4.54 | 0.02986 | 132.77 | 69.67 | 115.99 | -0.34 | -2.59 | 9.7 |
| U16306 | 3311 | chondroitin sulfate proteoglycan 2 (versican) | #N/A | #N/A | 48.35 | 56.91 | 35.99 | 8.07 | 4.58 | 16.58 |
| U17760 | 3314 | laminin, beta 3 (nicein (125kD), kalinin (140kD), BM600 (125kD)) | 3.54 | 0.01853 | 103.13 | 111.96 | 72.83 | 6.99 | -3.15 | 21.08 |
| U21049 | 3324 | epithelial protein up-regulated in carcinoma, membrane associated protein 17 | 7.53 | 0.01667 | 202.38 | 248.15 | 119.31 | -14.32 | -12.21 | 19.43 |
| U38847 | 3356 | TAR (HIV) RNA-binding protein 1 | #N/A | #N/A | 72.74 | 66.76 | 36.14 | 15.7 | 17.43 | 10.2 |
| U40990 | 3358 | potassium voltage-gated channel, KQT-like subfamily, member 1 | 3.18 | 0.00093 | 128.02 | 142.31 | 43.16 | 40.88 | 42.64 | 23.09 |
| U51095 | 3381 | caudal type homeo box transcription factor 1 | 4.76 | 0.02664 | 130.81 | 143.82 | 93.4 | 5.83 | 5.55 | 8.97 |
| U53786 | 3389 | envoplakin | #N/A | #N/A | 221.51 | 73.95 | 249.37 | -20.54 | -20.08 | 16.22 |
| U66661 | 3405 | gamma-aminobutyric acid (GABA) A receptor, epsilon | #N/A | #N/A | 55.33 | 44.93 | 29.26 | 16.58 | 14.81 | 11.96 |
| U77413 | 3426 | O-linked N-acetylglucosamine (GlcNAc) transferase (UDP-N-acetylglucosamine;polypeptide-N-acetylglucosaminyl transferase) | #N/A | #N/A | 59.38 | 59.78 | 48.05 | 1.2 | 5.23 | 13.8 |
| U89606 | 3451 | pyridoxal (pyridoxine, vitamin B6) kinase | 3.58 | 0.00322 | 103.6 | 97.56 | 58.85 | 15.19 | 18.94 | 24.5 |

TABLE 9A-continued

Genes and ESTs expressed only in Metastatic Liver Tumor vs Normal2

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| X13956 | 3698 | EST | 3.2 | 0.00321 | 79.19 | 75.13 | 39.53 | 15.11 | 18.02 | 14.55 |
| X14850 | 3703 | H2A histone family, memberX | 4.11 | 0.0001 | 118.41 | 97.53 | 52.6 | 11.6 | 13.26 | 30.46 |
| | | v-abl Abelson murine leukemia viral oncogene | | | | | | | | |
| X16416 | 3710 | homolog 1 | #N/A | #N/A | 82.49 | 90.74 | 16.7 | 36.59 | 38 | 14.59 |
| X57766 | 3742 | matrix metalloproteinase 11 (stromelysin 3) | #N/A | #N/A | 166.25 | 142.96 | 124.34 | 63.38 | 62.13 | 25.48 |
| X63629 | 3759 | cadherin 3, P-cadherin (placental) | 3.02 | 0.01654 | 67.22 | 76.67 | 29.17 | -4.24 | -6.82 | 16.9 |
| X67325 | 3772 | interferon, alpha-inducible protein 27 | 9.67 | 0.03245 | 962.87 | 412.22 | 1361.55 | 26.81 | 48.73 | 69.77 |
| X76180 | 3792 | sodium channel, nonvoltage-gated 1 alpha | 11.68 | 0 | 320.05 | 268.84 | 127.86 | 22.38 | 23.9 | 15.02 |
| | | FXYD domain-containing ion transport regulator | | | | | | | | |
| X93036 | 3827 | 3 | 42.36 | 0.00167 | 1322.91 | 783.61 | 1219 | -83.87 | -85.84 | 40.53 |
| Y00503 | 3846 | keratin 19 | 14.19 | 0.00217 | 362.5 | 427.85 | 240.73 | 7.02 | 10.74 | 10.98 |
| | | SRY (sex-determining region Y)-box 9 (campomelic dysplasia, autosomal sex- | | | | | | | | |
| Z46629 | 3935 | reversal) | #N/A | #N/A | 39.69 | 40.61 | 13.99 | 6.21 | 8.06 | 9.16 |
| | | lectin, galactoside-binding, soluble, 9 (galectin | | | | | | | | |
| AB006782 | 1541 | 9) | #N/A | #N/A | 475.47 | 430.44 | 192.68 | 222.25 | 213.37 | 51.25 |
| X83228 | 3807 | cadherin 17, LI cadherin (liver-intestine) | 10.58 | 0.02147 | 342.12 | 423.87 | 282.49 | -8.87 | -6.9 | 8.55 |
| | | HMT1 (hnRNP methyltransferase, S. | | | | | | | | |
| Y10807 | 3857 | cerevisiae)-like 2 | 4.28 | 0.00124 | 393.27 | 449.97 | 142.94 | 96 | 90.42 | 44.52 |
| U48705 | 3369 | discoidin domain receptor family, member 1 | 5.94 | 0.01323 | 178.04 | 200.63 | 102.82 | -1.87 | -6.25 | 25.81 |
| | | small nuclear ribonucleoprotein 70kD | | | | | | | | |
| X04654 | 3678 | polypeptide (RNP antigen) | #N/A | #N/A | 98.11 | 89.35 | 38.15 | 42.22 | 41.24 | 17.18 |
| | | CD44 antigen (homing function and India | | | | | | | | |
| HG2981-HT3127 | | blood group system) | #N/A | #N/A | 48.43 | 47.46 | 47.03 | 8.05 | 9.25 | 7.17 |
| HG371-HT26388 | | mucin 1, transmembrane | 8.44 | 0.00268 | 310.61 | 203.35 | 303.26 | 19.1 | 2.63 | 34.66 |
| J05582 | 2121 | mucin 1, transmembrane | 5.39 | 0.00056 | 114 | 114.74 | 42.09 | -6.01 | -4.53 | 13.68 |
| M16364 | 2269 | creatine kinase, brain | 12.69 | 0.03633 | 683.38 | 491.19 | 929.94 | -72.18 | -70.9 | 40.37 |
| X54667 | 3728 | cystatin S, cystatin SN | 8.53 | 0.00059 | 273.96 | 169.94 | 217.11 | -10.09 | -15.68 | 74.89 |
| M29277 | 2316 | melanoma adhesion molecule | 3.91 | 0.00112 | 269.54 | 313.13 | 82.76 | 80.09 | 81.21 | 48.32 |
| X57348 | 3741 | stratifin | 12.53 | 0.0013 | 308.28 | 241.69 | 194.79 | -63.66 | -76.43 | 44.95 |
| U07969 | 3288 | cadherin 17, LI cadherin (liver-intestine) | 10.78 | 0.02002 | 428.65 | 383.68 | 390.23 | 15.78 | 12.82 | 12.06 |
| M12125 | 2241 | tropomyosin 2 (beta) | 10.83 | 0.00191 | 291.63 | 158.55 | 229.08 | 13.01 | 16.33 | 11.64 |
| | | transcription factor 3 (E2A immunoglobulin | | | | | | | | |
| M31523 | 2329 | enhancer binding factors E12/E47) | #N/A | #N/A | 59.78 | 62.53 | 10.63 | 18.65 | 21.63 | 8.94 |
| X99133 | 3839 | lipocalin 2 (oncogene 24p3) | 6.27 | 0.0453 | 284.56 | 129.1 | 434.01 | -28.39 | -19.41 | 26.24 |
| | | sulfotransferase family 1A, phenol-preferring, | | | | | | | | |
| U20499 | 3320 | member 3 | 5.5 | 0.00299 | 316.7 | 231.67 | 222.02 | 48.34 | 54.37 | 24.69 |
| L42583 | 2215 | keratin 6A | #N/A | #N/A | 116.33 | 111.15 | 91.3 | 60.92 | 51.12 | 22.52 |

TABLE 9B

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| AA027766 | 58 | microvascular endothelial differentiation gene 1 | #N/A | #N/A | 16.71 | 16.37 | 7.36 | 25.05 | 26.19 | 13.26 |
| AA028976 | 63 | EST | #N/A | #N/A | 9.46 | 10.28 | 18.91 | 72.06 | 47.28 | 55.89 |
| AA041208 | 96 | NADH dehydrogenase (ubiquinone) 1 beta subcomplex, 8 (19kD, ASHI) | #N/A | #N/A | 234.76 | 302.34 | 215.51 | 448.34 | 390 | 234.61 |
| AA044095 | 102 | EST | #N/A | #N/A | 29.41 | 18.4 | 35.04 | 31.85 | 24.92 | 38.98 |
| AA044842 | 105 | Autosomal Highly Conserved Protein | 5.21 | 0.0009 | 16.66 | 16.52 | 18 | 167.15 | 159.32 | 123.77 |
| AA047151 | 116 | EST | 7.13 | 0.00007 | 17.55 | 17.5 | 10.09 | 188.62 | 185.41 | 80.5 |
| AA056319 | 139 | EST | #N/A | #N/A | 21.89 | 17.62 | 12.89 | 29.23 | 26.53 | 11.96 |
| AA092376 | 196 | 15 kDa selenoprotein | #N/A | #N/A | 16.78 | 14.2 | 28.1 | 59.07 | 57.94 | 24.97 |
| AA092596 | 197 | bone morphogenetic protein 6 | 3.46 | 0.02532 | 30.18 | 22.69 | 61.67 | 148.47 | 171.15 | 77.57 |
| AA092716 | 198 | HLA-B associated transcript-3 | 13.97 | 0.00009 | 62.83 | 63.53 | 42.33 | 952.09 | 817.41 | 545.31 |
| AA143019 | 309 | EST | 6.75 | 0.00009 | -0.4 | -5.82 | 18.62 | 192.42 | 176.13 | 136.81 |
| AA157401 | 346 | S-adenosylhomocysteine hydrolase-like 1 | #N/A | #N/A | 15.44 | 13.27 | 14.06 | 61.17 | 65.58 | 27.48 |
| AA174202 | 375 | EST | #N/A | #N/A | 55.99 | 38.87 | 72.55 | 120.99 | 128.88 | 62.33 |
| AA195179 | 415 | eukaryotic translation initiation factor 4A, isoform 2 | #N/A | #N/A | 30.71 | 38.24 | 25.48 | 85.7 | 87.87 | 42.11 |
| AA233225 | 468 | MRS1 protein | #N/A | #N/A | 25.16 | 30.66 | 26.03 | 54.1 | 55.8 | 22.69 |
| AA234634 | 486 | CCAAT/enhancer binding protein (C/EBP), delta | 7.48 | 0.03318 | 158.16 | 49.12 | 223.12 | 621.92 | 588.94 | 332.64 |
| AA234687 | 487 | EST | #N/A | #N/A | -8.8 | -12.38 | 20.12 | 61.87 | 47.79 | 57.62 |
| AA234817 | 490 | EST | 6.22 | 0.00099 | 31.51 | 20.97 | 34.92 | 222.41 | 156.99 | 133.06 |
| AA247453 | 533 | EST | 3.09 | 0.0015 | 32.38 | 37.86 | 21.04 | 120.43 | 133.44 | 58.12 |
| AA292440 | 709 | DKFZP566B133 protein | #N/A | #N/A | 122.1 | 125.27 | 37.73 | 370.32 | 318.31 | 181.37 |
| AA296821 | 723 | EST | #N/A | #N/A | 15.47 | 10.65 | 21.91 | 57.72 | 71.28 | 33.61 |
| AA298180 | 726 | EST | 3.11 | 0.00747 | 19.6 | 25.9 | 18.83 | 109.91 | 84.28 | 88.07 |
| AA316672 | 734 | fatty-acid-Coenzyme A ligase, long-chain 3 | #N/A | #N/A | 34.62 | 38.08 | 17.08 | 71.9 | 73.01 | 27.47 |
| AA328684 | 737 | EST | #N/A | #N/A | 49.88 | 48.15 | 31.41 | 115.97 | 114.66 | 46.25 |
| AA397841 | 780 | EST | 8.21 | 0 | 7.72 | 3.33 | 18.47 | 214.17 | 189.93 | 116.41 |
| AA400333 | 815 | tumor necrosis factor alpha-inducible cellular protein containing leucine zipper domains; Huntingtin interacting protein L; transcription factor IIIA-interacting protein | #N/A | #N/A | 27.22 | 27.33 | 24.37 | 62.54 | 58.6 | 31.69 |
| AA404214 | 846 | EST | #N/A | #N/A | 35.28 | 48.54 | 23.52 | 70.66 | 66.71 | 55.97 |
| AA424307 | 944 | EST | 5.73 | 0.0074 | 44.98 | 21.05 | 54.01 | 202.82 | 194.92 | 68.07 |
| AA447876 | 1109 | EST | #N/A | #N/A | 13.05 | 6.78 | 34.07 | 27.08 | 22.86 | 22.46 |
| AA456687 | 1197 | EST | 3.08 | 0.01189 | 17.88 | 37.03 | 53.32 | 130.65 | 118.55 | 65.44 |
| AA479266 | 1312 | EST | #N/A | #N/A | 18.04 | 21.7 | 25.73 | 42.53 | 38.32 | 18.46 |
| AB000114 | 1532 | osteomodulin | #N/A | #N/A | -2.62 | -0.81 | 29.14 | 31.94 | 25.4 | 20.87 |
| AF007216 | 1550 | solute carrier family 4, sodium bicarbonate cotransporter, member 4 | 5.79 | 0.00005 | 14.85 | 9.84 | 13.93 | 157.72 | 162.44 | 99.26 |
| C02532 | 1563 | EST | #N/A | #N/A | 10.12 | 16.41 | 16.79 | 32.27 | 34.25 | 11.02 |
| C15871 | 1575 | EST | 3.26 | 0.00046 | 13.83 | 18.19 | 16.99 | 79.77 | 83.41 | 40.17 |
| C16420 | 1576 | EST | 5.95 | 0.00119 | 26.92 | 20.84 | 24.82 | 205.53 | 234.17 | 120.92 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| C18029 | 1577 | tumor susceptibility gene 101 | #N/A | #N/A | 27.46 | 26.72 | 26.09 | 94.81 | 95.79 | 33.89 |
| D12620 | 1601 | cytochrome P450, subfamily IVF, polypeptide 2, cytochrome P450, subfamily IVF, polypeptide 3 (leukotriene B4 omega hydroxylase) | 35.09 | 0.00015 | 41.08 | 36.71 | 10.11 | 604.7 | 631.98 | 249.32 |
| D13243 | 1602 | pyruvate kinase, liver and RBC | 20.22 | 0 | −35.85 | −34.85 | 51.7 | 579.28 | 445.53 | 502 |
| D14012 | 1612 | HGF activator | 12.75 | 0.0035 | 160.15 | 216.05 | 107.03 | 1705.96 | 1963.23 | 794.42 |
| D16626 | 1622 | histidine ammonia-lyase | 22.66 | 0 | 11.74 | 8.13 | 16.04 | 538.78 | 535.2 | 166.14 |
| D16626 | 1622 | histidine ammonia-lyase | 22.66 | 0 | 12.06 | 22.91 | 55.95 | 289.6 | 256.22 | 113.59 |
| D45288 | 1661 | EST | #N/A | #N/A | −33.07 | 27.77 | 31.63 | 32.56 | 42.02 | |
| D50312 | 1669 | potassium inwardly-rectifying channel, subfamily J, member 8 | #N/A | #N/A | −2.39 | 3.94 | 24.71 | 76.55 | 72.56 | 48.96 |
| D57823 | 1690 | Sec23 (S. cerevisiae) homolog A | 4.43 | 0 | 13.37 | 13.08 | 8.38 | 94.25 | 87.66 | 30.56 |
| D57916 | 1691 | EST | #N/A | #N/A | 67.05 | 42.08 | 79.49 | 126.25 | 103.85 | 69.38 |
| D61991 | 1706 | EST | 4.84 | 0.00005 | 22.03 | 21.01 | 10.8 | 131.66 | 150.48 | 60.06 |
| D62103 | 1707 | EST | 4.11 | 0.0263 | 96.52 | 111.02 | 79.07 | 349.4 | 258.95 | 229.11 |
| H19089 | 1894 | EST | #N/A | #N/A | 76.83 | 44.82 | 89.14 | 76.54 | 74.4 | 40.21 |
| H20627 | 1898 | EST | #N/A | #N/A | 30.59 | 30.04 | 23.84 | 79.8 | 87.46 | 43.37 |
| H39627 | 1920 | EST | #N/A | #N/A | 73.92 | 101.48 | 54.09 | 155.43 | 158.44 | 39.98 |
| H61002 | 1967 | EST | #N/A | #N/A | 68.96 | 23.38 | 102.25 | 88.87 | 93.79 | 36.34 |
| H66367 | 1977 | EST | 6.68 | 0.0001 | −5.44 | −2.13 | 18.66 | 155.38 | 149.31 | 70.77 |
| H72650 | 1994 | EST | #N/A | #N/A | 81.21 | 98.79 | 41.38 | 122 | 125 | 42.24 |
| J00098 | 2086 | apolipoprotein A-I, apolipoprotein C-III | #N/A | #N/A | 96.71 | 29.74 | 269.46 | 9836.26 | 8356.89 | 8217.05 |
| K03192 | 2127 | cytochrome P450, subfamily IIA (phenobarbital-inducible), polypeptide 6 cytochrome P450, subfamily IIA | 69.92 | 0 | 3.07 | 9.83 | 30.14 | 1767.25 | 1790.36 | 741.7 |
| K03192 | 2127 | (phenobarbital-inducible), polypeptide 6 | 69.92 | 0 | −1.32 | −6.49 | 12.52 | 1087.08 | 1034.79 | 451.92 |
| L11244 | 2155 | complement component 4-binding protein, beta | 43.33 | 0 | 0.49 | −8.84 | 36.95 | 1147.16 | 1114.71 | 441.14 |
| L11244 | 2155 | complement component 4-binding protein, beta | 43.33 | 0 | −13.27 | −16.78 | 12.92 | 292.9 | 341.12 | 114.93 |
| L26336 | 2185 | heat shock 70kD protein 2 | #N/A | #N/A | 15.67 | 14.08 | 10.72 | 31.12 | 33.86 | 10.1 |
| L41067 | 2213 | nuclear factor of activated T-cells, cytoplasmic 3 | 4.96 | 0.00473 | 57.54 | 60.41 | 36.65 | 261.77 | 228.95 | 119.65 |
| L41067 | 2213 | nuclear factor of activated T-cells, cytoplasmic 3 | 4.96 | 0.00473 | 30.25 | 13.66 | 32.44 | 73.87 | 77.38 | 52.02 |
| L44424 | 2216 | UMP-CMP kinase | #N/A | #N/A | 23.79 | 18.2 | 26.85 | 57.57 | 43.3 | 36.92 |
| M12712 | 2246 | protein C (inactivator of coagulation factors Va and VIIIa) | 7.37 | 0.01866 | 107.12 | 177.74 | 113.63 | 646.94 | 628.19 | 326.15 |
| M12759 | 2247 | EST | #N/A | #N/A | 27.23 | 21.91 | 28.99 | 97.65 | 103.06 | 53.91 |
| M14777 | 2263 | glutathione S-transferase A2, glutathione S-transferase A3 | #N/A | #N/A | −24.81 | −27.52 | 27.54 | 2842.35 | 2790.19 | 1048.69 |
| M16974 | 2277 | complement component 8, alpha polypeptide | 49.47 | 0.00046 | 28.24 | −6.62 | 84.02 | 1843.82 | 1920.94 | 524.62 |
| M26393 | 2309 | acyl-Coenzyme A dehydrogenase, C-2 to C-3 short chain | 16.27 | 0.00007 | 16.81 | 12.39 | 48.16 | 677.3 | 775.54 | 358.47 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| M30185 | 2321 | cholesteryl ester transfer protein, plasma | 3.83 | 0.0013 | −37.15 | −29.18 | 28.09 | 93.07 | 86.04 | 61.35 |
| M61854 | 2370 | cytochrome P450, subfamily IIC (mephenytoin 4-hydroxylase) | 3.3 | 0.04185 | 52.7 | 55.56 | 44.01 | 321.6 | 166.36 | 430.71 |
| M95767 | 2431 | chitobiase, di-N-acetyl- | 4.94 | 0.00004 | 26.01 | 37.13 | 21.53 | 173.07 | 153.03 | 95 |
| N27670 | 2473 | progesterone membrane binding protein | 6.15 | 0.00321 | 38.66 | 15.48 | 47.19 | 252.94 | 292.34 | 133.48 |
| N40320 | 2513 | EST | 7.56 | 0.01584 | 99.72 | 83.43 | 128.45 | 558.37 | 595.16 | 250.67 |
| N57464 | 2575 | CCAAT/enhancer binding protein (C/EBP), delta | 14.69 | 0.00018 | 22.28 | 11.43 | 38.78 | 429.29 | 442.58 | 169.83 |
| N75120 | 2689 | EST | #N/A | #N/A | 20.59 | 23.42 | 10.65 | 61.42 | 58.88 | 13.84 |
| N87590 | 2706 | EST | #N/A | #N/A | 1.04 | −3.72 | 9.99 | 64.67 | 59.2 | 35.53 |
| N94146 | 2738 | EST | 8.05 | 0 | 28.92 | 34.7 | 14.14 | 258.82 | 265.55 | 101.53 |
| N99542 | 2746 | orosomucoid 1 | 8.41 | 0.00001 | 6.74 | 10.14 | 21.89 | 226.06 | 187.68 | 146.11 |
| R19808 | 2795 | EST | #N/A | #N/A | 9.95 | 12.2 | 25.55 | 27.53 | 25.43 | 10.61 |
| R31641 | 2813 | EST | 9.96 | 0.00011 | 29.02 | 21.83 | 31.18 | 350.89 | 330.68 | 166.29 |
| R63545 | 2926 | EST | 5.4 | 0.00202 | 2.58 | 9.54 | 17.4 | 157.98 | 128.33 | 139.55 |
| R64534 | 2933 | EST | #N/A | #N/A | 12.11 | 14.54 | 5.77 | 40.32 | 40.98 | 17.27 |
| R71459 | 2952 | differentially expressed in adenocarcinoma of the lung | #N/A | #N/A | 16.9 | 11.46 | 16.47 | 37.42 | 30.98 | 20.83 |
| R77539 | 2964 | EST | #N/A | #N/A | 5.91 | 14.55 | 25.48 | 70.5 | 59.8 | 31.72 |
| R82229 | 2974 | phosphatidylserine decarboxylase | 3.08 | 0.03455 | 84.63 | 80.61 | 67.01 | 228.19 | 232.06 | 58.36 |
| R98073 | 3008 | EST | 46.87 | 0 | −4.33 | −9.52 | 11.43 | 1161.51 | 1291.95 | 564.26 |
| S62539 | 3021 | insulin receptor substrate 1 | 3.7 | 0.01307 | 28.26 | 13.05 | 40.92 | 132.59 | 97.52 | 103.35 |
| S72370 | 3029 | pyruvate carboxylase | 5.31 | 0.00075 | 3.83 | 5.81 | 23.1 | 113.03 | 118.49 | 50.19 |
| T08879 | 3048 | cathepsin F | 5.29 | 0.0008 | 17.98 | 14.06 | 12.92 | 156.33 | 180.88 | 79.67 |
| T57140 | 3151 | paraoxonase 3 | 28.8 | 0 | −1.37 | −7.55 | 22.26 | 825.16 | 979.66 | 487.32 |
| T68083 | 3184 | short-chain dehydrogenase/reductase 1 | 4.03 | 0.01593 | 65.11 | 47.59 | 67.87 | 263.22 | 280.22 | 136.48 |
| T68510 | 3186 | EST | 3.87 | 0.00617 | 0.88 | −1.97 | 11.33 | 113.31 | 94.26 | 103.92 |
| T69384 | 3197 | phytanoyl-CoA hydroxylase (Refsum disease) | 5.88 | 0.01219 | 37.94 | 19.8 | 90.03 | 232.84 | 205.78 | 126.44 |
| T83397 | 3232 | KIAA1051 protein | 63.6 | 0 | −17.97 | −4.64 | 35.51 | 1404.6 | 1421.69 | 605.99 |
| T95813 | 3261 | UDP glycosyltransferase 2 family, polypeptide B15 | 38.38 | 0.00008 | 56.83 | 42.22 | 56.86 | 2271.29 | 1809.29 | 1537.82 |
| U06641 | 3286 | follistatin-like 1 | 24.32 | 0.00001 | 56.39 | 62.92 | 54.9 | 1762.46 | 1615.25 | 1206.06 |
| U06863 | 3287 | apolipoprotein C-IV | 3.09 | 0.00091 | 43.48 | 45.73 | 14.83 | 141.97 | 149.4 | 59.45 |
| U32576 | 3346 | apolipoprotein C-IV | 18.59 | 0.00005 | 311.97 | 318.75 | 271.42 | 1299.4 | 1145.33 | 698.02 |
| U32576 | 3346 | myosin VIIA (Usher syndrome 1B (autosomal recessive, severe)) | 18.59 | 0.00005 | −7.01 | −23.2 | 62.7 | 606.88 | 608.66 | 224.72 |
| U39226 | 3357 | deoxyribonuclease 1-like 3 | #N/A | #N/A | 33.54 | 31.07 | 8.59 | 53.24 | 50.47 | 20.86 |
| U56814 | 3392 | dermatan sulphate proteoglycan 3 | 29.43 | 0.00003 | 5.04 | 11.75 | 22.3 | 853.78 | 1073.24 | 434.79 |
| U59111 | 3396 | ATP-binding cassette, sub-family A (ABC1), member 5 | #N/A | #N/A | 32.34 | 26.73 | 15.11 | 68.69 | 64.44 | 32.48 |
| U66672 | 3406 | glutamic-pyruvate transaminase (alanine aminotransferase) | #N/A | #N/A | 78.03 | 41.24 | 72.76 | 105.45 | 97.64 | 60.15 |
| U70732 | 3414 | glutamic-pyruvate transaminase (alanine aminotransferase) | 27.63 | 0 | −47.95 | −65.21 | 50.88 | 696.22 | 732.8 | 284.7 |
| U70732 | 3414 | glutamic-pyruvate transaminase (alanine aminotransferase) | 27.63 | 0 | −1.44 | 3.98 | 66.42 | 201.88 | 218.68 | 136.17 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| U82108 | 3440 | solute carrier family 9 (sodium/hydrogen exchanger), isoform 3 regulatory factor 2 | 3.19 | 0.01545 | 58.61 | 78.15 | 43.49 | 130.34 | 122.39 | 73.74 |
| U95090 | 3463 | nephrosis 1, congenital, Finnish type (nephrin) | 14.01 | 0.00018 | 40.49 | 30.15 | 38.71 | 554.93 | 539.41 | 183.55 |
| U95090 | 3463 | nephrosis 1, congenital, Finnish type (nephrin) | 14.01 | 0.00018 | 4.97 | 5.87 | 18.32 | 188.83 | 201.08 | 88.01 |
| W02027 | 3464 | EST | #N/A | #N/A | 7.28 | 2.64 | 14.09 | 30.56 | 28.52 | 12.47 |
| W03796 | 3467 | EST | 8.3 | 0.0032 | 8.13 | −19.16 | 75.11 | 336.51 | 383.56 | 190.14 |
| W16686 | 3475 | basic helix-loop-helix domain containing, class B, 2 | #N/A | #N/A | 46.29 | −6.45 | 123.94 | 100.9 | 83.13 | 79.01 |
| W27503 | 3485 | KIAA0679 protein | #N/A | #N/A | 17.31 | 17.31 | 21.95 | 27.71 | 27.51 | 5.28 |
| W28235 | 3486 | EST | #N/A | #N/A | 95.97 | 150.37 | 81.4 | 271.36 | 307.26 | 108.42 |
| W28824 | 3492 | EST | 15.8 | 0.00006 | −1.99 | −5.59 | 17.64 | 441.67 | 509.29 | 251 |
| W36290 | 3500 | Kreisler (mouse) maf-related leucine zipper homolog | 3.94 | 0.02718 | 48.52 | 10.45 | 73.21 | 157.7 | 156.24 | 65.15 |
| W38778 | 3504 | EST | #N/A | #N/A | −55.97 | −63.87 | 44.35 | 78.01 | 37.07 | 137.01 |
| W52581 | 3540 | CD36 antigen (collagen type I receptor, thrombospondin receptor)-like 2 (lysosomal integral membrane protein II) | 3.08 | 0.00091 | 10.92 | 8.89 | 10.63 | 71.35 | 58.02 | 37.28 |
| W58520 | 3549 | nucleoporin 88kD | #N/A | #N/A | 24.77 | 26.75 | 16.56 | 81.88 | 87.47 | 37.77 |
| W81053 | 3607 | EST | 4.91 | 0.00164 | −21.38 | −13.04 | 24.17 | 135.84 | 109.34 | 113.36 |
| X02160 | 3668 | insulin receptor | 5.29 | 0.0001 | 10.06 | 8.21 | 10.89 | 77.32 | 65.71 | 45.53 |
| X07618 | 3688 | cytochrome P450, subfamily IID (debrisoquine, sparteine, etc., -metabolising), polypeptide 7a (pseudogene) | 35.79 | 0.00065 | 59.61 | 12.32 | 101.97 | 1429.98 | 1631.04 | 671.55 |
| X07618 | 3688 | cytochrome P450, subfamily IID (debrisoquine, sparteine, etc., -metabolising), polypeptide 7a (pseudogene) | 35.79 | 0.00065 | 40.81 | 38.21 | 14.35 | 609.22 | 605.91 | 330.02 |
| X14787 | 3701 | thrombospondin 1 | 3.69 | 0.01115 | 21.81 | 22.87 | 7.7 | 143.24 | 86.81 | 166.32 |
| X16260 | 3707 | inter-alpha (globulin) inhibitor, H1 polypeptide | 44.65 | 0.00933 | 40.4 | 36.54 | 67 | 1261.99 | 1133 | 523.31 |
| X60673 | 3749 | adenylate kinase 3 | 8.3 | 0.00016 | 23.02 | 32.17 | 44.24 | 331.58 | 324.75 | 164.03 |
| X92475 | 3821 | ITBA1 gene | #N/A | #N/A | 56.74 | 63.84 | 25.6 | 66.2 | 63.72 | 20.36 |
| Y00317 | 3842 | UDP glycosyltransferase 2 family, polypeptide B4 | 18.34 | 0.00001 | −9.82 | −11.91 | 20.96 | 456.09 | 477.28 | 257.07 |
| Y00317 | 3842 | UDP glycosyltransferase 2 family, polypeptide B4 | 18.34 | 0.00001 | 11.31 | 14.85 | 7.33 | 231.32 | 282.35 | 122.76 |
| Y10659 | 3856 | interleukin 13 receptor, alpha 1 | 4.22 | 0.00061 | 18.27 | 12.85 | 25.15 | 123.23 | 134.47 | 49.24 |
| Y10659 | 3856 | interleukin 13 receptor, alpha 1 | 4.22 | 0.00061 | 15.82 | 16.3 | 16.79 | 81.75 | 89.09 | 37.01 |
| Y12711 | 3858 | progesterone binding protein | 14.83 | 0.00285 | 26.37 | 16.12 | 99.79 | 1061.83 | 935.43 | 829.85 |
| Z29481 | 3874 | 3-hydroxyanthranilate 3,4-dioxygenase | 6.39 | 0.00029 | 546.48 | 440.33 | 293.12 | 2012.12 | 1797.38 | 944.18 |
| Z30425 | 3875 | nuclear receptor subfamily 1, group I, member 3 | 26.64 | 0 | 5.66 | 7.49 | 8.02 | 181.6 | 192.48 | 76.65 |
| Z48475 | 3940 | glucokinase (hexokinase 4) regulatory protein | 13.84 | 0 | −42.61 | −53.52 | 23.46 | 305.23 | 239.52 | 155.98 |
| AA004707 | 10 | copper chaperone for superoxide dismutase | #N/A | #N/A | 217.76 | 217.72 | 144.41 | 502.14 | 479.38 | 161.01 |
| AA005202 | 12 | retinol-binding protein 4, interstitial | 3.18 | 0.00106 | 43.46 | 41.24 | 9.66 | 163.36 | 107.5 | 110.2 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| AA010619 | 27 | EST | 8.55 | 0.00057 | 21.58 | 5.47 | 42.99 | 279.66 | 268.6 | 154.98 |
| AA017146 | 36 | EST | 10.1 | 0.00052 | 30.35 | 22.85 | 50.05 | 414.24 | 435.09 | 193.39 |
| AA019715 | 41 | EST | #N/A | #N/A | 8.03 | 8.03 | 6.49 | 15.9 | 14.58 | 7.82 |
| AA024866 | 49 | EST | #N/A | #N/A | 10.89 | 7.87 | 8.56 | 31.16 | 30.56 | 14.26 |
| AA025930 | 52 | EST | 3.59 | 0.00372 | 33.24 | 25.62 | 26.11 | 115.2 | 110.13 | 45.17 |
| AA032250 | 73 | EST | 3.56 | 0.0009 | 10.56 | 13.86 | 9.55 | 84.44 | 83.69 | 50.06 |
| AA043790 | 99 | KIAA0937 protein | #N/A | #N/A | 5.63 | 7.44 | 12.94 | 32.16 | 31.34 | 10.66 |
| AA045481 | 107 | EST | #N/A | #N/A | 28.81 | 21.88 | 17.14 | 71.32 | 63.94 | 38.49 |
| AA046747 | 114 | EST | 4.82 | 0.00022 | -5.19 | -4.2 | 10.73 | 113.78 | 88.54 | 66.41 |
| AA053917 | 131 | EST | #N/A | #N/A | -18.24 | -11.6 | 21.61 | 56.08 | 38.68 | 82.71 |
| AA055992 | 136 | calumenin | 3.51 | 0.00604 | 80.45 | 65.8 | 47.34 | 276.06 | 265.13 | 141.34 |
| AA056735 | 142 | SEC24 (S. cerevisiae) related gene family, member D | #N/A | #N/A | 4.59 | 10.03 | 14.42 | 29.84 | 28.43 | 10.97 |
| AA076672 | 172 | EST | #N/A | #N/A | 86.18 | 87.53 | 60.88 | 122.82 | 105.84 | 54.8 |
| AA084286 | 176 | paternally expressed gene 3 | #N/A | #N/A | -2.06 | 0.32 | 14.88 | 30.7 | 26.84 | 20.69 |
| AA084318 | 177 | EST | #N/A | #N/A | 9.73 | 3.97 | 17.06 | 30.63 | 32.37 | 11.48 |
| AA098864 | 205 | EST | #N/A | #N/A | 30.42 | 31.06 | 18.38 | 56.43 | 52.57 | 21.3 |
| AA102098 | 218 | EST | #N/A | #N/A | -1.8 | -5.18 | 15.21 | 21.79 | 20.01 | 6.78 |
| AA102571 | 220 | EST | #N/A | #N/A | 8.7 | 12.32 | 15.12 | 17.15 | 15.33 | 7.6 |
| AA116075 | 234 | EST | #N/A | #N/A | 29.71 | 23.88 | 10 | 62.94 | 64.79 | 25.13 |
| AA121140 | 235 | EST | 3.33 | 0.00058 | 6.67 | 5.82 | 3.73 | 74.84 | 83.56 | 31.9 |
| AA121257 | 236 | EST | #N/A | #N/A | 21.76 | 21.21 | 32.49 | 42.39 | 43.62 | 11.55 |
| AA128177 | 258 | sequence-specific single-stranded-DNA-binding protein | #N/A | #N/A | 11.71 | 6.05 | 16.96 | 44.4 | 33.57 | 33.54 |
| AA133215 | 277 | calcitonin receptor-like receptor activity modifying protein 1 | 4.55 | 0.02092 | 76.1 | 37.86 | 72.97 | 250.94 | 266.82 | 64.2 |
| AA136611 | 303 | EST | #N/A | #N/A | 9.05 | 6.82 | 8.39 | 48.23 | 42.67 | 13.53 |
| AA136940 | 305 | EST | #N/A | #N/A | 40.81 | 41.78 | 20.7 | 79.13 | 73.37 | 41.89 |
| AA147626 | 316 | EST | #N/A | #N/A | 37.93 | 20.43 | 44.09 | 82.38 | 75.98 | 37.45 |
| AA147646 | 317 | DKFZP586A0522 protein | 21.82 | 0 | 15.59 | 14.85 | 24.51 | 610.52 | 685.45 | 288.9 |
| AA148480 | 318 | flavin containing monooxygenase 5 | 19.64 | 0 | 18.26 | 14.26 | 14.85 | 521.95 | 407.11 | 247.99 |
| AA148539 | 319 | EST | #N/A | #N/A | 9.96 | 9.87 | 8.65 | 28.88 | 25.89 | 6.73 |
| AA150205 | 328 | EST | #N/A | #N/A | -1.1 | -1.72 | 9.15 | 8.12 | 7.44 | 9.59 |
| AA150284 | 329 | EST | #N/A | #N/A | 28.51 | 25.35 | 17.97 | 41.67 | 43.94 | 18.29 |
| AA151243 | 334 | EST | #N/A | #N/A | 1.13 | -0.17 | 14.55 | 43.61 | 42.74 | 11.08 |
| AA182030 | 387 | EST | 8.32 | 0.00018 | 14.05 | 16.82 | 12.13 | 222.23 | 220.01 | 117.56 |
| AA182568 | 388 | STAT induced STAT inhibitor-2 | 10.92 | 0.00099 | 23.5 | 18.15 | 21.15 | 501.87 | 386.2 | 478.02 |
| AA187437 | 389 | EST | #N/A | #N/A | 33.59 | 47.3 | 26.91 | 62.23 | 63 | 25.01 |
| AA193671 | 405 | KIAA0580 protein | #N/A | #N/A | 40.18 | 43.2 | 23.51 | 64.83 | 38.29 | 71.28 |
| AA195657 | 419 | EST | #N/A | #N/A | 5.72 | 7.44 | 9.74 | 157.7 | 136.21 | 100.68 |
| AA211370 | 432 | EST | 6.44 | 0.00016 | 27.26 | 29.44 | 16.5 | 44.85 | 45.87 | 21.25 |
| AA227968 | 461 | histone deacetylase 6 | #N/A | #N/A | 177.49 | 137.57 | 94.86 | 349.29 | 340.4 | 101.81 |
| AA233126 | 466 | EST | #N/A | #N/A | 48.86 | 59.64 | 33.59 | 88.56 | 74.17 | 35.35 |
| AA233369 | 471 | histidine ammonia-lyase | 9.06 | 0.0008 | 49.39 | 47.92 | 39.8 | 425.35 | 405.81 | 214.85 |
| AA233763 | 472 | EST | 4.61 | 0.00004 | 25.29 | 36.26 | 17.49 | 146.52 | 139.66 | 60.53 |
| AA234717 | 489 | EST | #N/A | #N/A | 10.99 | 5.01 | 20.04 | 50.22 | 53.32 | 31.32 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| AA234831 | 491 | EST | 3.42 | 0.00206 | 23.54 | 21.62 | 28.81 | 112.19 | 119 | 49.23 |
| AA242822 | 524 | EST | #N/A | #N/A | 9.44 | 13.66 | 8.25 | 27.21 | 25.96 | 16.64 |
| AA243654 | 532 | EST | #N/A | #N/A | 0.67 | 3.93 | 11.08 | 69.19 | 62.85 | 48.63 |
| AA251114 | 539 | prostate cancer overexpressed gene 1 | 6.6 | 0.00039 | 28.47 | 18.55 | 28.89 | 219.81 | 202.99 | 87.55 |
| AA251776 | 545 | jun D proto-oncogene | #N/A | #N/A | 30.8 | 23.59 | 32.23 | 51.25 | 46.83 | 15.96 |
| AA251845 | 548 | EST | #N/A | #N/A | 269.35 | 283.55 | 60.62 | 477.47 | 411.47 | 377.99 |
| AA253410 | 564 | EST | #N/A | #N/A | 18.46 | 7.23 | 42.79 | 49.37 | 26.82 | 45.2 |
| AA255546 | 569 | EST | 4 | 0.00301 | 61.04 | 67.88 | 31.64 | 260.34 | 224.12 | 142.84 |
| AA256990 | 585 | EST | #N/A | #N/A | 8.43 | 11.36 | 27.79 | 15.63 | 16.56 | 6.89 |
| AA258158 | 588 | EST | 13.15 | 0.00001 | 7.91 | 2.43 | 17.94 | 44.84 | 34.32 | 35.63 |
| AA259064 | 602 | EST | #N/A | #N/A | 15.32 | -1.37 | 28.67 | 401.93 | 394.99 | 178.23 |
| AA278670 | 616 | EST | #N/A | #N/A | 7.44 | 11.47 | 12.63 | 54.24 | 49.98 | 28.69 |
| AA278824 | 619 | EST | #N/A | #N/A | 26.85 | 31.59 | 11.72 | 83.48 | 91.25 | 30.24 |
| AA278853 | 621 | EST | #N/A | #N/A | 10.28 | 11.7 | 21.49 | 42.68 | 43.68 | 17.64 |
| AA279341 | 625 | EST | #N/A | #N/A | 67.56 | 80.37 | 50.19 | 132.89 | 118.11 | 67.28 |
| AA281545 | 645 | EST | 3.64 | 0.00002 | 6.52 | -0.81 | 16.89 | 87.27 | 85.27 | 34.29 |
| AA281770 | 649 | seven in absentia (Drosophila) homolog 1 | 3.96 | 0.00094 | 7.67 | 4.72 | 15.41 | 103.75 | 79.4 | 70.74 |
| AA281796 | 650 | mannose-P-dolichol utilization defect 1 | 3.3 | 0.04108 | 65.08 | 53.58 | 57.86 | 170.88 | 165.02 | 41.87 |
| AA283066 | 666 | EST | #N/A | #N/A | 21.18 | 25.64 | 13.39 | 67.44 | 59.46 | 35.89 |
| AA284795 | 678 | phosphatidylethanolamine N-methyltransferase | 10.03 | 0.00019 | 44.8 | 62.07 | 44.12 | 514.93 | 591.52 | 206.4 |
| AA286710 | 683 | lymphocyte adaptor protein | #N/A | #N/A | 37.88 | 39.15 | 30.32 | 82.93 | 86.15 | 45.58 |
| AA287566 | 690 | KIAA0187 gene product | 9.07 | 0.00013 | 4.86 | 6.24 | 7.4 | 246.24 | 201.66 | 228.64 |
| AA291293 | 698 | EST | #N/A | #N/A | 17.35 | 18.07 | 17.24 | 33.6 | 33.3 | 5.56 |
| AA342918 | 750 | EST | #N/A | #N/A | 23.67 | 31.68 | 25.77 | 69.4 | 73.71 | 18.13 |
| AA365691 | 763 | EST | #N/A | #N/A | 48.01 | 47.17 | 25.37 | 28.69 | 26.73 | 13.89 |
| AA397904 | 781 | EST | #N/A | #N/A | 22.74 | 18.55 | 19.05 | 59.75 | 54.83 | 32.24 |
| AA398124 | 787 | growth factor receptor-bound protein 14 | 7.82 | 0.00009 | 3.4 | 5.86 | 7.61 | 189.27 | 167.23 | 110.44 |
| AA393386 | 793 | EST | 5.71 | 0.00007 | 10.59 | 16.25 | 21.59 | 153.16 | 164.38 | 83.94 |
| AA398423 | 795 | EST | 8.26 | 0.00063 | -17.3 | -16.19 | 23.92 | 230.91 | 250.5 | 156.29 |
| AA398674 | 798 | thrombospondin 1 | #N/A | #N/A | -27.87 | 14.49 | 146.65 | 137.87 | 96.14 | 119.21 |
| AA400979 | 825 | calcitonin receptor-like receptor activity modifying protein 3 | 6.65 | 0.01051 | 48.89 | 21.04 | 80.4 | 276.38 | 267.3 | 88.7 |
| AA401091 | 826 | EST | #N/A | #N/A | 31.88 | 32.59 | 43.51 | 30.55 | 19.82 | 28.68 |
| AA402224 | 836 | growth arrest and DNA-damage-inducible, gamma | 14.41 | 0.00012 | 37.55 | 48.88 | 48.58 | 749.36 | 812.2 | 443.66 |
| AA402610 | 839 | EST | #N/A | #N/A | 3.02 | 6.69 | 13.83 | 27.54 | 23.2 | 17.78 |
| AA402656 | 841 | KIAA0548 protein | 12.05 | 0.00001 | -2.56 | 18.8 | 40.57 | 342.11 | 315.47 | 205.61 |
| AA404248 | 847 | EST | #N/A | #N/A | 11.96 | 11.18 | 10.84 | 40.92 | 35.06 | 17.49 |
| AA405495 | 859 | EST | #N/A | #N/A | 26.12 | 22.63 | 43.42 | 79 | 82.8 | 30.16 |
| AA405744 | 863 | EST | #N/A | #N/A | 61.18 | 28.74 | 58.71 | 64.39 | 57.95 | 35.67 |
| AA406363 | 874 | EST | #N/A | #N/A | 6.85 | 5.69 | 15.69 | 35.62 | 35.06 | 13.69 |
| AA406610 | 880 | EST | #N/A | #N/A | 5.99 | 6.04 | 4.63 | 35.94 | 34.84 | 11.57 |
| AA410255 | 882 | EST | 7.56 | 0.00043 | 0.82 | 4.15 | 11.49 | 195.75 | 236.93 | 110.49 |
| AA411795 | 892 | EST | #N/A | #N/A | 72.18 | 53.17 | 44.28 | 130.27 | 131.65 | 23.71 |
| AA412063 | 895 | EST | 8.26 | 0.00001 | 11.36 | 14.03 | 19.55 | 220.12 | 187.85 | 149.43 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| AA412149 | 897 | KIAA0480 gene product | #N/A | #N/A | 14.07 | 10.08 | 14.16 | 37.43 | 32.4 | 15.56 |
| AA412520 | 903 | EST | #N/A | #N/A | 18.84 | 14.4 | 14.11 | 80.29 | 103.19 | 41.98 |
| AA412700 | 904 | ubiquitin-conjugating enzyme E2L 6 | #N/A | #N/A | 139.65 | 95.44 | 135.61 | 275.39 | 273.98 | 112.87 |
| AA418398 | 921 | EST | #N/A | #N/A | 0.1 | −6.02 | 17.92 | 30.41 | 32 | 20.72 |
| AA421051 | 928 | serum-inducible kinase | #N/A | #N/A | 42.94 | 7.14 | 87.89 | 51.27 | 45.65 | 28 |
| AA421052 | 929 | branched chain alpha-ketoacid dehydrogenase kinase | 3.52 | 0.00869 | 77.76 | 94.75 | 43.63 | 251.45 | 221.35 | 109.93 |
| AA425214 | 950 | EST | #N/A | #N/A | 2.71 | 2.07 | 4.88 | 21.4 | 20.31 | 10.15 |
| AA426643 | 970 | EST | #N/A | #N/A | 9.96 | 0.97 | 18.11 | 48.26 | 47.37 | 23.47 |
| AA427537 | 974 | DKFZP566I153 protein | #N/A | #N/A | 183.26 | 156.56 | 68.58 | 259.57 | 242.97 | 79.81 |
| AA427579 | 975 | regulator of G-protein signalling 14 | #N/A | #N/A | 13.35 | 13.28 | 16.49 | 34.79 | 25.25 | 25.11 |
| AA427819 | 980 | midline 2 | 3.44 | 0.00063 | 25.98 | 17.06 | 14.91 | 97.03 | 93.49 | 31.39 |
| AA428150 | 985 | EST | 5.24 | 0.00167 | 41.92 | 35.06 | 30.53 | 213.96 | 217.27 | 76.08 |
| AA428325 | 988 | EST | 8.36 | 0.00002 | −0.52 | 3.28 | 16.92 | 194.02 | 167.37 | 111.11 |
| AA429478 | 998 | EST | 3.41 | 0.02599 | 55.86 | 65.19 | 47.48 | 192.7 | 196 | 89.2 |
| AA435591 | 1038 | kinesin family member 3B | 3.5 | 0.0001 | 3.57 | 3.68 | 10.34 | 75.9 | 81.12 | 29.32 |
| AA436156 | 1051 | EST | #N/A | #N/A | 22.66 | 7.78 | 34.68 | 54.98 | 48.35 | 38.09 |
| AA436548 | 1054 | EST | #N/A | #N/A | 5.08 | 5.93 | 5.2 | 40.27 | 38.99 | 22.22 |
| AA436880 | 1058 | EST | 3.22 | 0.00699 | 4.71 | 9.21 | 13.85 | 86.89 | 68.41 | 66.5 |
| AA437295 | 1062 | ribosomal protein L7a | 4.35 | 0.00347 | 19.67 | 20.38 | 43.07 | 139.16 | 140.38 | 70.9 |
| AA443658 | 1079 | transmembrane 7 superfamily member 2 | 9.06 | 0.00048 | 4.48 | 17.91 | 24.51 | 276.02 | 194.73 | 227.48 |
| AA447802 | 1108 | EST | #N/A | #N/A | 15.64 | 17.7 | 13.81 | 21.51 | 21.34 | 7.37 |
| AA449108 | 1118 | EST | #N/A | #N/A | 10.9 | 18.13 | 15.28 | 52.58 | 57.3 | 23.76 |
| AA449297 | 1121 | EST | 3.78 | 0.00039 | 3.76 | 0.63 | 19.01 | 91.67 | 81.15 | 55.17 |
| AA454667 | 1167 | EST | #N/A | #N/A | 21.25 | 12.77 | 23.4 | 83.02 | 75.81 | 56.63 |
| AA455111 | 1173 | heterogeneous nuclear ribonucleoprotein C (C1/C2) | #N/A | #N/A | −31.71 | −40.39 | 38.45 | 38.96 | 36.83 | 26.21 |
| AA455261 | 1175 | chromobox homolog 7 | #N/A | #N/A | 32.5 | 45.54 | 26.51 | 66.78 | 66.08 | 30.15 |
| AA455865 | 1180 | phosphatidylinositol glycan, class B | 5.41 | 0.00004 | 11.68 | 8.67 | 10.65 | 133.15 | 134.74 | 63.3 |
| AA455987 | 1183 | EST | 5.36 | 0.00029 | 20.54 | 17.51 | 15.24 | 128.55 | 130.64 | 17.07 |
| AA455988 | 1184 | butyrobetaine (gamma), 2-oxoglutarate dioxygenase (gamma-butyrobetaine hydroxylase) | 15.54 | 0.00001 | 10.13 | 11.88 | 8.38 | 354.42 | 375.91 | 141.08 |
| AA456075 | 1186 | RAD23 (S. cerevisiae) homolog A | #N/A | #N/A | 33.34 | 38.35 | 32.93 | 90.47 | 66.92 | 66.03 |
| AA456080 | 1187 | EST | #N/A | #N/A | 32.35 | 17.59 | 33.21 | 27.76 | 26.18 | 12.38 |
| AA456147 | 1188 | general transcription factor IIIA | 4.23 | 0.00088 | 4.61 | 0.17 | 9.08 | 102.1 | 89.95 | 63.84 |
| AA456289 | 1189 | EST | 15.31 | 0.00004 | 18.07 | 17.84 | 39.22 | 512.64 | 542.52 | 303.15 |
| AA456612 | 1195 | EST | #N/A | #N/A | 164.11 | 136.36 | 117.01 | 254.26 | 266.45 | 84.11 |
| AA458652 | 1202 | EST | 8.26 | 0.00001 | 19.3 | 18.21 | 17.18 | 203.23 | 218.67 | 53.52 |
| AA459005 | 1210 | EST | #N/A | #N/A | −3.57 | 12.22 | 40.05 | 49.76 | 42.58 | 28.85 |
| AA461448 | 1240 | EST | #N/A | #N/A | 1.74 | −4.19 | 22.52 | 58.65 | 56.06 | 32.42 |
| AA464606 | 1261 | MRS1 protein | #N/A | #N/A | 24.35 | 19.03 | 39.62 | 59.55 | 36.75 | 57.76 |
| AA465720 | 1274 | EST | #N/A | #N/A | 11.5 | 21.33 | 37.22 | 93.06 | 108.97 | 43.26 |
| AA470153 | 1275 | solute carrier family 21 (organic anion transporter), member 9 | 13.26 | 0.00315 | 47.49 | 48.57 | 116.54 | 726.75 | 713.23 | 297.62 |
| | | homolog of mouse quaking QKI (KH domain | | | | | | | | |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| AA478104 | 1296 | RNA binding protein) | #N/A | #N/A | −7.07 | −11.44 | 23.2 | 62.06 | 47.17 | 56.07 |
| AA478441 | 1302 | cathepsin F | 5.07 | 0.00752 | 53.85 | 67.48 | 43.52 | 243.44 | 243.61 | 69.17 |
| AA479148 | 1311 | EST | 38.05 | 0 | 6.2 | 1.32 | 14.38 | 895.91 | 847.72 | 362.53 |
| AA479488 | 1313 | S-adenosylhomocysteine hydrolase-like 1 | 4 | 0.0269 | 75.18 | 60.93 | 59.8 | 241.1 | 222.96 | 112.87 |
| AA480091 | 1323 | EST | 8.59 | 0.00156 | 48.08 | 25.74 | 51.03 | 444.29 | 309.38 | 367.89 |
| AA487195 | 1354 | EST | #N/A | #N/A | 8.73 | 7.94 | 9.21 | 21.04 | 14.67 | 16.52 |
| AA487576 | 1357 | EST | #N/A | #N/A | −12.17 | −14.87 | 17.17 | 26.05 | 25.27 | 11.13 |
| AA489009 | 1366 | EST | #N/A | #N/A | 15.19 | 18.01 | 8.67 | 59.19 | 45.15 | 41.42 |
| AA490964 | 1384 | EST | #N/A | #N/A | 20.3 | 17.53 | 11.39 | 47.7 | 41.84 | 25.18 |
| AA495803 | 1392 | EST | #N/A | #N/A | 95.29 | 83.46 | 90.72 | 94.07 | 93.85 | 37.65 |
| AA495924 | 1395 | kinesin family member 3B | #N/A | #N/A | 4.16 | 3.28 | 2.95 | 35.69 | 34.43 | 19.93 |
| AA496053 | 1396 | EST | 3.28 | 0.00095 | 5.36 | 2.22 | 17.58 | 81.79 | 94.01 | 42.77 |
| AA496936 | 1403 | EST | #N/A | #N/A | 17.71 | 9.86 | 20.19 | 30.24 | 34.4 | 14.77 |
| AA504324 | 1412 | EST | #N/A | #N/A | 45.99 | 38.81 | 31.27 | 74.31 | 72.05 | 31.59 |
| AA521290 | 1421 | EST | 4.53 | 0.0148 | 46.54 | 22.84 | 63.63 | 166.84 | 174.65 | 58.28 |
| AA598412 | 1425 | EST | #N/A | #N/A | −2.4 | −5.93 | 29.83 | 59 | 52.53 | 29.41 |
| AA598453 | 1429 | EST | #N/A | #N/A | 7.27 | 7.06 | 9.67 | 67.15 | 54.25 | 41.65 |
| AA599107 | 1443 | EST | #N/A | #N/A | 53.34 | 10 | 88.85 | 77.28 | 58.08 | 40.75 |
| AA599214 | 1446 | EST | #N/A | #N/A | 10.94 | 7.36 | 12.27 | 34.58 | 36 | 14.54 |
| AA608546 | 1463 | EST | 12.52 | 0.00003 | −19.59 | −29.07 | 29.39 | 310.07 | 300.44 | 189.6 |
| AA608723 | 1467 | EST | #N/A | #N/A | 17.44 | 15.29 | 13.31 | 66.54 | 70.38 | 20.94 |
| AA609316 | 1481 | EGF-like-domain, multiple 5 | 7.97 | 0.00011 | 22.6 | 21.61 | 25.56 | 236.54 | 226.79 | 65.9 |
| AA609519 | 1482 | EST | 8.13 | 0.00009 | 29.3 | 22.08 | 22.59 | 261.82 | 243.76 | 105.33 |
| AA620965 | 1511 | NOT3 (negative regulator of transcription 3, yeast) homolog similar to Caenorhabditis elegans protein C42C1.9 | #N/A | #N/A | 4.34 | 8.96 | 16.51 | 48.05 | 40.77 | 32.06 |
| AA621209 | 1516 | EST | 6.34 | 0.00144 | 22.77 | 19.95 | 46.78 | 214.61 | 167.05 | 138.24 |
| AA621235 | 1517 | EST | 3.44 | 0.0021 | 26.29 | 24.68 | 23.17 | 114.75 | 113.36 | 65.35 |
| D56989 | 1687 | EST | #N/A | #N/A | 8.83 | 6.61 | 9.79 | 77.62 | 55.56 | 72.14 |
| D59294 | 1693 | EST | #N/A | #N/A | 1.31 | 0.89 | 6.58 | 22.83 | 20.84 | 14.1 |
| F04611 | 1792 | EST | 23.96 | 0.00018 | 42.65 | 18.88 | 62.74 | 1011.12 | 1040.46 | 589.37 |
| F04677 | 1794 | EST | #N/A | #N/A | 138.06 | 123.28 | 34.39 | 355.75 | 310.97 | 168.21 |
| F09350 | 1801 | EST | 4.79 | 0.00088 | 13.91 | −6.46 | 33.97 | 147.64 | 130.28 | 79.24 |
| F09687 | 1806 | EST | #N/A | #N/A | 12.72 | 8.26 | 28.12 | 58.85 | 57.03 | 31.82 |
| F09729 | 1807 | EST | #N/A | #N/A | 9.35 | 20.58 | 23.17 | 55.49 | 55.78 | 27.37 |
| F09979 | 1809 | EST | 4.36 | 0.02555 | 6.98 | 6.51 | 20.72 | 226.47 | 116.41 | 288.21 |
| F10149 | 1810 | EST | #N/A | #N/A | 111.86 | 108.46 | 60.06 | 257.05 | 276.87 | 165.09 |
| F10381 | 1817 | KIAA0541 protein | #N/A | #N/A | 22.16 | 25.03 | 8.75 | 64.94 | 71.82 | 26.24 |
| F10418 | 1818 | EST | #N/A | #N/A | 44.91 | 44.45 | 22.72 | 64.3 | 52.54 | 31.96 |
| F13624 | 1825 | breast cancer anti-estrogen resistance 3 | #N/A | #N/A | 27.76 | 19.2 | 32.49 | 90.8 | 73.79 | 59.27 |
| F13782 | 1827 | LIM binding domain 2 | 4.17 | 0.00109 | −0.64 | 5.61 | 22.4 | 100.8 | 119.01 | 55.07 |
| H01059 | 1830 | solute carrier family 16 (monocarboxylic acid transporters), member 4 | #N/A | #N/A | 9.13 | 9.22 | 13.53 | 32.73 | 34.27 | 21.05 |
| H02855 | 1832 | EST | 5.96 | 0.00458 | 5.06 | 1.15 | 14.13 | 261.57 | 93.25 | 407.93 |
| H05970 | 1849 | EST | #N/A | #N/A | 9.16 | 12.81 | 14.19 | 68.16 | 65.08 | 40.19 |
| H09331 | 1865 | EST | #N/A | #N/A | 313.2 | 309.79 | 122.67 | 512.04 | 486.42 | 149.27 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| H09353 | 1866 | EST | 23.06 | 0.00094 | 45.11 | 18.95 | 65.29 | 782.6 | 824.74 | 226.28 |
| H10661 | 1871 | EST | 4.54 | 0.00276 | 31.29 | 18.75 | 28.5 | 132.09 | 124.86 | 64.37 |
| H12593 | 1880 | zinc-finger protein 265 | 10.72 | 0.0056 | 39.96 | −9.15 | 111.74 | 515.58 | 506.07 | 224.5 |
| H19504 | 1895 | EST | 3.13 | 0.04948 | 77.07 | 49.48 | 64.05 | 227.6 | 221.91 | 125.23 |
| H20543 | 1897 | DKFZP586B1621 protein | 31.03 | 0.00074 | 62.11 | 36.98 | 80.24 | 1684.92 | 1680.81 | 731.79 |
| H24081 | 1901 | KIAA1035 protein | #N/A | #N/A | 19.72 | 18.46 | 5.69 | 24.15 | 27.08 | 9.52 |
| H25124 | 1903 | EST | 3.65 | 0.00004 | 20.47 | 14.4 | 12.59 | 95.09 | 85.36 | 34.91 |
| H29568 | 1914 | EST | 11.45 | 0.00058 | 232.54 | 140.09 | 218.85 | 2206.49 | 1884.76 | 783.84 |
| H30270 | 1915 | EST | 17.09 | 0.00001 | 61.64 | 60.29 | 25.01 | 1224.59 | 1332.66 | 695.76 |
| H49417 | 1939 | ATP-binding cassette, sub-family C (CFTR/MRP), member 6 | #N/A | #N/A | 16.93 | 17.31 | 8.56 | 62.68 | 54.75 | 48.37 |
| H52251 | 1942 | EST | #N/A | #N/A | 25.41 | 22.3 | 15.29 | 33.86 | 34.48 | 19.95 |
| H53829 | 1946 | EST | #N/A | #N/A | 44.31 | 40.52 | 36.62 | 99.9 | 98.22 | 46.1 |
| H56965 | 1952 | EST | #N/A | #N/A | 0.18 | 0.68 | 12.9 | 61.03 | 73.89 | 30.12 |
| H57850 | 1958 | protein phosphatase 2 (formerly 2A), regulatory subunit A (PR 65), beta isoform | 3.02 | 0.00123 | 41.36 | 36.05 | 15.14 | 131.12 | 130.36 | 53.67 |
| H58692 | 1960 | formyltetrahydrofolate dehydrogenase | 81.41 | 0 | −2.66 | 5.46 | 16.1 | 1886.69 | 1520.43 | 1129.35 |
| H60317 | 1965 | EST | #N/A | #N/A | 18.86 | 22.34 | 11.81 | 38.92 | 39.1 | 18.67 |
| H69565 | 1987 | EST | 4.11 | 0.00002 | 15.45 | 16.92 | 9.4 | 95.6 | 94.91 | 42.92 |
| H70485 | 1988 | EST | #N/A | #N/A | 113.44 | 81.62 | 63.73 | 232.9 | 256.86 | 107.1 |
| H70554 | 1989 | EST | 10.99 | 0 | −11.73 | −19.98 | 33.09 | 292.66 | 288.78 | 153.17 |
| H87765 | 2017 | KIAA0626 gene product | 3.86 | 0.00131 | 5.2 | 7.91 | 19.6 | 94.26 | 93.78 | 60.64 |
| H89980 | 2026 | protein phosphatase 1, regulatory (inhibitor) subunit 5 | 31.13 | 0.00006 | 12.16 | 13.82 | 12.3 | 990.48 | 1005.21 | 755.6 |
| H90417 | 2028 | EST | 4.17 | 0.015 | 14.23 | −10.79 | 70.02 | 191.04 | 154.37 | 125.5 |
| H93381 | 2036 | EST | 24.23 | 0 | 6.08 | −0.69 | 28.81 | 621.48 | 640.77 | 214.25 |
| H95079 | 2046 | EST | #N/A | #N/A | 7.05 | 11.03 | 7.33 | 39.79 | 33.3 | 29.08 |
| H95089 | 2047 | EST | #N/A | #N/A | 13.05 | 13.54 | 4.03 | 31.99 | 31.89 | 13.19 |
| H95358 | 2049 | EST | 3.17 | 0.00182 | −5.85 | −5.95 | 11.57 | 74.74 | 72.66 | 42.36 |
| H95978 | 2052 | EST | 8.55 | 0.00046 | 12.28 | 14.38 | 10.71 | 240.91 | 246.43 | 147.67 |
| H98083 | 2067 | EST | 5.09 | 0.00025 | 11.73 | 11.11 | 3.97 | 121.51 | 104.88 | 70.52 |
| N22404 | 2449 | EST | 3.99 | 0.01152 | 30.59 | 23.97 | 55.32 | 193.63 | 130.09 | 162.83 |
| N22434 | 2450 | EST | 4.37 | 0.01725 | 100.96 | 66.55 | 110.62 | 334.51 | 328.98 | 150.7 |
| N24879 | 2459 | EST | 9.44 | 0.00008 | 6.2 | 5.49 | 23.52 | 280.93 | 337.77 | 165.77 |
| N24973 | 2461 | EST | #N/A | #N/A | 30.46 | 28.45 | 11.29 | 56.57 | 59.09 | 22.87 |
| N25262 | 2464 | EST | #N/A | #N/A | 31.16 | 28.04 | 9.03 | 64.13 | 64.97 | 18.29 |
| N27524 | 2471 | EST | 3.13 | 0.00216 | 14.18 | 22.08 | 20.51 | 87.67 | 98.26 | 42.62 |
| N29353 | 2476 | kynurenine 3-monooxygenase (kynurenine 3-hydroxylase) | 4.78 | 0.00019 | −4.7 | −5.88 | 13.94 | 109.79 | 101.27 | 53.38 |
| N29543 | 2478 | EST | #N/A | #N/A | 11.66 | 9.07 | 5.04 | 59.21 | 51.22 | 30.43 |
| N29740 | 2479 | EST | #N/A | #N/A | 48.71 | 27.45 | 46.9 | 80.01 | 77.9 | 37.18 |
| N31952 | 2489 | EST | 3.13 | 0.01481 | 36.21 | 27.5 | 25.04 | 133.49 | 147.66 | 83.03 |
| N34804 | 2496 | DKFZP434f214 protein | 8.08 | 0.00028 | 6.99 | 5.94 | 33.73 | 344.08 | 176.4 | 532.11 |
| N34919 | 2498 | EST | 7.39 | 0 | 8 | 6.82 | 52.96 | 44.23 | 24.23 | |
| N36085 | 2504 | EST | 20.98 | #N/A | 19.21 | 13.89 | 58.28 | 58 | 22.95 | |
| N45320 | 2518 | EST | 11.39 | #N/A | 11.26 | 7.06 | 50.75 | 36 | 39.19 | |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| N45998 | 2519 | EST | 3.14 | 0.00337 | 28.42 | 22.62 | 13.52 | 99.42 | 110.53 | 49.55 |
| N48315 | 2526 | adaptor-related protein complex 2, mu 1 subunit | 5.3 | 0.0149 | 62.03 | 30.66 | 52.29 | 368.37 | 331.28 | 260.93 |
| N48674 | 2529 | EST | 4.06 | 0.00028 | 2.7 | 4.57 | 10.52 | 94.61 | 72.82 | 54.62 |
| N50038 | 2540 | EST | #N/A | #N/A | 0.25 | 5.19 | 45.95 | 47.04 | 41.45 | 16.56 |
| N54053 | 2560 | secreted phosphoprotein 2, 24kD | 60.39 | 0.00087 | 44.3 | -18.16 | 166.47 | 2749.73 | 2790.77 | 1230.33 |
| N54604 | 2569 | EST | 3.72 | 0.00741 | 2.36 | 2.08 | 35.23 | 133.06 | 119.1 | 109.95 |
| N54792 | 2570 | cytidine monophosphate-N-acetylneuraminic acid hydroxylase (CMP-N-acetylneuraminate monooxygenase) | 3.23 | 0.00099 | 28.36 | 27.42 | 6.39 | 110.19 | 77.69 | 87.32 |
| N59089 | 2580 | EST | 4.74 | 0.00055 | 38.4 | 36.58 | 24.6 | 215.54 | 167.6 | 133.64 |
| N59543 | 2586 | PDZ domain containing 1 | 9.96 | 0.00052 | 1.2 | -2.89 | 17.29 | 303.49 | 259.23 | 225.96 |
| N62922 | 2595 | EST | #N/A | #N/A | 14.92 | 14.15 | 2.75 | 54.94 | 52.4 | 18.93 |
| N63047 | 2596 | EST | #N/A | #N/A | 4.13 | 0.93 | 9.72 | 14.78 | 15.63 | 8.24 |
| N63698 | 2603 | EST | 7.92 | 0.00001 | 19.14 | 18.14 | 12.14 | 221.25 | 212.4 | 122.32 |
| N64436 | 2608 | EST | 3.51 | 0.00441 | 24.46 | 20.38 | 21.08 | 119.24 | 133.44 | 70.66 |
| N65959 | 2611 | EST | 5.43 | 0.00044 | 3.51 | 3.25 | 22.24 | 142.87 | 149.26 | 79.26 |
| N66613 | 2616 | EST | #N/A | #N/A | 25.61 | 22.34 | 26.39 | 62.58 | 50.13 | 51.99 |
| N68871 | 2637 | EST | 4.3 | #N/A | 4.3 | 4.02 | 8.66 | 34.08 | 36.71 | 14.33 |
| N70305 | 2654 | EST | 4.41 | 0.00078 | -13.99 | -13.48 | 10.76 | 105.8 | 97.72 | 72.15 |
| N71542 | 2664 | kidney- and liver-specific gene | 21.05 | 0 | -14.76 | -18.28 | 14.3 | 471.65 | 486.43 | 226.63 |
| N71935 | 2666 | multiple PDZ domain protein | 16.28 | 0 | 12.84 | 19.17 | 14.1 | 410.92 | 422.1 | 218.42 |
| N73883 | 2681 | EST | 9.35 | 0 | 18.47 | 23.48 | 17.67 | 256.78 | 276.41 | 95.34 |
| N74025 | 2684 | deiodinase, iodothyronine, type I | 22.79 | 0 | -7.64 | 2.14 | 15.95 | 527.67 | 515.68 | 256.99 |
| N74422 | 2685 | EST | 30.32 | 0 | 23.57 | 28.41 | 36.93 | 1063.07 | 1094.48 | 371.26 |
| N74624 | 2687 | collectin sub-family member 10 (C-type lectin) | #N/A | #N/A | 33.8 | 34.24 | 5.13 | 71.81 | 62.09 | 43.57 |
| N75072 | 2688 | EST | 3.73 | 0.00379 | 5.14 | 6.21 | 15.5 | 104.12 | 104.99 | 81.79 |
| N76086 | 2694 | EST | #N/A | #N/A | 8.23 | 7.19 | 6.54 | 55.55 | 55.02 | 35.47 |
| N91882 | 2719 | alpha2,3-sialyltransferase | 14.52 | 0.00024 | -0.18 | 0.18 | 34.36 | 512.3 | 550.51 | 320.62 |
| N93191 | 2729 | EST | 3.25 | 0.00232 | 174.54 | 168.53 | 56.36 | 659.95 | 565.08 | 409.15 |
| N93403 | 2733 | EST | #N/A | #N/A | 4.44 | 7.63 | 11.8 | 48.84 | 38.39 | 30.93 |
| N93764 | 2736 | EST | 5.92 | 0.0109 | 113.46 | 68.13 | 96.98 | 771.74 | 792.59 | 504.88 |
| R05490 | 2760 | SEC24 (S. cerevisiae) related gene family, member B | 3.03 | 0.00317 | 5.87 | 3.49 | 12.23 | 75.28 | 78.17 | 48.59 |
| R06002 | 2762 | EST | 10.15 | 0.00003 | 10.52 | 8.26 | 20.8 | 292.89 | 264.17 | 160.28 |
| R06543 | 2768 | EST | #N/A | #N/A | 61.75 | 61.42 | 88.77 | 163.57 | 144.04 | 96.98 |
| R06746 | 2770 | EST | 15.77 | 0.00009 | 13.37 | 7.19 | 39.24 | 455.48 | 410.16 | 191.35 |
| R06860 | 2772 | EST | #N/A | #N/A | 84.61 | 75.89 | 71.35 | 104.51 | 116.59 | 44.71 |
| R08564 | 2779 | plasminogen-like | 60.18 | 0.00091 | 69.78 | 24 | 105.91 | 2485.63 | 2384.62 | 531.43 |
| R09053 | 2782 | EST | 5.9 | 0.0002 | 6.45 | 17.17 | 35.01 | 186.87 | 204.61 | 113.19 |
| R10287 | 2784 | EST | 11.2 | 0.0003 | 7.46 | 4.94 | 35.03 | 376.82 | 434.91 | 198.74 |
| R10684 | 2787 | EST | 5.51 | 0.00741 | 28.67 | 1.31 | 62.39 | 217.05 | 221.32 | 122.94 |
| R12472 | 2788 | EST | 55.18 | 0.00011 | 32.21 | 3.13 | 76.26 | 2002.79 | 1930.03 | 1097.37 |
| R12579 | 2789 | EST | 3.5 | 0.00137 | 54.49 | 37.84 | 26.65 | 198.7 | 194.59 | 92.03 |
| R33146 | 2818 | EST | 7 | 0.00043 | 3.32 | 2.1 | 10.76 | 179.67 | 195.02 | 107 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| R34362 | 2821 | KIAA0327 gene product | 5.4 | 0.04615 | 621.7 | 353.73 | 689.66 | 2107.55 | 2121.04 | 1000.75 |
| R39238 | 2835 | synaptojanin 1 | #N/A | #N/A | 16.06 | 16.03 | 9.94 | 26.8 | 23.84 | 16.46 |
| R43347 | 2848 | downregulated in renal cell carcinoma | 5.37 | 0.00103 | 36.93 | 32.68 | 30.41 | 105.66 | 100.62 | 28.62 |
| R43365 | 2849 | EST | 5.71 | 0 | 5.57 | 6.67 | 12.18 | 150.58 | 112.8 | 122.96 |
| R43910 | 2851 | EST | 36.5 | 0.00001 | 23.41 | 24.6 | 11.1 | 156.7 | 166.34 | 52.21 |
| R49602 | 2884 | EST | 5.03 | 0.00761 | 19.25 | 9.65 | 26.41 | 970.39 | 905.54 | 322.69 |
| R51831 | 2890 | EST | 12.79 | 0.00001 | 5.89 | 2.5 | 44.67 | 221.54 | 195.97 | 179.99 |
| R52822 | 2895 | EST | #N/A | #N/A | 10.78 | 0.35 | 28.51 | 380.07 | 441.17 | 180.12 |
| R53044 | 2897 | KIAA0981 protein | #N/A | #N/A | 17.84 | 25.74 | 11.45 | 48.77 | 44.34 | 18.43 |
| R53891 | 2899 | EST | #N/A | #N/A | 9.88 | 5.59 | 10.68 | 66.28 | 52.16 | 49.21 |
| R59312 | 2912 | EST | #N/A | #N/A | 34.37 | 35.83 | 22.13 | 94.44 | 91.55 | 36.35 |
| R59722 | 2915 | EST | 19.74 | 0.00016 | 18.78 | -4.94 | 51.34 | 628.69 | 642.78 | 316.88 |
| R60959 | 2918 | EST | #N/A | #N/A | 31.21 | 23.86 | 17.79 | 72.94 | 69.87 | 45.25 |
| R63734 | 2927 | fatty-acid-Coenzyme A ligase, long-chain 3 | #N/A | #N/A | 13.28 | 17.42 | 12.17 | 42.74 | 39.66 | 18.51 |
| R65593 | 2934 | kynurenine 3-monooxygenase (kynurenine 3-hydroxylase) | 21.27 | 0.00007 | 28.84 | 18.5 | 43.46 | 704.58 | 812.38 | 352.86 |
| R70319 | 2945 | EST | #N/A | #N/A | 5.34 | 2.91 | 8.92 | 29.23 | 29.18 | 10.78 |
| R70791 | 2948 | EST | #N/A | #N/A | 127.11 | 110.15 | 41.83 | 73.19 | 57.2 | 56.17 |
| R73468 | 2956 | EST | #N/A | #N/A | 9.97 | 10.43 | 9.69 | 38.29 | 44.82 | 17.14 |
| R73816 | 2960 | EST | 11.53 | 0.00259 | -26.88 | -30.68 | 10.09 | 462.31 | 374.67 | 450.91 |
| R78713 | 2967 | EST | #N/A | #N/A | 0.27 | -1.59 | 8.92 | 70.57 | 57.33 | 56.37 |
| R91060 | 2980 | EST | #N/A | #N/A | 59.14 | 37.15 | 56.04 | 85.88 | 61.99 | 68.99 |
| R93507 | 2990 | EST | #N/A | #N/A | 19.53 | 20.08 | 11 | 67.62 | 67.56 | 44.22 |
| R93714 | 2991 | fetuin B | 10.42 | 0.00043 | -60.74 | -65.14 | 57.99 | 280.62 | 301.36 | 203.86 |
| R93908 | 2993 | EST | 5.8 | 0.02699 | 66.75 | 29.54 | 129.46 | 348.58 | 301.29 | 173.81 |
| R94674 | 2995 | EST | 10.76 | 0.00008 | 0.91 | 4.15 | 14.66 | 269.49 | 288.56 | 148.06 |
| R96822 | 2999 | EST | 8.25 | 0.00008 | 16.45 | 17.01 | 30.67 | 250.81 | 257.18 | 131.85 |
| R97419 | 3003 | cytochrome P450, subfamily VIIIB (sterol 12-alpha-hydroxylase), polypeptide 1 | 65.07 | 0.0039 | 152.16 | -3.42 | 302.56 | 4114.39 | 3837.4 | 1458.43 |
| R97804 | 3007 | EST | #N/A | #N/A | 144.46 | 187.67 | 95.8 | 193.05 | 201.89 | 61.84 |
| R98413 | 3011 | EST | 9.71 | 0.00007 | 38.74 | 28.05 | 21.96 | 402.49 | 443.47 | 212.95 |
| R99014 | 3014 | EST | #N/A | #N/A | 26.99 | 17.82 | 29.49 | 49.82 | 52.35 | 18 |
| T16306 | 3067 | EST | #N/A | #N/A | 24.23 | 23.64 | 24.91 | 58.82 | 63.62 | 22.35 |
| T40895 | 3116 | protein tyrosine phosphatase type IVA, member 1 | #N/A | #N/A | 1575.59 | 2039.82 | 1098.29 | 4148.86 | 2440.28 | 4169.52 |
| T46901 | 3122 | EST | 77.28 | 0.0006 | 11.33 | -31.1 | 121.66 | 2608.54 | 2853.98 | 691.43 |
| T50773 | 3135 | apolipoprotein C-IV | #N/A | #N/A | 94.77 | 43.61 | 169.6 | 8473.97 | 6484.47 | 7036.85 |
| T58756 | 3155 | EST | 13.39 | 0.00013 | 7.38 | -19.91 | 46.26 | 390.04 | 386.76 | 164.41 |
| T58775 | 3156 | small inducible cytokine subfamily A (Cys-Cys), member 16 | 21.18 | 0.00006 | 11.93 | -0.59 | 34.83 | 577.14 | 540.96 | 205.27 |
| T67520 | 3181 | EST | #N/A | #N/A | 52.46 | 49.25 | 28.02 | 105.56 | 113.95 | 38.23 |
| T67931 | 3183 | fibrinogen, B beta polypeptide | 49.55 | 0 | -22.74 | -22.4 | 23.54 | 1187.95 | 1000.67 | 692.18 |
| T69305 | 3196 | EST | #N/A | #N/A | -107.09 | -119.3 | 45.51 | 4052.6 | 4262.37 | 3025.26 |
| T71978 | 3204 | EST | 4.39 | 0.0017 | 41.46 | 58.86 | 43.93 | 218.38 | 208.73 | 89.39 |
| T72502 | 3207 | EST | 8.87 | 0.00009 | 24.11 | 24.41 | 28.19 | 308.87 | 271.27 | 179.15 |
| T73442 | 3212 | EST | 94.41 | 0 | 28.55 | 25.96 | 25.95 | 3170.29 | 3275.73 | 1073.74 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| T74608 | 3215 | hydroxyacid oxidase (glycolate oxidase) 1 | 14.03 | 0 | −3.14 | −1.78 | 23.12 | 360.97 | 328.7 | 194.85 |
| T82323 | 3230 | immunoglobulin superfamily, member 4 | 10.14 | 0 | 14.47 | 5.07 | 19.91 | 264.33 | 229.92 | 135.46 |
| T87224 | 3240 | EST | #N/A | #N/A | 584.24 | 451.54 | 184.49 | 909.33 | 851.86 | 431.47 |
| T90037 | 3245 | EST | 3.99 | 0.0016 | 23.17 | 25.82 | 23.62 | 150.67 | 107.18 | 126.19 |
| T90520 | 3248 | EST | 8.67 | 0.00072 | 9.05 | −7.07 | 25.65 | 306.39 | 362.5 | 204.34 |
| W15417 | 3472 | KIAA0699 protein | #N/A | #N/A | 30.82 | 20.85 | 38.03 | 83.24 | 81.29 | 49.83 |
| W48860 | 3534 | EST | #N/A | #N/A | 36.89 | 39 | 14.08 | 52.69 | 41.31 | 21.1 |
| W60186 | 3554 | EST | 3.24 | 0.00228 | 19.15 | 26.5 | 27.35 | 101.92 | 109.68 | 47.85 |
| W63741 | 3563 | EST | #N/A | #N/A | −11.85 | −13.73 | 14.25 | 28.54 | 17.1 | 44.58 |
| W67147 | 3565 | deleted in liver cancer 1 | 9.74 | 0.00002 | 16.09 | 9.11 | 24.66 | 282.59 | 235.29 | 169.33 |
| W67199 | 3566 | EST | 3.09 | 0.01528 | 30.05 | 35 | 12.16 | 123.27 | 117.99 | 90.47 |
| W72382 | 3581 | oxidative 3 alpha hydroxysteroid dehydrogenase; retinal dehydrogenase | #N/A | #N/A | 37.21 | 6.21 | 66.91 | 3403.46 | 3255.54 | 1538.23 |
| W72471 | 3582 | EST | #N/A | #N/A | 17.93 | 13.32 | 10.61 | 71.51 | 76.9 | 29.33 |
| W85765 | 3615 | EST | 3.83 | 0.00379 | 3.6 | 1.46 | 7.87 | 108.99 | 77.01 | 109.58 |
| W85886 | 3618 | EST | 3.46 | 0.00814 | −6.09 | −2.4 | 11.46 | 99.92 | 68.44 | 97.4 |
| W86431 | 3624 | protein C inhibitor (plasminogen activator inhibitor III) | 14.94 | 0.00152 | 3.16 | 5.55 | 12.03 | 606.44 | 395.34 | 590.7 |
| W86600 | 3625 | EST | 32.14 | 0 | 12.67 | 7.49 | 15.61 | 792.37 | 807.74 | 313.83 |
| W88946 | 3636 | putative glycine-N-acyltransferase | 58.26 | 0 | 2.16 | −22.13 | 39.9 | 1717.54 | 1821.77 | 502.55 |
| W90018 | 3639 | EST | #N/A | #N/A | −2.1 | 4.12 | 13.16 | 59.32 | 53.19 | 41.68 |
| W90396 | 3642 | EST | #N/A | #N/A | 16.1 | 15.26 | 11.11 | 23.65 | 22.93 | 10.28 |
| W94942 | 3658 | dual specificity phosphatase 10 | 7.23 | 0.00137 | 19.36 | 16.05 | 11.9 | 250.16 | 281.49 | 160.43 |
| W95041 | 3659 | EST | 12.79 | 0.00001 | 6.66 | 5.17 | 3.55 | 291.2 | 298.05 | 115.81 |
| Z38161 | 3881 | EST | 4.38 | 0.0011 | 11.84 | 12.14 | 6.32 | 111.16 | 107.62 | 80.11 |
| Z38910 | 3895 | EST | #N/A | #N/A | 0.68 | 2.75 | 12.7 | 35.49 | 32.21 | 23.55 |
| Z39394 | 3901 | EST | 10.11 | 0.00001 | 10.11 | 10.43 | 11.1 | 24.06 | 22.96 | 11.11 |
| Z39622 | 3907 | EST | 4.4 | 0.00001 | 19.65 | 21.87 | 11.97 | 110.87 | 115.21 | 36.19 |
| Z39976 | 3912 | EST | 5.76 | 0.00012 | 13.09 | 7.15 | 18.64 | 165.45 | 151.05 | 98.9 |
| Z40259 | 3916 | EST | 8.18 | 0.00002 | 14.39 | 8.61 | 11.98 | 218.4 | 223.24 | 122.06 |
| Z41271 | 3927 | ariadne, Drosophila, homolog of | #N/A | #N/A | 51.96 | 64.49 | 36.28 | 145.09 | 126.18 | 57.57 |
| Z41634 | 3931 | EST | #N/A | #N/A | 16.4 | 16.07 | 3 | 51.19 | 48.49 | 33 |
| AA001902 | 5 | KIAA0305 gene product | #N/A | #N/A | 14.88 | 17.06 | 8.8 | 29.11 | 28.6 | 23.36 |
| AA001903 | 6 | EST | #N/A | #N/A | 6.64 | 0.97 | 14.07 | 26.52 | 28.7 | 13.21 |
| AA004669 | 9 | EST | #N/A | #N/A | 8.66 | 10.77 | 8.65 | 33.32 | 25.36 | 31.12 |
| AA009719 | 20 | peroxisomal membrane protein 2 (22kD) | 47.12 | 0.00008 | −50.14 | −51.69 | 47.17 | 1370.32 | 1503.99 | 715.62 |
| AA010205 | 23 | EST | 7.41 | 0 | 14.43 | 17.64 | 14.87 | 187.55 | 154.99 | 92.13 |
| AA010360 | 24 | EST | 6.55 | 0.00027 | 12.5 | 14.77 | 8.62 | 169.99 | 135.98 | 129.2 |
| AA013095 | 33 | potassium voltage-gated channel, shaker-related subfamily, beta member 1, | #N/A | #N/A | 7.81 | 3.06 | 19.71 | 18.56 | 15.83 | 8.24 |
| AA015768 | 34 | EST | 15.3 | 0.00008 | 12.22 | 14.2 | 11.71 | 417.95 | 472.1 | 248.15 |
| AA016021 | 35 | ubiquitin-like 3 | #N/A | #N/A | 13.88 | 16.21 | 13.21 | 65.65 | 51.44 | 46.44 |
| AA018867 | 39 | EST | 42.87 | 0.00002 | 45.29 | 29.28 | 52.68 | 1944.56 | 2160.33 | 1142.41 |
| AA024511 | 46 | EST | 7.82 | #N/A | 7.82 | 3.08 | 12.06 | 62.54 | 58.34 | 27.73 |
| AA031360 | 67 | suppressor of Ty (S.cerevisiae) 3 homolog | #N/A | #N/A | 13.46 | 12.87 | 10.49 | 26.25 | 24.36 | 9.3 |
| AA034365 | 76 | EST | #N/A | #N/A | 119.5 | 39.46 | 171.27 | 216.28 | 159.86 | 152.39 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| AA039616 | 90 | EST | 9.36 | 0.00009 | 2.48 | −4.83 | 14.2 | 238.71 | 224.42 | 125.28 |
| AA040087 | 92 | EST | 4.13 | 0.00123 | 34.99 | 27.32 | 18.99 | 156.63 | 148.88 | 90.44 |
| AA040291 | 94 | KIAA0669 gene product | 3.55 | 0.00308 | 12.98 | 12.72 | 16.36 | 101.69 | 98.94 | 80.43 |
| AA046457 | 111 | EST | 3.2 | 0.00513 | 77.66 | 80.71 | 27.66 | 304.54 | 264.9 | 233.62 |
| AA056482 | 141 | EST | 4.82 | 0.00199 | 10.09 | 19.17 | 14.96 | 135.83 | 132.94 | 97.88 |
| AA074885 | 161 | macrophage receptor with collagenous structure | 11.05 | 0.00786 | 79.55 | 25.58 | 153.64 | 652.03 | 761.74 | 300.57 |
| AA075298 | 163 | EST | #N/A | #N/A | 46.45 | 36.93 | 42.61 | 129.13 | 121.57 | 70.36 |
| AA086201 | 185 | EST | 5.8 | 0.00012 | 21.29 | 24.75 | 14.37 | 177.39 | 182.95 | 95.51 |
| AA099225 | 206 | EST | 7.33 | 0.00062 | 4.37 | 1.35 | 6.08 | 212.68 | 163.45 | 194.31 |
| AA099571 | 209 | MD-2 protein | #N/A | #N/A | 10.12 | 4.61 | 19.11 | 55.77 | 62.72 | 31.71 |
| AA115933 | 231 | KIAA1098 protein | #N/A | #N/A | 8.62 | 6.46 | 10.77 | 33.88 | 34.38 | 16.63 |
| AA126059 | 246 | EST | 3.08 | 0.00706 | 102.34 | 104.33 | 40.8 | 380.92 | 280.71 | 316.4 |
| AA127514 | 253 | EST | 3.4 | 0.00045 | 11.36 | 10.76 | 6.8 | 74.71 | 76.5 | 36.07 |
| AA127646 | 254 | schwannomin interacting protein 1 | #N/A | #N/A | 6.76 | −0.26 | 12.36 | 44.24 | 41.48 | 20.02 |
| AA129465 | 263 | EST | #N/A | #N/A | 7.9 | 10.16 | 24.29 | 61.62 | 59.75 | 34.37 |
| AA133214 | 276 | meningioma expressed antigen 6 (coiled-coil proline-rich) | #N/A | #N/A | 3.16 | 7.46 | 14.35 | 65.17 | 56.11 | 51.18 |
| AA133457 | 280 | EST | #N/A | #N/A | 233.92 | 279.32 | 161.44 | 456.09 | 475.45 | 114 |
| AA136333 | 300 | zinc finger protein | #N/A | #N/A | 17.23 | 17.21 | 5.7 | 45.55 | 39.88 | 25.1 |
| AA167550 | 361 | EST | #N/A | #N/A | 4.38 | 7.64 | 6.98 | 28.69 | 26.29 | 16.06 |
| AA171529 | 365 | EST | #N/A | #N/A | −1.76 | −4.58 | 6.37 | 51.3 | 47.89 | 33.98 |
| AA179004 | 377 | EST | 14.34 | 0.00008 | −33.2 | −28.97 | 78.62 | 503.76 | 495.87 | 326.16 |
| AA191310 | 397 | protein phosphatase 2 (formerly 2A), regulatory subunitA (PR 65), beta isoform | 7.28 | 0 | 26.23 | 29.87 | 6.93 | 206.65 | 209.15 | 77.34 |
| AA195463 | 416 | EST | #N/A | #N/A | 5.44 | 6.92 | 3.77 | 51.81 | 64.76 | 26.85 |
| AA195515 | 417 | EST | #N/A | #N/A | 7.27 | 3.56 | 8.61 | 51.59 | 49.91 | 23.13 |
| AA197311 | 422 | intercellular adhesion molecule 1 (CD54), human rhinovirus receptor | 6.07 | 0.00053 | −19.49 | 1.63 | 43.72 | 154.69 | 175.76 | 83.19 |
| AA199603 | 423 | EST | #N/A | #N/A | 14.97 | 24.27 | 28.57 | 54.95 | 55.7 | 19.61 |
| AA223902 | 450 | EST | 9.91 | 0.00003 | 7.98 | −3.32 | 28.42 | 292.86 | 294.78 | 156.98 |
| AA226925 | 452 | EST | #N/A | #N/A | 11.94 | 9.22 | 7.55 | 49.69 | 48.29 | 27.49 |
| AA232114 | 463 | epoxide hydrolase 2, cytoplasmic | 24.34 | 0.00007 | 63.09 | 46.66 | 60.38 | 1455.28 | 1626.11 | 664.36 |
| AA233152 | 467 | EST | 12.95 | 0 | −29.09 | −28.01 | 34.42 | 299.54 | 291.48 | 156.26 |
| AA233797 | 473 | sperm associated antigen 7 | #N/A | #N/A | 54.72 | 50.23 | 11.36 | 116.14 | 127.3 | 54.24 |
| AA233837 | 474 | EST | 4.79 | 0.0034 | 18.96 | 19.45 | 40.67 | 214.77 | 118.28 | 278.62 |
| AA235288 | 494 | PTPL1-associated RhoGAP 1 | 3.7 | 0.00643 | 34.06 | 30.95 | 14.36 | 169.9 | 113.81 | 138.05 |
| AA250958 | 538 | EST | #N/A | #N/A | 53.41 | 53.63 | 22.55 | 99.74 | 114.71 | 55.23 |
| AA255903 | 573 | CD39-like 4 | 5.67 | 0.01687 | 72.5 | 39.23 | 108.92 | 383.56 | 374.1 | 211.92 |
| AA256341 | 578 | EST | 7.37 | 0.00091 | 17.81 | 2.34 | 28.59 | 280.57 | 324.08 | 170.98 |
| M279916 | 633 | EST | #N/A | #N/A | 61.08 | 56.18 | 25.7 | 115.24 | 102.89 | 58.77 |
| AA280413 | 638 | spleen focus forming virus (SFFV) proviral integration oncogene spi1 | 4.46 | 0.02062 | 64.05 | 69.15 | 51.55 | 339.15 | 353.53 | 235.59 |
| AA282541 | 661 | EST | #N/A | #N/A | 7.18 | 5.97 | 14.25 | 31.31 | 29.9 | 13.53 |
| AA343142 | 751 | EST | 20.87 | 0.00003 | −12.34 | −21.46 | 30.45 | 610.64 | 636.83 | 438.33 |
| AA397919 | 785 | EST | #N/A | #N/A | 108.63 | 144.35 | 84.25 | 243.79 | 199.62 | 185.4 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| AA398280 | 792 | EST | 12.43 | 0.00134 | −114.74 | −71.05 | 103.33 | 433.45 | 423.73 | 356.61 |
| AA404352 | 850 | EST | 7 | 0.00059 | 26.7 | 20.02 | 33.28 | 213.01 | 172.11 | 108 |
| AA406546 | 879 | EST | #N/A | #N/A | −1.45 | −7.89 | 15.19 | 46.62 | 50.65 | 26.97 |
| AA416936 | 910 | 5-methyltetrahydrofolate-homocysteine methyltransferase reductase | 4.98 | 0.00632 | 82.04 | 85.81 | 69.18 | 427.41 | 366.53 | 235.63 |
| AA424798 | 947 | EST | 17.45 | 0.00352 | 48.63 | 15.48 | 171.26 | 879.91 | 873.25 | 489.59 |
| AA428900 | 992 | EST | 7.01 | 0.00037 | 66.25 | 66.77 | 15.35 | 615.96 | 619.42 | 441.72 |
| AA429038 | 995 | EST | 3.29 | 0.00927 | 13.39 | 1.93 | 28.01 | 108.66 | 87.59 | 86.11 |
| AA434225 | 1035 | serum constituent protein | #N/A | #N/A | 1010.84 | 876.42 | 674.94 | 1022.5 | 746.49 | 681.49 |
| AA463729 | 1250 | EST | 4.07 | 0.00676 | 19.31 | 19.05 | 13.37 | 150.62 | 116.86 | 156.67 |
| AA479961 | 1320 | EST | #N/A | #N/A | 33.49 | 28.45 | 10.58 | 88.13 | 89.35 | 36.9 |
| AA490947 | 1383 | EST | #N/A | #N/A | 34.15 | 35 | 21.49 | 56.24 | 38.75 | 49.85 |
| AA599199 | 1444 | endothelin converting enzyme 1 | #N/A | #N/A | 187.77 | 108.97 | 225.55 | 695.29 | 680.26 | 375.12 |
| AA621315 | 1521 | catenin (cadherin-associated protein), alpha-like 1 | #N/A | #N/A | 191.28 | 141.04 | 182.69 | 313.23 | 281.93 | 134.57 |
| C20982 | 1582 | aldehyde dehydrogenase 5 family, member A1 (succinate-semialdehyde dehydrogenase) | #N/A | #N/A | 68.8 | 85.38 | 28.73 | 104.44 | 88.12 | 66.28 |
| C21130 | 1583 | EST | 8.79 | 0.00008 | 17.56 | 8.6 | 19.19 | 277.18 | 238.8 | 188.55 |
| D11835 | 1598 | low density lipoprotein receptor (familial hypercholesterolemia) | 21.76 | 0.00307 | 76.38 | 23.21 | 131.25 | 895.7 | 910.39 | 322.98 |
| D45714 | 1664 | EST | 5.64 | 0.00384 | 34.3 | 29.86 | 13.09 | 301.07 | 218.14 | 282.7 |
| F04944 | 1795 | acyl-Coenzyme A oxidase | 4.01 | 0.00242 | 40.92 | 33.99 | 28.07 | 191.04 | 192.25 | 99.98 |
| F10276 | 1814 | dual specificity phosphatase 6 | 8.13 | 0.0001 | 19.64 | 13.06 | 12.33 | 240.65 | 275.65 | 138.17 |
| H11739 | 1876 | glycine dehydrogenase (decarboxylating; glycine decarboxylase, glycine cleavage system protein P) | 10.33 | 0.00023 | −21.2 | −37.69 | 28.32 | 290.05 | 210.37 | 244.67 |
| H68239 | 1983 | EST | #N/A | #N/A | 26.96 | 17.94 | 15.81 | 66.76 | 66.18 | 51.67 |
| H79820 | 2004 | EST | 3.25 | 0.01466 | 10.64 | 2 | 22.28 | 113.3 | 113.19 | 95.96 |
| H82966 | 2011 | apolipoprotein B (including Ag(x) antigen) | 3.42 | 0.00769 | 0.2 | 1 | 15.26 | 100.93 | 77.36 | 96.78 |
| H96392 | 2053 | EST | #N/A | #N/A | 12.6 | 9.93 | 33.15 | 35.98 | 53.46 | 42.74 |
| N22938 | 2452 | serum amyloid A4, constitutive | 35.39 | 0.00128 | 163.4 | 145.31 | 160.24 | 4244.44 | 3330.35 | 2358.25 |
| N32071 | 2490 | EST | 8.75 | 0.00006 | 40.89 | 43.12 | 15.37 | 421.21 | 488.49 | 238.4 |
| N47469 | 2521 | EST | 3.34 | 0.00329 | 20.35 | 13.91 | 20.65 | 104.74 | 99.87 | 61.84 |
| N48155 | 2524 | EST | #N/A | #N/A | 17.08 | 16.77 | 14.66 | 97.37 | 54.69 | 99.7 |
| N51117 | 2543 | EST | 9.68 | 0.00081 | 8.23 | 4.5 | 11.88 | 327.53 | 296.4 | 266.42 |
| N52845 | 2553 | EST | 5.53 | 0.00088 | 28.56 | 30.14 | 14.95 | 219.38 | 230.31 | 149.67 |
| N53757 | 2559 | EST | 3.97 | 0.00255 | 99.49 | 80.7 | 56.09 | 365.45 | 324.21 | 118.42 |
| N55272 | 2573 | EST | #N/A | #N/A | 22.71 | 13.6 | 24.4 | 45.08 | 47.45 | 14.77 |
| N59550 | 2587 | EST | 25.56 | 0.00024 | 19.9 | 2.53 | 65.91 | 855.88 | 774.72 | 358.3 |
| N64017 | 2605 | EST | 5.27 | 0.00022 | 5.45 | 8.71 | 8.71 | 122.34 | 135.27 | 55.58 |
| N67974 | 2629 | activating transcription factor 4 (tax-responsive enhancer element B67) | #N/A | #N/A | 5.67 | −0.08 | 15.97 | 82.1 | 74.13 | 59.47 |
| N70358 | 2656 | growth hormone receptor | 34.35 | 0 | 20.93 | 29.26 | 36.06 | 1449.57 | 1157.97 | 1115.22 |
| N73561 | 2675 | EST | 12.96 | 0.00011 | 17.04 | 4.48 | 25.06 | 516.79 | 458.57 | 393.69 |
| N80129 | 2702 | metallothionein 1L | 66.48 | 0.00415 | 179.8 | 104.5 | 643.06 | 10421.47 | 6358.88 | 9618.38 |
| N93470 | 2735 | EST | 5.27 | 0.00022 | 14.01 | 8.69 | 17.09 | 77.86 | 66.84 | 70.45 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| R02365 | 2754 | glucose-6-phosphatase, catalytic (glycogen storage disease type I, von Gierke disease) | 17.17 | 0.00124 | 0.92 | −5.3 | 9.39 | 768.72 | 444.03 | 841.02 |
| R06977 | 2774 | glucokinase (hexokinase 4) regulatory protein | 6.1 | 0.00049 | −47.7 | −38.97 | 37.79 | 152.22 | 150.69 | 87.15 |
| R43174 | 2847 | paraoxonase 1 | 74.04 | 0.00038 | 47.94 | −8.83 | 119.68 | 2926.85 | 3104.07 | 1318.41 |
| R67970 | 2939 | gamma-glutamyl carboxylase | 9.45 | 0.00212 | 85.44 | 59.33 | 76.67 | 655.11 | 692.66 | 267.95 |
| R98105 | 3010 | EST | #N/A | #N/A | 132.16 | 97.16 | 141.15 | 373.83 | 342.91 | 215.89 |
| R98624 | 3012 | EST | 21.32 | 0 | 15.01 | 4.48 | 22.97 | 686.81 | 542.22 | 466.97 |
| R99591 | 3015 | CD5 antigen-like (scavenger receptor cysteine rich family) | 9.52 | 0.00006 | 87.08 | 72.59 | 28.25 | 1035.39 | 904.92 | 691.83 |
| T48075 | 3129 | hemoglobin, alpha 1 | 32.56 | 0.00172 | 246.19 | 164.89 | 271.65 | 7193.85 | 5199.28 | 6317.01 |
| T51617 | 3137 | solute carrier family 22 (extraneuronal monoamine transporter), member 3 | 17.67 | 0.00018 | 29.08 | 19.44 | 56.17 | 669.34 | 725.25 | 402.58 |
| T51930 | 3138 | EST | 9.99 | 0.00066 | 8.27 | 9.41 | 5.97 | 325.48 | 218.59 | 298.12 |
| T67705 | 3182 | asialoglycoprotein receptor 2 | 31.6 | 0.00705 | 168.64 | 37.91 | 284.26 | 2403.76 | 2437.4 | 683.22 |
| T68711 | 3187 | EST | 37.65 | 0.00036 | 19.73 | −26.69 | 95.05 | 1388.67 | 1074.67 | 890.91 |
| T69284 | 3195 | mannose-binding lectin (protein C) 2, soluble (opsonic defect) | 36.53 | 0 | 9.82 | 0.32 | 17.14 | 1147.2 | 618.07 | 972.57 |
| T72171 | 3205 | thyroxin-binding globulin | 10.41 | 0.00163 | 5.48 | −20.52 | 54.58 | 492.89 | 371.71 | 454.89 |
| T72906 | 3209 | EST | 7.56 | 0.00062 | 4.88 | 3.04 | 14.04 | 233.73 | 199.26 | 211.99 |
| T73739 | 3213 | alanine-glyoxylate aminotransferase (oxalosis I; hyperoxaluria I; glycolicaciduria; serine-pyruvate aminotransferase) | 16.18 | 0.00277 | 1891.22 | 896.45 | 2229.6 | 26094.38 | 15281.08 | 25947.4 |
| W42429 | 3506 | EST | #N/A | #N/A | 98.32 | 80.07 | 52.23 | 252.63 | 300.68 | 162.35 |
| W58756 | 3551 | EST | 12.17 | 0.00087 | 93.37 | 88.97 | 71.48 | 1363.71 | 1064.26 | 1032.27 |
| W70131 | 3574 | EST | #N/A | #N/A | 108.21 | 30.68 | 183.05 | 118.49 | 100.66 | 53.4 |
| W72044 | 3577 | insulin induced gene 1 | 24.58 | 0.00001 | 41.6 | 36.28 | 36.46 | 1133.09 | 940.16 | 723.6 |
| W72079 | 3578 | EST | 6.36 | 0.00641 | 46.78 | 17.94 | 66.71 | 261.7 | 214.62 | 175.87 |
| W72972 | 3584 | EST | 5.61 | 0.00939 | 44.7 | 26.44 | 80.59 | 277.4 | 270.63 | 183.07 |
| W73382 | 3588 | EST | #N/A | #N/A | 62.97 | 39.05 | 67.26 | 87.32 | 89.49 | 28.17 |
| W85847 | 3616 | EST | 7.28 | 0.00024 | 4.15 | 5.29 | 9.26 | 187.31 | 160.02 | 130.73 |
| W87454 | 3629 | homogentisate 1,2-dioxygenase (homogentisate oxidase) | 7.93 | 0.00149 | 11.36 | 5.83 | 39.02 | 336.07 | 275.03 | 315.24 |
| W92148 | 3647 | kininogen | 51.09 | 0.00376 | 220.31 | 42.96 | 427.59 | 3697.54 | 4015.04 | 1444.99 |
| Z41356 | 3929 | EST | #N/A | #N/A | 4.46 | 15.94 | 28.44 | 82.7 | 48.14 | 71.73 |
| AA112209 | 223 | acyl-Coenzyme A dehydrogenase, long chain | 3.37 | 0.00084 | 29.77 | 28.31 | 11.33 | 116 | 100.18 | 66.07 |
| AA149253 | 323 | EST | 5.12 | 0.00863 | 78.65 | 75.3 | 61.14 | 401.77 | 301.06 | 333.03 |
| AA211418 | 434 | EST | #N/A | #N/A | 65.81 | 70.1 | 37.84 | 223.56 | 214.42 | 151.4 |
| AA227480 | 456 | EST | 3.31 | 0.02413 | 48 | 62.07 | 33.49 | 195.79 | 162.34 | 182.76 |
| AA235507 | 498 | pim-2 oncogene | 3.28 | 0.00249 | 22.14 | 37.31 | 26.61 | 111.91 | 126.75 | 58.39 |
| AA257057 | 586 | golgi autoantigen, golgin subfamily a, 5 | 8.11 | 0.00379 | 42.36 | 16.78 | 47.02 | 451.86 | 462.6 | 343.05 |
| AA258353 | 593 | EST | 5.28 | 0.00193 | 71.76 | 84 | 37.77 | 347.7 | 363.14 | 106.2 |
| AA279158 | 623 | EST | #N/A | #N/A | 50 | 46.97 | 19.41 | 87.9 | 72.44 | 38.36 |
| AA282956 | 664 | EST | #N/A | #N/A | 0.28 | −9.07 | 30.81 | 59.89 | 51.54 | 35.5 |
| AA285053 | 681 | EST | 6.95 | 0.00125 | 12.65 | 14.54 | 23.53 | 238.16 | 242.27 | 169.12 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| AA312946 | 731 | EST | 9.21 | 0.00106 | 12.32 | 13.78 | 12.24 | 300.22 | 304.56 | 213.18 |
| AA344866 | 752 | complement component 8, gamma polypeptide | 7.28 | 0.00206 | 292.65 | 305.28 | 176.61 | 1845.16 | 1679.29 | 561.04 |
| AA363203 | 761 | EST | #N/A | #N/A | 35.7 | 40.27 | 34.51 | 78.45 | 75.11 | 47.8 |
| AA381125 | 772 | EST | 15.48 | 0 | 17.66 | 13.82 | 13.2 | 412.26 | 344.45 | 217.56 |
| AA400030 | 806 | EST | 3.98 | 0.00088 | 8.99 | 12.21 | 11.35 | 97.83 | 115.15 | 52.04 |
| AA400080 | 807 | EST | #N/A | #N/A | 25.33 | 23.57 | 27.54 | 61.21 | 60.21 | 29.91 |
| AA400258 | 812 | EST | 11.89 | 0.00478 | 85.31 | 36.81 | 139.93 | 827.48 | 884.35 | 562.14 |
| AA400934 | 824 | EST | 4.98 | 0.02013 | 75.44 | 67.21 | 77.7 | 305.09 | 307.45 | 125.76 |
| AA401562 | 830 | EST | 50.45 | 0.00301 | 155.46 | 63.87 | 317.6 | 3745.71 | 3628.4 | 1635.98 |
| AA401825 | 831 | EST | #N/A | #N/A | 24.3 | 26.82 | 18.04 | 65.22 | 57.51 | 46.54 |
| AA405494 | 858 | EST | #N/A | #N/A | 10.03 | 9.53 | 7.62 | 59.95 | 44.88 | 50.8 |
| AA412068 | 896 | EST | #N/A | #N/A | 30.52 | 29.79 | 13.4 | 81.26 | 74.52 | 35.68 |
| AA417078 | 916 | EST | 4.1 | 0.00414 | 36.75 | 35.35 | 15.12 | 189.88 | 171.1 | 150.02 |
| AA419608 | 925 | EST | 9.19 | 0.00005 | 51.89 | 51.37 | 25.93 | 524.34 | 571.05 | 296.46 |
| AA419622 | 926 | EST | 4.62 | 0.00386 | 24.88 | 17.15 | 26 | 158.88 | 162.5 | 112.57 |
| AA421561 | 933 | insulin-like growth factor 2 (somatomedin A) | 9.98 | 0.00007 | 79.46 | 77.34 | 41.63 | 921.91 | 703.16 | 679.72 |
| AA429651 | 1002 | KIAA0871 protein | #N/A | #N/A | 15.52 | 13.25 | 17.03 | 44.75 | 41.91 | 28.67 |
| AA432166 | 1030 | succinate dehydrogenase complex, subunit C, integral membrane protein, 15kD | #N/A | #N/A | 10.94 | 14.1 | 42.99 | 33.86 | 42.75 | 27.46 |
| AA435753 | 1045 | EST | 4.71 | 0.00078 | 198.97 | 193.33 | 110.58 | 970.79 | 830.39 | 567.79 |
| AA443934 | 1083 | GTP-binding protein Rho7 | 3.09 | 0.00214 | 30.32 | 35.97 | 13.76 | 115.87 | 113.7 | 66.78 |
| AA446342 | 1088 | seven in absentia (Drosophila) homolog 1 | 4.84 | 0.00015 | 9.92 | 9.12 | 4.58 | 110.73 | 115.89 | 53.13 |
| AA448300 | 1116 | FXYD domain-containing ion transport regulator 1 (phospholemman) | 0.00001 | 118.64 | 24.97 | 70.34 | 2849.54 | 2905.51 | 994.41 | 789.64 |
| AA452158 | 1141 | ras homolog gene family, member B | 28.96 | 0.00064 | -103.87 | -106.99 | 71.68 | 1071.9 | 1164.8 | 70.02 |
| AA453770 | 1157 | EST | 6.04 | 0.00524 | 46.33 | 25.95 | 53.45 | 217.46 | 212.4 | 258.82 |
| AA454177 | 1164 | EST | 10.3 | 0.0008 | 9.16 | 14.72 | 11.39 | 324.16 | 253.23 | 66.93 |
| AA455896 | 1181 | glypican 1 | 3.46 | 0.00887 | 16.1 | 4.35 | 40.39 | 120.52 | 137.84 | 68.09 |
| AA456326 | 1191 | EST | 3.35 | 0.00489 | 17.08 | 2.74 | 30.38 | 111.5 | 102.17 | 49.27 |
| AA456845 | 1198 | KIAA0680 gene product | #N/A | #N/A | 23.95 | 17.11 | 17.99 | 67.15 | 63.46 | 39.92 |
| AA459256 | 1212 | lectin, mannose-binding, 1 | 3.01 | 0.00094 | 3.83 | 8.1 | 8.32 | 65.91 | 63.36 | 108.17 |
| AA460661 | 1229 | EST | 7.02 | 0.00053 | -1.52 | -6.03 | 15.81 | 184.62 | 198.21 | 46.64 |
| AA463876 | 1252 | EST | 3.31 | 0.00109 | 9.81 | 11.89 | 10.39 | 73.95 | 73.76 | 52.43 |
| AA465381 | 1272 | EST | #N/A | #N/A | 88.83 | 36.24 | 130.22 | 102.73 | 113.07 | 97.49 |
| AA479968 | 1321 | arylsulfatase A | 9.01 | 0.00224 | 37.97 | 20.36 | 45.8 | 331.32 | 312.63 | 63.6 |
| AA480997 | 1324 | MADS box transcription enhancer factor 2, polypeptide A (myocyte enhancer factor 2A) | #N/A | #N/A | 16 | 20.58 | 9.93 | 68.53 | 55.62 | 23.22 |
| AA481057 | 1325 | EST | #N/A | #N/A | 16.3 | 18.55 | 8.1 | 33.83 | 37.89 | 55.07 |
| AA486407 | 1347 | EST | #N/A | #N/A | 33.22 | 47.88 | 28.61 | 81.72 | 97.02 | 95.59 |
| AA486567 | 1350 | EST | 5 | 0.00002 | 4.65 | 2.5 | 21.62 | 131.53 | 98.76 | 31.84 |
| AA486794 | 1351 | EST | #N/A | #N/A | 49.57 | 52.25 | 18.73 | 78.8 | 72.55 | 119.11 |
| AA487503 | 1356 | EST | 8.85 | 0.00012 | 13.8 | 17.99 | 8.76 | 220.45 | 255.47 | 54.46 |
| AA490882 | 1381 | EST | 3.29 | 0.00319 | 20.67 | 13.84 | 27.06 | 100.67 | 98.47 | 33.37 |
| AA490890 | 1382 | EST | 3.02 | 0.00007 | 20.26 | 21.34 | 9.23 | 75.61 | 65.02 | 17.68 |
| AA496927 | 1402 | EST | #N/A | #N/A | 24.89 | 26.85 | 9.47 | 58.2 | 58.42 | |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| AA598685 | 1435 | lectin, galactoside-binding, soluble, 8 (galectin 8) | #N/A | #N/A | 16.45 | 11.35 | 11.87 | 55.9 | 55.08 | 42.18 |
| AA599365 | 1449 | decorin | #N/A | #N/A | 36.41 | 34.43 | 21.53 | 83.84 | 84.81 | 43.41 |
| AA600248 | 1461 | EST | #N/A | #N/A | 59.11 | 59.91 | 32.47 | 80.55 | 71.14 | 61.42 |
| AA609715 | 1488 | EST | #N/A | #N/A | −1.49 | −3.92 | 10.63 | 29.09 | 33.14 | 17.26 |
| AA621796 | 1531 | kinesin family member 3B | 4.44 | 0.00032 | 21.81 | 23.64 | 8.64 | 128.01 | 124.81 | 70.04 |
| C20653 | 1578 | EST | 10.59 | 0.00001 | 7.99 | 2.12 | 11.85 | 251.82 | 299.09 | 106.09 |
| D11802 | 1597 | angiotensinogen | 5.65 | 0.00009 | 55.88 | 52.43 | 25.14 | 319.73 | 291.02 | 132.07 |
| D45529 | 1662 | EST | 3.82 | 0.00193 | 12.24 | −3.36 | 29.18 | 126.63 | 109.06 | 70.64 |
| D59954 | 1698 | EST | 6.7 | 0 | 6.09 | 9.79 | 34.83 | 184.48 | 158.33 | 79.55 |
| D60769 | 1703 | KIAA0096 protein | 4.31 | 0.00142 | 13.44 | 13.91 | 10.95 | 119.96 | 107.2 | 86.36 |
| F10380 | 1816 | butyrobetaine (gamma), 2-oxoglutarate dioxygenase (gamma-butyrobetaine hydroxylase) | #N/A | #N/A | 36.92 | 34.01 | 13.56 | 106.49 | 93.71 | 83.35 |
| F10874 | 1823 | EST | 4.19 | 0.00025 | 233.85 | 209.96 | 107.99 | 1016.95 | 990.04 | 477.31 |
| H03348 | 1833 | claudin 1 | 5.77 | 0.0001 | 1.48 | 7.75 | 17.79 | 135.1 | 134.05 | 75.43 |
| H16098 | 1885 | EST | #N/A | #N/A | 45.29 | 37.73 | 26.92 | 87.28 | 94.49 | 38.15 |
| H17472 | 1888 | EST | #N/A | #N/A | 12.2 | 9.54 | 8.57 | 31.08 | 31.66 | 13.28 |
| H47838 | 1936 | carboxypeptidase B2 (plasma) | 16.74 | 0.00002 | −26.99 | −41.82 | 25.87 | 401.55 | 412.78 | 188.81 |
| H56584 | 1951 | 4-nitrophenylphosphatase domain and non-neuronal SNAP25-like 1 | 9.5 | 0 | 1.95 | 10.13 | 31.43 | 223.03 | 233.37 | 105.28 |
| H69138 | 1986 | v-Ki-ras2 Kirsten rat sarcoma 2 viral oncogene homolog | 6.76 | 0.00142 | 42.88 | 30.87 | 38.35 | 328.51 | 313.13 | 218.8 |
| H70627 | 1990 | EST | #N/A | #N/A | 17.89 | 17.62 | 8.85 | 42.72 | 41.34 | 11.7 |
| H73535 | 1996 | EST | 6.89 | 0.00202 | 154.24 | 97.36 | 149.45 | 912.39 | 956.58 | 383.35 |
| H77494 | 1999 | EST | #N/A | #N/A | 9.65 | 6.64 | 15.53 | 42.67 | 47.73 | 27.54 |
| H81070 | 2006 | RNA helicase-related protein | 25.74 | 0.00126 | 93.43 | 62.01 | 121.29 | 2044.42 | 2051.11 | 615.84 |
| H81964 | 2008 | SEC14 (S. cerevisiae)-like 1 | #N/A | #N/A | 9.95 | 15.7 | 12.54 | 29.9 | 21.14 | 20.56 |
| H82424 | 2009 | EST | #N/A | #N/A | 41.99 | 48.17 | 21.1 | 65.11 | 69.41 | 36.73 |
| H82735 | 2010 | NOT3 (negative regulator of transcription 3, yeast) homolog | #N/A | #N/A | −1.13 | 6.14 | 29.78 | 58.77 | 54.86 | 35.76 |
| H83109 | 2012 | EST | 16.55 | 0.00001 | 2.74 | 4.43 | 21.21 | 417.46 | 421.97 | 224.35 |
| H93562 | 2038 | proline synthetase co-transcribed (bacterial homolog) | 3.17 | 0.00113 | 20.83 | 14.13 | 20.46 | 89.3 | 84.36 | 37.72 |
| H93745 | 2040 | GS2 gene | #N/A | #N/A | 4.52 | 8.01 | 8.31 | 47.92 | 46.53 | 28.87 |
| H96897 | 2056 | KIAA0336 gene product | #N/A | #N/A | 35.22 | 19.98 | 42.05 | 48.46 | 50.39 | 33.36 |
| H97587 | 2060 | endothelin receptor type B | #N/A | #N/A | −5.07 | −3.35 | 14.02 | 39.65 | 36.54 | 21.7 |
| H97670 | 2061 | EST | #N/A | #N/A | 23.31 | 29.71 | 31.35 | 101.35 | 128.08 | 56.78 |
| H99393 | 2076 | endothelin receptor type B | 3.43 | 0.00093 | 4.63 | 9.33 | 11.96 | 79.18 | 70.67 | 42.71 |
| N21626 | 2444 | EST | #N/A | #N/A | 29.77 | 24.63 | 25.09 | 59.18 | 46.15 | 33.56 |
| N35247 | 2499 | EST | #N/A | #N/A | 39.9 | 33.56 | 15.03 | 117.08 | 116.14 | 57.05 |
| N54311 | 2563 | EST | 4.82 | 0.00183 | 9.77 | 9.36 | 25.17 | 160.29 | 130.17 | 124.7 |
| N57934 | 2576 | formiminotransferase cyclodeaminase | 13.81 | 0.00171 | 806.55 | 477.9 | 939.39 | 9051.2 | 6373.16 | 8542.52 |
| N59532 | 2584 | aminomethyltransferase (glycine cleavage system protein T) 6.73 | 0.00005 | 12.43 | 2.55 | 17.66 | 196.37 | 155.84 | 122.13 | 35.76 |
| N62523 | 2591 | hepatic leukemia factor | 5.02 | 0.00087 | 9.04 | 6.67 | 16.46 | 144.8 | 148.62 | 85.03 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| N63172 | 2598 | cell division cycle 42 (GTP-binding protein, 25kD) | #N/A | #N/A | 26.88 | 33.1 | 24.75 | 60.99 | 57.64 | 40.01 |
| N66130 | 2613 | progesterone membrane binding protein | 3.98 | 0.0106 | 29.02 | 21.05 | 33.88 | 172.14 | 181.78 | 114.84 |
| N67009 | 2621 | prion protein (p27-30) (Creutzfeld-Jakob disease, Gerstmann-Strausler-Scheinker syndrome, fatal familial insomnia) | 3.55 | 0.00956 | 25.95 | 11.35 | 38.17 | 122.85 | 124.39 | 65.69 |
| N67105 | 2623 | EST | 5.01 | 0.00176 | -0.75 | 0.21 | 16.38 | 143.36 | 102.9 | 121.4 |
| N67876 | 2627 | insulin-like growth factor 1 (somatomedin C) | 8.89 | 0.00042 | 11.81 | 15.88 | 8.82 | 267.41 | 145.79 | 238.35 |
| N68133 | 2632 | EST | #N/A | #N/A | 2.35 | -5.53 | 16.59 | 58.69 | 37.21 | 57.82 |
| N68596 | 2635 | betaine-homocysteine methyltransferase | 40.99 | 0 | -6.75 | -13.81 | 19.15 | 1061.81 | 1013.27 | 574.42 |
| N72200 | 2668 | EST | #N/A | #N/A | 12.93 | 14.15 | 14.26 | 57.8 | 56.14 | 30.12 |
| R05309 | 2758 | EST | 3.72 | 0.0008 | 21.94 | 13.92 | 18.75 | 96.81 | 100.54 | 31.73 |
| R06271 | 2765 | EST | 6.14 | 0.00063 | 23.1 | 18.95 | 21.07 | 208.75 | 221.65 | 107.72 |
| R06273 | 2766 | EST | #N/A | #N/A | 138 | 103.77 | 75.66 | 235.98 | 183.78 | 122.56 |
| R31104 | 2810 | EST | #N/A | #N/A | -6.45 | 0.74 | 37.65 | 32.27 | 26.77 | 13.57 |
| R40395 | 2840 | lecithin-cholesterol acyltransferase | 37.33 | 0.00032 | 0.98 | -46.23 | 77.82 | 1192.03 | 1230.66 | 281.28 |
| R40556 | 2842 | EST | 3.57 | 0.00184 | 8.98 | 8.28 | 11.75 | 91.55 | 95.59 | 58.66 |
| R40946 | 2844 | crystallin, zeta (quinone reductase) | 6.14 | 0.00156 | 18.65 | 19.52 | 14.3 | 205.48 | 220.3 | 137.27 |
| R45480 | 2862 | cyclin K | #N/A | #N/A | 27.21 | 17.36 | 21.39 | 71.04 | 79.77 | 50.88 |
| R62519 | 2925 | EST | 10.83 | 0.00243 | 73.01 | 104.54 | 56.5 | 707.38 | 751.42 | 357.22 |
| T56281 | 3150 | RNA helicase-related protein | 32.34 | 0.00002 | 71.16 | 62.87 | 44.81 | 2132.07 | 2146.52 | 824.76 |
| T59148 | 3157 | carbamoyl-phosphate synthetase 1, mitochondrial | 88.89 | 0 | 17.1 | 2.26 | 49.29 | 3384.09 | 3845.28 | 2295.81 |
| T61256 | 3161 | ketohexokinase (fructokinase) | 13.59 | 0.00425 | 55.8 | 29.78 | 120.62 | 752.99 | 846.1 | 315.74 |
| T61654 | 3165 | apolipoprotein A-I | #N/A | #N/A | 66.98 | -33.89 | 208.52 | 9388.4 | 4297.02 | 12058.3 |
| T64933 | 3173 | EST | #N/A | #N/A | 1.58 | 10.35 | 17.94 | 52.88 | 40.46 | 54.68 |
| T65443 | 3174 | EST | 11.15 | 0.00006 | 10.45 | 9.99 | 13.16 | 70.03 | 75.01 | 29 |
| T66189 | 3177 | glutaryl-Coenzyme A dehydrogenase | 8.61 | 0.00003 | 17.08 | 20.49 | 23.82 | 269.19 | 301.13 | 136.96 |
| T68855 | 3188 | EST | 34.04 | 0 | 8.38 | 6.98 | 9 | 800.27 | 911.26 | 406.27 |
| T69020 | 3192 | EST | 5.39 | 0.00383 | 32.69 | 17.15 | 46.31 | 202.05 | 208.64 | 90.02 |
| T69164 | 3194 | EST | 4.38 | 0.00548 | 34.31 | 17.81 | 30.85 | 173.2 | 167.2 | 85.34 |
| T74542 | 3214 | UDP glycosyltransferase 2 family, polypeptide B10 | 32.36 | 0.00004 | 27.96 | 25.04 | 64.23 | 1374.78 | 1445.94 | 869.3 |
| T84084 | 3233 | EST | #N/A | #N/A | 21.47 | 21.35 | 9.96 | 68.96 | 66.69 | 27.4 |
| T84491 | 3234 | CUG triplet repeat, RNA-binding protein 2 | #N/A | #N/A | 32.84 | 34.93 | 8.15 | 79.08 | 80.41 | 33.03 |
| T86482 | 3237 | transferrin | 11.15 | 0.00006 | 7.6 | 9.41 | 12.34 | 316.82 | 197.03 | 302.36 |
| T91161 | 3252 | EST | 3.48 | 0.00002 | 9.95 | 2.64 | 11.55 | 77.85 | 70.8 | 30.28 |
| W45560 | 3522 | EST | 5.06 | 0.00996 | 86.81 | 62.95 | 81.92 | 369.61 | 354.89 | 158.02 |
| W79422 | 3601 | fumarylacetoacetate | 14.94 | 0.00059 | -18.4 | -19.27 | 33.52 | 467.37 | 554.19 | 306.71 |
| W87480 | 3630 | STAT induced STAT inhibitor-2 | 3.24 | 0.01063 | 31.91 | 26.07 | 30.44 | 129.06 | 119.73 | 80.94 |
| W87606 | 3632 | protein Z, vitamin K-dependent plasma glycoprotein | 9.23 | 0.00085 | 2.53 | -1.74 | 9.98 | 268.59 | 280.44 | 184.7 |
| Z38192 | 3882 | EST | 3.35 | 0.00184 | -0.28 | -4.75 | 17.86 | 87.12 | 87.23 | 52.58 |
| Z39833 | 3910 | GTP-binding protein | 16.89 | 0.00034 | 35.79 | 41.07 | 84.59 | 957.61 | 1080.1 | 674.72 |
| AF000573 | 1543 | homogentisate 1,2-dioxygenase (homogentisate oxidase) | 13.76 | 0.00002 | 9.05 | 13.23 | 17.33 | 380.3 | 348.9 | 256.4 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| D12485 | 1600 | phosphodiesterase I/nucleotide pyrophosphatase 1 (homologous to mouse Ly-41 antigen) | 4.57 | 0.00008 | −2.69 | −0.53 | 9.86 | 101.7 | 90.07 | 46.62 |
| D14664 | 1616 | KIAA0022 gene product | 8.98 | 0.00011 | 14.15 | 13.51 | 9.07 | 233.08 | 248.97 | 111.44 |
| D14686 | 1617 | aminomethyltransferase (glycine cleavage system protein T) | #N/A | #N/A | 76.93 | 90.12 | 29.68 | 171.07 | 190.08 | 34.32 |
| D14695 | 1618 | KIAA0025 gene product; MMS-inducible gene | 6.48 | 0 | 28.53 | 28.21 | 12 | 196.04 | 197.12 | 77.25 |
| D16350 | 1620 | SA (rat hypertension-associated) homolog | 3.83 | 0.00117 | 27.34 | 29.05 | 12.27 | 128.95 | 133.42 | 74.27 |
| D31716 | 1647 | basic transcription element binding protein 1 | 5.35 | 0.00086 | 16.08 | 23.65 | 17.64 | 166.06 | 203.79 | 87.22 |
| D31815 | 1648 | regucalcin (senescence marker protein-30) | 10.55 | 0.00037 | 11.48 | 10.25 | 7 | 298.48 | 281.03 | 183.56 |
| D49742 | 1668 | hyaluronan-binding protein 2 | 18.13 | 0.00012 | 11.38 | −0.72 | 41.45 | 509.66 | 531.78 | 127.5 |
| D50582 | 1670 | potassium inwardly-rectifying channel, subfamily J, member 11 | #N/A | #N/A | 61.44 | 65.47 | 28.34 | 70.38 | 76.35 | 25.4 |
| D63160 | 1709 | ficolin (collagen/fibrinogen domain-containing lectin) 2 (hucolin) | 4.01 | 0.00391 | 51.13 | 46.11 | 30.07 | 219.26 | 228.53 | 125.06 |
| D76435 | 1716 | Zic family member 1 (odd-paired Drosophila homolog) | #N/A | #N/A | 7.52 | 9.44 | 7.51 | 28.48 | 22.05 | 16.54 |
| D78011 | 1717 | dihydropyrimidinase | 21.37 | 0.00003 | 22.34 | 11.34 | 31.83 | 640.3 | 680.03 | 206.48 |
| D85181 | 1750 | sterol-C5-desaturase (fungal ERG3, delta-5-desaturase)-like | 9.56 | 0.00005 | 31.54 | 25.11 | 23.09 | 350.04 | 388.34 | 151.37 |
| D85433 | 1751 | EST | #N/A | #N/A | 45.14 | 48.1 | 33.75 | 45.46 | 44.56 | 22.01 |
| D86983 | 1758 | p53-responsive gene 2 | #N/A | #N/A | 44.18 | 43.24 | 14.93 | 56.19 | 53 | 16.12 |
| D87075 | 1760 | solute carrier family 23 (nucleobase transporters), member 1 | 4.15 | 0.00067 | 5.77 | −0.83 | 26.24 | 119.77 | 104.75 | 72.62 |
| D90282 | 1769 | carbamoyl-phosphate synthetase 1, mitochondrial | 27.29 | 0.00002 | 8.24 | 12.24 | 8.02 | 712.98 | 819.32 | 415.69 |
| H46990 | 1933 | cytochrome P450, subfamily IIE (ethanol-inducible) | 3.2 | 0.00095 | −0.27 | −6.33 | 16.23 | 72.1 | 71.1 | 37.01 |
| HG1148-HT1148 |  | EST | 17.51 | 0.00024 | 11.81 | 2.35 | 49.19 | 501.82 | 482.3 | 169.87 |
| HG2167-HT2237 |  | A kinase (PRKA) anchor protein 13 | #N/A | #N/A | 12.53 | 10.98 | 18.36 | 61.94 | 62.5 | 16.73 |
| HG2755-HT2862 |  | plastin 3 (T isoform) | 11.01 | #N/A | 50.51 | 23.74 | 81.64 | 158.94 | 142.23 | 112.33 |
| HG4533-HT4938 |  | protease inhibitor 4 (kallistatin) | 18.98 | 0.00001 | 35.74 | 42.24 | 20.68 | 479.23 | 562.95 | 221.2 |
| J02943 | 2090 | corticosteroid binding globulin | 18.98 | 0.00087 | 57.44 | 39.79 | 44.72 | 880.54 | 924.99 | 144.24 |
| J03810 | 2099 | solute carrier family 2 (facilitated glucose transporter), member 2 | 21.99 | 0.00004 | 21.12 | 16.81 | 24.34 | 571.66 | 593.24 | 118.08 |
| J04056 | 2104 | carbonyl reductase 1 | 5.19 | 0.00001 | 9.77 | 22.83 | 29.45 | 145.33 | 139.19 | 73.11 |
| J05037 | 2116 | serine dehydratase | 16.24 | 0.00015 | 12.71 | 32.78 | 67.98 | 626.47 | 497.97 | 306.18 |
| J05158 | 2117 | carboxypeptidase N, polypeptide 2, 83kD | 8.52 | 0 | 2.27 | −7.78 | 21.43 | 209.63 | 218.19 | 81.01 |
| K02100 | 2123 | ornithine carbamoyltransferase | 10.24 | 0.00009 | 6.1 | 3.97 | 11.14 | 253.26 | 300.99 | 126.18 |
| K02402 | 2125 | coagulation factor IX (plasma thromboplastic component, Christmas disease, hemophilia B) | 28.81 | 0.00001 | 10.4 | 2.94 | 28.08 | 742.92 | 734.01 | 215.88 |
| L00972 | 2133 | cystathionine-beta-synthase glucan (1,4-alpha-), branching enzyme 1 (glycogen branching enzyme, Andersen | 7.19 | 0.00008 | 30.44 | 29.08 | 21.44 | 268.9 | 253.33 | 153.24 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| L07956 | 2148 | disease, glycogen storage disease type IV) | 5.6 | 0.00029 | 19.13 | 18.57 | 16.75 | 166.17 | 184.57 | 75.67 |
| L09717 | 2153 | lysosomal-associated membrane protein 2 | 4.06 | 0.00034 | 16.78 | 9.78 | 21.83 | 115.12 | 111.26 | 57.66 |
|  |  | murine leukemia viral (bmi-1) oncogene |  |  |  |  |  |  |  |  |
| L13689 | 2164 | homolog | #N/A | #N/A | 32.33 | 34.76 | 18.57 | 63.42 | 77.84 | 36.39 |
| L19871 | 2172 | activating transcription factor 3 | #N/A | #N/A | 72.2 | 31 | 78.72 | 98.22 | 85.66 | 61.41 |
| L27050 | 2186 | apolipoprotein F | 10.26 | 0.00026 | −23.8 | −20.7 | 14.43 | 258.1 | 252.65 | 124.08 |
| L27841 | 2187 | pericentriolar material 1 | #N/A | #N/A | 58.75 | 58.95 | 40.61 | 90.06 | 82.71 | 28.43 |
| L32140 | 2192 | afamin | 17.31 | 0.00003 | 9.44 | 16 | 10.75 | 426.89 | 464.97 | 221.11 |
| L32179 | 2193 | arylacetamide deacetylase (esterase) | 23.83 | 0 | 22.94 | 24.96 | 16.06 | 688.97 | 675.71 | 305.75 |
| L33799 | 2196 | procollagen C-endopeptidase enhancer | #N/A | #N/A | 87.45 | 73.5 | 89.14 | 230.54 | 248.1 | 130.08 |
|  |  | bile acid Coenzyme A: amino acid N- |  |  |  |  |  |  |  |  |
| L34081 | 2199 | acyltransferase (glycine N-cholyoyltransferase) | 11.96 | 0.00008 | 6.09 | 4.41 | 14.12 | 314.27 | 330.42 | 174.43 |
| L48516 | 2220 | paraoxonase 3 | 22.21 | 0.00004 | 36.05 | 28.85 | 37.25 | 896.92 | 896.69 | 337.05 |
| M10058 | 2230 | asialoglycoprotein receptor 1 | 23.96 | 0 | −47.64 | −42.75 | 75.52 | 591.6 | 603.68 | 188.25 |
| M11437 | 2238 | kininogen | 18.38 | 0.00006 | 20.84 | 10.7 | 36.84 | 535.53 | 529.53 | 186.97 |
| M11567 | 2239 | angiogenin, ribonuclease, RNase A family, 5 | 32.25 | 0.0001 | 2.5 | −18.19 | 58.03 | 1019.17 | 968.25 | 273.9 |
| M12625 | 2245 | lecithin-cholesterol acyltransferase | 4.55 | 0.01584 | 110.15 | 128.06 | 73.94 | 447.22 | 425.61 | 138.52 |
| M13143 | 2249 | kallikrein B plasma, (Fletcher factor) 1 | 10.39 | 0.00019 | 38.55 | 37.19 | 32.81 | 402.05 | 441.15 | 122.27 |
| M13699 | 2253 | ceruloplasmin (ferroxidase) | 15.85 | 0.00012 | 36.21 | 37.43 | 44.51 | 688.89 | 638.74 | 329.28 |
| M14091 | 2257 | thyroxin-binding globulin | 10.66 | 0.00024 | 1.76 | 2.84 | 9.9 | 269.26 | 284.66 | 119.28 |
| M15656 | 2268 | aldolase B, fructose-bisphosphate | 96.66 | 0 | −44.61 | −66.97 | 59.8 | 2911.78 | 2539.75 | 1883.04 |
|  |  | coagulation factor V (proaccelerin, labile |  |  |  |  |  |  |  |  |
| M16967 | 2275 | factor) | 5.56 | 0.00047 | 22.71 | 26.49 | 30.11 | 204.85 | 248.05 | 88.92 |
| M16973 | 2276 | complement component 8, beta polypeptide | 22.75 | 0.00001 | 20.03 | 23.43 | 31.9 | 686.99 | 714.82 | 203.16 |
| M17466 | 2279 | coagulation factor XII (Hageman factor) | 9.76 | 0.00285 | 94.21 | 63.47 | 93.18 | 706.11 | 724.27 | 261.46 |
|  |  | coagulation factor XI (plasma thromboplastin |  |  |  |  |  |  |  |  |
| M20218 | 2288 | antecedent) | 6.4 | 0.00004 | 38.74 | 45.83 | 14.62 | 247.85 | 259.47 | 69.46 |
| M20786 | 2290 | alpha-2-plasmin inhibitor | 16.95 | 0.00709 | 58.96 | −14.12 | 171 | 1074.45 | 1132.06 | 620.06 |
|  |  | alanyl (membrane) aminopeptidase |  |  |  |  |  |  |  |  |
| M22324 | 2295 | (aminopeptidase N, aminopeptidase M, microsomal aminopeptidase, CD13, p150) | #N/A | #N/A | 224.68 | 25.21 | 471.53 | 365.81 | 363.02 | 134.32 |
| M29194 | 2315 | lipase, hepatic | 12.18 | 0.00012 | 18.97 | 11.91 | 30.61 | 352.8 | 332.28 | 87.49 |
| M30269 | 2323 | nidogen (enactin) | 3.4 | 0.00026 | 19.81 | 26.36 | 14.57 | 96.8 | 94.16 | 42.52 |
| M63967 | 2378 | aldehyde dehydrogenase 5 | 4.04 | 0.00058 | 34.59 | 36.64 | 5.46 | 164.38 | 178.74 | 87.39 |
| M64174 | 2379 | Janus kinase 1 (a protein tyrosine kinase) | #N/A | #N/A | 10.42 | 10.81 | 15.82 | 59.51 | 59.38 | 27.77 |
| M64554 | 2380 | coagulation factor XIII, B polypeptide | 5.87 | 0.00011 | −4.73 | −4.91 | 7.92 | 137.26 | 136.8 | 72.05 |
|  |  | glycine dehydrogenase (decarboxylating; glycine decarboxylase, glycine cleavage |  |  |  |  |  |  |  |  |
| M64590 | 2381 | system protein P) | 6.41 | 0.00002 | 14.28 | 17.87 | 8.65 | 152.26 | 127.72 | 82.96 |
| M64929 | 2383 | protein phosphatase 2 (formerly 2A), regulatory subunit B (PR 52), alpha isoform | #N/A | #N/A | 64.63 | 38.82 | 95.31 | 106.38 | 88.13 | 67.95 |
|  |  | protein C inhibitor (plasminogen activator |  |  |  |  |  |  |  |  |
| M68516 | 2387 | inhibitor III) | 20.54 | 0 | −1.34 | −11.78 | 20.54 | 466.81 | 481.06 | 119.75 |
| M68840 | 2388 | monoamine oxidase A | 3.96 | 0.01396 | 42.09 | 28.9 | 45.52 | 182 | 201.64 | 94.09 |
| M69177 | 2391 | monoamine oxidase B | 11.64 | 0.00001 | 21.97 | 20.41 | 20.83 | 322.15 | 340.27 | 94 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| M74719 | 2395 | transcription factor 4 | #N/A | #N/A | 8.97 | 15.15 | 10.62 | 46.89 | 44.78 | 12.66 |
| M75106 | 2396 | carboxypeptidase B2 (plasma) | 40.63 | 0 | 19.77 | 30.19 | 22.24 | 1170.81 | 1124.59 | 329.77 |
| M76665 | 2397 | hydroxysteroid (11-beta) dehydrogenase 1 | 19.22 | 0.00004 | 33.41 | 17.51 | 23.86 | 628.97 | 670.88 | 196.22 |
| M83772 | 2408 | flavin containing monooxygenase 3 | 19.54 | 0 | 6.88 | −0.95 | 15.39 | 504.14 | 595.51 | 245.03 |
| | | SWI/SNF related, matrix associated, actin dependent regulator of chromatin, subfamily | | | | | | | | |
| M88163 | 2415 | a, member 1 | 3.37 | 0.00098 | 17.39 | 17.52 | 7.25 | 84.41 | 91.86 | 41.42 |
| M88338 | 2416 | serum constituent protein | #N/A | #N/A | 134.22 | 128.76 | 53.79 | 155.51 | 140.27 | 70.28 |
| M88468 | 2417 | mevalonate kinase (mevalonic aciduria) | #N/A | #N/A | 89.85 | 108.13 | 54.23 | 214.81 | 260.33 | 86.76 |
| | | methylmalonate-semialdehyde | | | | | | | | |
| M93405 | 2423 | dehydrogenase | 23.06 | 0 | 16.51 | 27.77 | 20.66 | 679.66 | 734.58 | 307.25 |
| M94065 | 2424 | dihydroorotate dehydrogenase | 6.47 | 0.00013 | 30.26 | 20.14 | 17.64 | 202.13 | 183.44 | 86.43 |
| | | electron-transferring-flavoprotein | | | | | | | | |
| S69232 | 3026 | dehydrogenase | 4.9 | 0.00017 | 2.73 | 4.9 | 4.29 | 113.33 | 103.27 | 60.93 |
| S70004 | 3028 | glycogen synthase 2 (liver) | 9.96 | 0.00001 | −0.03 | −4.28 | 11.42 | 225.1 | 212.32 | 102.76 |
| S82240 | 3038 | ras homolog gene family, member E | #N/A | #N/A | 19.9 | 6.78 | 30.8 | 75.14 | 74.07 | 40.43 |
| U00115 | 3271 | B-cell CLL/lymphoma 6 (zinc finger protein 51) | 5.18 | 0.00045 | 16.17 | 10.31 | 26.94 | 132.13 | 133.88 | 32.06 |
| U01120 | 3273 | glucose-6-phosphatase, catalytic (glycogen storage disease type I, von Gierke disease) | 13.41 | 0.00147 | 83.05 | 45.5 | 91.8 | 878.33 | 693.43 | 495.6 |
| U03056 | 3279 | hyaluronoglucosaminidase 1 | 6.64 | 0 | 12.68 | 11.77 | 4.73 | 139.32 | 137.21 | 43.97 |
| | | complement component 8, gamma | | | | | | | | |
| U08198 | 3291 | polypeptide | 19.71 | 0 | −29.27 | −38.32 | 47.54 | 544.28 | 630.51 | 234.87 |
| U11313 | 3296 | sterol carrier protein 2 | 5.44 | 0.00187 | 17.39 | 0.82 | 35.86 | 181.8 | 228.15 | 99.25 |
| U12778 | 3300 | acyl-Coenzyme A dehydrogenase, short/branched chain | 5.68 | 0.00116 | 5.23 | 6.16 | 7.33 | 147.06 | 158.14 | 91.5 |
| | | sulfotransferase family 2A, dehydroepiandrosterone (DHEA) -preferring, | | | | | | | | |
| U13061 | 3301 | member 1 | 11.32 | 0.00048 | 9.86 | 7.49 | 19.46 | 369.12 | 431.45 | 213.83 |
| U15174 | 3309 | BCL2/adenovirus E1B 19kD-interacting protein 3 | #N/A | #N/A | 41.72 | 11.86 | 49.01 | 129.19 | 138.02 | 68.72 |
| U15932 | 3310 | dual specificity phosphatase 5 | #N/A | #N/A | 47.94 | 27.05 | 47.87 | 86.73 | 86.97 | 38.45 |
| U17989 | 3315 | nuclear autoantigen | #N/A | 0.02825 | 14.21 | 12.72 | 6.13 | 44.22 | 41.28 | 19.09 |
| U19523 | 3319 | GTP cyclohydrolase 1 (dopa-responsive dystonia) | 5.25 | 0.00029 | 12.84 | 12.26 | 15.75 | 136.86 | 142.71 | 66.64 |
| U20530 | 3321 | secreted phosphoprotein 2, 24kD | 16.93 | 0 | 12.63 | 11.54 | 9.93 | 383.92 | 421.24 | 128.02 |
| | | nuclear receptor subfamily 1, group H, | | | | | | | | |
| U22662 | 3328 | member 3 | #N/A | #N/A | 5.71 | 14.46 | 20.18 | 63.21 | 58.72 | 37.5 |
| U31342 | 3343 | nucleobindin 1 | #N/A | #N/A | 77.59 | 66.2 | 40.03 | 183.59 | 197.29 | 58.86 |
| U32989 | 3347 | tryptophan 2,3-dioxygenase | 10.07 | 0.02825 | 166.12 | 22.7 | 333.99 | 527.61 | 473.11 | 268.8 |
| | | cytochrome P450, subfamily III (arachidonic | | | | | | | | |
| U37143 | 3353 | acid epoxygenase) polypeptide 2 | #N/A | #N/A | 33.79 | 28.24 | 31.46 | 116.06 | 131.46 | 48.68 |
| U37547 | 3354 | apoptosis inhibitor 1 | #N/A | #N/A | 29.52 | 19.51 | 48.74 | 93.6 | 112.45 | 52.27 |
| | | aldehyde dehydrogenase 10 (fatty aldehyde | | | | | | | | |
| U46689 | 3365 | dehydrogenase) | 3.5 | 0.01292 | 31.22 | 25.36 | 49.19 | 124.41 | 136.16 | 53.23 |
| | | protein phosphatase 1, regulatory (inhibitor) | | | | | | | | |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| U48707 | 3370 | subunit 1A | 14.22 | 0 | -1.33 | -1.45 | 20.92 | 319.97 | 310.24 | 125.51 |
| U49082 | 3372 | transporter protein | 9.17 | 0.00088 | 71.87 | 46.71 | 56.13 | 563.34 | 515.31 | 179.82 |
| U49248 | 3373 | ATP-binding cassette, sub-family C (CFTR/MRP), member 2 | 7.06 | 0.00067 | 30.01 | 26.03 | 36.14 | 231.96 | 249.25 | 91.2 |
| U50929 | 3379 | betaine-homocysteine methyltransferase | 36.91 | 0 | 8.63 | 2.82 | 20.35 | 898.57 | 865.9 | 313.61 |
| U57094 | 3393 | RAB27A, member RAS oncogene family | #N/A | #N/A | 30.85 | 31.58 | 23.86 | 93.06 | 93.79 | 50.75 |
| U59423 | 3398 | MAD (mothers against decapentaplegic, Drosophila) homolog 1 | #N/A | #N/A | 17.46 | 16.81 | 10.17 | 60.5 | 51.09 | 37.25 |
| U68233 | 3411 | nuclear receptor subfamily 1, group H, member 4 | 6.76 | 0.00022 | 19.94 | 9.8 | 29.99 | 198.25 | 233.6 | 83.71 |
| U69141 | 3413 | glutaryl-Coenzyme A dehydrogenase | 3.06 | 0.00053 | 35.13 | 27.91 | 13.89 | 108.36 | 119.26 | 34.82 |
| U72515 | 3415 | putative protein similar to nessy (Drosophila) | #N/A | #N/A | 45.44 | 58.93 | 45.12 | 137.35 | 138.01 | 55.38 |
| U73514 | 3418 | hydroxyacyl-Coenzyme A dehydrogenase, type II | 3.79 | 0.01392 | 9.85 | -22.7 | 56.91 | 159.74 | 161.9 | 127.8 |
| U77396 | 3425 | LPS-induced TNF-alpha factor | 4.47 | 0.00108 | 30.53 | 33.74 | 31.54 | 169.83 | 141.36 | 87.43 |
| U77594 | 3427 | retinoic acid receptor responder (tazarotene induced)2 | 11.95 | 0.00527 | 94.59 | 122.86 | 71.01 | 838.98 | 864.02 | 313.87 |
| U79716 | 3436 | reelin | 3.51 | 0.00053 | 14.44 | 9.15 | 15.58 | 90.6 | 101.49 | 36.51 |
| U81607 | 3439 | A kinase (PRKA) anchor protein (gravin) 12 | #N/A | #N/A | 18.75 | 8.46 | 50.91 | 82.7 | 78.31 | 62.79 |
| U83461 | 3443 | solute carrier family 31 (copper transporters), member 2 | #N/A | #N/A | 24.64 | 21.28 | 13.16 | 51.79 | 48.53 | 20.85 |
| U85193 | 3446 | nuclear factor I/B | #N/A | #N/A | 21.84 | 23.61 | 4.44 | 72.71 | 68.69 | 32.02 |
| U90544 | 3453 | solute carrier family 17 (sodium phosphate), member 2 | 6.42 | 0.00023 | -3.14 | -5.18 | 19.12 | 157.41 | 168.92 | 63.8 |
| X02750 | 3670 | protein C (inactivator of coagulation factors Va and VIIIa) | 7.04 | 0.00079 | 55.79 | 52.95 | 30.08 | 373.11 | 367.46 | 95.74 |
| X06562 | 3683 | growth hormone receptor | 10.87 | 0.00001 | 10.46 | 6.89 | 15.53 | 291.31 | 314.9 | 160.29 |
| X07732 | 3690 | hepsin (transmembrane protease, serine 1) | 28.21 | 0 | -8.34 | -12 | 39.24 | 678.15 | 672.42 | 183.61 |
| X07767 | 3691 | protein kinase, cAMP-dependent, catalytic, alpha | 5.94 | 0.00028 | 16.15 | 19.43 | 11.48 | 152.58 | 160.88 | 73.73 |
| X12662 | 3694 | arginase, liver | 20.59 | 0 | 11.33 | 10.15 | 12.81 | 486.71 | 479.11 | 199.71 |
| X13227 | 3695 | D-amino-acid oxidase | 4.81 | 0.0002 | 25.1 | 33.95 | 26.2 | 166.22 | 147.21 | 77.49 |
| X14813 | 3702 | acetyl-Coenzyme A acyltransferase 1 (peroxisomal 3-oxoacyl-Coenzyme A thiolase) | 11.61 | 0.0002 | 59.4 | 71.51 | 42.45 | 712.58 | 704.45 | 258.91 |
| X15393 | 3704 | motilin | #N/A | #N/A | 70.16 | 55.83 | 27.07 | 113.93 | 117.96 | 26.14 |
| X16663 | 3711 | hematopoietic cell-specific Lyn substrate 1 | #N/A | #N/A | 48.32 | 28.69 | 56.44 | 81.51 | 83.53 | 33.75 |
| X17094 | 3714 | paired basic amino acid cleaving enzyme (furin, membrane associated receptor protein) | 8.5 | 0 | -1.85 | 7.01 | 25.41 | 190.11 | 216.35 | 74.11 |
| X53414 | 3725 | alanine-glyoxylate aminotransferase (oxalosis I; hyperoxaluria I; glycolicaciduria; serine-pyruvate aminotransferase) | 13.87 | 0.00003 | 138.92 | 110.29 | 90.59 | 1856.57 | 1888.79 | 846.06 |
| X54380 | 3727 | pregnancy-zone protein | 8.44 | 0.00059 | 4.93 | 3.19 | 19.26 | 274.41 | 255.4 | 203.47 |
| X56411 | 3734 | alcohol dehydrogenase 4 (class II), pi polypeptide | 25.14 | 0.00144 | 55.53 | 11.29 | 102.45 | 991.98 | 943.64 | 448.31 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| X57025 | 3739 | insulin-like growth factor 1 (somatomedin C) | 4.72 | 0.00087 | 5.88 | 10.95 | 10.22 | 120.82 | 100.54 | 85.16 |
| X63359 | 3756 | UDP glycosyltransferase 2 family, polypeptide B10 | 13.66 | 0.00051 | 55.28 | 48.57 | 41.25 | 669.93 | 732.6 | 161.42 |
| X63417 | 3757 | c-myc promoter-binding protein | #N/A | #N/A | 28.85 | 27.75 | 24.56 | 68.08 | 56.34 | 33.18 |
| X76105 | 3791 | death-associated protein | 3.02 | 0.00944 | 30.12 | 33.72 | 31.36 | 108.68 | 118.36 | 56.76 |
| X78992 | 3799 | butyrate response factor 2 (EGF-response factor 2) | 4.69 | 0.01995 | 64.86 | 31.76 | 66.31 | 318.26 | 336.95 | 207.43 |
| X79981 | 3803 | cadherin 5, VE-cadherin (vascular epithelium) | #N/A | #N/A | 45.01 | 41.07 | 11.65 | 80.92 | 80.1 | 8.57 |
| X90999 | 3817 | hydroxyacyl glutathione hydrolase; glyoxalase 2 | 5.27 | 0.00047 | 16.15 | 26.83 | 26.47 | 170.37 | 179.54 | 76.98 |
| X91148 | 3818 | microsomal triglyceride transfer protein (large polypeptide, 88kD) | 5.91 | 0.00045 | 15.37 | 3.85 | 31.49 | 173.77 | 189.11 | 83.82 |
| X92396 | 3820 | synaptobrevin-like 1 | #N/A | #N/A | 40.87 | 17.73 | 57.17 | 67.49 | 61.23 | 31.24 |
| X95190 | 3829 | acyl-Coenzyme A oxidase 2, branched chain | 12.81 | 0 | −80.53 | −76.73 | 37.81 | 285.88 | 349.39 | 119.31 |
| X97160 | 3835 | transcription factor binding to IGHM enhancer 3 | #N/A | #N/A | 61.31 | 49.54 | 30.41 | 75.26 | 66.36 | 29.46 |
| Z28339 | 3872 | aldo-keto reductase family 1, member D1 (delta 4-3-ketosteriod-5-beta-reductase) | 24.66 | 0 | 3.67 | 3.48 | 5.1 | 527.72 | 552.17 | 156.66 |
| Z47553 | 3936 | flavin containing monooxygenase 5 | 6.17 | 0.0011 | 4.86 | 1.26 | 8.96 | 141.98 | 165.57 | 59.33 |
| Z48054 | 3938 | peroxisome receptor 1 | #N/A | #N/A | 46.89 | 51.87 | 23.55 | 78.16 | 80.88 | 26.87 |
| Z48633 | 3941 | EST | #N/A | #N/A | −5.51 | −6.39 | 13.15 | 36.84 | 40.63 | 26.33 |
| Z49269 | 3942 | small inducible cytokine subfamily A (Cys-Cys), member 14 | 18.46 | 0.00001 | 1.88 | −25.63 | 41.94 | 526.13 | 532.29 | 166.67 |
| Z49878 | 3943 | guanidinoacetate N-methyltransferase | 13.96 | 0.00021 | 44.63 | 45.34 | 41.76 | 615.57 | 659.09 | 196.31 |
| K02766 | 2126 | complement component 9 | 21.24 | 0 | 23.15 | 14.02 | 21.18 | 652.66 | 656.14 | 320.1 |
| L04751 | 2138 | cytochrome P450, subfamily IVA, polypeptide 11 | 36.79 | 0.00004 | 32.39 | 23.29 | 32.64 | 1164.28 | 1183.4 | 334.08 |
| M24283 | 2303 | intercellular adhesion molecule 1 (CD54), human rhinovirus receptor | 3.19 | 0.04985 | 77.88 | 34.05 | 69.45 | 207.07 | 183.74 | 121.4 |
| M61853 | 2369 | cytochrome P450, subfamily IIC (mephenytoin 4-hydroxylase), polypeptide 18 | 7.82 | 0.00024 | 12.17 | 12.44 | 4.36 | 191.94 | 204.27 | 91.68 |
| S77410 | 3034 | angiotensin receptor 1 | 10.4 | 0 | 18.77 | 17.34 | 10.85 | 266.59 | 284.37 | 98.14 |
| U20938 | 3323 | dihydropyrimidine dehydrogenase | 3.92 | 0.00053 | 6.66 | 6.08 | 7.12 | 90.66 | 97.02 | 44.64 |
| U60061 | 3399 | fasciculation and elongation protein zeta 2 (zygin II) | #N/A | #N/A | 61.44 | 29.18 | 68.3 | 55.02 | 66.29 | 38.2 |
| X15422 | 3705 | mannose-binding lectin (protein C) 2, soluble (opsonic defect) | 8.29 | 0.00015 | 2.28 | 2.69 | 7.25 | 208.25 | 221.14 | 123.22 |
| X16323 | 3708 | hepatocyte growth factor (hepapoietin A; scatter factor) | #N/A | #N/A | 10.65 | 6.56 | 6.59 | 32.58 | 30.52 | 9.66 |
| Y00097 | 3841 | annexin A6 | 3.4 | 0.00233 | 19.43 | 16.39 | 33.67 | 105.39 | 104.75 | 39.99 |
| M15465 | 2266 | pyruvate kinase, liver and RBC | 6.1 | 0.00069 | 3.06 | 3.32 | 11.38 | 158.56 | 132.57 | 102.11 |
| D13814 | 1611 | angiotensin receptor 1, angiotensin receptor 1B | 3.12 | 0.00101 | 13.86 | 10.01 | 12.82 | 79.69 | 75.71 | 45.03 |
| HG2383-HT4824 | | cystathionine-beta-synthase | 13.57 | 0.00035 | −0.01 | 2.09 | 10.74 | 377.07 | 375.12 | 210.67 |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| HG2730-HT2827 | | fibrinogen; A alpha polypeptide | 25.1 | 0 | 17.62 | 12.16 | 24.49 | 720.93 | 681.36 | 269.11 |
| HG2743-HT2846 | | caldesmon 1 | 3.33 | 0.00135 | 27.49 | 25.6 | 21.89 | 103.56 | 92.79 | 35.98 |
| M83216 | 2406 | caldesmon 1 | 4.27 | 0.00037 | 7.89 | 2.98 | 12.17 | 105.21 | 109.38 | 55.62 |
| J03242 | 2092 | insulin-like growth factor 2 (somatomedin A) | 4.01 | 0.00042 | 40.37 | 45.32 | 15.53 | 179.86 | 172.23 | 104.64 |
| J04093 | 2106 | UDP glycosyltransferase 1 | 18.92 | 0 | 8.62 | 8.7 | 12.9 | 462.51 | 511 | 215.46 |
| M13232 | 2251 | coagulation factor VII (serum prothrombin conversion accelerator) | 5.9 | 0.00014 | 43.46 | 42.59 | 18.46 | 248.65 | 275.82 | 70.94 |
| Y00339 | 3844 | carbonic anhydrase II | 6.89 | 0 | 6.23 | -1.39 | 18.22 | 168.76 | 178.44 | 69.52 |
| X02176 | 3669 | complement component 9 | 9.61 | 0.00004 | 47.28 | 46.34 | 28.54 | 507.56 | 507.21 | 261.45 |
| U37055 | 3352 | macrophage stimulating 1 (hepatocyte growth factor-like), macrophage stimulating, pseudogene 9 | 18.28 | 0 | -7.37 | -38.2 | 47.48 | 549.49 | 626.51 | 217.69 |
| X65727 | 3765 | glutathione S-transferase A2, glutathione S-transferase A3 | 73.64 | 0 | 21.03 | 17.39 | 15.18 | 2162.22 | 2183.18 | 1435.52 |
| U80226 | 3438 | 4-aminobutyrate aminotransferase | #N/A | #N/A | 39.69 | 51.46 | 20.33 | 86.94 | 91.76 | 24.15 |
| U19495 | 3318 | stromal cell-derived factor 1 | 4.59 | 0.00011 | 7.17 | 5.76 | 5.65 | 103.81 | 114.61 | 50.36 |
| U08006 | 3289 | complement component 8, alpha polypeptide | 16 | 0.00111 | 47.06 | 31.92 | 47.52 | 633.01 | 661.72 | 102.98 |
| M23234 | 2299 | ATP-binding cassette, sub-family B (MDR/TAP), member 4 | 10.05 | 0 | -4.37 | -11.49 | 29.05 | 255.03 | 242.93 | 112.08 |
| M30257 | 2322 | vascular cell adhesion molecule 1 | 3.11 | 0.00064 | 17.33 | 13.46 | 10.06 | 78.1 | 82.04 | 35.74 |
| M86873 | 2413 | plasminogen, plasminogen-like | 17.54 | 0 | -3.92 | -8.08 | 6.71 | 410.11 | 403.69 | 218.51 |
| M65134 | 2385 | complement component 5 | 12.01 | 0.00012 | 2.31 | 3.66 | 7.43 | 303.27 | 337.95 | 151.33 |
| X65962 | 3766 | cytochrome P450, subfamily IIC (mephenytoin 4-hydroxylase) | 5.47 | 0.00014 | 36.73 | 31.48 | 11.66 | 247.79 | 149.39 | 208.59 |
| M98399 | 2436 | CD36 antigen (collagen type I receptor, thrombospondin receptor) | #N/A | #N/A | 4.71 | 4.58 | 5.51 | 47.65 | 38.28 | 35.2 |
| X86401 | 3812 | glycine amidinotransferase (L-arginine: glycine amidinotransferase) | 22.7 | 0 | 19.17 | 9.16 | 19.13 | 646 | 721.34 | 274.64 |
| U08854 | 3292 | UDP glycosyltransferase 2 family, polypeptide B15 | 7.38 | 0.00005 | 10.72 | 6.45 | 10.71 | 181.08 | 184.97 | 91.81 |
| U51010 | 3380 | nicotinamide N-methyltransferase | 27.79 | 0.00366 | 105.25 | 43.72 | 204.23 | 1589.66 | 1590.62 | 536.04 |
| X07619 | 3689 | cytochrome P450, subfamily IID (debrisoquine, sparteine, etc., -metabolising), polypeptide 7a (pseudogene) | 4.96 | 0.00004 | 32.26 | 33.56 | 10.88 | 177.56 | 206.15 | 77.69 |
| X64877 | 3763 | H factor (complement)-like 3 | 14.6 | 0 | 14.6 | 7.51 | 21.01 | 387.8 | 402.95 | 151.23 |
| X64877 | 3763 | H factor (complement)-like 3 | 12.33 | 0 | 6.14 | 8.26 | 14.25 | 262.65 | 268.29 | 84.84 |
| X98337 | 3837 | complement factor H related 3, complement factor H related 4 | 13.5 | 0.00001 | 18.76 | 22.2 | 33.33 | 411.51 | 375.08 | 169.37 |
| X94563 | 3828 | EST | 3.52 | 0.00928 | 76.79 | 66.4 | 52.64 | 274.91 | 244.92 | 177.63 |
| D90042 | 1767 | N-acetyltransferase 2 (arylamine N-acetyltransferase) | 7.06 | 0 | 5.13 | 18.92 | 32.5 | 167.38 | 176.16 | 66.7 |
| M10943 | 2234 | metallothionein 1F (functional) | 3.88 | 0 | 53.15 | 52.73 | 8.81 | 217.65 | 186.71 | 86.73 |
| | | aldo-keto reductase family 1, member C4 (chlordecone reductase; 3-alpha hydroxysteroid dehydrogenase, type I; | | | | | | | | |

TABLE 9B-continued

Genes and ESTs expressed only in Normal2 vs Metastatic Liver Tumor

| Fragment Name | SEQ ID: | Known Gene Name | fold change in metas | p value | metastatic: Mean | metastatic: Median | metastatic: Std Dev | normal set 2: Mean | normal set 2: Median | normal set 2: Std Dev |
|---|---|---|---|---|---|---|---|---|---|---|
| S68287 | 3024 | dihydrodiol dehydrogenase 4) | 24.11 | 0 | 6.23 | 6.37 | 9.75 | 510.59 | 569.32 | 165.14 |
| U02388 | 3277 | cytochrome P450, subfamily IVF, polypeptide 2 | 9.38 | 0.00001 | −4.93 | −3.43 | 18.14 | 207.48 | 207.15 | 90.12 |
| U05861 | 3284 | aldo-keto reductase family 1, member C1 (dihydrodiol dehydrogenase 1; 20-alpha (3-alpha)-hydroxysteroid dehydrogenase) | 23.22 | 0.00002 | 47.98 | 44.41 | 21.91 | 1070.69 | 962.74 | 359.01 |
| L11931 | 2159 | serine hydroxymethyltransferase 1 (soluble) | 7.27 | 0.00041 | −18.81 | −31.65 | 26.43 | 188.25 | 181.11 | 114.89 |
| L32961 | 2194 | 4-aminobutyrate amino transferase | #N/A | #N/A | 15.64 | 7.44 | 15.63 | 76.44 | 79.62 | 26.55 |
| M16594 | 2272 | glutathione S-transferase A2 | 73.21 | 0 | −3.62 | −9.74 | 18.15 | 1602.11 | 1787.28 | 655.41 |
| L00389 | 2132 | cytochrome P450, subfamily I (aromatic compound-inducible), polypeptide 2 | #N/A | #N/A | 69.38 | 86.39 | 64.81 | 222.59 | 184.81 | 121.16 |
| M33317 | 2338 | cytochrome P450, subfamily IIA (phenobarbital-inducible), polypeptide 7 | 32.63 | 0 | 44.53 | 35.06 | 29.77 | 1613.89 | 1437.34 | 1086.43 |
| U22029 | 3326 | cytochrome P450, subfamily IIA (phenobarbital-inducible), polypeptide 7 | 71.98 | 0 | 5.05 | 10.11 | 21.51 | 1968.7 | 1339.04 | 1937.45 |
| X13930 | 3697 | cytochrome P450, subfamily IIA (phenobarbital-inducible, polypeptide 6 | 38.52 | 0 | 52.66 | 64.02 | 31.42 | 2408.66 | 1948.18 | 1843.46 |

SEQUENCE LISTING

The patent contains a lengthy "Sequence Listing" section. A copy of the "Sequence Listing" is available in electronic form from the USPTO web site (http://seqdata.uspto.gov/sequence.html?DocID=6974667B2). An electronic copy of the "Sequence Listing" will also be available from the USPTO upon request and payment of the fee set forth in 37 CFR 1.19(b)(3).

What is claimed is:

1. A method of diagnosing hepatocellular carcinoma in a human patient, compnsing:
   (a) detecting the level of expression in a tissue sample of ten or more genes from Tables 3A, 3B, 5, 7A, 7B, 8A, and 8B; wherein differential expression of the genes in Tables 3A, 3B, 5, 7A, 7B, 8A, and 8B is indicative of hepatocellular carcinoma.

2. A method of detecting the progression of hepatocellular carcinoma in a human patient, comprising:
   (a) detecting the level of expression in a tissue sample of ten or more genes from Tables 3A, 3B, 5, 7A, 7B, 8A, and 8B; wherein differential expression of the genes in Tables 3A, 3B, 5, 7A, 7B, 8A, and 8B is indicative of hepatocellular carcinoma progression.

3. A method of monitoring the treatment of a human patient with hepatocellular carcinoma, comprising:
   (a) administering a pharmaceutical composition to the patient;
   (b) detecting the level of expression of ten or more genes from Tables 3A, 3B, 5, 7A, 7B 8A and 8B from a cell or tissue sample from the patient; and
   (c) comparing the patient gene expression detected in step (b) to gene expression from a cell population comprising normal liver cells or to gene expression from a cell population comprising hepatocellular carcinoma cells or both.

4. A method of diagnosing a metastatic liver cancer in a human patient, comprising:
   (a) detecting the level of expression in a tissue sample of ten or more genes from Tables 4A, 4B, 5, 6A, 6B, 9A and 9B; wherein differential expression of the genes in Tables 4A, 4B, 5, 6A, 6B, 9A, and 9B is indicative of metastatic liver cancer.

5. A method of detecting the progression of a metastatic liver cancer in a human patient, comprising:
   (a) detecting the level of expression in a tissue sample of ten or more genes from Tables 4A, 4B, 5, 6A, 6B, 9A and 9B; wherein differential expression of the genes in Tables 4A, 4B, 5, 6A, 6B, 9A, and 9B is indicative of metastatic liver cancer progression.

6. A method of monitoring the treatment of a human patient with metastatic liver cancer, comprising:
   (a) administering a pharmaceutical composition to the patient;
   (b) detecting the level of expression of ten or more genes from Tables 4A, 4B, 5, 6A, 6B, 9A and 9B from a cell or tissue sample from the patient; and
   (c) comparing the patient gene expression detected in step (b) to gene expression from a cell population comprising normal liver cells or to gene expression from a cell population comprising metastatic liver tumor cells or both.

7. A method of differentiating metastatic liver cancer from hepatocellular carcinoma in a human patient, comprising:
   (a) detecting the level of expression in a tissue sample of ten or more genes from Tables 3–9; wherein differential expression of the genes in Tables 3–9 is indicative of metastatic liver cancer rather than hepatocellular carcinoma.

8. A method of claim 1 or 4, wherein the level of expression of 100 or more genes from one or more tables selected from the group consisting of Tables 3A, 3B, 4A, 4B, 5, 6A, 6B, 7A, 7B, 8A, 8B, 9A and 9B is detected.

9. A method of claim 1 or 4, wherein the level of expression is compared to the gene information in one or more tables selected from the group consisting of Tables 3A, 3B, 4A, 4B, 5, 6A, 6B, 7A, 7B, 8A, 8B, 9A and 9B.

10. A method of diagnosing hepatocellular carcinoma or metastatic liver cancer in a human patient comprising:
    (a) detecting the level of expression of ten or more genes from Tables 3–9 from a tissue sample from the patient; and
    (b) comparing the gene expression detected in step (a) to a database comprising part of the data in Tables 3–9; wherein differential expression of the genes detected in step (a) is indicative of hepatocellular carcinoma or metastatic liver cancer.

11. A method of claim 10, wherein the cancer is hepatocellular carcinoma.

12. A method of claim 10, wherein the cancer is metastatic liver cancer.

13. A method of claim 10, wherein the database comprises all of the data from Tables 3–9.

14. A method of claim 10, wherein the database comprises gene expression information for all of the genes from Tables 3–9.

15. A method of diagnosing hepatocellular carcinoma in a human patient, comprising:
    (a) detecting the level of expression in a liver tissue sample of ten or more mRNA species from Table 3A, 3B, 5, 7A, 7B, 8A or 8B; and
    (b) comparing the detected level of expression to the level of expression of said ten or more mRNA species in a hepatocellular carcinoma liver tissue sample, thereby diagnosing hepatocellular carcinoma in the patient.

16. A method of diagnosing metastatic liver cancer in a human patient, comprising:
    (a) detecting the level of expression in a liver tissue sample of ten or more mRNA species from Table 4A, 4B, 5, 6A, 6B, 9A or 9B; and
    (b) comparing the detected level of expression to the level of expression of said ten or more mRNA species in a metastatic liver cancer tissue sample, thereby diagnosing metastatic liver cancer in the patient.

17. A method of claim 15, wherein the level of expression of said ten or more mRNA species in a hepatocellular carcinoma liver sample is in Table 3A, 3B, 5, 7A, 7B, 8A or 8B.

18. A method of claim 16, wherein the level of expression of said ten or more mRNA species in a metastatic liver cancer sample is in Table 4A, 4B, 5, 6A, 6B, 9A or 9B.

* * * * *